US005861427A

United States Patent [19]
Kluender et al.

[11] Patent Number: 5,861,427
[45] Date of Patent: Jan. 19, 1999

[54] SUBSTITUTED 4-BIARYLBUTYRIC ACID DERIVATIVES AS MATRIX METALLOPROTEASE INHIBITORS

[76] Inventors: Harold Clinton Eugene Kluender, 27 Academy Rd., Trumbull, Conn. 06611; Guenter Hans Herbert Heinz Benz, Am Bolkumer-Busch 5, D-42553 Velbert, Germany; David Ross Brittelli, 240 Stony Creek Rd., Branford, Conn. 06405; Brian Richard Dixon, 1220 Johnson Rd., Woodbridge, Conn. 06525; Michael Christopher VanZandt, 56 Barker Hill Dr., Guiliford, Conn. 06437; Scott McClelland Wilhelm, 255 Midland Dr.; Donald John Wolanin, 320 Longmeadow Rd., both of Orange, Conn. 06477

[21] Appl. No.: 866,679

[22] Filed: May 30, 1997

Related U.S. Application Data

[63] Continuation of Ser. No. 465,626, Jun. 5, 1995, abandoned, which is a continuation of Ser. No. 339,846, Nov. 15, 1994, abandoned.

[51] Int. Cl.⁶ .................. A61K 31/40; A61K 31/535; C07D 204/02; C07D 265/30
[52] U.S. Cl. .................. 514/417; 514/238.8; 548/468; 548/473; 548/477; 548/478; 548/479; 548/470; 544/171
[58] Field of Search ................... 548/468, 473, 548/477, 478, 470; 514/419, 238.8; 544/171

[56] References Cited

U.S. PATENT DOCUMENTS

| | | | |
|---|---|---|---|
| 3,182,061 | 5/1965 | Goldschmidt | 260/520 |
| 3,624,142 | 11/1971 | Shen et al. | 260/515 A |
| 3,652,646 | 3/1972 | Leigh et al. | 260/473 G |
| 3,707,549 | 12/1972 | Mills | 260/470 |
| 3,749,750 | 7/1973 | Wei | 260/470 |
| 3,754,021 | 8/1973 | Shen et al. | 260/515 A |
| 3,784,701 | 1/1974 | Tomcufcik et al. | 424/317 |
| 3,867,434 | 2/1975 | Diamond | 260/515 A |
| 3,876,800 | 4/1975 | Kruasz et al. | 424/317 |
| 3,882,174 | 5/1975 | Seeger et al. | 260/558 R |
| 3,917,846 | 11/1975 | Diamond et al. | 424/317 |
| 3,962,228 | 6/1976 | Wei et al. | 260/243 C |
| 3,993,683 | 11/1976 | Nickl et al. | 260/470 |
| 3,997,589 | 12/1976 | Seeger et al. | 260/469 |
| 4,008,323 | 2/1977 | Cousse et al. | 424/250 |
| 4,021,479 | 5/1977 | Seeger et al. | 260/520 B |
| 4,049,823 | 9/1977 | Schacht et al. | 424/308 |
| 4,058,558 | 11/1977 | Cousse et al. | 260/515 |
| 4,151,302 | 4/1979 | Gante et al. | 424/317 |
| 4,168,385 | 9/1979 | Trust et al. | 560/56 |
| 4,219,668 | 8/1980 | Chiccarelli | 562/469 |
| 4,247,466 | 1/1981 | Chiccarelli | 260/343.6 |
| 4,271,191 | 6/1981 | Mazoyer | 424/317 |
| 4,304,788 | 12/1981 | Edge | 424/308 |
| 4,310,544 | 1/1982 | Edge | 424/308 |
| 4,472,316 | 9/1984 | Sota et al. | 260/455 R |
| 4,577,025 | 3/1986 | Arai et al. | 546/198 |
| 4,594,197 | 6/1986 | Tomisawa et al. | 558/255 |
| 4,683,331 | 7/1987 | Kuchar et al. | 562/459 |
| 4,933,367 | 6/1990 | Wolff et al. | 514/570 |
| 4,937,243 | 6/1990 | Markwell et al. | 514/237.8 |
| 5,098,613 | 3/1992 | Bollinger et al. | 260/413 |
| 5,109,000 | 4/1992 | Markwell et al. | 514/237.8 |
| 5,124,322 | 6/1992 | Hughes | 514/183 |
| 5,177,204 | 1/1993 | Kuchar et al. | 544/126 |
| 5,462,954 | 10/1995 | Baker et al. | 514/381 |
| 5,473,100 | 12/1995 | Isomura et al. | 562/26 |
| 5,525,629 | 6/1996 | Crimmin et al. | 514/542 |
| 5,591,891 | 1/1997 | Fournie-Zaluski et al. | 567/426 |

FOREIGN PATENT DOCUMENTS

| | | |
|---|---|---|
| 667498 | 11/1965 | Belgium . |
| 0180290 | 5/1986 | European Pat. Off. . |
| 0275024 | 7/1988 | European Pat. Off. . |
| 2104632 | 5/1972 | France . |
| 2503140 | 10/1982 | France . |
| 2854475 | 7/1980 | Germany . |
| 60-209539 | 10/1985 | Japan . |
| 61-200963 | 9/1986 | Japan . |

(List continued on next page.)

OTHER PUBLICATIONS

Chiccarelli et al., "Disposition and Metabolism of Fenbufen in several Laboratory Animals", Arzneim–Forsch./Drug Res., 30(1), 707–715 (1980).

(List continued on next page.)

*Primary Examiner*—Deborah C. Lambkin

[57] ABSTRACT

Inhibitors for matrix metalloproteases, pharmaceutical compositions containing them, and a process for using them treat a variety of physiological conditions. The compounds of the invention have the generalized formula

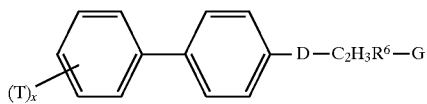

wherein each T is a substituent group; x is 0, 1, or 2; the group D represents

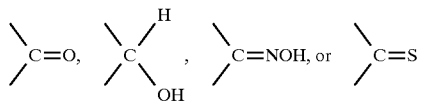

the group R6 represents a variety of possible substituent groups on the carbon chain between D and G, and the group G represents M,

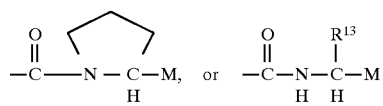

in which M represents $-CO_2H$, $-CON(R^{11})_2$, or $-CO_2R^{12}$; and $R^{13}$ represents any of the side chains of the 19 noncyclic naturally occurring amino acids.

16 Claims, No Drawings

FOREIGN PATENT DOCUMENTS

| | | |
|---|---|---|
| 61-200964 | 9/1986 | Japan . |
| 62-132825 | 6/1987 | Japan . |
| 63-88168 | 4/1988 | Japan . |
| 0465879 | 1/1992 | Japan . |
| 4128262 | 4/1992 | Japan . |
| 0488682 | 6/1992 | Japan . |
| 62-34754 | 8/1994 | Japan . |
| 1565616 | 4/1980 | United Kingdom . |

OTHER PUBLICATIONS

Child et al., "A New Non–steroidal Anti–inflammatory Analgesic: γ–Oxo (1,1'–biphenyl)–4–butanoic Acid (Fenbufen)", Arzneim–Forsch./ Drug Res., 30(I), 695–702 (1980).

Child et al., "Fenbufen, a New Anti–Inflammatory Analgesic: Synthesis and Structure–Activity Relationships of Analogs", J. Pharma. Sci., 66(4), 466–476 (1977).

Cousse et al., "Synthèse, structure et activité hypocholestérolémiante d'une série d'acides γ–oxo butyriques subsitutés et dérivés", Eur. J. Med. Chem., 22, 45–57 (1987).

Curran, W. V. and Ross, A., "6–Phenyl–4, 5–dihydro–3(2H)–pyridazinones. A Series of Hypotensive Agents", J. Med. Chem., 17(3), 273–281 (1974).

Farbenind, I. G., "Compounds having capillary action", Chem. Abstracts, 30, $7729^3$ (1936).

Kameo et al., "Studies on Antirheumatic Agents: 3–Benzoylpropionic Acid Derivatives", Chem. Pharm. Bull., 36(6), 2050–2060 (1988).

Kawashima et al., "Structure–Activity Studies of 3–Benzoylpropionic Acid Derivatives Suppressing Adjuvant Arthritis", Chem. Pharm. Bull., 40(3), 774–777 (1992).

Tomisawa et al., "Studies on Hypolipidemic Agents. II. 3–(4–Phenoxybenzoyl)–propionic Acid Derivatives", Chem. Pharm. Bull., 33(6), 2386–2394 (1985).

Weizmann et al., "A New Method for the Synthesis of β–Phenyl–Naphthalene Derivatives", Chemistry and Industry, pp. 402–404, Jun. 8, 1940.

Sammour et al., "Alkylation of Aromatic Hydrocarbons with β–Aroylacrylic Acids", J. Prakt. Chemie, 314, 5–6, 906–914(1972).

El–Hashash et al., "Reactions of 3,5–Disubstituted–2–Furanone with Amines, Grignard Reagents, Toluene and Xyelen", Indian Journal of Heterocyclic Chemistry, 5, 231–232 (1996).

Kameo et al., "Studies on Hypolipidemic Agents. IV. 3–[4–(Phenylthio) benzoyl] propionic Acids Derivatives", Chem.Pharm. Bull., 37(5), 1260–1267 (1989).

Takeshita et al., "Immunopharmacological Studies of New 3–Benzoyl–4–Mercaptobutyric Acid Derivatives. II Immunosuppressive Effects", Drugs Exptl.Clin.Res., XIV (5), 311–318 (1988).

Fournel et al., "Differential induction profile of drug–metabolizing enzymes after treatment with hypolipidemic agents", Xenobiotica, 17(4), 445–457 (1987).

Kuchar et al., "Quantitative Relations Between Structure and Anti Inflammatory Activity of Ayloxaolkanoic Acids", Collection Czechoslovak Chem.Commun., 53, 1862–1872 (1988).

Chem.Abstr. Accession No. 108: 31304. Kuchar, et al., Metabolic Model and QSAR of Long–acting Anti–inflammatory Arylaliphatic Acids, 1988.

SUBSTITUTED 4-BIARYLBUTYRIC ACID DERIVATIVES AS MATRIX METALLOPROTEASE INHIBITORS

This application is a continuation of Ser. No. 08/465,626 filed Jun. 6, 1995, abandoned, which is a continuation of Ser. No. 08/339,846 filed Nov. 15, 1994, abandoned.

FIELD

This invention relates to enzyme inhibitors, and more particularly, to novel 4-biarylbutyric or 5-biarylpentanoic acid compounds or derivatives thereof useful for inhibiting matrix metalloproteases.

BACKGROUND

The matrix metalloproteases (aka. matrix metalloendoproteinases or MMPs) are a family of zinc endoproteinases which include, but are not limited to, interstitial collagenase (aka. MMP-1), stromelysin (aka. proteoglycanase, transin, or MMP-3), gelatinase A (aka. 72 kDα-gelatinase or MMP-2) and gelatinase B (aka. 95 kDα-gelatinase or MMP-9). These MMPs are secreted by a variety of cells including fibroblasts and chondrocytes, along with natural proteinatious inhibitors known as TIMPs (Tissue Inhibitor of MetalloProteinase).

All of these MMPs are capable of destroying a variety of connective tissue components of articular cartilage or basement membranes. Each MMP is secreted as an inactive proenzyme which must be cleaved in a subsequent step before it is able to exert its own proteolytic activity. In addition to the matrix destroying effect, certain of these MMPs such as MMP-3 have been implemented as the in vivo activator for other MMPs such as MMP-1 and MMP-9 (A. Ho, H. Nagase, Arch Biochem Biophys., 267, 211–16 (1988); Y. Ogata, J. J. Enghild, H. Nagase, J. Biol. Chem., 267, 3581–84 (1992)). Thus, a cascade of proteolytic activity can be initiated by an excess of MMP-3. It follows that specific MMP-3 inhibitors should limit the activity of other MMPs that are not directly inhibited by such inhibitors.

It has also been reported that MMP-3 can cleave and thereby inactivate the endogenous inhibitors of other proteinases such as elastase (P. G.Winyard, Z. Zhang, K. Chidwick, D. R. Blake, R. W. Carrell G., Murphy, FEBS Letts., 279, 1, 91–94 (1991)). Inhibitors of MMP-3 could thus influence the activity of other destructive proteinases by modifying the level of their endogenous inhibitors.

A number of diseases are thought to be mediated by excess or undesired matrix-destroying metalloprotease activity or by an imbalance in the ratio of the MMPs to the TIMPs. These include: a) osteoarthritis (Woessner, et al., J. Biochelogical Chem., 259(6), 3633–3638 (1984); J. Rheumatol., 10, 852–860 (1883)), b) rheumatoid arthritis (D. E. Mullins, et al., Biochim. Biophys. Acta, 695, 117–214 (1983); Arthritis and Rheumatism, 20, 1231–1239 (1977); Arthritis and Rheumatism, 34, 1076–1105 (1991)), c) septic arthritis (R. J. Williams, et al., Arthr. Rheum., 33, 533–41 (1990)), d) tumor metastasis (R. Reich, et al., Cancer Res., 48, 3307–3312 (1988), and LM. Matrisian, et al., Proc. Nat'l. Acad. Sci., USA, 83, 9413–7 (1986)), e) periodontal diseases (C. M. Overall, et al., J. Periodontal Res., 22, 81–88 (1987)), f) corneal ulceration (F.R. Burns, et al., Invest. Opthalmol., 30, 1569–1575 (1989)), g) proteinuria (W. H. Baricos, et al., Biochem. J., 254, 609–612 (1988)), h) coronary thrombosis from atherosclerotic plaque rupture (A. M. Henney, et al., Proc. Nat'l. Acad. Sci. USA, 88, 8154–8158 (1991)), i) aneurysnial aortic disease (N. Vine and J. T. Powell, Clin. Sci., 81, 233–9 (1991)), j) birth control (J. F. Woessner, et al., Steroids, 54, 491–499 (1989)), k) dystrophobic epidermolysis bullosa (A. Kronberger, et al., J. Invest. Dermatol., 79, 208–211 (1982)), and 1) degenerative cartilage loss following traumatic joint injury, conditions leading to inflammatory responses, osteopenias mediated by MMP activity, tempero mandibular joint disease, demyelating diseases of the nervous system, etc. (J. Neurochem., 50, 688–694 (1988)).

The need for new therapies is especially important in the case of arthritic diseases. The primary disabling effect of oeteoarthritis (OA), rheumatoid arthritis (RA) and septic arthritis is the progressive loss of articular cartilage and thereby normal joint function. No marketed pharmaceutical agent is able to prevent or slow this cartilage loss, although nonsteroidal antiinflammatory drugs (NSAIDs) have been given to control pain and swelling. The end result of these diseases is total loss of joint function which is only treatable by joint replacement surgery. MMP inhibitors are expected to halt or reverse the progression of cartilage loss and obviate or delay surgical intervention.

Several inhibitors of MMPs have been described in the literature. See, for example, U.S. Pat. No. 4,599,361; U.S. Pat. No. 5,190,937; EP 0574 758 A1, published Dec. 22, 1993; EP 026 436 A1 published Aug. 3, 1988; and EP 0520 573 A1, published Dec. 30, 1992. These compounds have peptide backbones with a zinc complexing group (hydroxamic acid, thiol, carboxylic acid or phosphinic acid) at one end and a variety of sidechains, both those found in the natural amino acids as well as those with more novel functional groups. Such small peptides are usually poorly absorbed, exhibiting low oral bioavailability. They are also subject to rapid proteolytic metabolism, thus having short half lives. See, for example, a search for orally active peptide-based renin inhibitors in which the best compound had a bioavailability of only 14% in monkeys: Saul H. Rosenberg, et al., J. Med. Chem., 36, 449–459 (1993).

Certain 3-biphenoylpropanoic and 4-biaryloylbutanoic acids are described in the literature as anti-inflammatory, anti-platelet aggregation, anti-phlogistic, anti-proliferative, hypolipidemic, antirheumatic, analgesic, and hypocholesterolemic agents. In none of these examples is a reference made to MMP inhibition as a mechanism for the claimed therapeutic effect. Certain related compounds are also used as intermediates in the preparation of liquid crystals.

Specifically U.S. Pat. No. 3,784,701 claims certain substituted benzoylpropionic acids to treat inflammation and pain. These compounds include 3-biphenoylpropanoic acid (aka fenbufen) shown below.

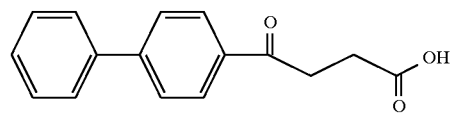

Fenbufen

R. G. Child, et al., J. Pharm. Sci., 66, 466–476 (1977) describes structure-activity relationships of several analogs of fenbufen. These include several compounds in which the biphenyl ring system is substituted or the propanoic acid portion is substituted with phenyl, halogen, hydroxyl or methyl, or the carboxylic acid or carbonyl functions are converted to a variety of derivatives. No compounds are described which contain a 4'-substituted biphenyl and a substituted propanoic acid portion combined in one molecule. The phenyl (compounds XLIV and LXXVII) and methyl (compound XLVIII) substituted compounds shown below were described as inactive.

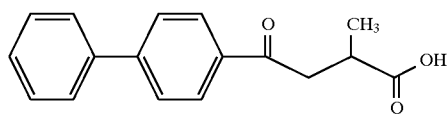

XLVIII

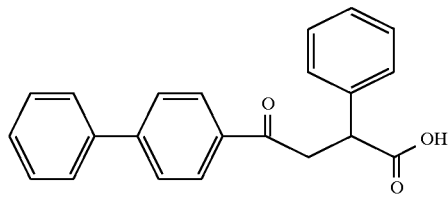

XLIX

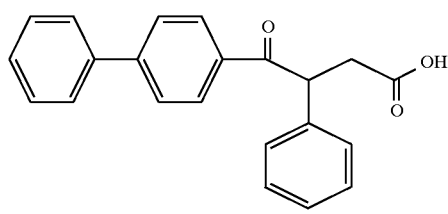

LXXVII

K. K. Kameo, et al., Chem. Pharm. Bull., 36, 2050–2060 and JP patent 62132825 describe certain substituted 3-biphenoylpropionic acid derivatives and analogs thereof including the following. Various compounds with other substituents on the propionic acid portion are described, but they do not contain biphenyl residues.

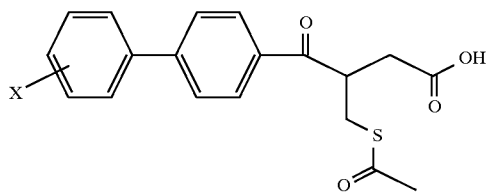

X = H, 4'-Br, 4'-Cl, 4'-CH$_3$ and 2'-Br

H. Cousse, et al., Eur. J. Med. Chem., 22, 45–57 (1987) describe the following methyl and methylene substituted 3-biphenoylpropanoic and -propenoic acids. The corresponding compounds in which the carbonyl is replaced with either CHOH or CH2 are also described.

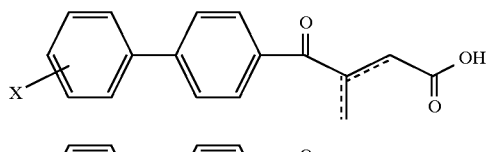

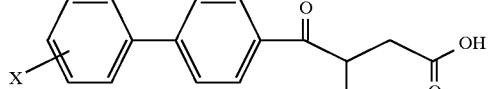

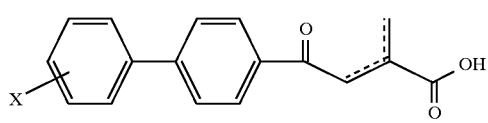

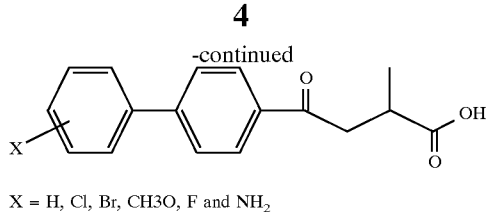

X = H, Cl, Br, CH3O, F and NH$_2$

German Patent Application No. 19 57 750 of Tomae also describes certain of the above methylene substituted biphenoylpropanoic acids.

M. A. El-Hashsh, et al., Revue Roum. Chim., 23, 1581–1588 (1978) describe products derived from β-aroylacrylic acid epoxides including the following biphenyl compound. No compounds substituted on the biphenyl portion are described.

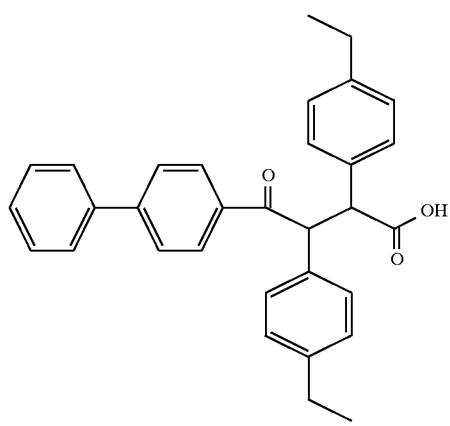

T. Kitamura, et al., Japanese Patent Application No. 84-65795 840404 describes certain biphenyl compounds used as intermediates for the production of liquid crystals including the following. The biphenyl is not substituted in these intermediates.

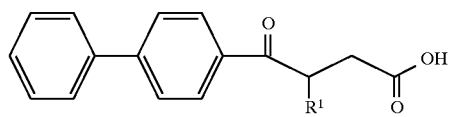

R$^1$ = alkyl of 1–10 carbons

German Patent No. 28 54 475 uses the following compound as an intermediate. The biphenyl group is not substituted.

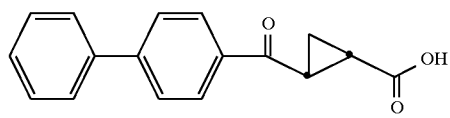

A. Sammou, et al., Egypt J. Chem., 15, 311–327 (1972) and J. Couquelet, et al., Bull. Soc. Chim. Fr., 9, 3196–9 (1971) describe certain dialkylamino substituted biphenoylpropanoic acids including the following. In no case is the biphenyl group substituted.

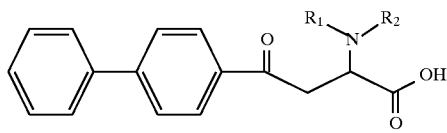

R₁, R₂ = alkyl, benzyl, H
and morpholine ring together with the Nitrogen

It would be desirable to have effective MMP inhibitors which possess improved bioavailablity and biological stability relative to the peptide-based compounds of the prior art, and which can be optimized for use against particular target MMPs. Such compounds are the subject of the present application.

SUMMARY

This invention relates to compounds having matrix metalloprotease inhibitory activity and the generalized formula:

$$(T)x\alpha\text{-B-D-E-G} . \tag{I}$$

In the above generalized formula (I), (T)xA represents a substituted or unsubstituted aromatic 6-membered ring or heteroaromatic 5–6 membered ring containing 1–2 atoms of N, O, or S. T represents one or more substituent groups, the subscript x represents the number of such substituent groups, and A represents the aromatic or heteroaromatic ring, designated as the A ring or A unit. When N is employed in conjunction with either S or O in the A ring, these heteroatoms are separated by at least one carbon atom.

The substituent group(s) T are independently selected from the group consisting of halogen; alkyl; haloalkyl; alkenyl; alkynyl; —(CH₂)ₚQ in which p is 0 or an integer of 1–4; and -alkenyl-Q in which the alkenyl moiety comprises 2–4 carbons. Q in the latter two groups is selected from the group consisting of aryl, heteroaryl, —CN, —CHO, —NO₂, —CO₂R², —OCOR², —SOR³, —SO₂R³, —CON(R²)₂, —SO₂N(R²)₂, —COR², —N(R²)₂, —N(R²)COR², —N(R²)CO₂R³, —N(R²)CON(R²)₂, —CHN₄, —OR⁴, and —SR⁴. In these formulae R² represents H, alkyl, aryl, heteroaryl, arylalkyl, or heteroaryl-alkyl; R3 represents alkyl, aryl, heteroaryl, arylalkyl, or heteroaryl-alkyl; and R4 represents H, alkyl, aryl, heteroaryl, arylalkyl, heteroaryl- alkyl, alkenyl, alkynyl, haloalkyl, acyl, or alkyleneoxy or polyalkyleneoxy terminated with H, alkyl, or phenyl. Unsaturation in a moiety which is attached to Q or which is part of Q is separated from any N, O, or S of Q by at least one carbon atom. The A ring may be unsubstituted or may carry up to 2 substituents T. Accordingly, the subscript x is 0, 1, or 2.

In the generalized formula (I), B represents an aromatic 6-membered ring or a heteroaromatic 5–6 membered ring containing 1–2 atoms of N, O, or S. It is referred to as the B ring or B unit. When N is employed in conjunction with either S or O in the B ring, these heteroatoms are separated by at least one carbon atom.

In the generalized formula (I), D represents

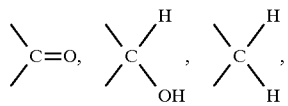

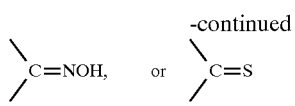

In the generalized formula (I), E represents a chain of n carbon atoms bearing m substituents R⁶, in which the R⁶ groups are independent substituents, or constitute Spiro or nonspiro rings.

Rings may be formed in two ways: a) two groups R⁶ are joined, and taken together with the chain atom(s) to which the two R6 group(s) are attached, and any intervening chain atoms, constitute a 3–7 membered ring, or b) one group R⁶ is joined to the chain on which this one group R⁶ resides, and taken together with the chain atom(s) to which the R⁶ group is attached, and any intervening chain atoms, constitutes a 314 7 membered ring. The number n of carbon atoms in the chain is 2 or 3, and the number m of R⁶ substituents is an integer of 114 3. The number of carbons in the totality of R⁶ groups is at least two.

Each group R⁶ is independently selected from the group consisting of:

alkyl provided that if the A unit is phenyl, the B unit is phenylene, m is 1, and n is 2, then x is 1 or 2;

aryl, provided that if said A unit is phenyl, said B unit is phenylene, said aryl group is phenyl, n is 2, and m is 1 or 2, then x is 1 or 2;

heteroaryl;

arylalkyl;

heteroaryl-alkyl;

alkenyl;

aryl-substituted alkenyl;

hetaryl-substituted alkenyl;

alkynyl;

aryl-substituted alkynyl;

heteroaryl-substituted alkynyl;

—(CH₂)ₜ R⁷, wherein t is 0 or an integer of 1–5 and R⁷ is selected from the group consisting of:
  N-phthalimidoyl;
  N-(1,2-naphthalenedicarboximidoyl);
  N-(2,3-naphthalenedicarboximidoyl);
  N-(1,8-naphthalenedicarboximidoyl);
  N-indoloyl;
  N-(2-pyrrolodinonyl);
  N-succinimidoyl;
  N-maleimidoyl;
  3-hydantoinyl;
  1,2,4-urazolyl;
  amido;
  urethane;
  urea; and
  nonaromatic substituted or unsubstituted heterocycles containing and connected through a N atom, and comprising one additional O or S; and
  amino;
  and corresponding heteroaryl moieties in which the aryl portion of an aryl-containing R⁷ group comprises 414 9 carbons and at least one N, O, or S heteroatom, but with the proviso that when R⁷ is a nonaromatic heterocycle or an amino group, and t is 0, m is 1, and n is 2, then x is 1 or 2; and —(CH₂)ᵥZR⁸ in which v is 0 or an integer of 1–4, Z represents

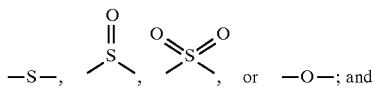 or —O—; and

R⁸ is selected from the group consisting of:
 alkyl;
 aryl;
 heteroaryl;
 arylalkyl;
 heteroaryl-alkyl; and
 —C(O)R⁹ in which R⁹ represents alkyl of at least two carbons, aryl, heteroaryl, arylalkyl, or heteroaryl-alkyl;
and with the further provisos that
 when R⁸ is —C(O)R⁹, Z is S or 0;
 when Z is 0, R⁸ may also be alkyleneoxy or polyalkyleneoxy terminated with H, alkyl, or phenyl; and
 when said A unit is phenyl, said B unit is phenylene, m is 1, n is 2, and v is 0, then x is 1 or 2; and trialkylsilyl-substituted alkyl.

Furthermore, aryl or heteroaryl portions of any of the T or R⁶ groups optionally may bear up to two substituents selected from the group consisting of —(CH₂)ᵧC(R¹¹)(R¹²)OH, —(CH₂)ᵧOR11, —(CH₂)ᵧSR¹¹, —(CH₂)ᵧS(O)R¹¹, —(CH₂)ᵧS(O)₂R¹¹, —(CH₂)ᵧSO₂N(R¹¹)₂, —(CH₂)ᵧN(R¹¹)₂, —(CH₂)ᵧN(R¹¹)COR¹², —OC(R¹¹)₂O— in which both oxygen atoms are connected to the aryl ring, —(CH₂)ᵧCOR¹¹, —(CH₂)ᵧCON(R¹¹)₂, —(CH₂)ᵧCO₂R¹¹, —(CH₂)ᵧOCOR¹¹, —halogen, —CHO, —CF₃, —NO₂, —CN, and —R¹², in which y is 0–4; R¹¹ represents H or lower alkyl; and R¹² represents lower alkyl.

In the generalized formula (I), G represents —PO₃H₂, —M,

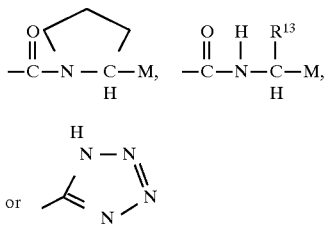

in which M represents —CO₂H, —CON(R¹¹)₂, or —CO₂R¹², and R13 represents any of the side chains of the 19 noncyclic naturally occurring amino acids. Pharmaceutically acceptable salts of these compounds are also within the scope of the invention.

In most related reference compounds of the prior art, the biphenyl portion of the molecule is unsubstituted, and the propanoic or butanoic acid portion is either unsubstituted or has a single methyl or phenyl group. Presence of the larger phenyl group has been reported to cause prior art compounds to be inactive as anti-inflammatory analgesic agents. See, for example, R. G. Child, et al., J. Pharm. Sci., 66, 466–476 (1977) By contrast, it has now been found that compounds which exhibit potent MMP inhibitory activity contain a substituent of significant size on the propanoic or butanoic portion of the molecule. The biphenyl portions of the best MMP inhibitors also preferably contain a substituent on the 4' position, although when the propanoic or butanoic portions are optimally substituted, the unsubstituted biphenyl compounds of the invention have sufficient activity to be considered realistic drug candidates.

In addition to the above-described compounds, the invention also relates to pharmaceutical compositions having matrix metalloprotease inhibitory activity, which compositions comprise a compound of the invention as described above, and a pharmaceutically acceptable carrier.

The invention also relates to a method of treating a mammal to achieve an effect, in which the effect is: alleviation of osteoarthritis, rheumatoid arthritis, septic arthritis, periodontal disease, corneal ulceration, proteinuria aneurysmal aortic disease, dystrophobic epidermolysis bullosa, conditions leading to inflammatory responses, osteopenias mediated by MMP activity, tempero mandibular joint disease, or demyelinating diseases of the nervous system; retardation of tumor metastasis or degenerative cartilage loss following traumatic joint injury; reduction of coronary thrombosis from atherosclerotic plaque rupture; or improved birth control; the method comprising administering an amount of a compound of the invention as described above which is effective to inhibit the activity of at least one matrix metalloprotease, resulting in achievement of the desired effect.

DETAILED DESCRIPTION

More particularly, the compounds of the present invention are materials having matrix metalloprotease inhibitory activity and the generalized formula:

$$(T)_x\text{-}\alpha\text{-B-D-E-G} \qquad (I)$$

in which $(T)_x$A represents a substituted or unsubstituted aromatic or heteroaromatic moiety selected from the group consisting of:

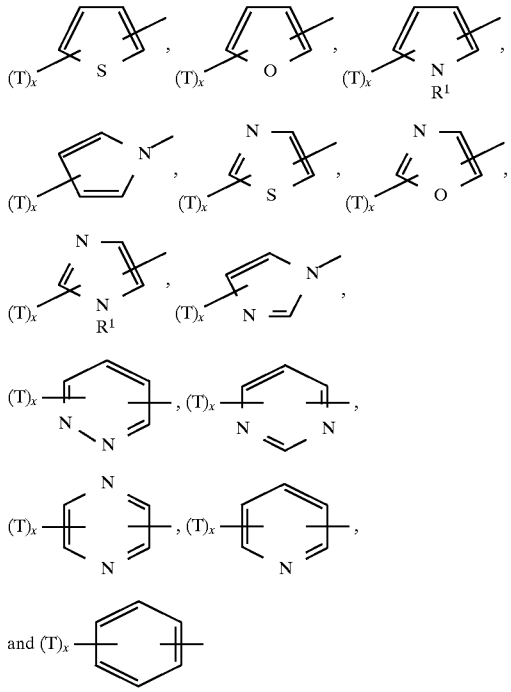

in which R¹ represents H or alkyl of 1–3 carbons.

In these structures, the aromatic ring is referred to as the A ring or A unit, and each T represents a substituent group, referred to as a T group or T unit. Substituent groups T are independently selected from the group consisting of: the halogens —F, —Cl, —Br, and —I; alkyl of 114 10 carbons; haloalkyl of 1–10 carbons; alkenyl of 2–10 carbons; alkynyl of 2–10 carbons; —(CH₂)ₚQ in which p is 0 or an integer 1–4, and -alkenyl-Q in which the alkenyl moiety comprises 2–4 carbons. Q in each of the latter two groups is selected from the group consisting of aryl of 6–10 carbons; heteroaryl comprising 4–9 carbons and at least one N, O, or S heteroatom; —CN; —CHO; —NO$_2$; —CO$_2$R$^2$; —OCOR$^2$; —SOR$^3$; —SO$_2$R$^3$; —CON(R$^2$)$_2$; —SO$_2$N(R$^2$)$_2$; —C(O)R$^2$; —N(R$^2$)$_2$; —N(R$^2$)COR$^2$; —N(R$^2$)CO$_2$R$^3$; —N(R$^2$)CON(R$^2$)$_2$; —CHN$_4$; —OR$^4$; and —SR$^4$. The groups R$^2$, R$^3$, and R$^4$ are defined as follows.

R$^2$ represents H; alkyl of 1–6 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

R$^3$ represents alkyl of 1–4 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

R$^4$ represents H; alkyl of 1–12 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; heteroaryl-alkyl in which the heteroaryl portion comprises 4–9 carbons and at least one N, O, or S heteroatom and the alkyl portion contains 1–4 carbons; alkenyl of 2–12 carbons; alkynyl of 2–12 carbons; —(C$_q$H$_{2q}$O)$_r$R$^5$ in which q is 1–3, r is 1–3, and R$^5$ is H provided q is greater than 1, or R$^5$ is alkyl of 1–4 carbons, or phenyl; —(CH$_2$)$_s$X in which s is 2–3 and X is halogen; or —C(O)R$^2$.

Any unsaturation in a moiety which is attached to Q or which is part of Q is separated from any N, O, or S of Q by at least one carbon atom, and the number of substituents, designated x, is 0, 1, or 2.

In the generalized formula (I), B represents an aromatic or heteroaromatic ring selected from the group consisting of:

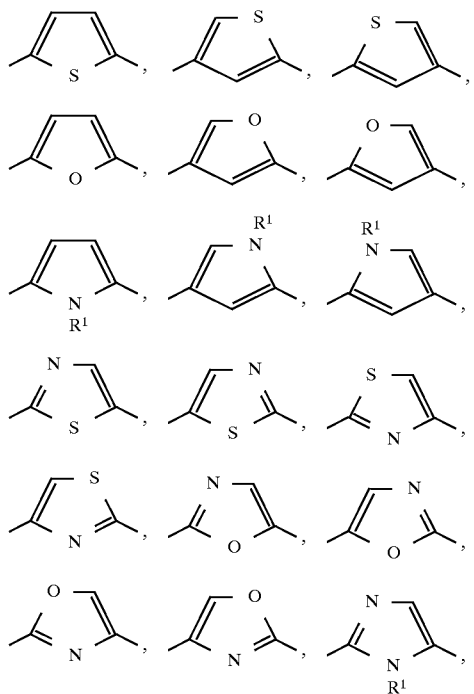

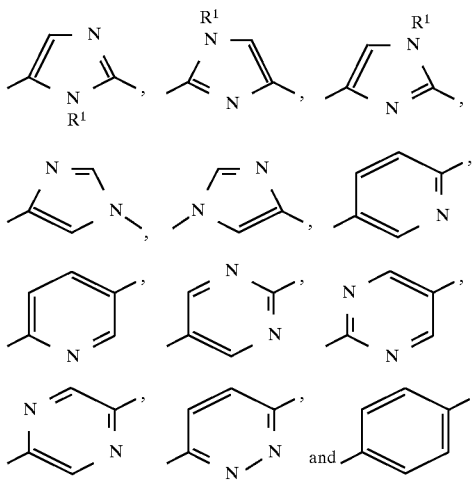

in which R$^1$ is defined as above. These rings are referred to as the B ring or B unit.

In the generalized formula (I), D represents the moieties

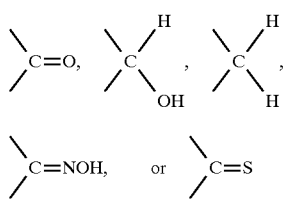

In the generalized formula (I), E represents a chain of n carbon atoms bearing m substituents R$^6$, referred to as R$^6$ groups or R$^6$ units. The R$^6$ groups are independent substituents, or constitute spiro or nonspiro rings. Rings may be formed in two ways: a) two groups R$^6$ are joined, and taken together with the chain atom(s) to which the two R6 group(s) are attached, and any intervening chain atoms, constitute a 3–7 membered ring, or b) one group R$^6$ is joined to the chain on which this one group R$^6$ resides, and taken together with the chain atom(s) to which the R$^6$ group is attached, and any intervening chain atoms, constitutes a 3–7 membered ring. The number n of carbon atoms in the chain is 2 or 3, and the number m of R$^6$ substituents is an integer of 1–3. The number of carbons in the totality of R$^6$ groups is at least two.

Each group R$^6$ is independently selected from the group consisting of the substituents listed below as items 1)–14).

1) An R$^6$ group may be alkyl of 1–10 carbons, provided that if the A unit is phenyl, the B unit is phenylene, m is 1, n is 2, and the alkyl group is located on the alpha carbon relative to the D unit, then x is 1 or 2.

2) An R$^6$ group may be aryl of 6–10 carbons, provided that if the A unit is phenyl, the B unit is phenylene, the aryl group is phenyl, n is 2, and m is 1 or 2, then x is 1 or 2.

3) An R$^6$ group may be heteroaryl comprising 4–9 carbons and at least one N, O, or S heteroatom.

4) An R$^6$ group may be arylalkyl in which the aryl portion contains 6–10 carbons and the alkyl portion contains 1–8 carbons.

5) An R$^6$ group may be heteroaryl-alkyl in which the heteroaryl portion comprises 4–9 carbons and at least one N, O, or S heteroatom, and the alkyl portion contains 1–8 carbons;

6) An $R^6$ group may be alkenyl of 2–10 carbons.
7) An $R^6$ group may be aryl-alkenyl in which the aryl portion contains 6–10 carbons and the alkenyl portion contains 2–5 carbons.
8) An $R^6$ group may be heteroaryl-alkenyl in which the heteroaryl portion comprises 4–9 carbons and at least one N, O, or S heteroatom and the alkenyl portion contains 2–5 carbons;
9) An $R^6$ group may be alkynyl of 2–10 carbons.
10) An $R^6$ group may be aryl-alkynyl in which the aryl portion contains 6–10 carbons and the alkynyl portion contains 2–5 carbons.
11) An $R^6$ group may be heteroaryl-alkynyl in which the heteroaryl portion comprises 4–9 carbons and at least one N, O, or S heteroatom and the alkynyl portion contains 2–5 carbons.
12) An $R^6$ group may be —(CH2)$_t$R$^7$ in which t is 0 or an integer of 1–5 and $R^7$ is selected from the group consisting of

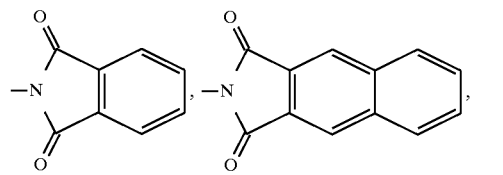

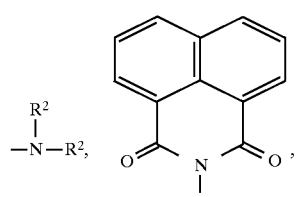

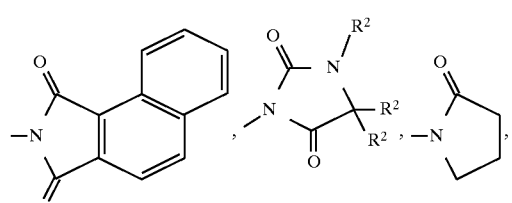

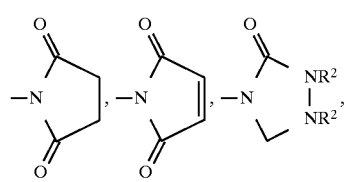

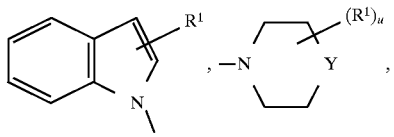

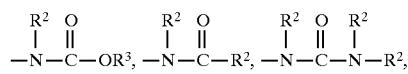

as well as corresponding heteroaryl moieties in which the aryl portion of an aryl-containing $R^7$ group comprises 4–9 carbons and at least one N, O, or S heteroatom. In such $R^7$ groups, Y represents O or S; $R^1$, $R^2$, and $R^3$ are as defined above; and u is 0, 1, or 2; provided that when $R^7$ is

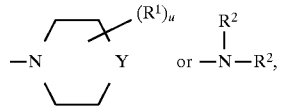

and the A unit is phenyl, the B unit is phenylene, m is 1, n is 2, and t is 0, then x is 1 or 2.

13) An $R^6$ group may be —(CH$_2$)$_v$ZR$^8$ in which v is 0 or an integer of 1 to 4; Z represents —S—, —S(O)—, —SO$_2$—, or —O—; and $R^8$ is selected from the group consisting of: alkyl of 1 to 12 carbons; aryl of 6 to 10 carbons; heteroaryl comprising 4–9 carbons and at least one N, O, or S heteroatom; arylalkyl in which the aryl portion contains 6 to 12 carbons and the alkyl portion contains 1 to 4 carbons; heteroaryl-alkyl in which the aryl portion comprises 4–9 carbons and at least one N, O, or S heteroatom and the alkyl portion contains 1–4 carbons; —C(O)R$^9$ in which $R^9$ represents alkyl of 2–6 carbons, aryl of 6–10 carbons, heteroaryl comprising 4–9 carbons and at least one N, O, or S heteroatom, or arylalkyl in which the aryl portion contains 6–10 carbons or is heteroaryl comprising 4–9 carbons and at least one N, O, or S heteroatom, and the alkyl portion contains 1–4 carbons, with the provisos that
when $R^8$ is —C(O)R$^9$, Z is —S— or —O—;
when Z is —O—, $R^8$ may also be —(C$_q$H$_{2q}$O)$_r$R$^5$ in which q, r, and $R^5$ are as defined above; and
when the A unit is phenyl, the B unit is phenylene, m is 1, n is .2, and v is 0, then x is 1 or 2; and 14) An $R^6$ group may be —(CH$_2$)$_w$SiR$^{10}$$_3$ in which w is an integer of 1 to 3, and $R^{10}$ represents alkyl of 1 to 2 carbons.

In addition, aryl or heteroaryl portions of any of the T or $R^6$ groups optionally may bear up to two substituents selected from the group consisting of —(CH$_2$)$_y$C(R$^{11}$)(R$^{12}$)OH, —(CH$_2$)$_y$OR$^{11}$, —(CH$_2$)$_y$SR$^{11}$, —(CH$_2$)$_y$S(O)R$^{11}$, —(CH$_2$)$_y$S(O)$_2$R$^{11}$, —(CH$_2$)$_y$SO$_2$N(R$^{11}$)$_2$, —(CH$_2$)$_y$N(R$^{11}$)$_2$, —(CH$_2$)$_y$N(R$^{11}$)COR$^{12}$, —OC(R$^{11}$)$_2$O— in which both oxygen atoms are connected to the aryl ring, —(CH$_2$)$_y$COR$^{11}$, —(CH$_2$)$_y$CON(R$^{11}$)$_2$, —(CH$_2$)$_y$CO$_2$R$^{11}$, —(CH$_2$)$_y$OCOR$^{11}$, —halogen, —CHO, —CF$_3$, —NO$_2$, —CN, and —R$^{12}$, in which y is 0–4; R$^{11}$ represents H or alkyl of 1–4 carbons; and R$^{12}$ represents alkyl of 1–4 carbons.

In the generalized formula (I), G represents —PO$_3$H$_2$, —M,

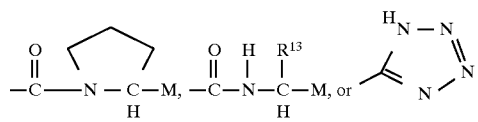

in which M represents —CO$_2$H, —CON(R$^{11}$)$_2$, or —CO$_2$R$^{12}$, and R$^{13}$ represents any of the side chains of the 19 noncyclic naturally occurring amino acids. Pharmaceutically acceptable salts of the compounds falling within the generalized formula (I) are also within the invention.

It is to be understood that as used herein, the term "alkyl" means straight, branched, cyclic, and polycyclic materials. The term "haloalkyl" means partially or fully halogenated alkyl groups such as —(CH$_2$)$_2$Cl, —CF$_3$ and —C$_6$F$_{13}$, for example.

The B ring of generalized formula (I) is a substituted or unsubstituted aromatic or heteroaromatic ring, in which any substituents are groups which do not cause the molecule to fail to fit the active site of the target enzyme, or disrupt the relative conformations of the A and B rings, such that they would be detrimental. Such groups may be moieties such as lower alkyl, lower alkoxy, CN, $NO_2$, halogen, etc., but are not to be limited to such groups.

In one of its embodiments, the invention relates to compounds of generalized formula (I) in which at least one of the units A, B, T, and $R^6$ comprises a heteroaromatic ring. Preferred heteroaromatic ring-containing compounds are those in which the heteroaryl groups are heteroaryl of 4–9 carbons comprising a 5–6 membered heteroaromatic ring containing O, S, or $NR^1$ when the ring is 5-membered, and N when said ring is 6-membered. Particularly preferred heteroaromatic ring-containing compounds are those in which at least one of the A and B units comprises a thiophene ring. When A unit is thiophene, it is preferably connected to B unit at position 2 and carries one substituent group T on position 5. When B Unit is thiophene, it is preferably connected through positions 2 and 5 to D and A units respectively.

In the generalized formula (I), the A and B rings are preferably phenyl and phenylene, respectively, the A ring preferably bears at least one substituent group T preferably located on the position furthest from the position of the A ring which is connected to the B ring, the D unit is preferably a carbonyl group, and the G unit is preferably a carboxyl group.

In another embodiment, the invention relates to compounds of generalized formula (I), in the E unit of which n is 2 and m is 1. These compounds thus possess two carbon atoms between the D unit and the G unit, and carry one substituent on this two-carbon chain.

In another of its embodiments, the invention relates to compounds of generalized formula (I) in which the A ring is a substituted or unsubstituted phenyl group, the B ring is p-phenylene, and aryl portions of any aryl-containing T and $R^6$ moieties contain only carbon in the rings. These compounds thus contain no heteroaromatic rings.

In another of its embodiments, the invention relates to compounds of generalized formula (I) in which m is 1 and $R^6$ is an independent substituent. These compounds are materials which contain only a single substituent $R^6$ on the E unit, and this substituent in not involved in a ring. Preferred compounds within this subset have the formula

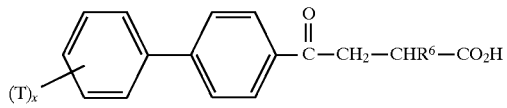

in which x is 1 or 2, and one substituent group T is located on the 4-position of the A ring, relative to the point of attachment between the A and B rings. Substituent group T of this subset is preferably the halogens —Cl, —Br or I or is an ether —$OR^4$. Most preferred compounds contain only one substituent T on the 4- position of the A ring relative to the attachment to B ring.

Preferred compounds of general formula (I) in which $R^6$ is —$(CH_2)_tR^7$ have t as an integer of 1–5. Preferred compounds of general formula (I) in which $R^6$ is —$(CH_2)_vZR^8$ have v as an integer of 1–4 and Z as —S— or —O—. Preferred compounds of general formula (I) in which $R^6$ is alkyl contain 4 or more carbons in said alkyl and those in which $R^6$ is arylalkyl contain 2–3 carbons in the alkyl portion of said arylalkyl.

In another of its embodiments, the invention relates to compounds of generalized formula (I) in which the number of substituents m on the E unit is 2 or 3; and when m is 2, both groups $R^6$ are independent substituents, or together constitute a spiro ring, or one group $R^6$ is an independent substituent and the other constitutes a Spiro ring; and when m is 3, two groups $R^6$ are independent substituents and one group $R^6$ constitutes a ring, or two groups R6 constitute a ring and one group R6 is an independent substituent, or three groups R6 are independent substituents. This subset therefore contains compounds in which the E unit is di- or tri-substituted, and in the disubstituted case any rings formed by one or both $R^6$ groups are spiro rings, and in the trisubstituted case, the $R^6$ groups may form either spiro or nonspiro rings.

In another of its embodiments, the invention relates to compounds of generalized formula (I) in which the number of substituents m on the E unit is 1 or 2; and when m is 1, the group $R^6$ constitutes a nonspiro ring; and when m is 2, both groups $R^6$ together constitute a nonspiro ring or one group R6 is an independent substituent and the other constitutes a nonspiro ring. This subset therefore contains compounds in which the E unit carries one or two substituents $R^6$, and at least one of these substituents is involved in a nonspiro ring.

More particularly, representative compounds of generalized formula (I) in which one or more of the substituent groups $R^6$ are involved in formation of nonspiro rings have E units of the following structures:

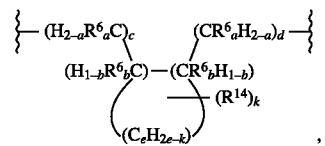

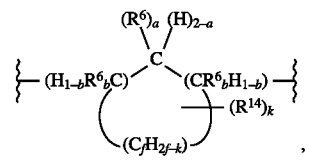

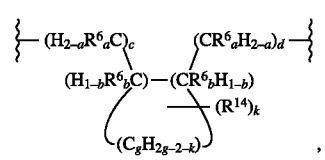

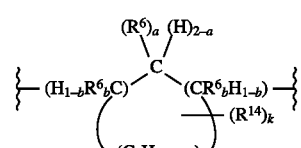

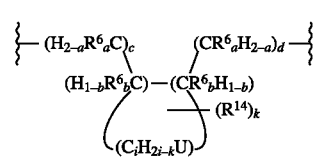

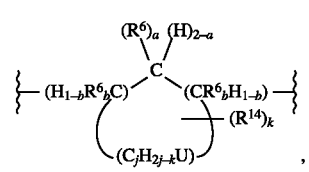

-continued

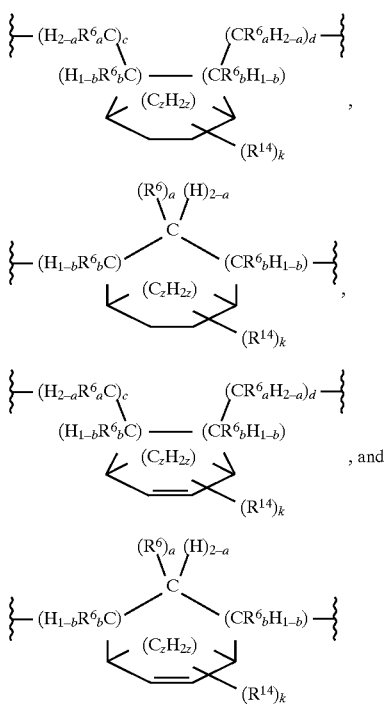

in which a is 0, 1, or 2; b is 0 or 1; c is 0 or 1; d is 0 or 1; c+d is 0 or 1; e is 1–5; f is 1–4; g is 3–5; h is 2–4; i is 0–4; j is 0–3; is 0–2; the total number of groups $R^6$ is 0, 1, or 2; U represents O, S, or $NR^1$; and z is 1 or 2; Each group $R^{14}$ is independently selected from the group consisting of: alkyl of 1–9 carbons; arylalkyl in which the alkyl portion contains 1–7 carbons and the aryl portion contains 6–10 carbons; alkenyl of 2–9 carbons; aryl-substituted alkenyl in which the alkenyl portion contains 2–4 carbons and the aryl portion contains 6–10 carbons; alkynyl of 2–9 carbons; aryl-substituted alkynyl in which the alkynyl portion contains 2–4 carbons and the aryl portion contains 6–10 carbons; aryl of 6–10 carbons; $-COR^2$; $-CO_2R^3$; $-CON(R^2)_2$; $-(CH_2)_tR^7$ in which t is 0 or an integer of 1–4; and $-(CH_2)_vZR^8$ in which v is 0 or an integer of 1 to 3, and Z represents $-S-$ or $-O-$. $R^1$, $R^7$, and $R^8$ have been defined above.

Preferred compounds of generalized formula (I) in which one or more of the substituent groups $R^6$ are involved in formation of nonspiro rings have E units of the following structures:

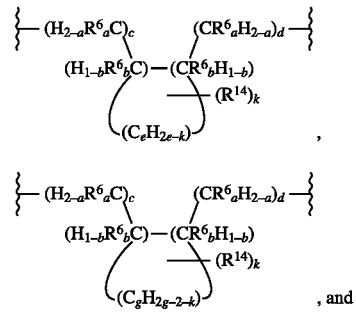

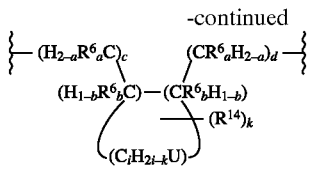

in which a, b, c, d, (c+d), e, g, i, k, the total number of groups $R^6$, U, and $R^{14}$ are as defined above.

The more preferred compounds of generalized formula (I) in which one or more of the substituent groups $R^6$ are involved in formation of nonspiro rings have the formula

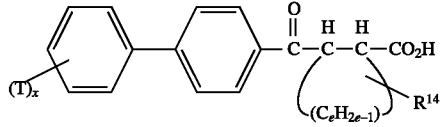

in which the subscript x is 1 or 2; one substituent T is located on the 4-position of the A ring, relative to the point of attachment between the A and B rings; e is 2 or 3; and $R^{14}$ is as defined above.

The invention also relates to certain intermediates useful in the synthesis of some of the claimed inhibitors. These intermediates are compounds having the generalized formula

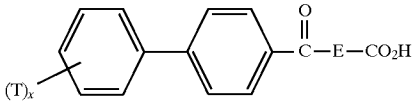

in which E represents

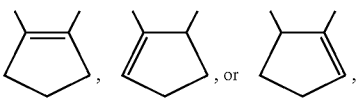

T represents a substituent group, and x is 1 or 2.

Those skilled in the art will appreciate that many of the compounds of the invention exist in enantiomeric or diastereomeric forms, and that it is understood by the art that such stereoisomers generally exhibit different activities in biological systems. This invention encompasses all possible stereoisomers which possess inhibitory activity against an MMP, regardless of their stereoisomeric designations, as well as mixtures of stereoisomers in which at least one member possesses inhibitory activity.

General Preparative Methods

All the compounds of the present invention may be prepared by chemical reactions and procedures which are known to the art, without the necessity for undue experimentation. Nevertheless, the following general preparative methods are presented to aid the reader in synthesizing the inhibitors, with more detailed particular examples being presented below in the experimental section describing the working examples.

All variable groups of these methods are as described in the generic description if they are not specifically defined below. The variable subscript n is independently defined for each method. When a variable group with a given symbol (i.e. $R^6$ or T) is used more than once in a given structure, it is to be understood that each of these groups may be independently varied within the range of definitions for that symbol.

General Method A

The compounds of this invention in which the rings A and B are substituted phenyl and phenylene respectively are conveniently prepared by use of a Friedel-Crafts reaction of a substituted biphenyl II with an activated acyl- containing intermediate such as the succinic or glutaric anhydride derivative III in the presence of a Lewis acid catalyst such as aluminum trichloride in an aprotic solvent such as 1,1,2, 2-tetrachloroethane. The well known Friedel-Crafts reaction can be accomplished with use of many alternative solvents and acid catalysts as described by E. Berliner, *Org. React.*, 5, 229 (1949) and H. Heaney, *Comp. Org. Synth.*, 2, 733 (1991).

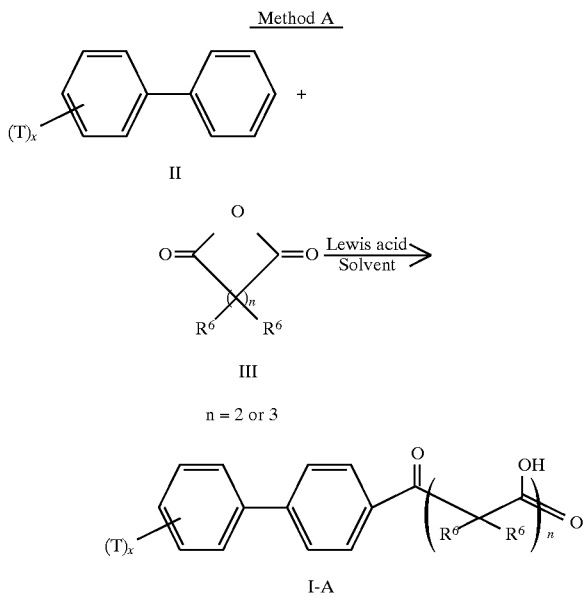

If the anhydride III is monosubstituted or multiply-substituted in an unsymmetrical way, the raw product I often exists as a mixture of isomers via attack of the anhydride from either of the two carbonyls. The resultant isomers can be separated into pure forms by crystallization or chromatography using standard methods known to those skilled in the art.

This method is especially useful for the preparation of cyclic compounds in which two $R^6$ groups are connected in a methylene chain to form a 3–7 member ring.

This method is also useful when double bonds are found either between C-2 and C-3 of a succinoyl chain (from maleic anhydride or 1-cyclopentene-1,2-dicarboxylic anhydride, for example) or when a double bond is found in a side chain, such as in the use of itaconic anhydride as starting material to yield products in which two $R^6$ groups as found on one chain carbon together form an exo-methylene ($=CH_2$) group.

General Method B

Other active acyl derivatives such as the acid chloride IV can be used instead of anhydride III. The resultant ester products I-B are then hydrolyzed by aqueous base in a way known to those skilled in the art to yield the more potent acids I.

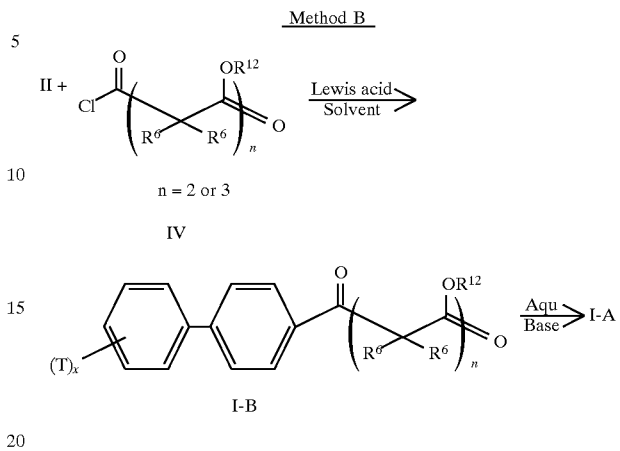

General Method C

Alternatively the compounds I can be prepared via a reaction sequence involving mono-alkylation of a dialkyl malonate VI with an alkyl halide to form intermediate VII, followed by alkylation with a halomethyl biphenyl ketone VII to yield intermediate IX. Compounds of structure IX are then hydrolyzed with aqueous base and then heated to decarboxylate the malonic acid intermediate and yield I (Method C-1). By using one equivalent of aqueous base the esters I-C with $R^{12}$ as alkyl are obtained, and using more than two equivalents of base the acid compounds ($R^{12}$ =H) are obtained. Optionally, heat is not used and the diacid or acid-ester I-B is obtained. Alternatively, the diester intermediate IX can be heated with a strong acid such as concentrated hydrochloric acid in acetic acid in a sealed tube at about 110° C. for about 24 hr.

Alternatively, the reaction of VI with VII can be conducted before that with the alkyl halide to yield the same IX (Method C-2).

Intermediates VII are formed from biphenyls II in a Friedel-Craft reaction with haloacetyl halides such as bromoacetyl bromide or chloroacetyl chloride. Alternatively, the biphenyl can be reacted with acetyl chloride or acetic anhydride and the resultant product halogenated with, for example, bromine to yield intermediates VIII (X =Br).

Method C has the advantage of yielding single regio isomers when Method A yields mixtures. Method C is especially useful when the side chains $R^6$ contain aromatic or heteroaromatic rings that may participate in intramolecular acylation reactions to give side products if Method A were to be used. This method is also very useful when the $R^6$ group adjacent to the carboxyl of the final compound contains heteroatoms such as oxygen, sulfur, or nitrogen, or more complex functions such as imide rings.

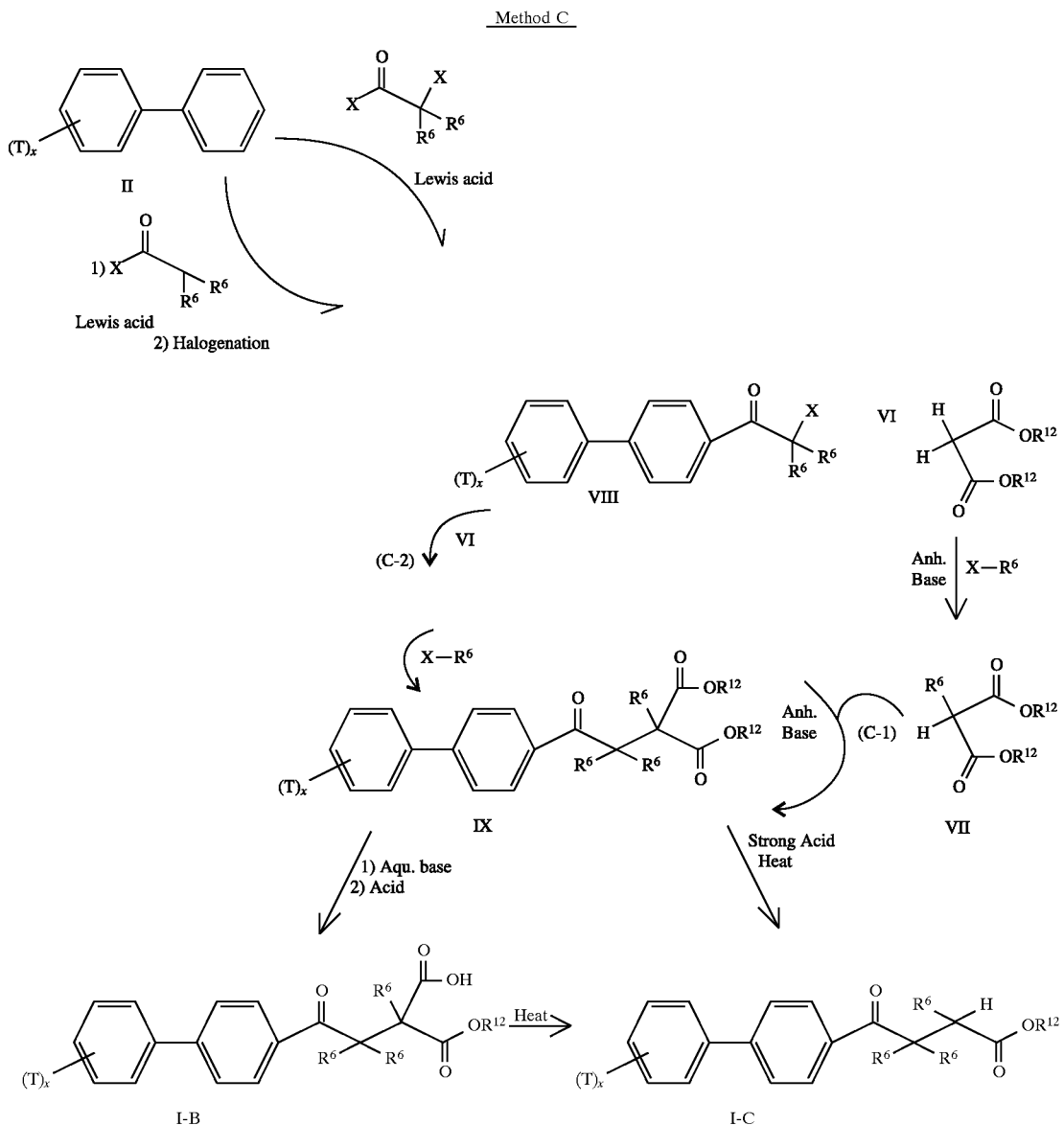

Method C

General Method D

Especially useful is the use of chiral HPLC to separate the enantiomers of racemic product mixtures (see, for example, D. Arit, B. Boemer, R Grosser and W. Lange, *Angew. Chem. Int. Ed. Engl.* 30 (1991) No. 12) . The compounds of this invention are prepared as pure enantiomers by use of a chiral auxiliary route—see, for example: D. A. Evans, Aldrichimica Acta, 15(2), 23 (1982) and other similar references known to one skilled in the art.

D-1.

Acid halide X is reacted with the lithium salt of chiral auxiliary XI (R is often isopropyl or benzyl) to yield intermediate XII, which in turn is akylated at low temperatures (typically under −50° C.) with halo-tert-butylacetyl compound XII to yield pure isomer XIV. The use of opposite chirality XI yields opposite chirality XIV. Conversion of XIV to the enantiomerically pure diacid XV is accomplished by treatment with lithium hydroxide/hydrogen peroxide in THF/water, followed by acids such as trifluoroacetic acid. The compound XV is then converted to enantiomerically pure anhydride III-A by treatment with acetyl chloride. The use of a Friedel-Crafts reaction as in method A then converts III-A to I-D.

D-2.

Biphenyl starting material II may also first be reacted in a Friedel-Crafts reaction as earlier described with succinic anhydride followed by Fisher esterification with a lower alcohol such as methanol in the presence of a strong acid such as sulfuric acid to form acyl derivative I-D-II. The carbonyl group of this material is then blocked as a ketal such as that formed by treatment with 1,2-bistrimethyl-silyloxyethane in the presence of a catalyst such as trimethyl-silyltriflate in a suitable solvent. Many other ketal derivatives and reaction conditions familiar to those skilled in the art can also be used in this step. Basic hydrolysis of the ester followed by reaction of the resultant I-D-III with XI in the presence of an amide coupling agent such as 1-(3-dimethylaminopropyl)-3-ethylcarbodiimide yields amide I-D-IV. Reaction of this chiral amide with an alkylating agent such as alkyl or arylalkyl triflate or halide yields enantiomerically enriched product I-D-V which can be converted to final product I-D-VI by treatment with a weak base such as lithium hydroxide/hydrogen peroxide and then acid. These deblocking steps can be conducted in either order.
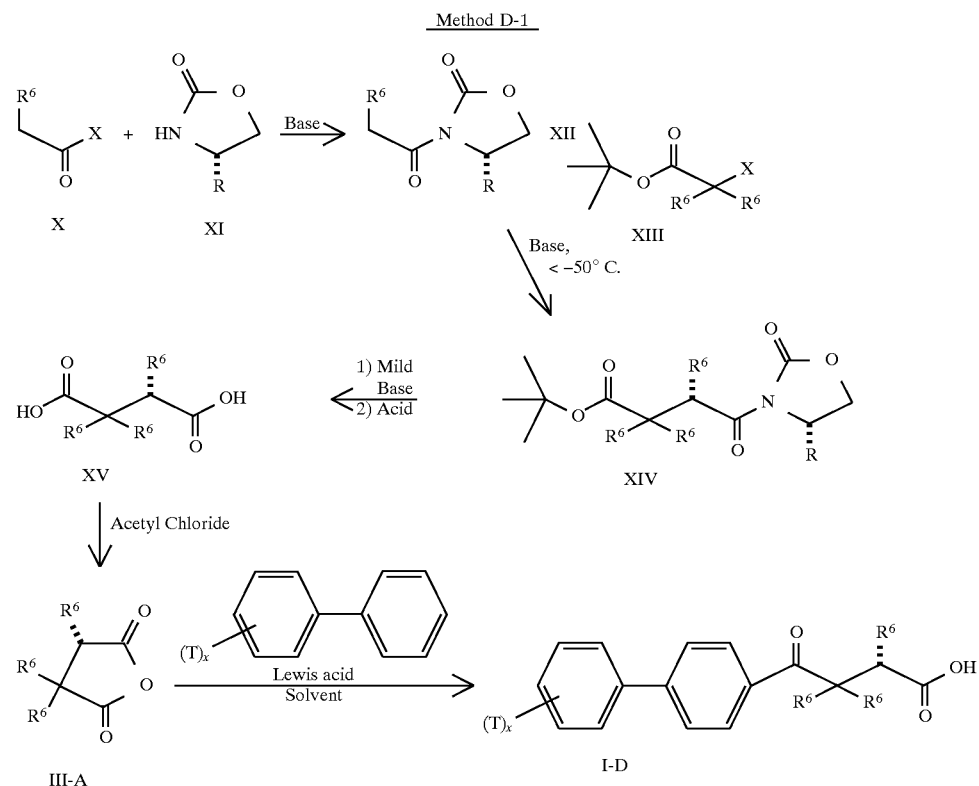
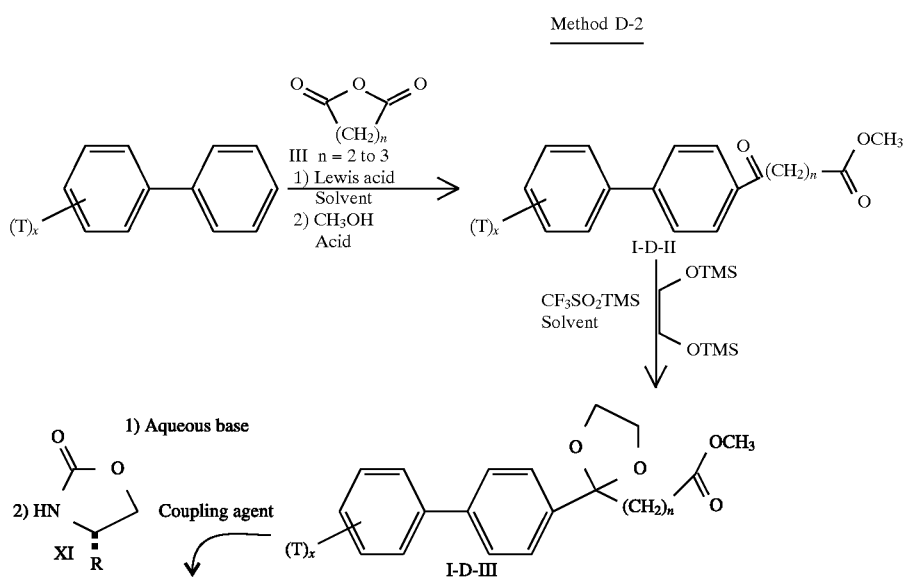

-continued
Method D-2

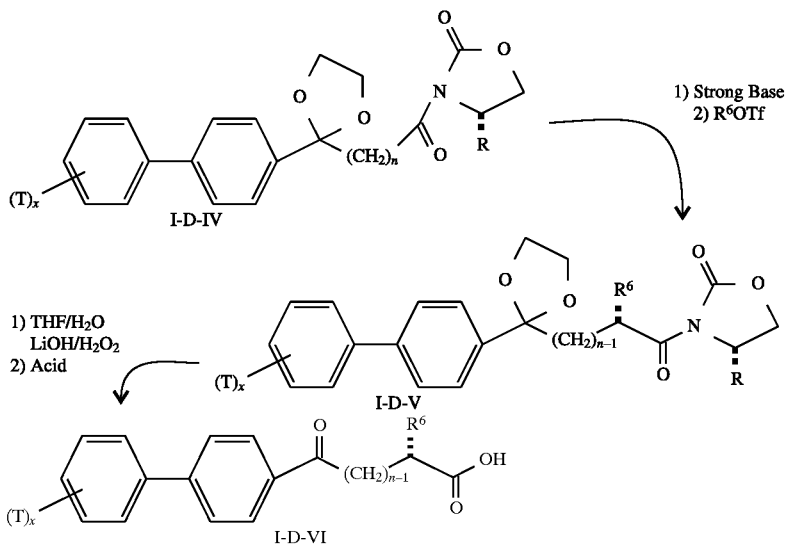

General Method E

Compounds in which $R^6$ are alkyl- or aryl- or heteroaryl- or acyl- or heteroarylcarbonyl-thiomethylene are prepared by methods analogous to those described in the patent WO 90/05719. Thus substituted itaconic anhydride XVI (n=1) is reacted under Friedel-Crafts conditions to yield acid I-E-1 which can be separated by chromatography or crystallization from small amounts of isomeric analogs of I-E-5. Alternatively, I-E-5 are obtained by reaction of invention compounds I-E-4 (from any of Methods A through D) with formaldehyde in the presence of a base.

Compounds I-E-1 or I-E-5 are then reacted with a mercapto derivative XVII or XVIII in the presence of a catalyst such as Potassium carbonate, ethyldiisobutylamine, tetrabutylammonium fluoride or free radical initiators such as azobisisobutyronitrile (AIBN) in a solvent such as dimethylformamide or tetrahydrofuran to yield invention compounds I-E-2, I-E-3, I-E-6 or I-E-7.

Method E

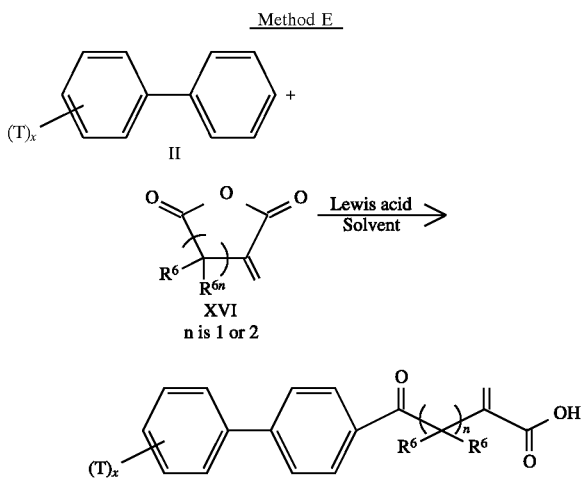

-continued
Method E

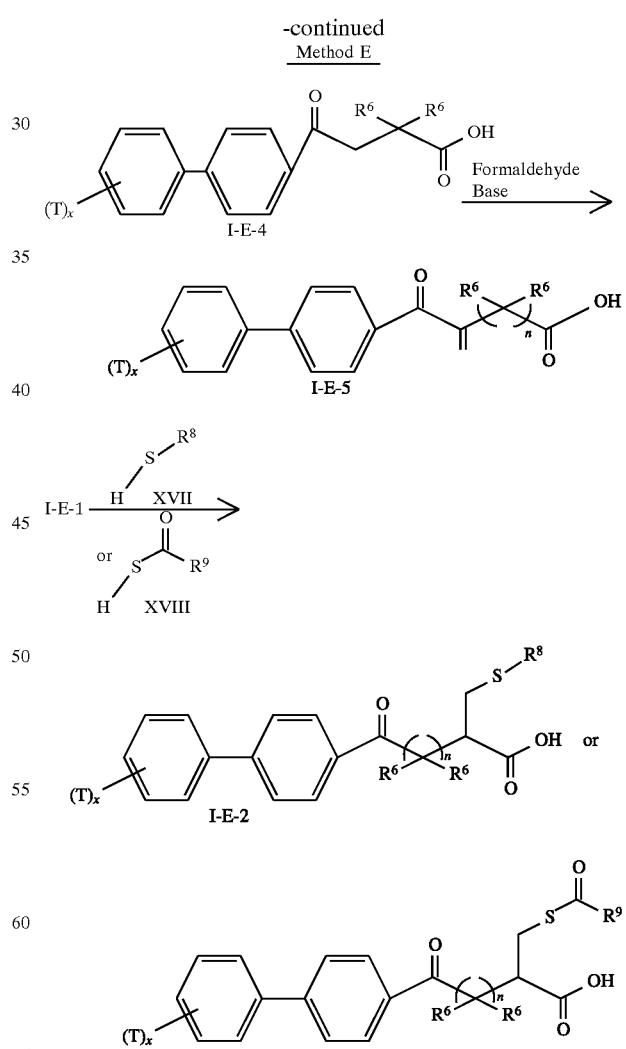

-continued
Method E

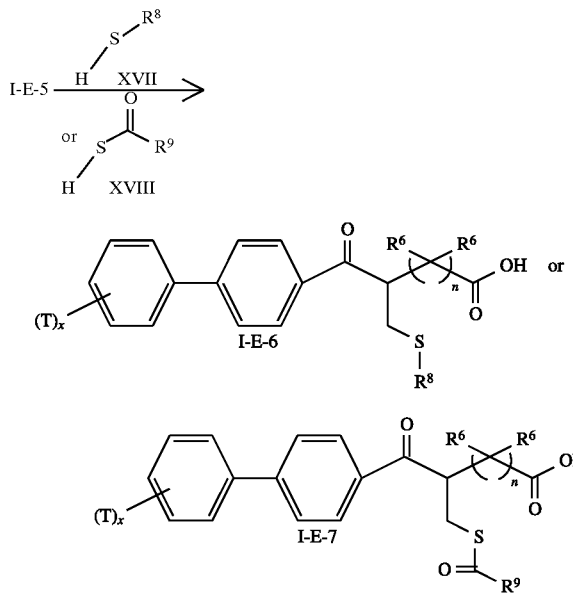

General Method F

Reaction of optionally substituted maleic anhydride XIX under Friedel-Crafts conditions with II yields invention compound I-F-1, which in turn is reacted with either of mercapto derivatives XVII or XVIII to yield invention compounds I-F-2 or I-F-3 or with substituted amine XX to yield invention compounds I-F-4.

General Method G

When they are not commercially available, the succinic anhydrides III-H are prepared via a Stobbe Condensation of a dialkyl succinate XXI with an aldehyde or ketone XXII to yield unsaturated hemiester XXIII, followed by catalytic hydrogenation to yield hemiester XXIV. This intermediate XXIV is then hydrolized to a diacid XXV and then converted to the anhydride III-H by reaction with acetyl chloride or acetic anhydride (Method G-1). For a review of the Stobbe condensation, including lists of suitable solvents and bases see W. S. Johnson and G. H. Daub, Org. React., 6, 1 (1951). Method G-1, as applied to the preparation of III-H ($R^6$=H, R=H, isopropyl and n-butyl), has been described by D. Wolanin, et al., U.S. Pat. No. 4,771,038, Sep. 13, 1988.

Alternatively the hemiester XXIV is converted by treatment with thionyl chloride or oxalyl chloride to the acid chloride IV-H (Method G-2).

Both the formation of the anhydride from the diacid and the hemiester acid chloride from the hemiester acid can be accomplished with several reagents familiar to those skilled in the art.

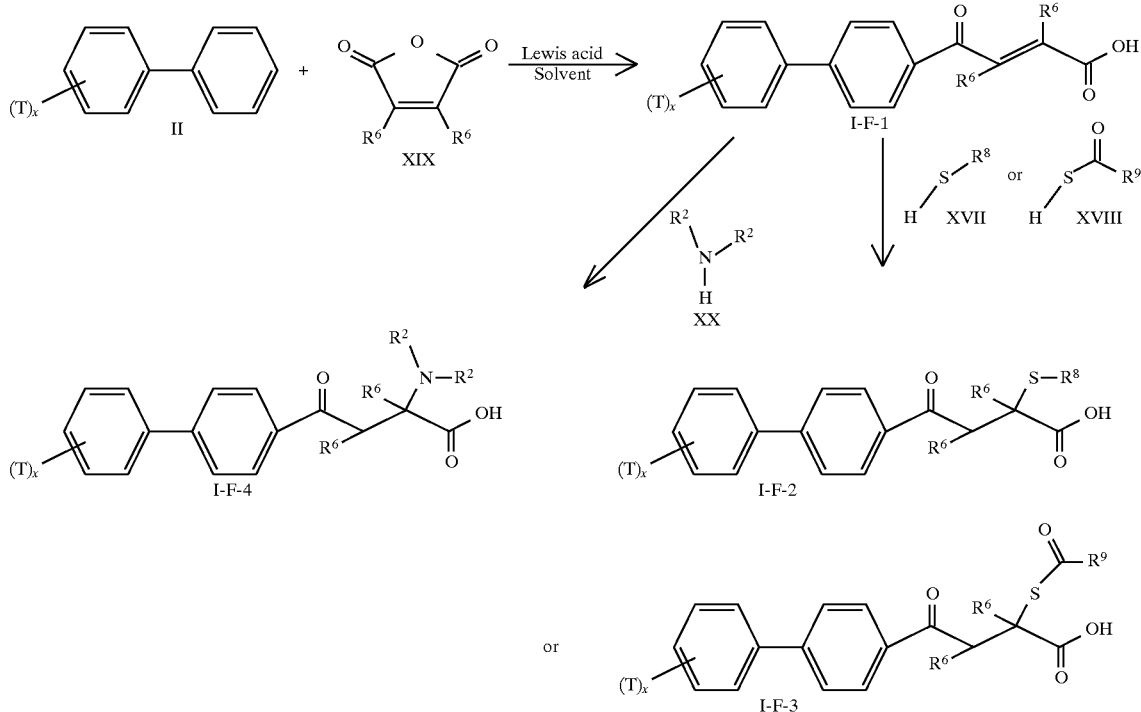

Method G

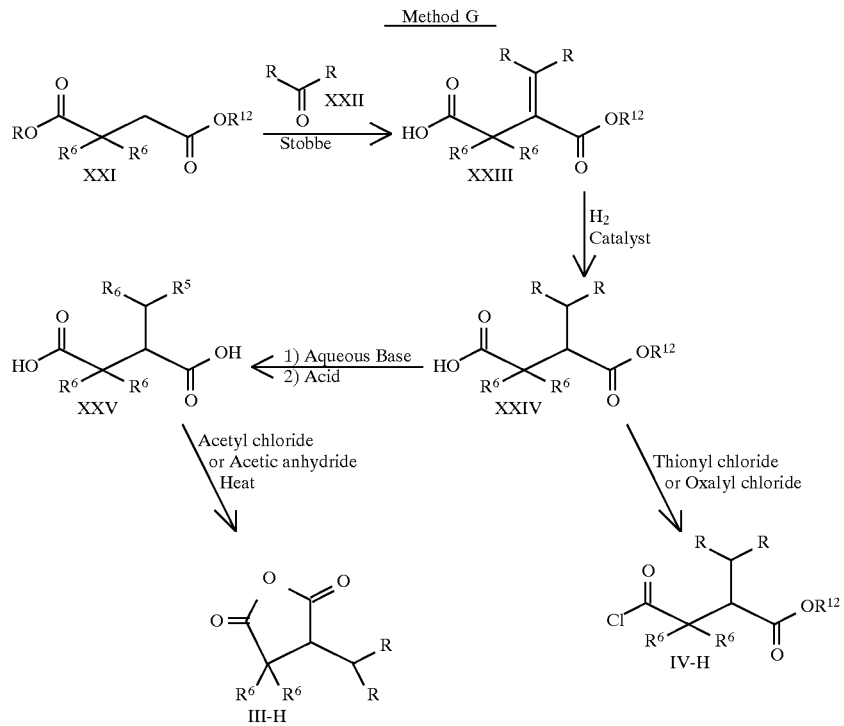

General Method H

Biaryl compounds such as those of this application may also be prepared by Suzuki or Stille cross-coupling reactions of aryl or heteroaryl metallic compounds in which the metal is zinc, tin, magnesium, lithium, boron, silicon, copper, cadmium or the like with an aryl or heteroaryl halide or triflate (trifluoromethane-sulfonate) or the like. In the drawing below., either Met or X is the metal and the other is the halide or triflate. Pd(com) is a soluble complex of palladium such as tetrakis(triphenylphosphine)-palladium(O) or bis-(triphenylphosphine)-palladium(II) chloride. These methods are well known to those skilled in the art. See, for example, A. Suzuki, Pure Appl. Chem., 66, 213–222 (1994); A. Suzuki, Pure Appl. Chem., 63, 419–422 (1991); and V. Farina and G. Roth, "Metal-Organic Chemistry" Volume 5 (Chapter 1), 1994 (in press).

The starting materials XXVII-A are readily formed using methods analogous to those of methods A, B or C but using a halobenzene rather than a biphenyl as starting material. When desired, the materials in which X is halo can be converted to those in which X is metal by reactions well known to those skilled in the art such as treatment of a bromo intermediate with hexamethyiditin and palladium tetrakistriphenylphosphine in toluene at reflux to yield the trimethyltin intermediate. The starting materials XXVII-B are most conveniently prepared by method C but using readily available heteroaryl rather than biphenyl starting materials. The intermediates XXVI-A and XXVI-B are either commercial or easily prepared from commercial materials by methods well known to those skilled in the art.

These general methods are useful for the preparation of compounds for which Friedel-Crafts reactions such as those of Methods A, B, C, D, E or F would lead to mixtures with various biaryl acylation patterns. Method H is also especially useful for the preparation of products in which the aryl groups A or B contain one or more heteroatoms (heteroaryls) such as those compounds that contain thiophene, furan, pyridine, pyrrole, oxazole, thiazole, pyrimidine or pyrazine rings or the like instead of phenyls (I-H-2, I-H-3 or I-H-4 below).

Method H (Furan may optionally be other heteroaryl)

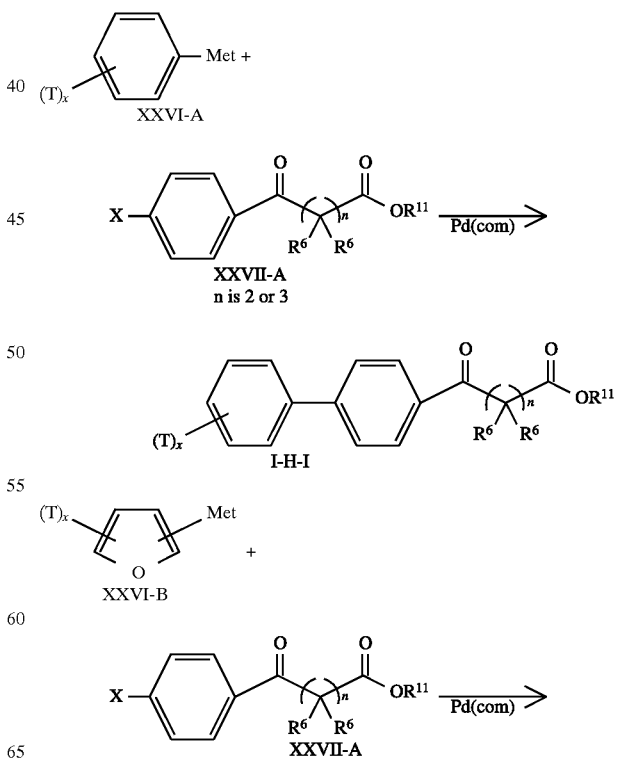

-continued
Method H (Furan may optionally be other heteroaryl)

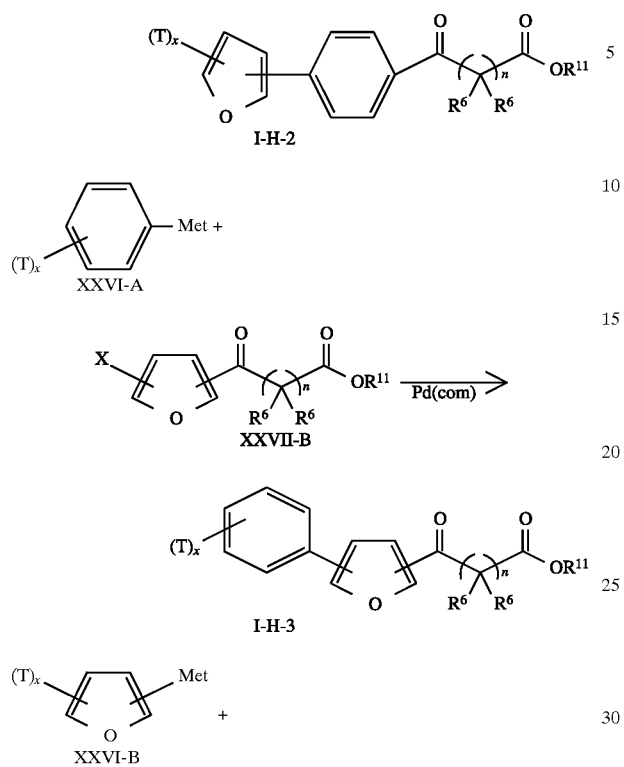

-continued
Method H (Furan may optionally be other heteroaryl)

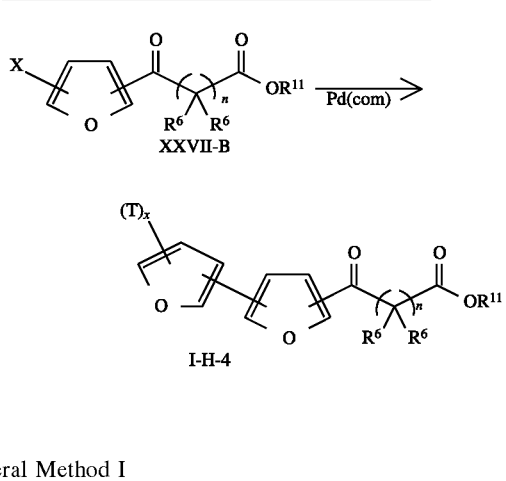

General Method I

When the $R^6$ groups of method F form together a 4–7 member carbocyclic ring as in Intermediate XXIX below, the double bond can be moved out of conjugation with the ketone group by treatment with two equivalents of a strong base such as lithium diisopropylamide or lithium hexamethylsilylamide or the like followed by acid quench to yield compounds with the structure XXX. Reaction of XXX with mercapto derivatives using methods analogous to those of General Method E then leads to cyclic compounds I-I-1 or I-I-2.

Method I

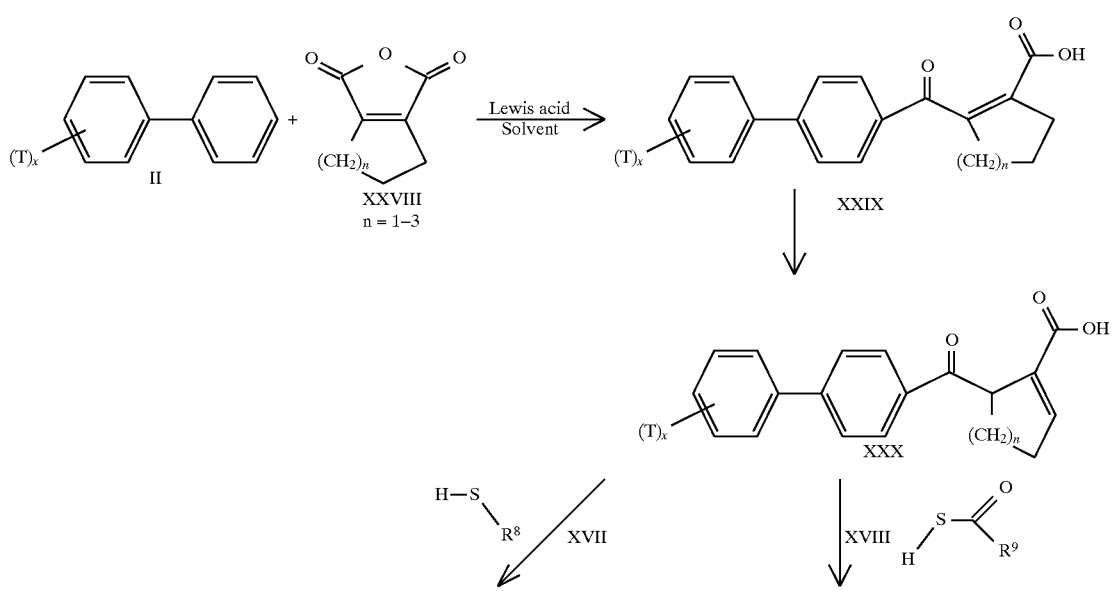

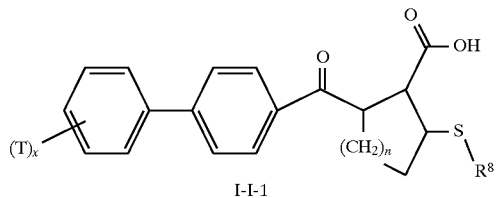

I-I-1

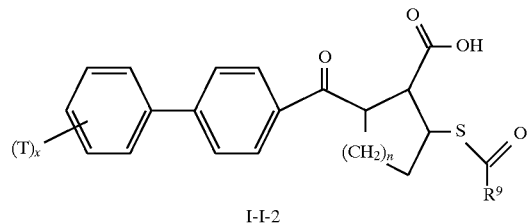

I-I-2

General Method J

Invention compounds in which two $R^6$ groups form a 4–7 member carbocyclic ring as in I-J below and $R^{14}$ is alkyl or arylalkyl are prepared according to method J. Starting material XXXI is reacted with two equivalents of a strong base such as lithium diisopropylamide (LDA) followed by an alkyl or arylalkyl halide ($R^{14}X$) to yield intermediate XXXII. This material is then reduced to the alcohol with a reducing agent capable of selective reduction of the ketone such as sodium borohydride, followed by dehydration with triphenylphosphine/diethyl azodicarboxylate (DEAD) in a suitable solvent such as THF at reflux to yield XXXIII. Hydrolysis of the ester with aqueous base followed by amide formation with $R^{12}ONHR^{12}$ (R is lower alkyl, but usually $CH_3$) in the presence of a coupling agent such as dicyclohexyldiimide (DCC) yields XXXIV. Other acyl activating groups well known to those skilled in the art such as acid chlorides or mixed anhydrides could be used instead of XXXIV. Substituted biphenyl halide XXXV is reacted with an alkyl lithium such as two equivalents of t-butyl lithium to yield lithiated biphenyl XXXVI which is then reacted with activated acyl compound XXXIV. The resultant intermediate XXXVII is then treated with diethylaluminum cyanide to yield intermediate XXXVIII which is then hydrolyzed with aqueous acid to yield invention compound I-J which is purified by chromatography on silica gel to afford pure isomers.

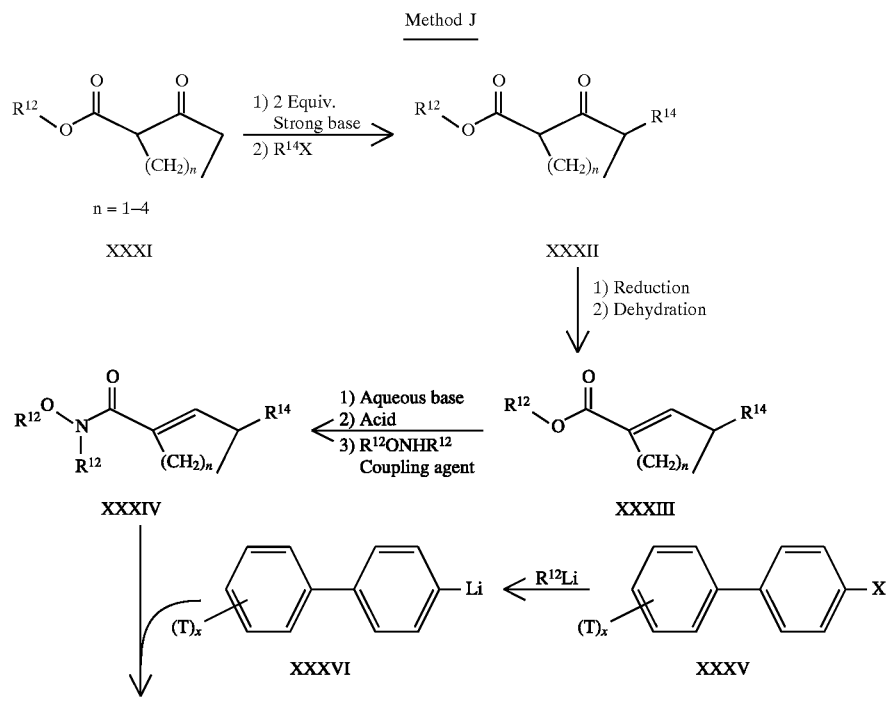

Method J

-continued
Method J

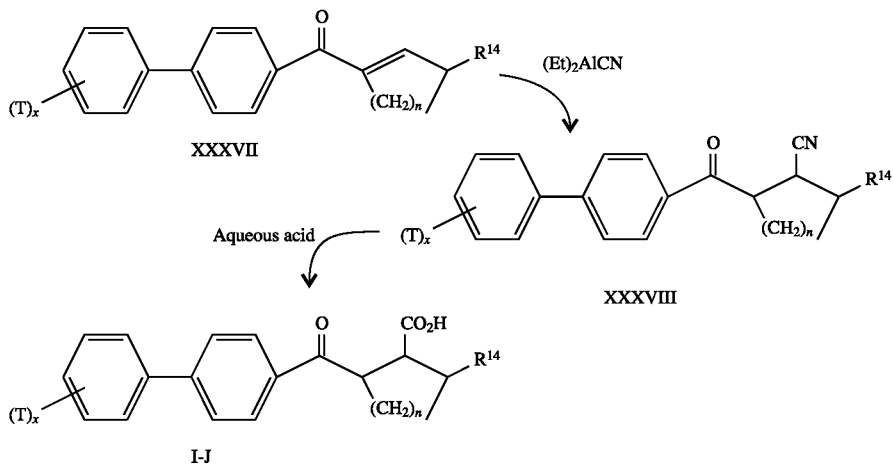

General Method K

Invention compounds in which two R6 groups together form a pyrrolidine ring are prepared according to method K. Starting material XXXIX (L-pyroglutaminol) is reacted under acid catalysis with benzaldehyde XXXX (may be substituted) to yield bicyclic derivative XXXXI. A double bond is then introduced using phenylselenenyl methodology well known to those skilled in the art to yield XXXXII, which, in turn, is reacted with a vinylcopper (I) complex to yield conjugate addition product XXXXIII. Such reactions in which Lig can be, for example, another equivalent of vinyl group or halide are well known to those skilled in the art. Hydride reduction (lithium aluminum hydride or the like) of XXXXIII followed by standard blocking with, for example, t-butyldimethylsilylchloride yields XXXXIV which in turn is reacted with an optionally substituted benzylchloroformate XXXXV to yield XXXXVI. Ozonolysis of this intermediate followed by reductive workup (dimethylsulfide, zinc/acetic acid or the like) leads to aldehyde XXXXVII. Reaction of this aldehyde with a biphenyl organometallic such as XXXVI yields alcohol XXXXVIII. Deblocking of the silyl group with, for example, tetrabutylammonium fluoride followed by oxidation with, for example, pyridiniumdichromate or the like yields claimed compound 1-K-1 in which $R^{14}$ is a carbobenzyloxy group.

Alternatively the carbobenzyloxy group is removed by reaction with hydrogen and a catalyst such as palladium on carbon to yield the unsubstituted invention compound 1-K-2 optionally followed by N-alkylation to yield compound 1-K-3. These final steps are well known to those skilled in the art. Alternatively the intermediate XXXXIV can be directly treated with ozone followed by the other steps of this method to yield 1-K-3 in which $R^{14}$ is optionally substituted benzyl rather than 1-K-1.

This method is especially useful to prepare single enantiomers because starting material XXXIX is available as either the isomer as drawn or as D-pyroglutaminol to yield enantiomeric products.

Method K

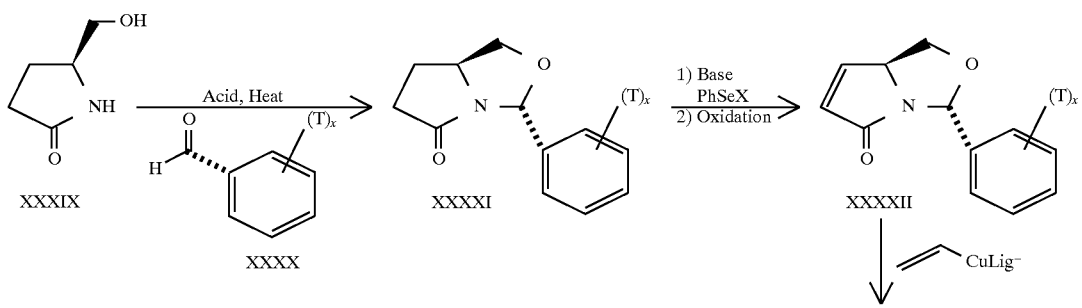

-continued
Method K

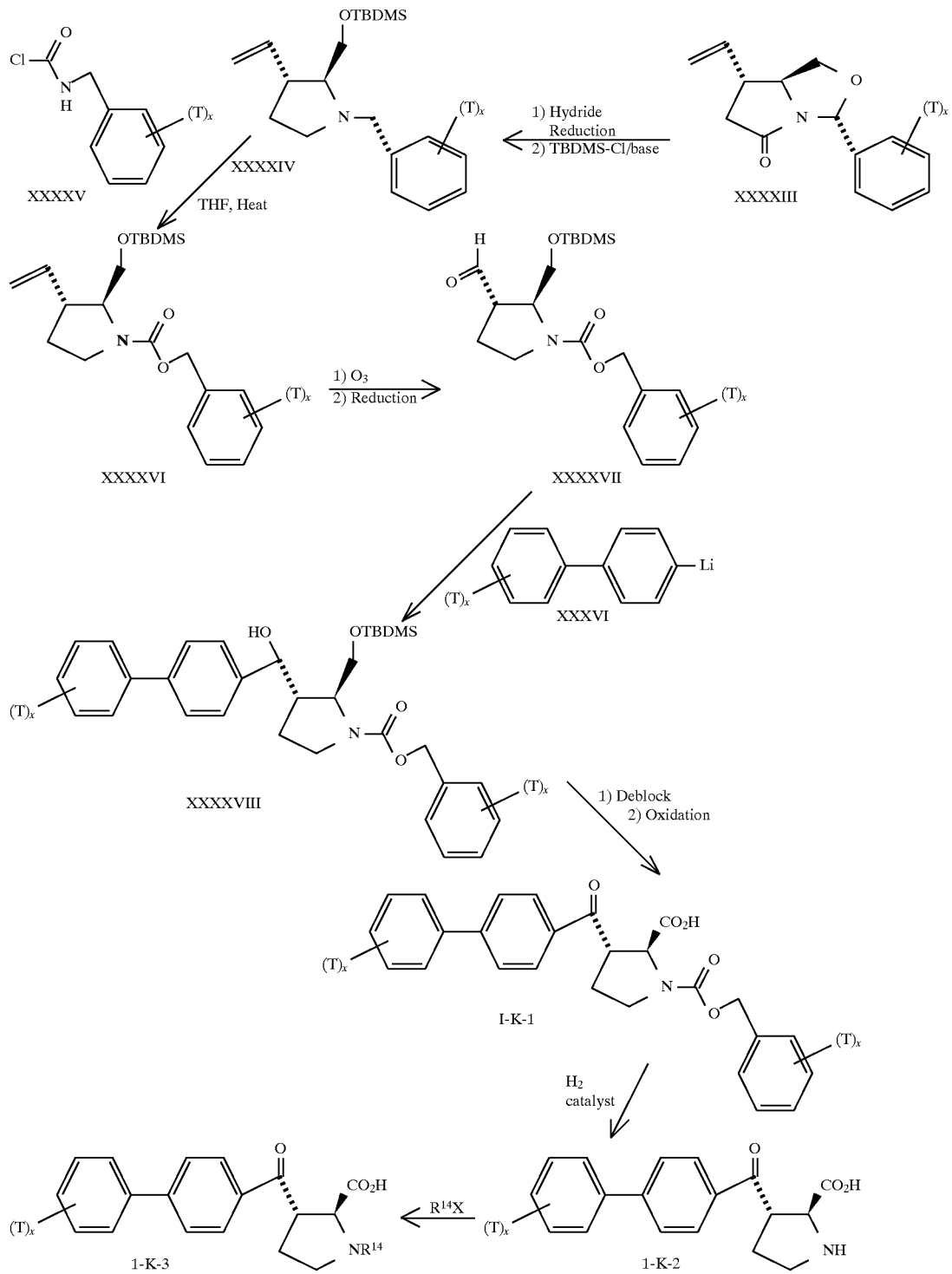

General Method L

The compounds of this invention in which E represents a substituted chain of 3 carbons are prepared by method L. Intermediates LI, if not available from commercial sources, are prepared by reaction of an activated biphenylcarboxylic acid derivative XXXXIX with substituted acetic acid L which has been converted to its bis anion with two equivalents of a strong base such as LDA followed by heating to decarboxylate the intermediate keto acid. LI is then treated with methylenemalonate derivative LII in the presence of a strong base such as sodium hydride to yield substituted malonate LIII. This malonate can be further alkylated under conditions familiar to those skilled in the art to yield LIV which in turn is treated with acid and then heated to yield invention compound 1-L-1. Alternatively the final alkylation can be omitted to yield products in which the R6 adjacent to the carboxyl is H. Alternatively LI can be alkylated with 3-halopropionate ester LV in the presence of base such as LDA to yield ester 1-L-2 which can then be hydrolyzed with aqueous base to yield invention compound 1-L-3 upon treatment with acid. This method is especially useful if any of the groups $R^6$ contain aromatic residues.

be simple alkyl or arylalkyl substituted or can be amino acid derivatives in which the carboxyl is blocked and the amino group is free.

The compounds of the present invention have been found to inhibit the matrix metalloproteases MMP-3, MMP-9 and MMP-2, and to a lesser extent MMP-1, and are therefore

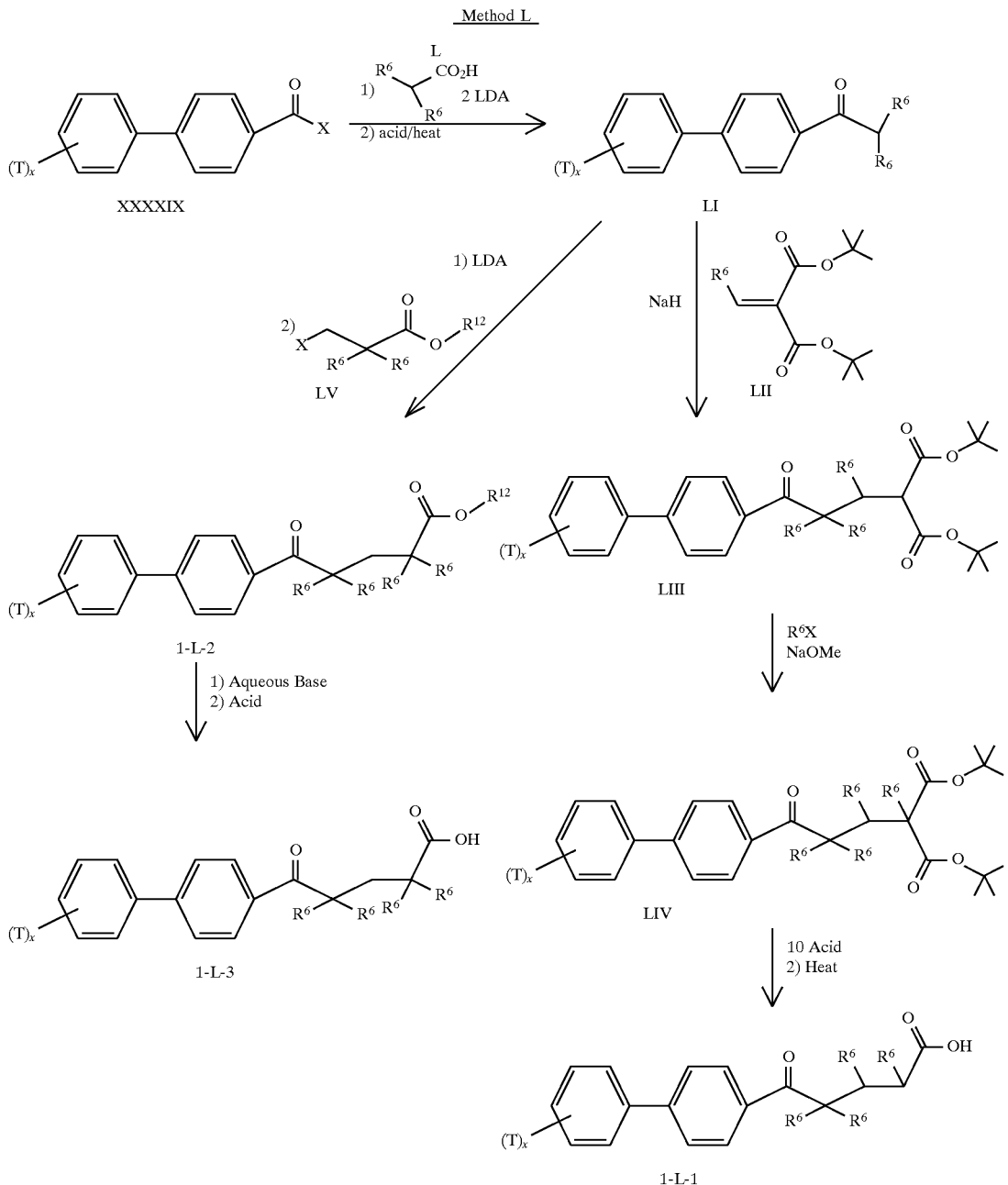

Method M

Amides of the acids of the invention compounds can be prepared from the acids by treatment in an appropriate solvent such as dichloromethane or dimethylformamide with a primary or secondary amine and a coupling agent such as dicyclohexylcarbodiimide. These reactions are well known to those skilled in the art. The amine component can useful for treating or preventing the conditions referred to in the background section. As other MMPs not listed above share a high degree of homology with those listed above, especially in the catalytic site, it is deemed that compounds of the invention should also inhibit such other MMPs to varying degrees. Varying the substituents on the biaryl portions of the molecules, as well as those of the propanoic or butanoic acid chains of the claimed compounds, has been demonstrated to affect the relative inhibition of the listed MMPs. Thus compounds of this general class can be "tuned" by selecting specific substituents such that inhibition of specific MMP(s) associated with specific pathological conditions can be enhanced while leaving non-involved MMPs less affected.

The method of treating matrix metalloprotease-mediated conditions may be practiced in mammals, including humans, which exhibit such conditions.

The inhibitors of the present invention are contemplated for use in veterinary and human applications. For such purposes, they will be employed in pharmaceutical compositions containing active ingredient(s) plus one or more pharmaceutically acceptable carriers, diluents, fillers, binders, and other excipients, depending on the administration mode and dosage form contemplated.

Administration of the inhibitors may be by any suitable mode known to those skilled in the art. Examples of suitable parenteral administration include intravenous, intraarticular, subcutaneous and intramuscular routes. Intravenous administration can be used to obtain acute regulation of peak plasma concentrations of the drug. Improved half-life and targeting of the drug to the joint cavities may be aided by entrapment of the drug in liposomes. It may be possible to improve the selectivity of liposomal targeting to the joint cavities by incorporation of ligands into the outside of the liposomes that bind to synovial-specific macromolecules. Alternatively intramuscular, intraarticular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia. Improved convenience and patient compliance may also be achieved by the use of either injector pens (e.g. the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Nasal delivery may be achieved by incorporation of the drug into bioadhesive particulate carriers (<200 $\mu$m) such as those comprising cellulose, polyacrylate or polycarbophil, in conjunction with suitable absorption enhancers such as phospholipids or acylcarnitines. Available systems include those developed by DanBiosys and Scios Nova.

Oral delivery may be achieved by incorporation of the drug into tablets, coated tablets, dragées, hard and soft gelatine capsules, solutions, emulsions or suspensions. Oral delivery may also be achieved by incorporation of the drug into enteric coated capsules designed to release the drug into the colon where digestive protease activity is low. Examples include the OROS-CT/Osmet™ and PULSINCAP™ systems from ALZA and Scherer Drug Delivery Systems respectively. Other systems use azo-crosslinked polymers that are degraded by colon specific bacterial azoreductases, or pH sensitive polyacrylate polymers that are activated by the rise in pH at the colon. The above systems may be used in conjunction with a wide range of available absorption enhancers.

Rectal delivery may be achieved by incorporation of the drug into suppositories.

The compounds of this invention can be manufactured into the above listed formulations by the addition of various therapeutically inert, inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target enzyme which must be inhibited in order to treat the condition.

The matrix metalloprotease inhibitors of the invention are useful not only for treatment of the physiological conditions discussed above, but are also useful in such activities as purification of metalloproteases and testing for matrix metalloprotease activity. Such activity testing can be both in vitro using natural or synthetic enzyme preparations or in vivo using, for example, animal models in which abnormal destructive enzyme levels are found spontaneously (use of genetically mutated or transgenic animals) or are induced by administration of exogenous agents or by surgery which disrupts joint stability.

Experimental

General Procedures:

All reactions were performed in flame-dried or oven-dried glassware under a positive pressure of argon and were stirred magnetically unless otherwise indicated. Sensitive liquids and solutions were transferred via syringe or cannula and were introduced into reaction vessels through rubber septa. Reaction product solutions were concentrated using a Buchi evaporator unless otherwise indicated.

Materials:

Commercial grade reagents and solvents were used without further purification except that diethyl ether and tetrahydrofuran were usually distilled under argon from benzophenone ketyl, and methylene chloride was distilled under argon from calcium hydride. Many of the specialty organic or organometallic starting materials and reagents were obtained from Aldrich, 1001 West Saint Paul Avenue, Milwaukee, Wis. 53233. Solvents are often obtained from EM Science as distributed by VWR Scientific.

Chromatography:

Analytical thin-layer chromatography (TLC) was performed on Whatman® pre-coated glass-backed silica gel 60 A F-254 250 $\mu$m plates. Visualization of spots was effected by one of the following techniques: (a) ultraviolet illumination, (b) exposure to iodine vapor, (c) immersion of the plate in a 10% solution of phosphomolybdic acid in ethanol followed by heating, and (d) immersion of the plate in a 3% solution of p-anisaldehyde in ethanol containing 0.5% concentrated sulfuric acid followed. by heating.

Column chromatography was performed using 230–400 mesh EM Science® silica gel.

Analytical high performance liquid chromatography (HPLC) was performed at 1 mL min$^{-1}$ on a 4.6×250 mm Microsorb® column monitored at 288 nm, and semipreparative HPLC was performed at 24 mL min⁻¹ on a 21.4×250 mm Microsorb® column monitored at 288 nm.

Instrumentation:

Melting points (mp) were determined with a Thomas-Hoover melting point apparatus and are uncorrected.

Proton ($^1$H) nuclear magnetic resonance (NMR) spectra were measured with a General. Electric GN-OMEGA 300 (300 MHz) spectrometer, and carbon thirteen ($^{13}$C) NMR spectra were measured with a General Electric GN-OMEGA 300 (75 MHz) spectrometer.

Mass spectral (MS) data were obtained on a Kratos Concept 1-H spectrometer by liquid-cesium secondary ion (LCIMS), an updated version of fast atom bombardment (FAB).

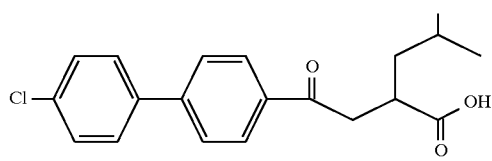

Example 1 (racemate)
Example 2 (−)
Example 3 (+)

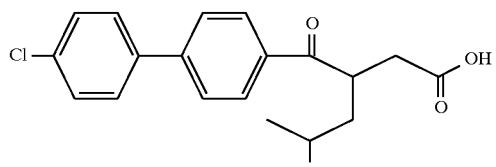

Example 4 (−)
Example 5 (+)

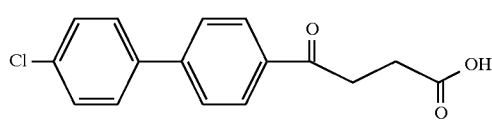

Example 6

Example 1, Example 2, Example 3, Example 4, Example 5, and Example 6 (Reference with Respect to Composition)

4-Chlorobiphenyl (2.859 g, 15.154 mmoles, supplied by TCI) was weighed into a 500 mL flask which had been purged with argon. Into this flask was transferred dihydro-3-(2-methylpropyl)-2,5-furandione (1.997 g, 15.110 mmoles, for preparation see below) with 1,1,2,2-tetachloroethane (50 mL). The solution was cooled in an ice bath and then aluminum trichloride (4.09 g) was slowly added as a solid. The ice bath was removed and the reaction was allowed to warm to room temperature. The mixture was then heated in an oil bath for a total of 2.5 hours at which time the reaction was cooled in an ice bath and quenched with 10% HCL solution (200 mL). The aqueous mixture was extracted thrice with ethyl acetate and the combined organic extracts washed once with brine. The solution was dried over MgSO$_4$ and concentrated in vacuuo. Purification by flash chromatography (hexane.ethyl acetate) provided an oil that was recrystallized twice (hexane-ethyl acetate) to provide 1.358 g of a light orange solid which was mostly one material. Chromatography (ethyl acetate-hexane) of a small amount of this material yielded 52.0 mg of Example 1 (mp=138.5°–139.5° C.) as a white fluffy solid and 4.0 mg of Example 6 (mp=185.5°–186.5 ° C.) as side product from succinic anhydride as a minor impurity of dihydro-3-(2-methylpropyl)-2,5-furandione.

The mother liquors from a similarly prepared batch of Example 1 were evaporated in vacuo and the residue evaluated by NMR spectroscopy to show the presence of an isomer, 5-methyl-3-[oxo-(4'-chloro-4-biphenyl)methyl] hexanoic acid, as a significant component. This residue was prepurified by flash silica chromatography (methylene chloride-methanol) to remove extraneous contaminants and then separated on a Chiralpak AD ® HPLC column (65% n-heptane, 35% (1% water+0.2% TFA in ethanol)) to yield enantiomers of the regioisomer (Example 4/Example 5 mixed) along with those of Example 1. Separation of pure Example 1 on the same system yielded only the isomers of this compound as Example 2 (first off) and Example 3 (second off). Re-chromatography of the regioisomer mixture on a Chiralcel OJ ® column gave pure samples of Example 5 (first off) and Example 4 (second off).

In a separate experiment run in a similar manner using pure succinic anhydride instead of the above anhydride, the only product was Example 6.

Example 1

TLC (methylene chloride-2.5% methanol) R$_f$=0.20; $^1$H NMR (DMSO-d$_6$) δ 12.12 (s, 0.6H), 8.03 (d,J=8.43 Hz, 2H), 7.80 (d, J=8.43 Hz, 2 H ), 7.76 (d, J=8.43 Hz, 2H), 7.53 ( d, J=8.43 Hz, 2H), 3.59 (d, J=9.16 Hz , d 3.30 solvent), 3.10 (dd, J=18.15 Hz, J=4.22 HZ, 1H), 2.85 (M, 1H), 1.65 (m, 1H), 1.50 (m, 1H), 1.33 (m, 1H), 0.88 ( d, J=6.6 Hz, 3H), 0.78 ( d, J=6.6 Hz, 3H); $^{13}$C NMR (DMSO-d$_6$) δ 8 199.13, 177.13, 144.2, 138.74, 136.59, 134.42, 130.15, 129.87, 129.77, 127.94, 41.96, 41.50, 39.27, 26.38, 23.53, 23.43; IR (soln) 1706.7, 1687.4, 1606.4 cm⁻¹; MS (FAB-LSIMS) 345 [M+H]⁺ (C$_{20}$H$_{21}$O$_3$Cl, FW=344.84); Anal. C: calcd, 69.66; found, 69.73. H: calcd, 6.14;

found, 6.20. Cl: calcd, 10.28, found, 10.35.

Example 2

[A] D=−26.3 (MEOH), >99.8%ee by chiral HPLC, $^1$H NMR identical to Example 1.

Example 3

[A] D=+25.4 (MEOH), >99.8%ee by chiral HPLC, $^1$H NMR identical to Example 1.

Example 4

[α]D −26.3 (MeOH); >99%ee by chiral HPLC; $^1$H NMR (CDCl$_3$) δ 8.05 (d, J=8 Hz, 2H), 7.66 (d, J=8 Hz, 2H), 7.56 (d, J=8 Hz, 2H), 7.45 (d, J=8 Hz, 2H), 3.9 (m, 1H), 2.98 (dd, J=9 Hz, J=17 Hz, 1H), 2.58 (dd, J=4 Hz, J=17 Hz, 1H), 1.3–1.7 (m, 3H), 1.01 (d, J=6 Hz, 3H), 0.87 (d, J=6 Hz, 3H); $^{13}$C NMR (CDCl$_3$) δ 203.09, 177.28, 145.19, 138.94, 135.87, 135.13, 129.82, 129.17, 127.88, 42.09, 40.86, 35.84, 26.52, 23.77, 22.61; MS (FAB-LSIMS) 345 [M+H]⁺ (C$_{20}$H$_{21}$O$_3$Cl, FW=344.84).

Example 5

[α]D+26.1 (MeOH); >99%ee by chiral HPLC; $^1$H NMR, $^{13}$C NMR and MS identical to Example 4.

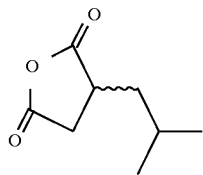

Dihydro-3-(2-methylpropyl)-2,5-furandione:

This intermediate was prepared according to the general procedures given in Wolanin, et al., U.S. Pat. No. 4,771,038 (Sep. 13, 1988 —Examples 6 and 5c). The $^1$H NMR spectra of the intermediates and final product matched those given in the experimental procedures of that patent.

Example 1

Later Preparations and General Procedure.

4-Chlorobiphenyl (14.8 mmoles, 1 EQ) was weighed into a 250 mL flask which had been purged with argon. Into this flask was transferred dihydro-3-(2-methyl.propyl)-2,5-furandione (14.9 mmoles, 1 EQ) with 1,1,2,2-tetachloroethane (50 mL). The solution was cooled in an ice bath and then aluminum trichloride (30.8 mmoles, 2.07 EQ) was slowly added as a solid. The ice bath was removed after approximately 30 minutes and the reaction was allowed to warm to room temperature and allowed to stir for at least 24 hours. It was then poured into cold 10% HCL solution and extracted three to five times with chloroform. The combined organic extracts washed once with brine, dried over MgSO$_4$ and concentrated in vacuo. Purification by flash chromatography (methylene chloride-methanol) provided an oil that was recrystallized twice (hexane- ethyl acetate) to provide 1.066 grams of white solid (Example 1). The mother liquors from recrystallization were a mixture of regioisomers and a small amount of Example 6.

The above general method was used to prepare the following series of substituted biphenyl products using either the substituted anhydride dihydro-3-(2-methylpropyl)-2,5-furandione or succinic anhydride along with the indicated substituted biphenyls:

FROM SUCCINIC ANHYDRIDE: EXAMPLE 6, EXAMPLE 7, EXAMPLE 8, EXAMPLE 9, EXAMPLE 10, EXAMPLE 11, EXAMPLE 12

From Dihydro-3-(2-methylpropyl)-2,5-furandione: Example 13, Example 14, Example 15, Example 16, Example17, Example18, Example 19, Example 20, Example 21, Example 22, Example 23

Example 6

From 4-chlorobiphenyl and pure succinic anhydride: T L C (methylene chloride-2.5% methanol) R$_f$=0.09; $^1$H NMR (DMSO-d$_6$) δ 8.04 (d, J=8.43 Hz, 2H), 7.81 (d, J=8.43 Hz, 2H), 7.76 (d, J=8.43 Hz, 2H), 7.53 (d, J=8.43 Hz, 2H), 3.26 (t, J=6.23 Hz, 2H), 2.56 (t, J=6.23 Hz, 2H); $^{13}$C NMR (DMSO-d$_6$) δ 199.13, 174.97, 144.24, 138.79, 136.60, 134.43, 130.17, 129.89, 129.75, 128.00, 34.25, 28.97; MS (FAB-LSIMS) 289 [M+H]+(C$_{16}$H$_{13}$O$_3$Cl, FW=288.73); Anal. C: calcd, 66.56; found, 66.46. H: calcd, 4.54; found, 4.45.

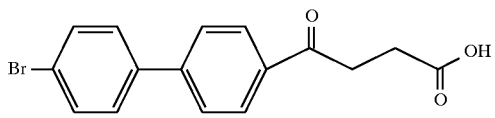

Example 7

Example 7 (Reference With Respect to Composition)

From 4-bromobiphenyl: MP 201.5°–202.0° C.; TLC (methylene chloride-2.5% methanol) R$_f$=0.11; $^1$H NMR (DMSO-d$_6$) δ 8.03 (d, J=8.46 Hz, 2H), 7.80 (d, J=8.46 Hz, 2H), 7.67 (m, 4H), 3.25 (t, J=6.25 Hz, 2H), 2.58 (t, J=6.25 Hz, 2H) ; $^{13}$C NMR (DMSO-d$_6$) δ 199.11, 174.94, 144.27, 139.13, 136.61, 133.08, 130.15, 129.73, 127.92, 123.08, 34.26, 28.96; MS (FAB-LSIMS) 333 [M+H]$^+$ (C$_{16}$H$_{13}$O$_3$Br, FW=333.18); Anal. C: calcd, 57.68; found, 57.41. H: calcd, 3.93; found, 4.00.

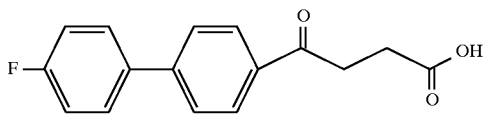

Example 8

Example 8 (Reference With Respect to Composition)

From 4-fluorobiphenyl: MP 176.0°–177.0° C.; TLC (methylene chloride-2.5% methanol) R$_f$=0.10; $^1$H NMR (DMSO-d$_6$) δ 12.13 (S, 1H), 8.03 (d, J=8.42 Hz, 2H), 7.79 (m, 4H), 7.31 ( t, J=9.02 Hz, 2H), 3.26 (t, J=6.16 Hz, 2H), 2.57 (t, J=6.01 Hz, 2H) ; $^{13}$C NMR (DMSO-d$_6$) δ 199.10, 174.95, 165.13, 161.86, 144.53, 136.47, 136.42, 136.29, 130.24,130.14, 129.68, 127.92, 117.17, 116.89, 32.22, 28.97; MS (FAB-LSIMS) 273 [M+H]$^+$(C$_{16}$H$_{13}$O$_3$F, FW=272.28); Anal. C: calcd, 70.58; found, 70.62. H: calcd, 4.81; found, 4.73.

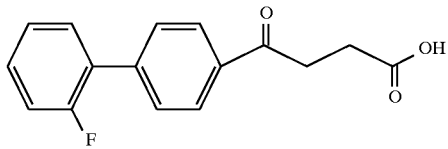

Example 9

Example 9 (Reference With Respect to Composition)

From 2-fluorobiphenyl: MP 158.0°–159.0° C.; TLC (methylene chloride-2.5% methanol) R$_f$=0.10; $^1$H NMR (DMSO-d$_6$) δ 12.15 (s, 1H), 8.06 (d, J=8.42 Hz, 2H), 7.69 (dd, J=1.5 Hz, J=8.42 Hz, 2H), 7.58 (m, 1H), 7.46 (m, 1H), 7.33 (m, 2H), 3.27 (t, J=6.31 Hz, 2H), 2.58 (t, J=6.31 Hz, 2H); $^{13}$C NMR (DMSO-d$_6$) δ 199.23, 174.9, 161.81, 158.54, 140.73, 136.66, 131.91, 131.88, 131.59, 131.48, 130.23, 130.20, 129.27, 128.36, 128.18, 126.23, 126.18, 117.51, 117.22, 34.26, 28.96; MS (FAB-LSIMS) 273 [M+H]$^+$ (C$_{16}$H$_{13}$O$_3$F, FW=272.28); Anal. C: calcd, 70.58; found, 70.47. H: calcd, 4.81; found, 4.89.

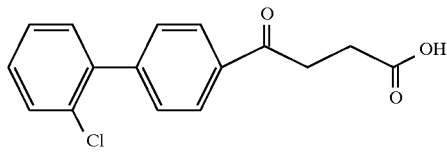

Example 10

Example 10 (Reference With Respect to Composition)

From 2-chlorobiphenyl: MP 175.0°–176.0° C.; TLC (methylene chloride-2.5% methanol) $R_f$=0.09; $^1$H NMR (DMSO-$d_6$) δ 12.16 (s, 1 H), 8.09 (d, J=8.12 Hz, 2H), 7.57, 7.39 (m, 6H), 3.27 (t, J=6.30 Hz, 2H), 2.59 (t, J=6.30 Hz, 2H); $^{13}$C NMR (DMSO-$d_6$) δ 99.24, 174.94, 144.37, 139.92, 136.68, 132.46, 132.24, 131.06, 130.91, 130.75, 128.91, 128.75, 34.24, 28.98; MS (FAB-LSIMS) 289 [M+H]$^+$ ($C_{16}H_{13}O_3Cl$, FW=288.73); Anal. C: calcd, 66.56; found, 66.17. H: calcd, 4.54; found, 4.57.

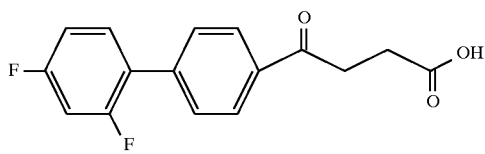

Example 11

Example 11 (Reference With Respect to Composition)

From 2,4-difluorobiphenyl: MP 133.0°–134.0° C.; TLC (methylene chloride-2.5% methanol) $R_f$=0.09; $^1$H NMR (DMSO-$d_6$) δ 12.15 (s, 1 H), 8.05 (d, J=8.42 Hz, 2H), 7.65, 7.40, 7.22 (m, 6H), 3.27 (t, J=6.31 Hz, 2H), 2.58 (t, J=6.0 Hz, 2H); $^{13}$C NMR (DMSO-$d_6$) δ 199.17, 174.94, 165.00, 164.84, 162.02, 161.86, 161.73, 161.56, 158.72, 158.56, 139.89, 136.68, 133.22, 133.16, 133.09, 133.03, 130.19, 130.15, 129.30, 125.03, 124.98, 124.87, 124.81, 120.25, 113.54, 113.50, 113.26, 113.21, 106.15, 105.80, 105.44, 34.24, 28.94; MS (FAB-LSIMS) 291 [M+H]$^+$ ($C_{16}H12O_3F_2$, FW=290.27); Anal. C: calcd, 66.21; found, 65.97. H: calcd, 4.17; found, 4.00.

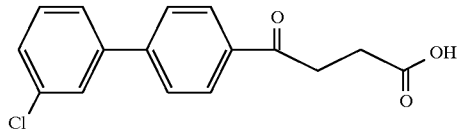

Example 12

Example 12 (Reference With Respect to Composition)

From 3-chlorobiphenyl: MP 147.0°–148.0° C.; $^1$H NMR (DMSO-$d_6$) δ 12.3 (bs, 1H), 8.03 (d, J=8 Hz, 2H), 7.4–7.9 (m, 6H), 3.25 (t, J=3 Hz, 2H), 2.60 (t, J=3 Hz, 2H); 13C NMR (DMSO-$d_6$) δ 198.0, 173.9, 142.9, 141.0, 135.7, 133.9, 130.9, 128.2, 128.2, 127.1, 126.7, 125.7, 33.2, 27.9; MS (FAB-LSIMS) 289 [M+H]$^+$ ($C_{16}H_{13}O_3Cl$, FW=290.27); Anal. C: calcd, 66.56; found, 65.9. H: calcd, 4.54; found, 4.56.

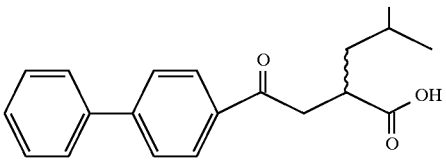

Example 13

Example 13

From biphenyl: MP 134.5°–135.0° C.; TLC (methylene chloride-2.5% methanol) $R_f$=0.19; $^1$H NMR (DMSO-$d_6$) δ 12.13 (s, 0.7H), 8.03 (d, J=8.43 Hz, 2H), 7.79 (d, J=8.43 Hz, 2H), 7.72 (d, J=8.43 Hz, 2H), 7.44 (d, J=8.43 Hz, 2H), 3.35 (dd, J=18.14 Hz, J=10.2 Hz, 1H), 3.09 (dd, J=17.96 Hz, J=4.4 Hz, 1H), 1.65 (m, 1H), 1.50 (m, 1H), 1.33 (m, 1H), 0.92 (d, J=6.6 Hz, 3H), 0.82 (d, J=6.6 Hz, 3H); $^{13}$C NMR (DMSO-$d_6$) δ 199.18, 177.77, 145.66, 139.99, 136.36, 130.20, 129.75, 129.50, 128.10, 128.00, 41.99, 41.50, 39.31, 26.40, 23.56, 23.45; MS (FAB-LSIMS) 311 [M+H]$^+$ ($C_{20}H_{22}O_3$, FW=310.38); Anal. C: calcd, 77.39; found, 77.25. H: calcd, 7.14; found, 7.12.

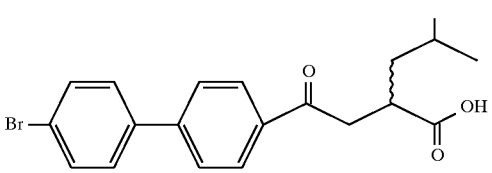

Example 14

Example 14

From 4-bromobiphenyl: MP 149.0°–150.0° C.; TLC (methylene chloride-2.5% methanol) $R_f$=0.16; $^1$H NMR (DMSO-$d_6$) δ 8.05 (d, J=10 Hz, 2H), 7.66 (m, 4H), 7.50 (d, J=10 Hz, 2H), 3.46 (dd, J=18 Hz, J=6 Hz, 1H), 3.12 (m, 2H), 1.72 (m, 2H), 1.42 (m, 1H), 1.02 (d, J=6 Hz, 3H), 0.90 (d, J=6 Hz, 3H); $^{13}$C NMR (DMSO-$d_6$) δ 198.22, 182.93, 151.79, 145.25, 139.36, 136.16, 132.78, 129.49, 129.45, 127.72, 123.37, 41.79, 41.30, 39.11, 26.55, 23.20, 23.03; MS (FAB-LSIMS) 389 [M+H]$^+$($C_{20}H_{21}O_3Br$, FW=389.28); Anal. C: calcd, 61.71; found, 61.88. H: calcd, 5.44; found, 5.40.

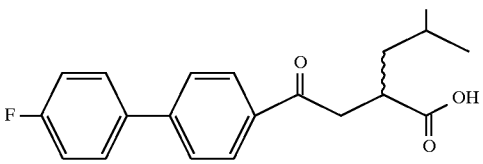

Example 15

Example 15

From 4-fluorobiphenyl: MP 117.5°–118.5° C.; TLC (methylene chloride-2.5% methanol) $R_f$=0.16; $^1$H NMR (DMSO-$d_6$) δ 8.04 (d, J=8.46 Hz, 2H), 7.61 (m, 4H), 7.16 (t, J=8.64 Hz, 2H), 3.47 (dd, J=17.29 Hz, J=8.45 Hz, 1H), 3.12 (m, 2H), 1.72 (m, 2H), 1.44 (m, 1H), 1.01 (d, J=6 Hz, 3H), 0.91 (d, J=6 Hz, 3H); $^{13}$C NMR (DMSO-$d_6$) δ 198.22, 182.72, 165.30, 162.02, 145.53, 136.63, 136.58, 135.85, 129.65, 129.54, 129.38, 127.75, 116.72, 116.43, 41.78, 41.27, 39.07, 26.54, 23.20, 22.98; MS (FAB-LSIMS) 329 [M+H]+ ($C_{20}H_{21}O_3F$, FW=328.39); Anal. C: calcd, 73.15; found, 73.30. H: calcd, 6.45; found, 6.43.

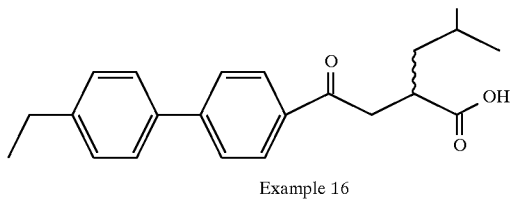

Example 16

Example 16

From 4-ethylbiphenyl: MP 153.0° C.; TLC (methylene chloride-2.5% methanol) $R_f$=0.16; $^1$H NMR (DMSO-$d_6$) δ 12.2 (s, 0.8H), 8.02 (d, J=8 Hz, 2H), 7.78 (d, J=8 Hz, 2H), 7.63 (d, J=8 Hz, 2H), 7.30 (d, J=8 Hz, 2H), 3.34 (dd-solvent), 3.08 (dd, J=18 Hz, J=6 Hz, 1H), 2.76 (m, 1H), 2.60 (q, J=18 Hz, J=6 Hz, 2H), 1.64 (m, 1H), 1.48 (m, 1H), 1.32 (m, 1H), 1.18 (t, J=6 Hz, 3H), 0.91 (d,J=6 Hz, 3H), 0.81 (d, J=6 Hz, 3H); 13C NMR (DMSO-$d_6$) δ 199.12, 177.77, 145.64, 145.30, 137.35, 136.09, 129.73, 129.63, 128.02, 127.69, 41.99, 41.46, 39.29, 28.95, 26.40, 23.56, 23.43, 16.63; MS (FAB-LSIMS) 339 [M+H]+ ($C_{22}H_{26}O_3$, FW=338.45); Anal. C: calcd, 78.08; found, 77.74. H: calcd, 7.74; found, 7.72.

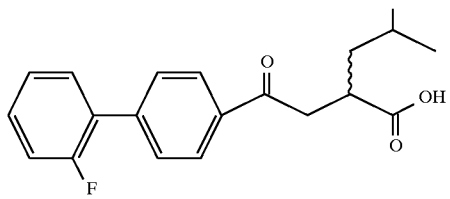

Example 17

Example 17

From 2-fluorobiphenyl: MP 119.0°–120.0° C.; TLC (methylene chloride-2.5% methanol) $R_f$=0.12; $^1$H NMR (DMSO-$d_6$) δ 12.18 (s, 0.7H), 8.09 (d, J=13 Hz, 2H), 7.96 (d, J=13 Hz, 2H), 7.78, 7.65, 7.44, (m, 4H), 3.35 (dd, J=17 Hz, J+10 Hz, 1H), 3.10 (dd, J=17 Hz, J=4 Hz, 1H), 2.85 (m, 1H), 1.64 (m, 1H), 1.50 (m, 1H), 1.32 (m, 1H), 1 0 0.91 (d, J=6 Hz, 3H), 0.81 (d, J.=6 Hz, 3H); 13C NMR (DMSO-$d_6$) δ 199.23, 177.74, 161.83, 158.57, 140.78, 136.68, 131.92, 131.88, 131.59, 131.49, 130.22, 130.19, 129.32, 128.36, 128.20, 126.24, 126.19, 117.51, 117.22, 41.97, 41.51, 39.29, 26.40, 23.53, 23.43; MS (FAB-LSIMS) 329 [M+H]+ ($C_{20}H_{21}O_3F$, FW=328.39); Anal. C: calcd, 73.15; found, 73.02. H: calcd, 6.45; found, 6.48.

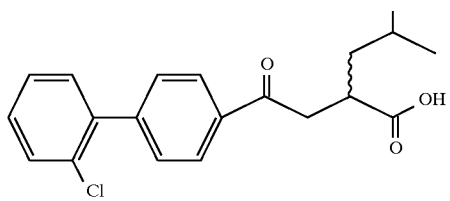

Example 18

Example 18

From 2-chlorobiphenyl: MP 118.0°–119.0° C.; TLC (methylene chloride-2.5% methanol) $R_f$=0.18; $^1$H NMR (DMSO-$d_6$) δ 8.05 (d, J=8.42 Hz, 2H), 7.56 (d, J=8.72 Hz, 2H), 7.50, 7.34 (m, 4H), 3.48 (dd, J=8.0 Hz, J=15 Hz, 1H), 3.20 (m, 2H), 1.72 (m, 2H), 1.45 (m, 1H), 1.02 (d, 1.02, J=6 Hz, 3H), 0.92 (d, J=6 Hz, 3H); 13C NMR (DMSO-$d_6$) δ 198.31, 182.54, 144.96, 140.02, 136.18, 132.96, 131.17, 130.78, 130.46, 129.90, 128.54, 127.67, 41.77, 41.31, 38.97, 26.54, 23.18, 23.02; MS (FAB-LSIMS) 345 [M+H]+ ($C_{20}H_{21}O_3F$, FW=328.37); Anal. C: calcd, 69.66; found, 69.41. H calcd, 6.14; found, 6.10. Cl: calcd, 10.28 found, 10.24.

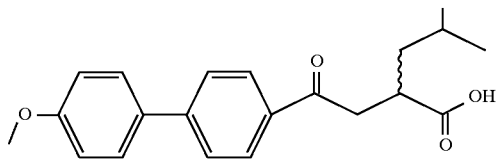

Example 19

Example 19

From 4-methoxybiphenyl: MP 141.0°–142.0° C.; TLC (methylene chloride-2.5% methanol) $R_f$=0.21; $^1$H NMR (DMSO-$d_6$) δ 8.02 (d, J=8.42 Hz, 2H), 7.65 (d, J=8.42 Hz, 2H), 7.59 (d, J=8.72 Hz, 2H), 7.01 (d, J=9.02 Hz, 2H), 3.87 (s, 3H) 3.46 (dd, J=15.0 Hz, J=8.0 Hz, 1H), 3.15 (m, 2H), 1.72 (m, 2H), 1.44 (m, 1H), 1.02 (d, J=6 Hz, 3H), 0.92 (d, J=6 Hz, 3H); $^{13}$C NMR (DMSO-$d_6$) δ 198.24, 182.64, 160.58, 146.74, 135.29, 132.87, 128.36, 129.04, 127.30, 115.07, 56.04, 41.80, 41.25, 39.08, 26.55, 23.21, 22.98; MS (FAB-LSIMS) 341 [M+H]+ ($C_{21}H_{24}O_4$, FW=340.42); Anal. C: calcd, 74.09; found, 73.98. H: calcd, 7.11; found, 7.09.

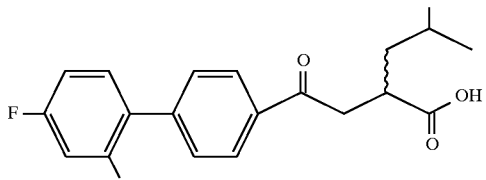

Example 20

Example 20

From 2,4-difluorobiphenyl: MP 133.0=134.0° C.;TLC (methylene chloride-2.5% methanol) $R_f$=0.17;$^1$H NMR (DMSO-$d_6$) δ 12.17 (s, 0.8H), 8.05 (d, J=7.7 Hz, 2H), 7.65, 7.40, 7.22 (m, 6H), 3.34 (m, 1 H and solvent), 3.11 (dd, J=18.02 Hz, J=4.04 Hz, 1H), 0.93 (d, J=6 Hz, 3H), 0.83 (d, J=6 Hz, 3H); $^{13}$C NMR (DMSO-$d_6$) δ 199.19, 177.73, 165.00, 164.84, 162.02, 161.86, 161.73, 161.56, 158.72, 158.54, 139.91, 136.69, 133.21, 133.16, 133.08, 133.03, 130.15, 130.12, 129.33, 125.02, 124.97, 124.86, 124.81, 113.52, 113.49, 113.24, 113.20, 106.14, 105.78, 105.43, 41.96, 41.49, 39.27, 26.38, 23.50, 23.40; MS (FAB-LSIMS) 347 [M+H]+($C_{20}H_{20}O_3F_2$ FW=346.38).

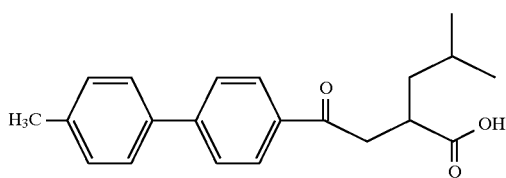

Example 21

Example 21

From 4-methylbiphenyl: MP 131.5=132.5° C.;TLC (methylene chloride-2.5% methanol) $R_f$=1.4; $^1$H NMR (CDCl$_3$) δ 8.03 (d, J=8.4 Hz, 2H), 7.67 (d, J=8.7 Hz, 2H), 7.54(d, J=8.1 Hz, 2H), 7.28 (d, J=8.1 Hz, 2H), 3.46 (m, 1H), 3.14 (m,2H), 2.42 (s, 3H), 1.73 (m, 2H), 1.43 (m, 1H), 0.99 (d, J=6.0 Hz, 3H), 0.94 (d, J=6.3 Hz, 3H); 13C NMR (CDCl$_3$) δ 198.29, 182.59, 146.55, 138.92, 137.58, 135.61, 130.35, 129.31, 127.76, 127.65, 41.80, 41.27, 39.07, 26.55, 23.21, 22.98, 21.34; MS (FAB-LSIMS) 325 [M+H]$^+$ (C$_{21}$H$_{24}$O$_3$ FW=324.42); Anal. C: calcd, 77.75; found, 77.51. H: calcd, 7.46; found, 7.40.

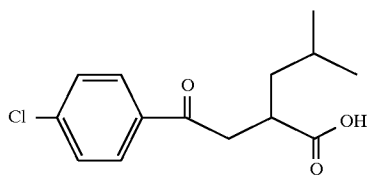

Example 22

Example 22 (Reference)

From 4-chlorobenzene: MP 123.5°–124.5° C.; $^1$H NMR (CDCl$_3$) δ 7.67 (d, J=9 Hz, 2H), 7.20 (d, J=8 Hz, 2H), 3.15 (dd, J=9 Hz, J=17 Hz, 1H), 3.15 (dd, J=9 Hz, J=17 Hz, 1H), 2.83 (m, 2H), 1.45 (m, 2H), 1.16 (m, 1H), 0.76 (d, J=6 Hz, 3H), 0.66 (d, J=6 Hz, 3H); 13C NMR (CDCl$_3$) δ 197.53, 182.72, 140.39, 135.46, 130.13, 129.60, 41.73, 41.15, 39.02, 26.50, 23.13, 22.98; MS (FAB-LSIMS) 269 [M+H]$^+$ (C$_{14}$H$_{17}$O$_3$Cl FW=268.74); Anal. C: calcd, 62.57; found, 62.50. H: calcd, 6.38; found, 6.39; Cl: calcd, 13.19; found, 13.18.

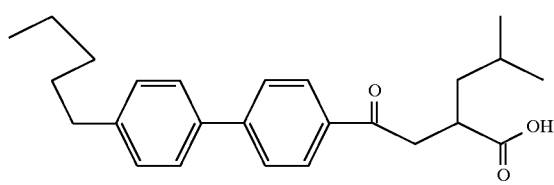

Example 23

Example 23

From 4-pentylbiphenyl: MP 101.0°–102.0° C.; $^1$H NMR (CDCl$_3$) δ 8.03 (d, J=8 Hz, 2H), 7.678 (d, J=8 Hz, 2H), 7.56 (d, J=8 Hz, 2H), 7.29 (d, J=8 Hz, 2H), 3.46 (dd, 1H), 3.10 (m, 2H), 2.67 (tr, J=7 Hz, 2H), 1.2–1.8 (m, 9H), 0.8–1.0 (m, 9H); $^{13}$C NMR (CDCl$_3$) δ 198.27, 182.54, 146.58, 143.99, 137.76, 135.57, 129.70, 129.31, 127.78, 127.67, 41.80, 41.27, 39.05, 36.27, 32.17, 31.80, 26.55, 23.21, 22.98, 14.70; MS (FAB-LSIMS) 381 [M+H]$^+$ (C$_{25}$H$_{32}$O$_3$ FW=324.42); Anal. C: calcd, 78.91; found, 78.85. H: calcd, 8.48; found, 8.46.

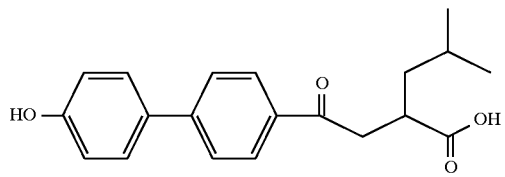

Example 24

Example 24

Example 19 (52.2 mg, 0.153 mmol) was dissolved in 2.5 ml glacial acetic acid and 1.5 ml conc. HBr. This mixture was stirred overnight at ambient temperature and then refluxed for 13 hours. The reaction was allowed to cool before water was added to precipitate crude solid. This was dissolved in ethyl acetate and washed with brine. The solution was dried over MgSO$_4$ and concentrated in vacuo to give a solid that recrystallized from hexane-ethyl acetate as 24.6 mg white crystals.

MP 188.0°–189.0° C.; TLC (methylene chloride- 2.5% methanol) $R_f$=0.07; 1 H NMR (DMSO-d$_6$) δ 8.02 (d, J=8.42 Hz, 2H), 7.65 (d, J=8.42 Hz, 2H), 7.59 (d, J=8.72 Hz, 2H), 7.01 (d, J=9.02 Hz, 2H), 3.87 (s, 3H) 3.46 (dd, J=15.0 Hz, J=8.0 Hz, 1H), 3.15 (m, 2H), 1.72 (m, 2H), 1.44 (m, 1H), 1.02 (d, J=6 Hz, 3H), 0.92 (d, J=6 Hz, 3 H ); $^{13}$C NMR (DMSO-d$_6$) δ 198.98, 177.76, 159.13, 145.69, 135.35, 130.53, 129.72, 129.30, 126.97, 116.99, 26.39, 23.56, 23.44; MS (FAB-LSIMS) 327 [M+H]$^+$ (C$_{20}$H$_{22}$O$_4$, FW=326.40); Anal. C: calcd, 73.60; found, 73.19. H: calcd, 6.76; found, 6.76.

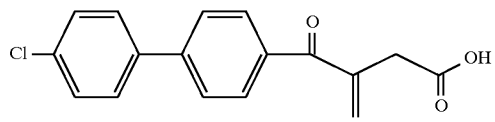

Example 25

Example 25 (Reference with respect to composition)

Example 6 (127.2 mg, 0.441 mmole) was dissolved in 2 ml of pyridine. To this solution was added 32 mg of paraformaldehyde and 0.5 ml of piperidine. The mixture was heated in an oil bath at 55°–60° C. for 6 hours, then allowed to stir at ambient temperature overnight. The reaction was poured into 10% HCl and extracted with EtOAc, washed with saturated brine, dried over MgSO$_4$, filtered and solvent was removed in vacuo to give a crude solid. This solid was dissolved in EtOAc and filtered through a cotton plug to remove insoluble material. The residue was recrystallized with Hexane-EtOAc to give 54.4 mg (41%) white crystals. MP 127.0°–128.0 ° C.; TLC (methylene chloride-2.5%methanol) $R_f$=0.05; $^1$H NMR (CDCl$_3$) δ 7.88 (d, J=9 Hz, 2H), 7.63 (d, J=9 Hz, 2 H), 7.55 (d, J=9 Hz, 2H), 7.44 (d, J=9 Hz, 2H), 6.07 (s, 1H), 5.2 (solvent), 5.87 (s, 1H), 3.60 (s, 2H); $^{13}$C NMR (CDCl$_3$) δ 197.27, 176.70, 144.72, 141.15, 139.00, 135.52, 135.06, 131.15, 130.28, 129.80, 129.17, 127.47, 38.70; MS (FAB-LSIMS) 301 [M+H]+ ($C_{17}H_{13}O_3Cl$, FW=300.74); Anal. C: calcd, 67.89; found, 67.64. H: calcd, 4.36; found, 4.31.

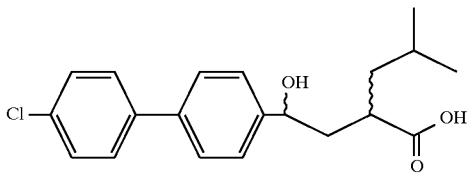

Example 26 Isomer A—First off chromatography column
Example 27 Isomer B—Second off chromatography column

Example 26 and Example 27

Example 1 (103.5 mg, 0.300 mmole) was dissolved in 20 ml of water with the addition of 30.0 mg (0.687 mmole) of sodium hydroxide. The solution was cooled in an ice bath and then 13.0 mg (0.344 mmoles) of sodium borohydride was added as a solid. Stirring continued for 1 hour. TLC (methylene chloride-2.5% methanol) indicated that starting material was still present, so the reaction was allowed to warm to room temperature overnight (16.5 hrs). Starting material was still present, so 13.0 mg more sodium borohydride was added at room temperature. The reaction was stirred for 2 hours and then quenched with 10% HCl and extracted twice with ethyl acetate. The combined organic extracts were washed once with brine and dried over $MgSO_4$. The solution was concentrated in vacuo to give 57.0 mg of a crude solid. This was purified by silica gel chromatography (methylene chloride-methanol) to give two major products Example 26 (7.9 mg) and Example 27 (19.1 mg).

Example 26

$^1$H NMR (MeOD-$d_3$) δ 7.56 (m, 4H), 7.38 (m, 4H), 4.66 (dd, J=9 Hz, J=3 Hz, 1H), 2.77 (m, 1H),1.95 (m, 1H), 1.75, 1.57 (m, 3H), 1.26 (m, 1H), 0.85 (d, J=6 Hz, 3H), 0.79 (d, J=6 Hz, 3H).

Example 27

$^1$H NMR (MeOD-$d_3$) δ 7.58 (m, 4H), 7.40 (m, 4H), 4.64 (t, J=6 Hz, 1H), 2.34 (m, 1H), 2.10 (m and solvent), 1.74 (m, 1H), 1.54 (m, 2H), 1.28 (m, 2H), 0.87 (d, J=6 Hz, 3H), 0.77 (d, J=6 Hz, 3H).

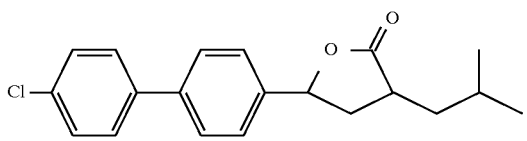

Example 28 and Example 29

Example 28 and Example 29 (Reference With Respect to Composition)

The lactones Example 28 and Example 29 were prepared by dissolving a mixture of Example 26 and Example 27 (51 mg) in 25 ml benzene along with camphor sulfonic acid (11 mg). This mixture was refluxed for 12 hours using a Dean-Stark trap. The resultant solution was washed with aqueous sodium bicarbonate, dried over $MgSO_4$ and evaporated in vacuo. The residue was purified by Silica gel chromatography with Hexane-EtOAc to give the separated lactones.

Example 28

$^1$H NMR (CDCl$_3$) δ 7.3–7.7 (m, 8H), 5.6 (m, 1H), 2.75 (m, 1H), 2.45 (m, 2H), 2.20 (solvent), 1.75 (m, 2H), 1.45 (m, 1H), 1.01 (d, J=7 Hz, 3H), 0.87 (d, J=7 Hz, 3H);$^{13}$C NMR (CDCl$_3$) δ 180.24, 140.57, 139.98, 139.51, 134.33, 129.68, 128.99, 127.98, 126.26, 79.98, 40.31, 37.73, 37.53, 31.61, 26.83, 23.66, 22.27; MS (FAB-LSIMS) 329 [M+H]$^+$ ($C_{20}H_{21}O_2Cl$ FW=328.87).

Example 29

$^1$H NMR (CDCl$_3$) δ (m, 8H), (m, 1H), (m, 1H), 2 (m, 2H), 2.20 (solvent), 1.75 (m, 2H), 1.45 (m, 1H), 1.01 ( d, J=7 Hz, 3H), 0.87 (d, J=7 Hz, 3H); MS (FAB-LSIMS) 328 [M]$^+$ ($C_{20}H_{21}O_2Cl$ FW=328.87).

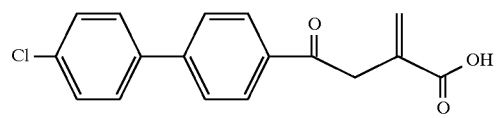

Example 30

Example 30 (Reference With Respect to Composition)

4-Chlorobiphenyl (1.0667 g, 5.654 mmoles)was weighed into a 250 mL flask which had been purged with argon. Into this flask was transferred itaconic anhydride (637.4 mg, 5.686 mmoles) with 1,1,2,2-tetrachloroethane (50 mL). The solution was cooled in an ice bath and then aluminum trichloride (1.8141 g) was slowly added as a solid. The ice bath was removed and the reaction was allowed to warm to room temperature. The reaction was stirred at room temperature for 24 hours, cooled in an ice bath and quenched with 10% HCL solution (200 mL). The aqueous mixture was extracted thrice with chloroform. The combined organic extracts were washed with saturated sodium bicarbonate which was then acidified with concentrated hydrochloric acid. The aqueous mixture was extracted thrice with chloroform and the combined organic extracts washed once with brine. The solution was dried over $MgSO_4$ and concentrated in vacuo. The white solid was recrystallized (hexane-ethyl acetate) to provide 598.8 mg of fluffy white solid Example 30 (mp=169°–170° C.).

TLC (methylene chloride-5%methanol) R$_f$ 0.14; $^1$H NMR (DMSO-$d_6$) δ 12.50 (bs, 0.6H), 8.05 (d, J=8.8 Hz, 2H), 7.83 (d, J=8.06 Hz, 2 H ), 7.78 (d, J=8.07 Hz, 2H), 7.55 ( d, J=8.8 Hz, 2H), 6.21 (d, J=1.46 Hz ,1H), 5.74 (bs, 1H), 4.06 (bs, 2H); $^{13}$C NMR (DMSO-$d_6$) δ 197.73, 168.62, 144.30, 138.76, 137.10, 136.49, 134.45, 130.17, 129.91, 129.10, 128.02, 42.74, 40.19; MS (FAB-LSIMS) 301 [M+H]$^+$ ($C_{17}H_{13}O_3Cl$, FW=300.57); Anal. C: calcd, 67.89; found, 67.76. H: calcd, 4.36; found, 4.34. Cl: calcd, 11.79; found, 11.82.

Example 31 and Example 32

The general method of Example 30 was used to prepare Example 31 and Example 32 by using either toluene or 2-chlorobiphenyl instead of 4-chlorobiphenyl as indicated below.

Example 31 (Reference)

From toluene: MP: 144.0°–145.5° C.; ¹H NMR (MeOD-d₃) δ 7.88 (d, J=8 Hz, 2H), 7.29 (d, J=8 Hz, 2 H ), 6.32 (s, 1H), 5.70 (s, 1H), 4.00 (s, 2H), 2.39 (s, 3H); ¹³C NMR (MeOD-d₃) δ 198.24, 169.01, 144.78, 136.40, 134.66, 129.59, 128.68, 128.25, 41.91, 20.87; MS (FAB-LSIMS) 205 [M+H]⁺ (C₁₂H₁₂O₃ , FW=204.23); Anal. C: calcd, 70.58; found, 70.62. H: calcd, 5.92; found, 5.93.

Example 32 (Reference With Respect to Composition)

From 2-chlorobiphenyl: MP: 186.0°–187.5° C.; ¹H NMR (DMSO-d₆) δ 12.6 (bs, 1H), 8.05 (d, J=8 Hz, 2H), 7.4–7.6 (m, 6H), 6.21 (s, 1H), 5.74 (s, 1H), 4.07 (s, 2H); ¹³C NMR (DMSO-d₆) δ 197.84, 168.64, 144.45, 139.89, 137.06, 136.58, 132.46, 132.24, 131.06, 130.93, 130.78, 129.09, 128.75, 120.00, 42.75; MS (FAB-LSIMS) 301 [M+H]⁺ (C₁₇H₁₃O₃Cl, FW=300.74); Anal. C: calcd, 67.89; found, 67.49. H: calcd, 4.36; found, 4.39.

Example 33 and Example 34

These compounds were prepared by a similar method to that used for Example 30, except that the indicated anhydrides were used instead of itaconic anhydride.

Example 33 (Reference With Respect to Composition)

From 2-methylsuccinic anhydride: MP 196°–197° C.; TLC (methylene chloride-10% methanol) R_f 0.566; ¹H NMR (DMSO-d6) δ 12.13 (s, 1H), 8.03 (d, J=8.22 Hz, 2H), 7.79 (m, 4H), 7.54 (m, 2H), 3.40 (m, 1H), 3.07 (m, 1H), 2.88 (m, 1H), 1.16 (d, J=7.16 Hz, 3H); ¹³C NMR (DMSO-d₆) δ 199.00, 177.91, 144.24, 138.76, 136.61, 134.42, 130.15, 129.88, 129.75, 127.99, 42.64, 35.60, 18.17; M S (FAB-LSIMS) 303 [M+H]⁺ (C₁₇H₁₅O₃Cl, FW=302.76); Anal. C: calcd, 67.44; found, 67.41. H: calcd, 4.99; found, 5.00. Cl: calcd, 11.71; found, 11.69.

Example 34 (Reference With Respect to Composition)

From maleic anhydride: ¹H NMR (DMSO-d₆) δ 13.25 (s, 1H), 8.10 (d, J=8 Hz, 2H), 7.75–7.95 (m, 6H), 7.55 (d, J=8 Hz, 2H), 6.7 (d, J=16 Hz, 1H); ¹³C NMR (DMSO-d₆) δ 190.0, 167.2, 144.8, 138.8, 137.2, 136.4, 134.8, 134.0, 130.8, 130.5, 128.0; MS (FAB-LSIMS) 287 [M+H]⁺ (C₁₆H₁₁O₃Cl, FW=286.76).

Example 35 (Reference)

This compound was prepared by a similar method to that used for Example 30, except that maleic anhydride was used instead of itaconic anhydride and 4-chlorodiphenyl ether was used instead of 4-chlorobiphenyl.

Example 35

MP: 155.0°–157.0° C.; ¹H NMR (MeOD-d₃) δ 8.03 (d, J=9 Hz, 2H), 7.92 (d, J=15 Hz, 1H), 7.41 (d, J=9 Hz, 2H), 7.1–7.0 (m, 4H), 6.75 (d, J=15 Hz, 1H); MS (FAB-LSIMS) 302 [M+H]⁺ (C₁₆H₁₁O₄Cl, FW=280.27).

Example 36

This compound was prepared in a similar manner to Example 1, except that the indicated anhydride was used instead of dihydro-3-(2-methylpropyl)-2,5-furandione. From 2-n-pentylsuccinic anhydride. This anhydride was prepared according to the procedures given for dihydro-3-(2-methylpropyl)-2,5-furandione, except that valeraldehyde was used instead of isobutyraldehyde.

MP 141°–142° C.; TLC (methylene chloride-10%methanol) R_f 0.563; ¹H NMR (DMSO-d₆) δ 12.22 (bs, 0.5H), 8.05 (d, J=8.36 Hz, 2H), 7.79 (m, 4H), 7 54 (d, J=8.6 Hz, 2H), 3.38 (m, 1H), 3.09 (m, 1H), 2.81 (m, 1H), 1.40 (m, 8H), 0.84 (t, J=6.69 Hz, 3H); ¹³C NMR: (DMSO-d₆) δ

199.21, 177.42, 144.24, 136.63, 130.17, 129.90, 129.78, 127.97, 41.09, 40.97, 32.57, 32.29, 27.26, 23.06, 15.00; MS (FAB-LSIMS) 359 [M+H]+ (C$_{21}$H$_{23}$O$_3$Cl, FW=358.87); Anal. C: calcd, 70.29; found, 70.54. H: calcd, 6.46; found, 6.47. Cl: calcd, 9.88; found, 10.15.

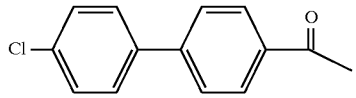

Example 37

Example 37 (Intermediate)

The general method of Example 30 was used to prepare Example 37 by using acetyl chloride instead of itaconic anhydride. The neutral product remained in the chloroform layer after sodium bicarbonate wash. This product-containing solution was treated with activated carbon, filtered and then evaporated. The resultant residue was recrystallized from ethyl acetate and hexane to yield product melting at 100°–101° C.

TLC (methylene chloride-2%methanol) R$_f$ 0.735; $^1$H NMR (CDCl$_3$) δ 8.04 (d, J=8.60 Hz, 2H), 7.65 (d, J=8.84 Hz, 2H), 7.56 (d, J=8.60 Hz, 2H), 7.45 (d, J=8.84 Hz, 2H), 2.65 (s, 3H); $^{13}$C NMR (CDCl$_3$) δ 197.62, 144 .44, 138.27, 136.04, 134.43, 129.13, 128.99, 128.49, 127.05, 26.66; MS (FAB-LSIMS) 231[M+H]+ (C$_{14}$HG$_{11}$OCl FW=230.69); Anal. C: calcd, 72.89; found, 72.91. H: calcd, 4.81; found, 4.74. Cl: calcd, 15.37; found, 15.11.

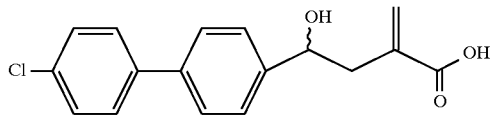

Example 38

Example 38 (Reference With Respect to Composition)

Example 30 (97.9 mg, 0.325 mmol) was dissolved in 1.0 ml of a 0.446M solution of potassium hydroxide in water. Slowly, 76.8 mg (2.030 mmol) of sodium borohydride was added. The mixture was stirred at room temperature for 15 hours. The reaction was quenched by addition of 6N HCl and extracted twice with ethyl acetate and the combined organic extracts washed once with brine. The solution was dried over MgSO$_4$ and concentrated in vacuo. The white solid was recrystallized (hexane-ethyl acetate) to provide 57.1 mg of white solid Example 38 (mp=118°–120° C.).

TLC (methylene chloride-5%methanol) R$_f$ 0.192; $^1$H NMR (DMSO-d$_6$) δ 12.25 (bs, 1H), 7.66(d, J=8.07 Hz, 2H), 7.60 (d, J=8.8 Hz, 2 H), 7.48 (d, J=8.07 Hz, 2H), 7.37 (d, J=8.07 Hz, 2H), 6.02 (bd, J=1.47 Hz, 1H), 5.53 (bs, 1H), 5.3 (bs, 1H), 4.72 (t, J=6.6 Hz, 1H), 2.53 (d, J=5.87 Hz, 2H); $^{13}$C NMR (DMSO-d$_6$) δ 129.94, 129.39, 127.64, 127.33, 71.98, 42.92. Weak signal to noise; these were the only distinguishable peaks. MS (FAB-LSIMS) 285 [M+H]+ (lactone formed during ionization) (C$_{17}$H$_{15}$O$_3$Cl, FW=302.76); Anal. C: calcd, 67.44; found, 66.77. H: calcd, 4.99; found, 4.94. Cl: calcd, 11.71; found, 11.31.

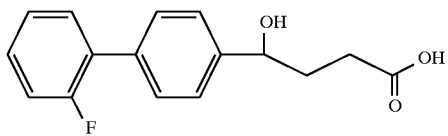

Example 39

Example 39 (Reference With Respect to Composition)

Example 39 was prepared from Example 9 in a way similar to the preparation of Example 38.

$^1$H NMR (DMSO-d$_6$) δ 12.1 (bs, 1H), 7.66(d, J=8.07 Hz, 2H), 7.2–7.6 (m, 8H), 5.3. (d, J=4 Hz, 1H), 4.6 (m, 1H), 2.3 (t, J=7 Hz, 2H), 2.8 (d, 2H); $^{13}$C NMR (DMSO-d$_6$) δ 176.37, 162.63, 159.37, 147.40, 135.39, 132.64, 132.59, 131.33, 131.22, 130.43, 130.40, 130.15, 129.98, 127.89, 126.84, 126.79, 118.12, 117.83, 72.92, 36.24, 32.21; MS (FAB-LSIMS) 257 [M+H]+ (lactone formed during ionization) (C$_{16}$H$_{15}$O$_3$F, FW=274.28); Anal. C: calcd, 67.83; found, 67.80. H: calcd, 5.12; found, 5.50, with calcd 0.5 H$_2$O.

Example 40

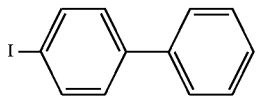

Step 1 —Preparation of 4-Iodobiphenyl.

A solution of trimethyltin chloride (5.5 g, 27.60 mmoles) in 5 mL of DME was added to a stirred suspension of small cubes of metallic sodium (1.9 g, 82.64 mg atom) in 15 mL of DME under an argon stream in an ice bath. When the addition was complete, the mixture was stirred and chilled in an ice bath for 2 hrs. (the color changed to green). The mixture was cannulated into another dry and under argon round bottom flask to remove excess sodium and cooled to 0° C. A solution of 4-bromobiphenyl (5.4 g, 22.70 mmoles) in 14 mL of DME was added dropwise to the chilled NaSnMe$_3$ solution. The resulting solution was stirred at room temperature overnight at which time TLC analysis showed complete reaction. R$_f$ of the trimethyltin product= 0.44 (silica, hexanes). The reaction mixture was then cooled in an ice bath and treated with iodine (6.6 g, 26.00 mmoles). After stirring at room temperature for 1.5 hrs, the mixture was diluted with EtOAc, washed with water, brine, dried over MgSO$_4$, and the solvent removed at reduced pressure. The crude product was then purified by column chromatography with hexanes to afford 5.5 g (86% yield) of white solid.

TLC (silica, hexanes) R$_f$=0.54; $^1$H NMR (CDCl$_3$) δ 7.78 (d , J=8.70 Hz, 2H), 7.32–7.59 (m, 6H); $^{13}$C NMR (CDCl$_3$) δ 140.69, 140.02, 137.80, 128.99, 128.89, 127.68, 126.87, 93.02.

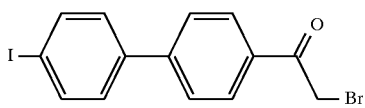

Step 2 —Preparation of 2-Bromo-4-(4-Iodophenyl)-acetophenone.

A solution of 4-iodobiphenyl from step 1 (1.35 g, 4.82 mmoles) in 25 mL of dry dichloroethane was treated with bromoacetyl bromide (0.47 mL, 5.21 mmoles) and cooled to 0° C. under a stream of argon. The cooled mixture was then treated with AlCl₃ (0.77 g, 5.77 mmoles) and allowed to stir at room temperature overnight. The reaction mixture was poured into cold 10% HCl and extracted thrice with methylene chloride. The combined extracts were then washed with brine, dried over MgSO₄, and concentrated at reduced pressure. Crystallization from EtOAc/hexanes afforded 1.1 g (58% yield) as light brown fine needles.

$^{1}$H NMR (CD₃OD) δ 8.17 (d, J=8.4 Hz, 2H), 7.95 (d, J=8.4 Hz, 2H), 7.94 (d, J=8.7 Hz, 2H), 7.66 (d, J=8.1 Hz, 2H), 5.05 (s, 2H); $^{13}$C NMR (CD₃OD) δ 200.86, 153.56, 147.68, 147.43, 142.61, 139.12, 25 138.71, 136.40, 104.93, 43.64.

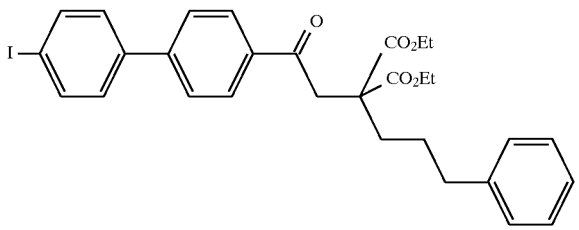

Step 3

A solution of diethyl-(3-phenyl)propyl malonate (product of step 1 from Example 87 preparation, 1.5 g, 5.28 mmoles) in 11 mL of dry THF was treated with NaH (0.12 g, 4.95 mmoles) under a stream of argon. The mixture was stirred at room temperature for 30 min at which time a homogenous mixture was obtained and the gas evolution ceased. A solution of 2-bromo-4-(4-iodophenyl)-acetophenone from step 2 (1.85g, 4.61 mmoles) in 20 mL of dry THF was added and the reaction mixture was allowed to stir at room temperature for 4 hrs, at which time a TLC analysis showed complete reaction. The mixture was then quenched with 2N HCl, diluted with EtOAc, and the layers were separated. The aqueous layer was extracted twice with EtOAc and the combined Extracts were washed with brine, dried over MgSO₄, and the solvent removed at reduced pressure. The crude product was chromatographed with a gradient 3%–40% EtOAc in hexanes to afford 2.28 g (83% yield) of pure product.

TLC (silica, EtOAc:hexanes, 1:4) $R_f$=0.37; $^{1}$H NMR (CDCl₃) δ 8.03 (d, J=9 Hz, 2H), 7.81 (d, J=8.4 Hz, 2H), 7.65 (d, J=8.7 Hz, 2H), 7.36 (d, J=8.4 Hz, 2H), 7.10–7.24 (m, 5H), 4.20 (q, J=7.2 Hz, 4H), 3.70 (s, 2H), 2.60 (t, J=7.6 Hz, 2H), 2.16–2.22 (m, 2H), 1.54–1.59 (m, 2H), 1.23 (t, J=7.2 Hz, 6H); $^{13}$C NMR (CDCl₃) δ 196.12, 170.88, 144.78, 141.65, 139.27, 138.08, 135.62, 129.00, 128.73, 128.28, 126.98, 125.84, 124.63, 119.57, 94.33, 61.51, 55.37, 41.28, 35.85, 32.70, 26.63, 13.97.

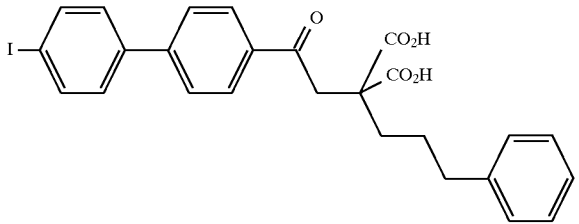

Step 4

A solution of the diethylester from step 3 (2.28 g, 3.81 mmoles) in THF (5 mL)/EtOH (15 mL) was treated with 5 eq of NaOH in 5 mL of water and allowed to stir at room temperature overnight. At this time, the reaction mixture was acidified with 2N HCl and the solvent removed at reduced pressure. The solid formed was then filtered, washed with water, and dried to afford 1.6 g (77 %) of pure product.

TLC (silica, CH₂Cl₂:MeOH, 9:1) $R_f$=0.14; $^{1}$H NMR (DMSO-d₆) δ 8.01 (d, J=7.8 Hz, 2H), 7.78–7.86 (m, 4H), 7.54 (d, J=8.4 Hz, 2H), 7.08–7.23 (m, 5H), 3.61 (s, 2H), 2.51 (t, J=7.5 Hz, 2H), 1.92–1.98 (m, 2H), 1.45–1.55 (m, 2H); $^{13}$C NMR (DMSO-d₆) δ 196.90, 172.65, 143.72, 141.85, 138.50, 138.07, 135.73, 129.32, 128.41, 126.96, 125.91, 95.37, 54.64, 41.43, 35.47, 32.93, 26.43.

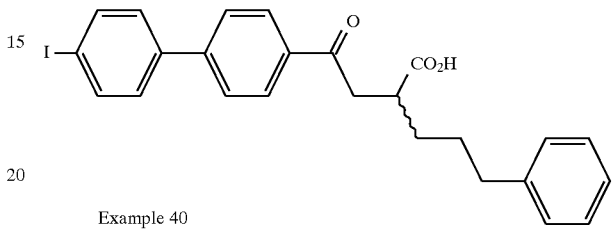

Example 40

Step 5 —Preparation of Example 40.

The diacid from step 4 (1.6 g, 2.95 mmoles) was dissolved in 30 mL of 1,4-dioxane and refluxed for 36 hrs. The reaction mixture was then cooled to room temperature and the solvent removed at reduced pressure. The residue obtained was crystallized from EtOAc/hexanes to afford 0.6 g (41% yield).

MP. 165°–165.5° C.; TLC (silica, CH₂Cl₂: MeOH, 9:1) $R_f$=0.41; $^{1}$H NMR (CDCl₃—CD₃OD) δ 7.96 (d, J=9 Hz, 2H), 7.74 (d, J=8.4 Hz, 2H), 7.57 (d, J=8.7 Hz, 2H), 7.29 (d, J=8.4 Hz, 2H), 7.08–7.24 (m, 5H), 3.42 (m, 1H), 2.95–3.06 (m, 2H), 2.57–2.64 (m, 2H), 1.57–1.78 (m, 4H); $^{13}$C NMR (CDCl₃—CD₃OD) δ 198.24, 177.71, 144.60, 141.81, 139.13, 137.93, 135.48, 128.86, 128.62, 128.23, 128.18, 126.85, 125.66, 94.14, 40.26, 39.94, 35.48, 31.46, 28.76; MS (FAB-LSIMS) 498.9 [M+H]⁺ (C₂₅H₂₃IO₃, FW=498.365); HRMS for C₂₅H₂₄IO₃ calcd. 499.07702; found 499.07782; Anal. C: calcd, 60.25; found, 60.23. H: calcd, 4.65; found, 4.63.

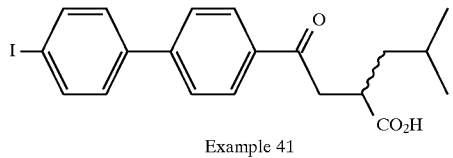

Example 41

Example 41

This compound was prepared in a similar manner to Example 40, except that the diethyl, isobutyl malonate was used instead of diethyl-(3-phenyl)propyl malonate.

TLC (methylene chloride—10% methanol) $R_f$ 0.54; $^{1}$H NMR (CDCl₃) δ 8.04 (d, J=8.2 Hz, 2H), 7.81 (d, J =8.2 Hz, 2H), 7.64 (d, J =7,9 Hz, 2H), 7.36 (d, J=8.5 Hz, 2H), 3.46 (dd, J₁=17.1 Hz, J₂=8.5 Hz, 1H), 3.19–3.11 (m, 1H), 1.76–1.65 (m, 2H), 1.49–1.36 (m, 1H), 0.99 (d, J=5.9 Hz, 3H), 0.93 (d, J=5.9 Hz, 3H); 13C NMR (CDCl₃) δ 197.51, 181.34, 144.70, 139.27, 138.05, 135.50, 128.99, 5 128.73, 126.98, 94.30, 41.08, 40.62, 38.29, 25.85, 22.49, 22.30; MS (FAB-LSIMS) 437 [M+H]⁺; HRMS (FAB) calcd. for C₂₀H₂₂IO₃ [M+H]⁺ 437.06137, found 481.06052; Elemental Analysis calcd. C 55.06, H 4.85; found C 54.90, H 4.79.

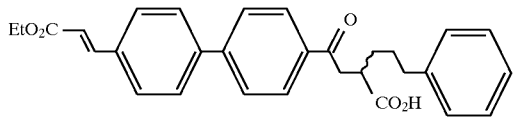

Example 42

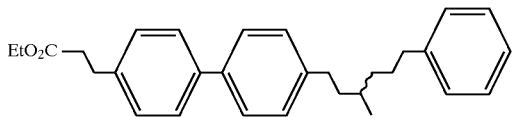

Example 44

Example 42

Example 40 (300 mg, 0.60 mmole) was dissolved in DMF (3 mL) and treated with ethyl acrylate (0.15 mL, 1.38 mmoles), Pd(OAc)2 (15 mg, 0.07 mmole), sodium bicarbonate (126 mg, 1.50 mmoles), and tetrabutylammonium chloride (69 mg, 0.24 mmole). The mixture was refluxed for 3 days at which time it was diluted with ethyl acetate and transferred to a separatory funnel. The organic layer was washed with water, brine, dried over $MgSO_4$, and the solvent removed at reduced pressure. The crude product was chromatographed with 0–4% methanol in methylene chloride to afford 120 mg of product.

MP 155°–157° C.; TLC (methylene chloride —5% methanol) $R_f$ 0.24; $^1H$ NMR ($CDCl_3$) δ 8.04 (d, J=8.3 Hz, 2H), 7.76–7.58 (m, 7H), 7.31–7.16 (m, 5H), 6.50 (d, J=16.09 Hz, 1H), 4.29 (q, J=6.9 Hz, 2H), 3.49 (dd, $J_1$=16.7 Hz, $J_2$=8.0 Hz, 1H), 3.17–3.05 (m, 2H), 2.67 (t, J=7.2 Hz, 2H), 1.86–1.66 (m, 4H), 1.36 (t, J=7.2 Hz, 3H); $^{13}C$ NMR ($CDCl_3$) δ 197.49, 179.63, 166.92, 144.86, 143.73, 141.78, 141.41, 135.51, 134.41, 128.74, 128.65, 128.39, 128.36, 127.69, 127.16, 125.87, 118.78, 60.61, 40.23, 39.81, 35.62, 31.44, 28.89, 14.31; MS (FAB-LSIMS) 471 [M+H]$^+$.

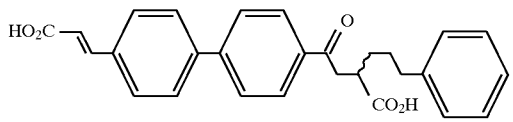

Example 42

Example 43

A suspension of Example 42 (28 mg, 0.06 mmole) in ethanol (1.5 mL) was treated with a solution of NaOH (14 mg, 0.35 mmole) in water (0.3 mL) and the mixture was stirred at room temperature overnight. At this time, it was quenched with 2N HCl and extracted with methylene chloride (2×10 mL). The combined extracts were washed with brine, dried over $MgSO_4$, and the solvent removed at reduced pressure to afford 23 mg (87%) of product.

MP 230°–232° C.; TLC (methylene chloride - 5% methanol) $R_f$ 0.05; $^1H$ NMR ($CDCl_3/DMSO-d_6$) δ 7.87 (d, J=8.3 Hz, 2H), 7.57–7.45 (m, 7H), 7.13–7.00 (m, 5H), 6.32 (d, J=15.8 Hz, 1H), 3.33 (dd, $J_1$17.9 Hz, $J_2$=9.2 Hz, 1H), 2.92–2.84 (m, 2H), 2.51–2.46 (m, 2H), 1.65–1.49 (m, 4H); $^{13}C$ NMR ($CDCl_3/DMSO-d_6$) δ 197.38, 176.79, 168.12, 144.12, 143.20, 141.62, 140.81, 135.38, 134.04, 128.26, 128.20, 127.95, 127.84, 127.21, 126.63, 125.30, 119.04, 40.05, 39.75, 35.25, 31.25, 28.58; MS (FAB-LSIMS) 443 [M+H]$^+$.

Example 44

A solution of Example 42 (60 mg, 0.13 mmole) in ethanol (2 mL) was treated with 10% Pd on C (10 mg) and the mixture was stirred at room temperature overnight under hydrogen gas balloon. At this time, the reaction mixture was filtered through celite and the solvent was removed at reduced pressure to afford 43 mg of product as oil.

TLC (methylene chloride—5% methanol) $R_f$ 0.33; $^1H$ NMR ($CDCl_3$) δ 7.53–7.48 (m, 4H), 7.30–7.15 (m, 9H), 4.15 (q, J=6.9 Hz, 2H), 2.99 (t, J=8.0 Hz, 2H), 2.72–2.59 (m, 6H), 2.51–2.45 (m, 1H), 2.10 1.95 (m, 1H), 1.83–1.58 (m, 5H), 1.25 (t, J=6.9 Hz, 3H); $^{13}C$ NMR ($CDCl_3$) δ 180.63, 172.95, 141.92, 140.40, 139.45, 138.98, 138.68, 128.83, 128.70, 128.36, 128.32, 127.03, 126.97, 125.82, 60.45, 44.51, 35.88, 35.67, 33.70, 33.14, 31.68, 30.57, 28.95, 14.21; M S (FAB-LSIMS) 458 [M]$^+$.

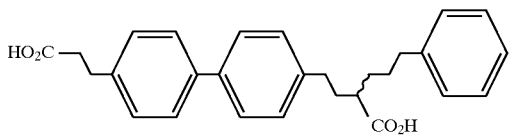

Example 45

Example 45

A suspension of Example 44 (15 mg, 0.03 mmole) in ethanol (1 mL) was treated with a solution of sodium hydroxide (9 mg, 0.23 mmole) in water (0.2 mL) and allowed to stir at room temperature for 1.5 days. The reaction mixture was then quenched with 2N HCl, diluted with ethyl acetate and the layers were separated. The organic layer was washed with brine, dried over $MgSO_4$, and the solvent was removed at reduced pressure to afford 12 mg of product. MP 131°–132° C.; $^1H$ NMR ($CDCl_3$) δ 7.52 (d, J=8.0 Hz, 2H), 7.48 (d, J=7.7 Hz, 2H), 7.30–7.15 (m, 9H), 2.87 (t, J=7.7 Hz, 2H), 2.78–2.40 (m, 7H), 2.10–1.98 (m, 1H), 1.91–1.81 (m, 1H), 1.78–1.53 (m, 4H); $^{13}C$ NMR ($CDCl_3$) δ 181.97, 178.53, 141.92, 140.07, 138.97, 138.92, 138.45, 129.10, 128.58, 128.36, 128.32, 126.95, 126.69, 125.82, 45.02, 35.66, 35.04, 33.62, 33.49, 31.94, 29.99, 28.95; MS (FAB-LSIMS) 430 [M]$^+$.

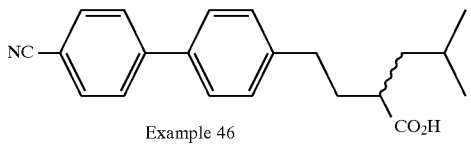

Example 46

Example 46

Example 41 (50 mg, 0.12 mmoles), Cu(I)CN (36 mg, 0.40 mmoles), and 0.7 mL of 1-methyl-2-pyrrolidinone were mixed and heated at 125° C. for 24 hr. The reaction mixture was diluted with methylene chloride and evaporated at reduced pressure. The crude product was then chromatographed with 0–8% methanol in methylene chloride on the MPLC to afford 26.5 mg (66% yield) of product.

TLC (methylene chloride —10% methanol) $R_f$ 0.48; $^1$H NMR (CDCl$_3$/CD$_3$OD) δ 8.06 (d, J=8.2 Hz, 2H), 7.65–7.76 (m, 6H), 3.45 (dd, J$_1$=17.0 Hz, J$_2$=7.9 Hz, 1H), 3.04–3.10 (m, 2H), 1.64–1.75 (m,2H), 1.38–1.42 (m, 1H), 0.96 (d, J=5.9 Hz, 3H), 0.91 (d, J=6.2 Hz, 3H); $^{13}$C NMR (CDCl$_3$/CD$_3$OD) δ 197.96, 178.20, 144.20, 143.49, 136.29, 132.64, 128.74, 127.81, 127.34, 118.52, 111.63, 53.34, 41.16, 40.82, 25.79, 22.36, 22.24; MS (FAB-LSIMS) 336 [M+H]$^+$; HRMS (FAB) calcd. for C$_{21}$H$_{22}$NO$_3$S [M+H]$^+$ 336.15997, Found 336.16129.

Example 47

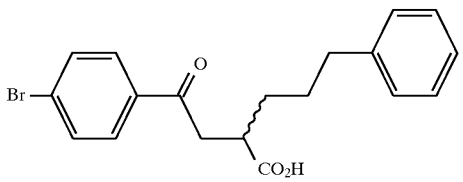

Step 1

This intermediate was prepared in a similar manner to Example 40 except 2,4'-dibromoacetophenone was used instead of 2-bromo-4-(4-iodophenyl)acetophenone. TLC (methylene chloride—10% methanol) $R_f$ 0.52;

$^1$H NMR (CDCl$_3$) δ 7.82 (d, J=8.8 Hz, 2H), 7.61 (d, J=8.5 Hz, 2H), 7.31–7.16 (m, 5H), 3.41 (dd, J$_1$=17.1 Hz, J$_2$=8.5 Hz, 1H), 3.15–3.06 (m, 1H), 2.99 (dd, J$_1$=17.1 Hz, J$_2$=4.4 Hz, 1H), 2.66 (t, J=7.4 Hz, 2H), 1.83–1.63 (m, 4H); $^{13}$C NMR (CDCl$_3$) δ 196.90, 181.13, 141.66, 135.09, 131.89, 129.52, 128.47, 128.34, 125.85, 39.94, 39.89, 35.54, 31.33, 28.79.

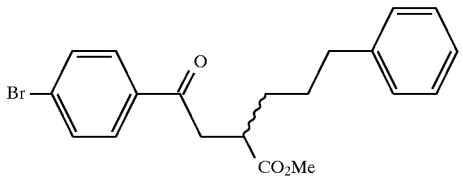

Step 2

Methylation of the product from step 1 with diazomethane in ethanol afforded quantitative yield of the methyl ester. T L C (hexanes, 10% ethyl acetate) $R_f$ 0.21;

$^1$H NMR (CDCl$_3$) δ 7.82 (d, J=8.5 Hz, 2H), 7.61 (d, J=8.2 Hz, 2H), 7.32–7.16 (m, 5H), 3.70 (s, 3H), 3.43 (dd, J$_1$=16.8 Hz, J$_2$=8.5 Hz, 1H), 3.13–3.05 (m, 1H), 3.98 (dd, J$_1$=17.1 Hz, J$_2$=4.4 Hz, 1H), 2.65 (t, J=7.1 Hz, 2H), 1.80–1.59 (m, 4H); $^{13}$C NMR (CDCl$_3$) δ 197.15, 175.82, 141.79, 135.25, 131.89, 129.54, 128.41, 128.34, 125.87, 51.84, 40.37, 40.07, 35.59, 31.68, 28.91.

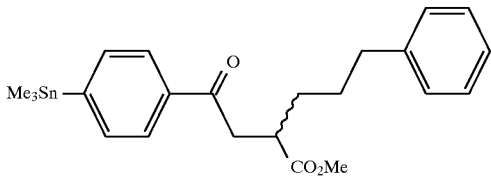

Step 3

The product from step 2 (1.85 g, 4.75 mmoles), hexamethylditin (2.00 g, 5.80 mmoles), and palladium tetrakistriphenylphosphine (44 mg, 0.038 mmoles) in 7 mL of toluene were refluxed for 3 hr under argon. TLC showed complete reaction. The reaction mixture was then cooled to room temperature, the solvent was removed at reduced pressure, and the residue was chromatographed on the MPLC with 3–30% ethyl acetate in hexanes to afford 2.25 g (100% yield) of the trimethyltin product.

TLC (hexanes—10% ethyl acetate) $R_f$ 0.26; $^1$H NMR (CDCl$_3$) δ 7.77 (d, J=7.9 Hz, 2H), 7.49 (d, J=7.9 Hz, 2H), 7.21–7.05 (m, 5H), 3.33 (dd, J$_1$=16.2, J$_2$=7.4 Hz, 1H), 3.01–2.89 (m, 2H), 2.56–2.51 (m, 2H), 1.66–1.47 (m, 4H), 0.22 (s, 9H); $^{13}$C NMR (CDCl$_3$) δ 197.15, 175.97, 150.37, 141.87, 136.17, 135.98, 128.34, 128.31, 126.89, 125.81, 51.76, 40.42, 40.13, 35.59, 31.73, 28.94, −9.58.

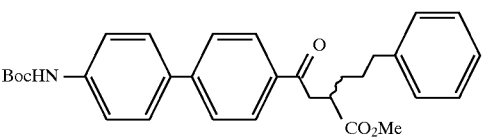

Step 4

4-Bromo-N-Boc-aniline (0.61 g, 2.24 mmoles), the product from step 3 (0.51 g, 1.08 mmoles), and palladium tetrakistriphenyl-phosphine (94 mg, 0.08 mmoles) in 9 mL of toluene were refluxed for 3 hr under argon. After TLC showed complete reaction, the reaction mixture was filtered, concentrated at reduced pressure, and chromatographed with 3–60% ethyl acetate in hexanes to afford 180 mg of product (33% yield) as the methyl ester.

TLC (hexanes—20% ethyl acetate) $R_f$ 0.26; $^1$H NMR (CDCl$_3$) δ 8.00 (d, J=8.2 Hz, 2H), 7.65 (d, J=8.2 Hz, 2H), 7.58 (d, J=8.2 Hz, 2H), 7.47 (d, J=8.5 Hz, 2H), 7.32–7.16 (m, 5H), 3.71 (s, 3H), 3.52–3.43 (m, 1H), 3.14–3.03 (m, 2H), 2.66 (t, J=7.1 Hz, 2H), 1.78–1.60 (m, 4H), 1.55 (s, 9H).

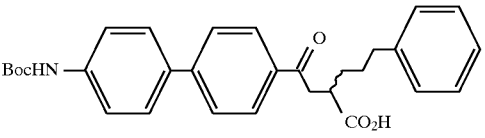

Example 47

Step 5 —Preparation of Example 47

The methyl ester (93 mg) was dissolved in 3 mL of ethanol and treated with 5 eq of sodium hydroxide in 0.5 mL of H$_2$O. The mixture was stirred at room temperature for 10 hr at which time TLC showed complete hydrolysis of the methyl ester. The reaction mixture was acidified with 2N HCl, diluted with ethyl acetate, and the layers were separated. The organic layer was washed with brine, dried over MgSO$_4$, and the solvent removed at reduced pressure to afford 82 mg of product.

MP 169°–171° C.; TLC (methylene chloride—4% methanol) $R_f$ 0.24; $^1$H NMR (CDCl$_3$/DMSO-d$_6$) δ 7.92 (d, J=8.2 Hz, 2H), 7.88 (s, 1H), 7.57 (d, J=8.2 Hz, 2H), 7.48 (broad s, 3H), 7.21–7.07 (m, 5H), 3.40 (dd, J$_1$=18.5 Hz, J$_2$=9.7 Hz, 1H), 3.01–2.92 (m, 2H), 2.60–2.51 (m, 2H), 1.72–1.58 (m, 4H), 1.48 (m, 9H); $^{13}$C NMR (CDCl$_3$/DMSO-d$_6$) δ 197.46, 176.94, 152.66, 144.86, 141.70, 139.06, 134.59, 133.28, 128.26, 128.02, 127.90, 127.18, 126.16, 125.35, 118.49, 40.07, 39.84, 35.33, 31.35, 28.65, 28.05; MS (FAB-LSIMS) 488 [M+H]$^+$; Elemental Analysis calcd. for C$_{30}$H$_{33}$NO$_5$ C 73.90, H 6.82, N 2.87; Elemental Analysis found. C 73.55, H 6.89, N 2.61.

Example 48, Example 49, Example 50, Example 51, Example 52, Example 53, Example 54, Example 55 and Example 56

These compounds were prepared in a similar manner to Example 47, except that the indicated bromides were used instead of 4-bromo-Boc-aniline in step 4:

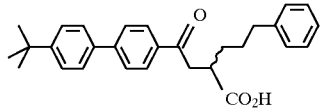

Example 48

Example 48

From 1-Bromo-t-butyl benzene: MP 124°–125° C.; TLC (methylene chloride—10% methanol) $R_f$ 0.48; $^1$H NMR (CDCl$_3$) δ 7.94 (d, J=8.2 Hz, 2H), 7.61 (d, J =8.2 Hz, 2H), 7.51 (d, J=8.2 Hz, 2H), 7.42 (d, J=8.2 Hz, 2H), 7.23–7.09 (m, 5H), 3.41 (dd, J$_1$=17.1 Hz, J$_2$=8.2 Hz, 1H), 3.11–2.99 (m, 2H), 2.59 (t, J=7.1 Hz, 2H), 1.78–1.58 (m, 4H), 1.30 (s, 9H); $^{13}$C NMR (CDCl$_3$) δ 197.61, 179.83, 151.50, 145.86, 141.81, 136.85, 134.88, 128.63, 128.37, 128.34, 127.02, 126.90, 125.92, 125.84, 40.18, 39.85, 35.62, 34.62, 31.44, 31.28, 28.91; MS (FAB-LSIMS) 429 [M+H]$^+$; HRMS (FAB) calcd. for C$_{29}$H$_{33}$O$_3$ [M+H]$^+$ 429.24297, Found 429.24094.

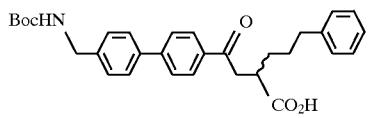

Example 49

Example 49

From 4-bromo-N-Boc-benzylamine: MP 156° C.; TLC (hexanes—50% ethyl acetate) $R_f$ 0.24; $^1$H NMR (CDCl$_3$) δ 8.03 (d, J=6.5 Hz, 2H), 7.67 (d, J=6.5 Hz, 2H), 7.60 (d, J=5.9 Hz, 2H), 7.40 (d, J=5.3 Hz, 2H), 7.32–7.19 (m, 5H), 4.95 (broad s, 1H), 4.40 (broad s, 2H), 3.49 (dd, J$_1$=17.3 Hz, J$_2$=7.9 Hz, 1H), 3.20–3.08 (m, 2H), 2.69 (t, J=5.2 Hz, 2H), 1.86–1.69 (m, 4H), 1.50 (s, 9H); MS (FAB-LSIMS) 502 [M+H]$^+$; HRMS (FAB) calcd. for C$_{31}$H$_{36}$NO$_5$ [M+H]$^+$ 502.25935, Found 502.25906; Elemental Analysis calcd. C 74.23, H 7.03, N 2.79; found. C 73.93, H 7.10, N 2.55.

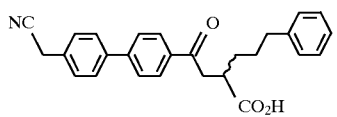

Example 50

Example 50

From 4-bromophenyl acetonitrile: MP 139°–140° C.; TLC (hexanes—70% ethyl acetate) $R_f$ 0.42; $^1$H NMR (CDCl$_3$/DMSO-d$_6$) δ 7.98 (d, J=8.2 Hz, 2H), 7.60 (d, J=8.2 Hz, 2H), 7.58 (d, J=7.9 Hz, 2H), 7.38 (d, J=7.9 Hz, 2H), 7.23–7.08 (m, 5H), 3.77 (s, 2H), 3.43 (dd, J$_1$=16.2 Hz, J$_2$=7.1 Hz, 1H), 3.07–2.94 (m, 2H), 2.64–2.57 (m, 2H), 1.79–1.58 (m, 4H);$^{13}$C NMR (CDCl$_3$/DMSO-d$_6$) δ 197.62, 177.18, 144.41, 141.84, 139.50, 135.54, 129.75, 128.49, 128.36, 128.18, 128.07, 127.71, 126.90, 125.53, 119.41, 40.27, 39.95, 35.49, 31.47, 28.79, 23.11; MS (FAB-LSIMS) 412 [M+H]$^+$; HRMS (FAB) calcd. for C$_{27}$H$_{26}$NO$_3$ [M+H]$^+$ 412.19127, Found 412.18979; Elemental Analysis calcd. C 78.81, H 6.12, N 3.40; found. C 78.45, H 6.14, N 3.22.

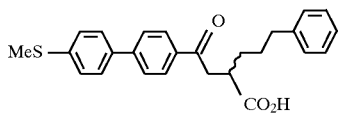

Example 51

Example 51

From 4-bromothioanisole: MP 174.5°–175° C.; TLC (hexanes—50% ethyl acetate) $R_f$ 0.32; $^1$H NMR (CDCl$_3$/DMSO-d$_6$) δ 7.62 (d, J=7.9 Hz, 2H), 7.28 (d, J=7.9 Hz, 2H), 7.18 (d, J=7.9 Hz, 2H), 6.94 (d, J=7.9 Hz, 2H), 6.89–6.74 (m, 5H), 3.07 (dd, J$_1$=17.9 Hz, J$_2$=9.7 Hz, 1H), 2.67–2.61 (m, 2H), 2.30–2.23 (m, 2H), 2.13 (s, 3H), 1.40–1.23 (m, 4H); $^{13}$C NMR (CDCl$_3$/DMSO-d$_6$) δ 196.72, 176.03, 143.76, 141.00, 138.17, 135.03, 134.28, 127.66, 127.37, 127.29, 126.47, 125.66, 125.55, 124.76, 39.42, 39.15, 34.64, 30.63, 28.02, 14.37; MS (FAB-LSIMS) 419 [M+H]$^+$; HRMS (FAB) calcd. for C$_{26}$H$_{27}$SO$_3$ [M+H]$^+$ 419.16809, Found 419.16895; Elemental Analysis calcd. for C$_{26}$H$_{26}$SO$_3$·0.25H$_2$O C 73.81, H 6.31; found C 73.51, H 6.23.

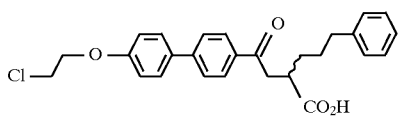

Example 52

Example 52

From 4-bromophenyl-2-chloroethyl ether: MP 155°–156° C.; TLC (hexanes—50% ethyl acetate) $R_f$ 0.12; $^1$H NMR (CDCl$_3$/DMSO-d$_6$) δ 7.90 (d, J=8.2 Hz, 2H), 7.54 (d, J=8.2 Hz, 2H), 7.49 (d, J=8.8 Hz, 2H), 7.19–6.89 (m, 7H), 4.20 (t, J=5.9 Hz, 2H), 3.76 (t, J=5.9 Hz, 2H), 3.38 (dd, J$_1$=18.8 Hz, J$_2$=8.8 Hz, 1H), 2.99–2.89 (m, 2H), 2.57–2.52 (m, 2H), 1.73–1.54 (m, 4H); $^{13}$C NMR (CDCl$_3$/DMSO-d$_6$) δ 197.54, 177.06, 158.20, 144.78, 141.79, 134.74, 132.62, 128.37, 128.16, 128.12, 128.00, 126.32, 125.45, 114.87, 67.83, 41.68, 40.16, 39.90, 35.43, 31.43, 28.74; MS (FAB-LSIMS) 451 [M+H]$^+$; HRMS (FAB) calcd. for C$_{27}$H$_{28}$ClO$_4$ [M+H]$^+$ 451.16761, Found 451.16565; Elemental Analysis calcd. for C$_{27}$H$_{27}$ClO$_4$·0.25H$_2$O C 781.20, H 5.98; found. C 71.21, H 6.10.

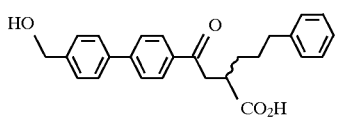

Example 53

Example 53

From 4-bromobenzyl alcohol: MP 165°–166° C.; TLC (hexanes—70% ethyl acetate) $R_f$ 0.21; $^1$H NMR (CDCl$_3$/DMSO-d$_6$) δ 7.83 (d, J=7.9 Hz, 2H), 7.49 (d, J=8.2 Hz, 2H), 7.42 (d, J=7.6 Hz, 2H), 7.30 (d, J=8.2 Hz, 2H), 7.10–6.97 (m, 5H), 4.51 (s, 2H), 3.28 (dd, J$_1$=17.9 Hz, J$_2$=7.9 Hz, 1H), 2.88–2.80 (m, 2H), 2.49–2.43 (m, 2H), 1.62–1.48 (m, 4H);

$^{13}$C NMR (CDCl$_3$/DMSO-d$_6$) δ 197.59, 177.01, 145.19, 141.78, 138.24, 135.09, 128.34, 128.11, 127.98, 127.12, 126.86, 126.71, 125.44, 63.84, 40.06, 39.80, 35.41, 31.40, 28.74; M S (FAB-LSIMS) 403 [M+H]$^+$; HRMS (FAB) calcd. for C$_{26}$H$_{27}$O$_4$ [M+H]$^+$ 403.19093, Found 403.19165.

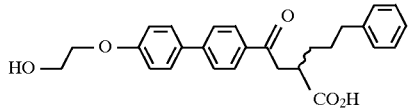

Example 54

Example 54

From 2-(4-bromophenoxy)ethanol: M P 167°–168° C.; T L C (methylene chloride—6% methanol) R$_f$ 0.25; $^1$H NMR (CDCl$_3$/DMSO-d$_6$) δ 7.80 (d, J=8.5 Hz, 2H), 7.44 (d, J=8.2 Hz, 2H), 7.38 (d, J=8.2 Hz, 2H), 7.09–6.82 (m, 5H), 3.93 (t, J=4.7 Hz, 2H), 3.75 (t, J=4.7 Hz, 2H), 3.28 (dd, J$_1$=J$_2$=9.7 Hz, 1H), 2.89–2.79 (m, 2H), 2.47–2.42 (m, 2H), 1.62–1.433 (m, 4H); $^{13}$C NMR (CDCl$_3$/DMSO-d$_6$) δ 197.28, 176.73, 158.77, 144.67, 141.54, 134.33, 131.60, 128.11, 127.86, 127.76, 125.97, 125.21, 114.56, 69.12, 60.16, 39.66, 35.17, 31.17, 28.50; MS (FAB-LSIMS) 433 [M+H]$^+$; HRMS (FAB) calcd. for C$_{27}$H$_{29}$O$_5$ [M+H]$^+$ 433.20150, Found 433.20145.

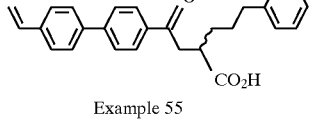

Example 55

Example 55

From 4-bromostyrene: MP 156°–157° C.; TLC (methylene chloride—10% methanol R$_f$ 0.47; $^1$H NMR (CDCl$_3$/DMSO-d$_6$) δ 7.88 (d, J=7.6 Hz, 2H), 7.54 (d, J=7.9 Hz, 2H), 7.46 (d, J=7.9 Hz, 2H), 7.37 (d, J=8.2 Hz, 2H), 7.14–6.99 (m, 5H), 6.61 (dd, J$_1$=17.3 Hz, J$_2$=10.5 Hz, 1H), 5.68 (d, J=17.3 Hz, 1H), 5.17 (d, J=10.9 Hz, 1H), 3.33 (dd, J$_1$=18.8 Hz, J$_2$=9.7 Hz, 1H), 2.92–2.85 (m, 2H), 2.55–2.48 (m, 2H), 1.67–1.49 (m, 4H); $^{13}$C NMR (CDCl$_3$/MSO-d$_6$) δ 197.43, 176.85, 144.67, 141.65, 138.61, 137.09, 135.74, 135.06, 128.24, 127.99, 127.87, 126.92, 126.50, 126.39, 125.34, 114.21, 40.07, 39.79, 35.30, 31.30, 28.62; MS (FAB-LSIMS) 433 [M+H]$^+$; Elemental Analysis calcd. for C$_{27}$H$_{26}$O$_3$·0.5 H$_2$O C 79.58, H 6.68; found C 79.72, H 6.66.

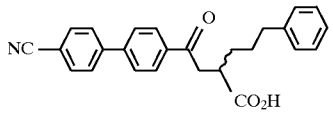

Example 56

Example 56

From 4-bromobenzonitrile: MP 199°–200° C. (dec.); TLC (hexanes—50% ethyl acetate) R$_f$ 0.25; $^1$H NMR (CDCl$_3$/DMSO-d$_6$) δ 7.77 (d, J=7.9 Hz, 2H), 7.51–7.40 (m, 6H), 6.99–6.86 (m, 5H), 3.20 (dd, J$_1$=18.5 Hz, J$_2$=9.7 Hz, 1H), 2.78–2.71 (m, 2H), 2.37–2.33 (m, 2H), 1.52–1.40 (m, 4H); $^{13}$C NMR (CDCl$_3$/DMSO-d$_6$) δ 197.03, 176.34, 143.47, 142.63, 141.26, 135.75, 131.99, 128.29, 127.65, 127.29, 126.69, 125.03, 117.94, 110.90, 39.79, 34.93, 30.91, 28.28; M S (FAB-LSIMS) 398 [M+H]$^+$; HRMS (FAB) calcd. for C$_{26}$H$_{24}$NO$_3$ [M+H]$^+$ 398.17562, Found 398.17703.

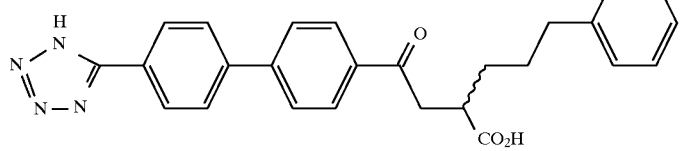

Example 57

Example 57

The methyl ester of Example 56 (81 mg, 0.2 mmole, from treatment of an ethanol solution of Example 56 with diazomethane followed by solvent evaporation in vucuo) was dissolved in 1 mL of toluene and treated with trimethyltin azide (62 mg, 0.3 mmole). The reaction mixture was refluxed for 5 days. At this time, the reaction mixture was cooled to room temperature, diluted with ethyl acetate, washed with brine and dried over MgSO$_4$. The crude product was chromatographed with 0–20% methanol in methylene chloride to afford 56 mg of the methyl ester tetrazole product. The methyl ester product was suspended in ethanol and treated with 2N NaOH solution (0.5 mL) and stirred at room temperature for 3 hrs. The reaction mixture was then quenched with 2N HCl, diluted with ethyl acetate, and the layers were separated. The organic layer was washed with brine and dried over MgSO$_4$ to afford 34 mg of Example 57 crystallized from ethyl acetate/hexanes.

Example 57

MP 176°–177° C.; TLC (methylene chloride—10% methanol) R$_f$0.11; $^1$H NMR (CDCl$_3$/CD$_3$OD) δ 8.10 (d, J=8.2 Hz, 2H), 8.01 (d, J=8.5 Hz, 2H), 7.74 (d, J=8.2 Hz, 2H), 7.68 (d, J=8.5 Hz, 2H), 7.25–7.11 (m, 5H), 3.46 (dd, J$_1$=18.5 Hz, J$_2$=9.9 Hz, 1H), 3.09–2.98 (m, 2H), 2.61–2.59 (m, 2H), 1.79–1.61 (m, 4H); $^{13}$C NMR (CDCl$_3$/CD$_3$OD) δ 198.17, 177.69, 144.36, 142.36, 141.83, 135.79, 128.66, 128.26, 128.21, 127.94, 127.61, 127.16, 125.71, 124.13, 40.36, 39.98, 35.56, 31.54, 28.84; MS (FAB-LSIMS) 441 [M+H]$^+$; Elemental Analysis calcd. for C$_{26}$H$_{24}$N$_4$O$_3$ C 70.89, H 5.49, N 12.72; Elemental Analysis found. C 70.81, H 5.44, N 12.41.

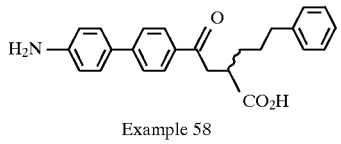

Example 58

Example 58

Example 47 (46 mg, 0.094 mmole) was dissolved in 1.5 mL of methylene chloride and treated with trifluoroacetic acid (0.16 mL, 2.06 mmoles). The mixture was stirred at room temperature for 32 hr, when TLC showed complete reaction. The solvent was removed at reduced pressure and the solid obtained was washed with ethyl acetate/hexanes to afford 40 mg of product as TFA salt.

MP 170°–174° C. (dec.); TLC (hexanes—70% ethyl acetate) $R_f$ 0.44; $^1$H NMR (CDCl$_3$/DMSO-d$_6$) δ 7.78 (d, J=7.9 Hz, 2H), 7.41 (d, J=7.9 Hz, 2H), 7.30 (m, 3H), 7.08–6.93 (m, 4H), 6.74 (d, J=8.2 Hz, 2H), 3.26 (dd, J$_1$=18.5 Hz, J$_2$=9.7 Hz, 1H), 2.86–2.79 (m, 2H), 2.46–2.38 (m, 2H), 1.56–1.44 (m, 4H); $^{13}$C NMR (CDCl$_3$/DMSO-d$_6$) δ 197.15, 176.64, 144.75, 143.36, 141.45, 134.02, 130.75, 128.05, 127.79, 127.69, 127.52, 125.55, 125.14, 116.68, 39.79, 39.61, 35.09, 31.10, 28.44; MS (FAB-LSIMS) 388 [M+H]$^+$; Elemental Analysis calcd. for C$_{25}$H$_{25}$NO$_3$·TFA C 64.67, H 5.23, N 2.79; found. C 64.66, H 5.23, N 2.61.

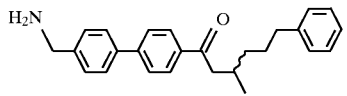

Example 59

Example 59

This compound was prepared in a similar manner to that of Example 58, except Example 49 was used instead of Example 47.

MP 146°–148° C.; TLC (methylene chloride—10% methanol) $R_f$ 0.10; $^1$H NMR (CDCl$_3$/DMSO-d$_6$) δ 8.44 (broad s, 2H), 7.75 (d, J=8.5 Hz, 2H), 7.38 (d, J=7.6 Hz, 2H), 7.40 (d, J=8.2 Hz, 2H), 7.29 (d, J=8.2 Hz, 2H), 7.02–6.82 (m, 5H), 3.85 (s, 2H), 3.20 (dd, J$_1$=18.5 Hz, J$_2$=9.7 Hz, 1H), 2.79–2.72 (m, 2H), 2.39–2.34 (m, 2H), 1.54–1.36 (m, 4H); $^{13}$C NMR (CDCl$_3$/DMSO-d$_6$) δ 197.20, 176.48, 143.91, 141.29, 139.35, 134.98, 132.85, 129.02, 127.99, 127.66, 127.58, 126.85, 126.35, 125.05, 42.16, 34.95, 30.94, 30.70, 28.29; MS (FAB-LSIMS) 402 [M+H]$^+$; HRMS (FAB) calcd. for C$_{26}$H$_{28}$NO$_3$ [M+H]$^+$ 402.20692, Found 402.20807.

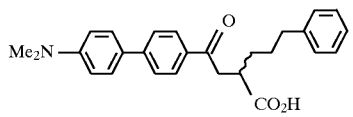

Example 60

Example 60

The methyl ester of Example 58 (50 mg, 0.13 mmoles) in methanol/tetrahydrofuran (0.7 mL / 0.4 mL) was treated with 37% aqueous formaldehyde (0.11 mL, 1.46 mmoles), glacial acetic acid (0.032 mL), and sodium cyanoborohydride (0.32 mL, 1.0M in THF, 0.32 mmoles). The reaction mixture was stirred at room temperature for 2 hr at which time the solvent was removed at reduced pressure and saturated potassium carbonate was added to the residue. Ethyl acetate was added to the mixture and the layers were separated. The aqueous layers was extracted with ethyl acetate and the combined extracts were washed with brine, dried over MgSO$_4$, and the solvent removed at reduced pressure to afford 47 mg (88% yield) of the methyl ester product.

TLC (hexanes—20% ethyl acetate) $R_f$ 0.35; $^1$H NMR (CDCl$_3$) δ 7.90 (d, J=8.5 Hz, 2H), 7.57 (d, J=8.2 Hz, 2H), 7.49 (d, J=8.8 Hz, 2H), 7.25–7.09 (m, 5H), 6.74 (d, J=8.5 Hz, 2H), 3.63 (s, 3H), 3.44–3.34 (m, 1H), 3.08–2.93 (m, 8H), 2.58 (t, J=7.1 Hz, 2H), 1.72–1.51 (m, 4H).

The methyl ester product (47 mg, 0.11 mmoles) was suspended in ethanol (2 mL) and treated with 10 eq of sodium hydroxide in H$_2$O (1 mL). The mixture was stirred at room temperature for 16 hr at which time TLC showed complete reaction. The ethanol was then removed at reduced pressure, the residue was diluted with ethyl acetate, and the mixture was acidified with 2N HCl. At this time, the layers were separated and the organic portion was washed with brine, dried over MgSO$_4$, and the solvent removed at reduced pressure to afford 48 mg (96% yield) of product as the hydrochloride salt.

Example 60

MP 166°–168° C.; TLC (methylene chloride—5% methanol) $R_f$ 0.14; $^1$H NMR (CDCl$_3$/DMSO-d$_6$) δ 7.92 (d, J=8.2 Hz, 2H), 7.59 (broad s, 4H), 7.53 (d, J=8.5 Hz, 2H), 7.18–7.05 (m, 5H), 3.38 (m, 1H), 3.08 (s, 6H), 2.98–2.88 (m, 2H), 2.56–2.52 (m, 2H), 1.67–1.58 (m, 4H); $^{13}$C NMR (CDCl$_3$/DMSO-d$_6$) δ 197.45, 176.92, 141.71, 128.58, 128.45, 128.05, 127.95, 126.69, 125.42, 119.35, 40.16, 39.84, 35.38, 35.25, 331.36, 28.70; MS (FAB-LSIMS) 416 [M+H]$^+$; HRMS (FAB) calcd. for C$_{27}$H$_{30}$NO$_3$ [M+H]$^+$ 416.22257, Found 416.22296.

Example 61

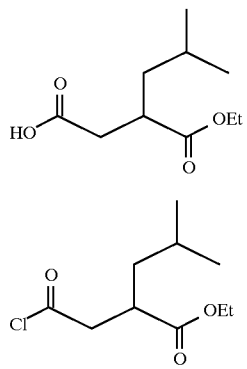

Step 1, 2 and 3

A three neck 2 L flask equipped with a mechanical stirrer was charged, under argon atmosphere, with a potassium tert-butoxide/tert-butanol solution ( 800 mL, 1.0M) and brought to reflux. Isobutyraldehyde ( 66.2 mL, 729 mmol) and diethyl succinate (151 mL, 907 mmol) were combined and added dropwise over 0.5 hours. The reaction solution was refluxed an additional 1.5 hours and cooled to ambient temperature. The solution was diluted with ethyl acetate (800 mL) and washed with 2N hydrochloric acid solution (500 mL). The ethyl acetate solution was separated and washed with 10% sodium carbonate solution (6×200 mL). The basic washings were combined and acidified with concentrated hydrochloric acid. Extraction of product was accomplished with ethyl acetate (5×250 mL). The washings were combined, dried over magnesium sulfate, and concentrated. A portion of this material was immediately hydrogenated with palladium on carbon using Parr apparatus. This afforded 90.18 grams of the desired acid ester compound shown above. This was then converted to the corresponding ester acid chloride by refluxing with oxalyl chloride (1 eq.)

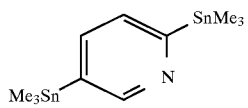

Step 4

A solution of trimethylsilyl tin chloride (21.8 G, 109.5 mmol) in freshly distilled dimethoxyethane (50 mL) was added to a suspension of sodium (7.6 G, 330 mL), naphthalene (200 mg, 1.56 mmol), and dimethoxyethane under argon atmosphere cooled to −20° C. After 2.5 hours, the suspension had turned to a dark green color. The solution was then decanted from excess sodium . A solution of 1,4 dibromopyridine (10 G, 42.2 mmol) and dimethoxyethane was added over 0.3 hours at 0° C. under argon. The solution was slowly warmed to ambient temperature, the poured into 500 mL water. The solution was washed with dichloromethane (4×250 mL) and the extracts were combined and dried over magnesium sulfate. Concentration afforded a brownish solid that was recrystallized from acetonitrile to afford 13.8 G of 1,4 bis-trimethylsilyl tin pyridine.

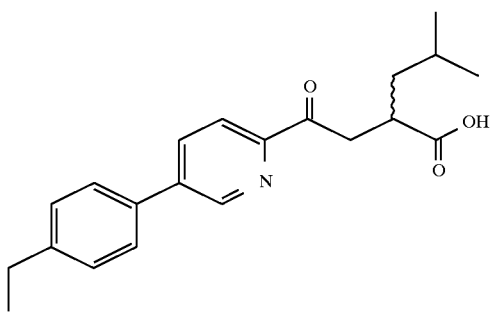

Example 61

Steps 5, 6 and 7 —Preparation of Example 61

Potassium carbonate (100 mg) was suspended in a solution of the acid chloride from step 3 (1.91 G, 9.6 mmol), the product of step 4 (3.9 G, 9.6 mmol) and toluene (50 mL). This was then refluxed 48 hours before being cooled to ambient temperature and diluted with ethyl acetate. Solids were filtered off and solvent removed. The remaining oil was chromatographed on silica with an ethyl acetate/hexane eluent. The resulting material was coupled to p-iodo ethyl benzene (1 eq.) by refluxing in a solution of tetrahydrofuran in the presence of bis-(triphenylphosphine) palladium (II) chloride (20 mole %). The coupled product was chromatographed on silica with ethyl acetate/ hexane and saponified by addition of sodium hydroxide to an aqueous/ ethanol solution. Acidification to pH 5 afforded a yellow solid which was filtered off and recrystallized from ethyl acetate/hexane. This afforded 53 mg of Example 61.

Example 61

MP 111°–112° C.; TLC (50% ethyl acetate/hexane) TLC $R_f$=0.44 $^1$H NMR (CDCl$_3$) δ 8.90(s, 1H); 8.12 (d, J=0.55 Hz, 1H); 8.02 (d, J=7.16 Hz, 1H); 7.56 (d, J=6.61 Hz, 2H); 7.35 (d, J=7.99 Hz, 2H); 3.69 (dd, J=18.74 Hz and 9.37 Hz, 1H); 3.40 (dd, J=18.46 Hz and 4.41 Hz, 1H); 3.17 (m, 1H); 2.75 (q, J=7.72 Hz, 2H); 1.75 (m, 2H); 1.48 (m, 1H); 1.30 (t, J=7.71 Hz, 3H); 0.99 (d, J=6.34 Hz, 3H); 0.93 (d, J=6.34 Hz, 3H); 13C NMR (CDCl$_3$) δ 200.04, 182.10, 151.97, 147.87, 146.03, 140.72, 135.48, 134.80, 129.49, 127.92, 122.70, 120.25, 41.77, 40.65, 38.96, 29.25, 26.47, 23.11, 23.05, 16.15; MS (FAB-LSIMS) 340 [M+H]$^+$, (C$_{21}$ H$_{25}$NO$_3$, FW=339.44).

Example 62, Example 63 and Example 64

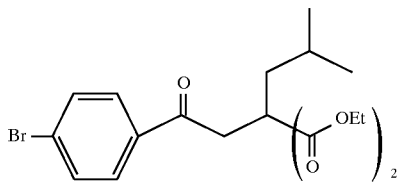

Step 1 (A)

A one-necked, 50-mL, round-bottomed flask equipped with a rubber septum and an argon needle inlet was charged with 7 mL THF, sodium hydride (0.058 g, 2.42 mmol) and cooled to 0° C. while diethyl isobutylmalonate (0.476 g, 0.491 mL, 2.20 mmol) was added dropwise via syringe over ca. 2 min. The resulting mixture was stirred for 30 min at 0° C. and 1 h at room temperature. The reaction mixture was then cooled to 0° C. while a solution of 2,4'-dibromoacetophenone (0.556 g, 2.00 mmol in 3 mL THF) was added dropwise via cannula over ca. 1 min. The resulting mixture was stirred for 30 min at 0° C. and 13 h at room temperature. A mixture of water (30 mL) and hexanes (50 mL) was added and the resulting aqueous phase was extracted with a second 20-mL portion of hexanes. The combined organic phases were dried over MgSO$_4$, filtered, and concentrated to provide a yellow oil. Column chromatography on 30 g of silica gel (gradient elution with 1–5% ethyl acetate-hexanes) afforded 0.53 g (64%) of product as a colorless oil:

TLC (5% ethyl acetate-hexanes) $R_f$=0.24; $^1$H NMR (CDCl$_3$, 300 MHz) δ 7.83 (d, J=8.8 Hz, 2H), 7.59 (d, J=8.5 Hz, 2H), 4.18 (q, J=7.0 Hz, 4H), 3.67 (s, 2H), 2.08 (d, J=6.3 Hz, 2H), 1.49–1.61 (m, 1H), 1.22 (t, J=7.0 Hz, 6H), and 0.83 (d, J=6.6 Hz, 6H); $^{13}$C NMR (CDCl$_3$, 75 MHz) δ 195.7, 171.2, 135.3, 131.9, 129.5, 128.5, 61.5, 55.0, 41.1, 41.0, 24.7, 23.6, and 13.9.

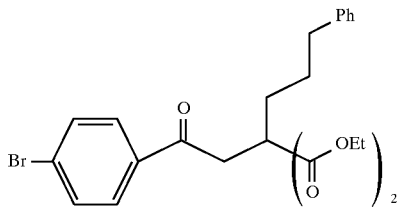

Step 1 (B)

Treatment of diethyl phenylpropylmalonate (1.00 g, 3.59 mmol) according to the general alkylation procedure of step 1 (A) afforded 1.11 g (71%) of product as a colorless oil:

TLC (10% ethyl acetate-hexanes) $R_f$=0.19; $^1$H NMR (CDCl$_3$, 300 MHz) δ 7.79 (d, J=8.8 Hz, 2H), 7.63 (d, J=8.8 Hz, 2H), 7.07–7.24 (m, 5H) 4.16 (q, J=7.0 Hz, 4H), 3.59 (s, 2H), 2.57 (br t, J=7.5 Hz, 2H), 2.11–2.16 (m, 2H), 1.49–1.54

(m, 4H), and 1.19 (t, J=7.0 Hz, 6H); $^{13}$C NMR (CDCl$_3$, 75 MHz) δ 195.7, 170.7, 141.6, 135.3, 131.9, 129.5, 128.3, 128.2, 125.9, 61.5, 55.3, 41.2, 35.8, 32.6, 26.6, and 13.9.

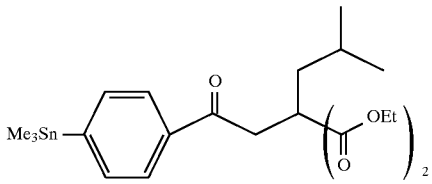

Step 2 (A)

A one-necked, 10-mL, round-bottomed flask equipped with a reflux condenser fitted with an argon inlet adapter was charged with 4 mL toluene, the product of step 1 (A) (0.100 g, 0.242 mmol), hexamethyl ditin (0.159 g, 0.484 mmol), tetrakis(triphenyl-phoshine)palladium (0.014 g, 0.0121 mmol), and heated at reflux for 24 h. The resulting mixture was concentrated to provide a black oil. Column chromatography on 15 g of silica gel (elution with 5% ethyl acetate-hexanes) afforded 0.107 g (89%) of Compound III as a colorless oil:

TLC (5% ethyl acetate-hexaries) R$_f$=0.33; $^1$H NMR (CDCl$_3$, 300 MHz) δ 7.90 (d, J=8.1 Hz, 2H), 7.59 (d, J=8.1 Hz, 2H), 4.18 (q, J=7.0 Hz, 4H), 3.72 (s, 2H), 2.10 (d, J=6.3 Hz, 2H), 1.51–1.60 (m, 1H), 1.22 (t, J=7.0 Hz, 6H), 0.83 (d, J=6.6 Hz, 6H), and 0.30 (s, 9H); $^{13}$C NMR (CDCl$_3$, 75 MHz) δ 197.0, 171.3, 150.5, 136.0, 126.8, 126.6, 61.4, 54.9, 41.1, 40.9, 24.7, 23.6, 13.9, and –9.6.

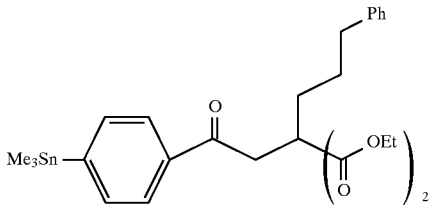

Step 2 (B)

Treatment of product from step 1 (B) (0.150 g, 0.316 mmol) according to the general procedure of step 2 (A) afforded 0.155 g (88%) of product as a colorless oil:

TLC (10% ethyl acetate-hexanes) R$_f$=0.19; $^1$H NMR (CDCl$_3$, 300 MHz) δ 7.86 (d, J=8.1 Hz, 2H), 7.56 (d, J=8.1 Hz, 2H), 7.07–7.24 (m, 5H) 4.16 (q, J=7.0 Hz, 4H), 3.64 (s, 2H), 2.56 (br t, J=7.7 Hz, 2H), 2.11–2.18 (m, 2H), 1.49–1.54 (m, 4H), 1.19 (t, J=7.0 Hz, 6H), and 0.30 (s, 9H); $^{13}$C NMR (CDCl$_3$, 75 MHz) δ 196.9, 170.9, 150.5, 141.7, 136.0, 135.8, 135.8, 128.3, 128.3, 125.8, 61.4, 55.3, 41.1, 35.9, 32.6, 26.6, 26.5, 14.0, and –9.6.

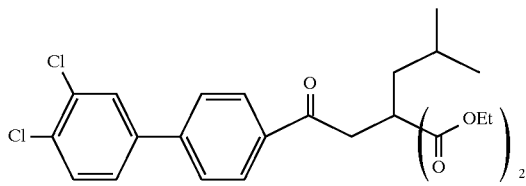

Step 3 (A)

A one-necked, 10-mL, round-bottomed flask equipped with a reflux condenser fitted with an argon inlet adapter was charged with 1 mL dimethoxyethane or toluene, the product of step 2 (A) (0.107 g, 0.215 mmol), 1-bromo-3,4-dichlorobenzene (0.097 g, 0.429 mmol), tetrakis(triphenylphosphine)palladium (0.025 g, 0.0216 mmol), and heated at reflux for 24 h. The resulting mixture was concentrated to provide a black oil. Column chromatography on 15 g of silica gel (elution with 5% ethyl acetate-hexanes) afforded 0.058 g (57%) of product as a white solid:

TLC (10% ethyl acetate-hexanes) R$_f$=0.26; $^1$H NMR (CDCl$_3$, 300 MHz) 8 8.04 (d, J=8.8 Hz, 2H), 7.68 (br s, 1H), 7.62 (d, J=8.8 Hz, 2H), 7.52 (d, J=8.5 Hz, 1H), 7.42 (d, J=8.5 Hz, 1H), 4.19 (q, J=7.0 Hz, 4H), 3.74 (s, 2H), 2.11 (d, J=6.6 Hz, 2H), 1.51–1.61 (m, 1H), 1.23 (t, J=7.0 Hz, 6H), and 0.85 (d, J=6.6 Hz, 6H); $^{13}$C NMR (CDCl$_3$, 75 MHz) δ 196.2, 171.3, 143.3, 139.8, 136.0, 133.2, 132.6, 130.9, 129.1, 128.8, 127.1, 126.5, 61.6, 55.0, 41.3, 41.1, 24.8, 23.7, and 14.0.

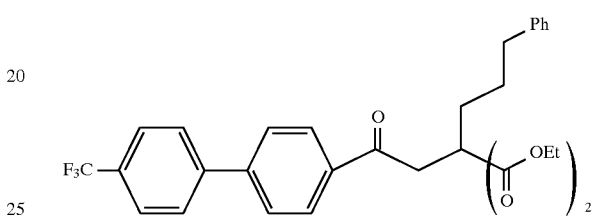

Step 3 (B)

Reaction of the product of step 2 (B) (0.079 g, 0.141 mmol) with 4-bromobenzotrifluoride in toluene according to the general coupling procedure of step 3 (A), afforded 0.069 g (91%) of product as a white solid:

TLC (10% ethyl acetate-hexanes) R$_f$=0.18; $^1$H NMR (CDCl$_3$, 300 MHz) δ 8.04 (d, J=8.5 Hz, 2H), 7.65–7.71 (m, 6H), 7.08–7.24 (m, 5H), 4.19 (q, J=7.0 Hz, 4H), 3.68 (s, 2H), 2.56 (br t, J=7.7 Hz, 2H), 2.15–2.20 (m, 2H), 1.49–1.58 (m, 4H), and 1.21 (t, J=7.0 Hz, 6H); $^{13}$C NMR (CDCl$_3$, 75 MHz) δ 196.1, 170.8, 144.3, 143.3, 141.6, 136.0, 130.4, 129.9, 128.7, 128.3, 127.4, 127.2, 125.9, 125.8, 122.3, 61.5, 55.4, 41.3, 35.8, 32.7, 26.6, and 13.9.

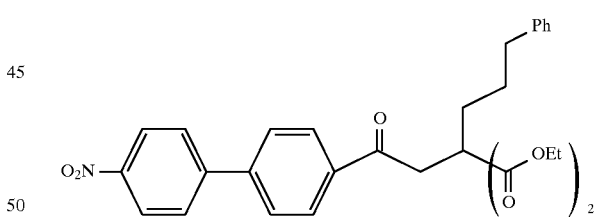

Step 3 (C)

Reaction of the product of step 2 (B) (0.058 g, 0.104 mmol) with 1-bromo-4-nitrobenzene in toluene according to the general coupling procedure of step 3 (A) afforded 0.042 g (78%) of product as a white solid:

TLC (10% ethyl acetate-hexanes) R$_f$=0.06; $^1$H NMR (CDCl$_3$, 300 MHz) δ 8.32 (d, J =8.7 Hz, 2H), 8.08 (d, J=8.5 Hz, 2H), 7.76 (d, J=8.5 Hz, 2H), 7.71 (d, J=8.7 Hz, 2H), 7.13–7.32 (m, 5H), 4.19 (q, J=7.0 Hz, 4H), 3.68 (s, 2H), 2.57 (br t, J=7.7 Hz, 2H), 2.12–2.21 (m, 2H), 1.49–1.62 (m, 4H), and 1.20 (t, J=7.0 Hz, 6H); $^{13}$C NMR (CDCl$_3$, 75 MHz) δ 196.0, 170.8, 147.6, 146.1, 143.3, 141.6, 136.5 128.8, 128.3, 128.1, 127.7, 127.6, 125.8, 124.2, 61.5, 55.4, 41.4, 35.8, 32.7, 26.6, and 14.0.

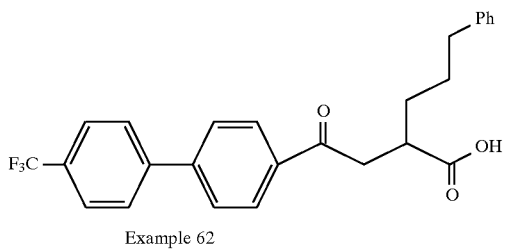

Example 62

Step 4 (B)—Preparation of Example 62

A one-necked, 10-mL, round-bottomed flask equipped with an argon inlet adapter was charged with 3 mL ethanol, product of step 3 (B) (0.069 g, 0.128 mmol), and 1 mL of an aqueous 25% sodium hydroxide solution. The resulting mixture was stirred for 10 h at room temperature. The reaction mixture was acidified with a 10% HCl solution, and extracted three times with 20-mL portions of ether. The organic phase was dried over $MgSO_4$, filtered, and concentrated to provide a yellow solid, which was dissolved in 2 mL of 1,4-dioxane and heated to reflux for 24 h in a one-necked, 10-mL, round-bottomed flask equipped with a reflux condenser fitted with an argon inlet adapter. The resulting mixture was concentrated to provide a yellow solid. Column chromatography on 10 g of silica gel (elution with 40% ethyl acetate-hexanes containing 1% acetic acid) afforded 0.033 g (59%) of Example 62 which was recrystallized once from ethyl acetate-hexanes to provide a white solid.

MP 165° C.; TLC (10% methanol-methylene chloride) $R_f$=0.50; HPLC (10% methanol-methylene chloride)$t_R$=7.6 min; $^1$H NMR (CDCl$_3$, 300 MHz) δ 8.04 (d, J=8.5 Hz, 2H), 7.65–7.71 (m, 6H), 7.14–7.29 (m, 5H), 3.47 (dd, J=8.1, 16.9 Hz, 1H), 3.03–3.16 (m, 2H), 2.65 (brt, J=7.0 Hz, 2H), and 1.66–1.80 (m, 4H); $^{13}$C NMR (CDCl$_3$, 75 MHz) δ 197.4, 180.8, 144.4, 143.3, 141.7, 135.9, 130.1, 128.8, 128.4, 128.3, 127.6, 127.5, 126.8, 125.9, 122.2, 40.2, 39.9, 35.6, 31.4, and 28.9; FAB-LCIMS: 441 [M+H]$^+$; HRMS: calcd. for $[C_{26}H_{23}F_3O_3+H]^+$: 441.16775; found: 441.16559.

Example 63

Step 4 (C)—Preparation of Example 63

Treatment of the product of step 3 (C) (0.042 g, 0.081 mmol) according to the general procedure of Example 62 afforded 0.023 g (68%) of Example 63 which was recrystallized once from ethyl acetate-hexanes to provide a white solid.

MP 183° C.; TLC (10% methanol-methylene chloride) $R_f$=0.50; HPLC (gradient elution 0.5–2.5% methanol-methylene chloride containing 0.1% TFA)$t_R$=13.7 min; $^1$H NMR (CDCl$_3$, 300 MHz) δ 8.32 (d, J=8.7 Hz, 2H), 8.07 (d, J=8.5 Hz, 2H), 7.76 (d, J=8.5 Hz, 2H), 7.69 (d, J=8.7 Hz, 2H), 7.13–7.32 (m, 5H), 3.47 (dd, J=8.1, 16.9 Hz, 1H), 3.01–3.12 (m, 2H), 2.64 (brt, J=7.0 Hz, 2H), and 1.66–1.80 (m, 4H); FAB-LCIMS: 418 [M+H]$^+$; HRMS: calcd. for $[C_{25}H_{23}NO_5+H]^+$: 418.16545; found: 418.16620.

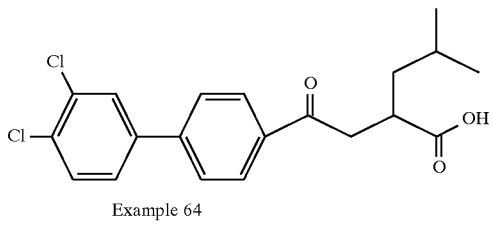

Example 64

Step 4 (A) - Preparation of Example 64

Treatment of the product of step 3 (A) (0.050 g, 0.104 mmol) according to the general procedure of Example 62 afforded 0.010 g (25%) of Example 64 which was recrystallized once from ethyl acetate-hexanes to provide a white solid.

MP 132° C. ; TLC (10% methanol-methylene chloride) $R_f$=0.49; HPLC (gradient elution 0.5–2.5% methanol-methylene chloride containing 0.1% TFA)$t_R$=12.7 min; $^1$H NMR (CDCl$_3$, 300 MHz) δ 8.02 (d, J=8.5 Hz, 2H), 7.68 (s, 1H), 7.61 (d, J=8.1 Hz, 2H), 7.52 (d, J=8.5 Hz, 2H), 7.42 (d, J=8.1 Hz, 2H), 3.43 (dd, J=8.1, 16.9 Hz, 1H), 3.03–3.16 (m, 2H), 1.63–1.73 (m, 2H), 1.38–1.43 (m, 1H), 0.97 (d, J=6.3 Hz, 3H), and 0.91 (d, J=6.3 Hz, 3H); FAB-LCIMS: 379 [M+H]$^+$; HRMS: calcd. for $[C_{20}H_{20}Cl_2O_3+H]^+$: 379.08678; found: 379.08682.

Example 65

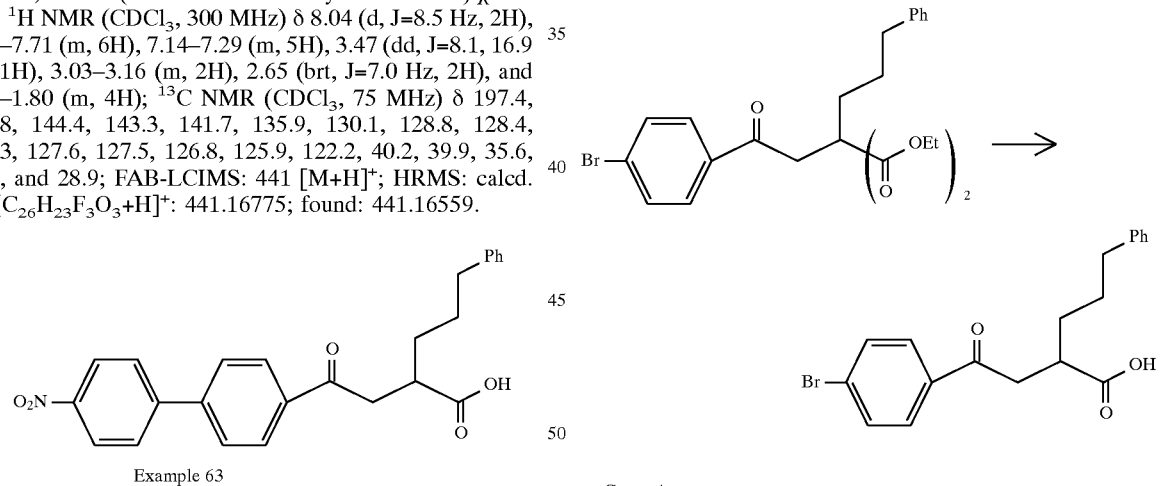

Step 1

Treatment of the product of step 1 (B) of the Example 62 preparation (13.34 g, 28.06 mmol) according to the general procedure of Example 62, step 4 (B) afforded 4.36 g (41%) of the above 4-bromophenyl intermediate which was recrystallized once from 1-chlorobutane to provide a white solid.

MP 147° C.; TLC (30% ethyl acetate-hexanes containing 1% acetic acid) $R_f$=0.29; $^1$H NMR (CDCl$_3$, 300 MHz) δ 7.79 (d, J=8.5 Hz, 2H), 7.58 (d, J=8.5 Hz, 2H), 7.14–7.28 (m, 5H), 3.38 (dd, J=8.8, 17.7 Hz, 1H), 3.06–3.10 (m, 1H), 2.97 (dd, J=4.4, 17.7 Hz, 1H), 2.63 (brt, J=7.0 Hz, 2H), and 1.61–1.81 (m, 4H); $^{13}$C NMR (CDCl$_3$, 75 MHz) δ 196.9, 180.8, 141.7, 135.1, 131.9, 129.6, 128.5, 128.4, 125.9, 40.0, 39.8, 35.6, 31.4, and 28.8.

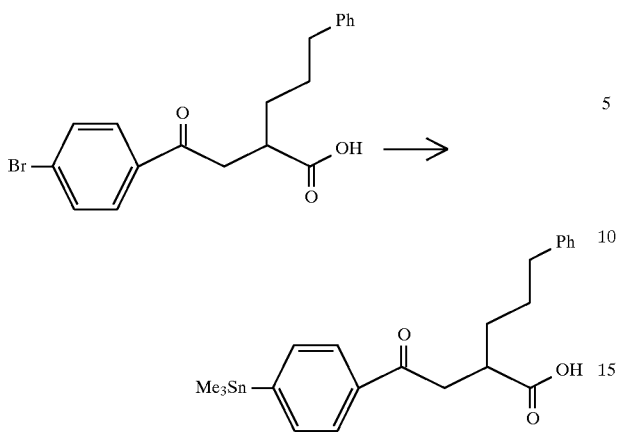

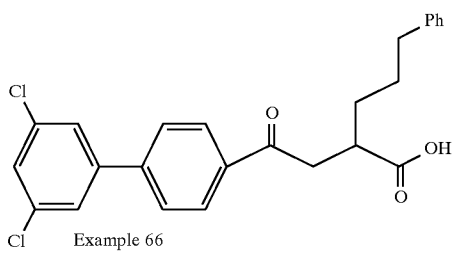

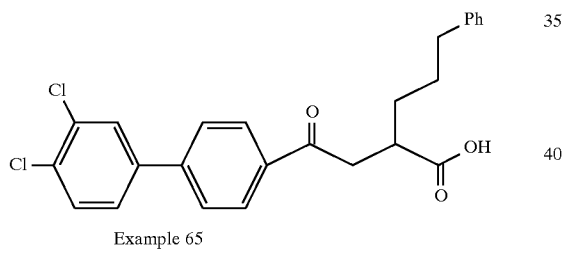

Step 2

Treatment of the 4-bromophenyl intermediate from step 1 (1.00 g, 2.66 mmol) in the presence of anhydrous $K_2CO_3$, according to the general procedure of step 2 (A) of the example 64 preparation afforded 0.706 g (58%) of the 4-trimethylstannylphenyl compound as a white solid:

TLC (30% ethyl acetate-hexanes containing 1% acetic acid) $R_f$=0.47; HPLC (gradient elution 0.5–2.5% methanol-methylene chloride containing 0.1% TFA)$t_R$=11.4 min; $^1$H NMR (CDCl$_3$, 300 MHz) δ 7.86 (d, J=8.1 Hz, 2H), 7.58 (d, J=8.1 Hz, 2H), 7.07–7.25 (m, 5H), 3.41 (dd, J=8.1, 17.1 Hz, 1H), 3.00–3.16 (m, 2H), 2.63 (brt, J=7.0 Hz, 2H), 1.66–1.80 (m, 4H), and 0.30 (s, 9H).

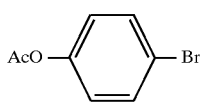

Example 65

Step 3 —Preparation of Example 65

A one-necked, 10-mL, round-bottomed flask equipped with a reflux condenser fitted with an argon inlet adapter was charged with 3 mL toluene, the product of step 2 (0.050 g, 0.108 mmol), 1-bromo-3,4-dichlorobenzene (0.049 g, 0.217 mmol), and tetrakis(triphenylphoshine)palladium (0.013 g, 0.0112 mmol). The resulting mixture was heated at reflux for 24 h, and then concentrated to provide a black oil. Column chromatography on 15 g of silica gel (elution with 20% ethyl acetate-hexanes containing 0.5% acetic acid) afforded 0.033 g (69%) of Example 65 which was recrystallized once from ethyl acetate-hexanes to provide a white solid.

M P 137° C.; TLC (elution with 30% ethyl acetate-hexanes containing 1% acetic acid) $R_f$=0.34; HPLC (gradient elution 0.5–2.5% methanol-methylene chloride containing 0.1% TFA)$t_R$=11.7 min;$^1$H NMR (CDCl$_3$, 300 MHz) δ 8.01 (d, J=8.1 Hz, 2H), 7.68 (br s, 1H), 7.61 (d, J=8.1 Hz, 2H), 7.52 (d, J=8.1 Hz, 2H), 7.42 (d, J=8.1 Hz, 2H), 7.13–7.32 (m, 5H), 3.46 (dd, J=8.1, 16.5 Hz, 1H), 3.03–3.15 (m, 2H), 2.65 (brt, J=7.0 Hz, 2H), and 1.66–1.80 (m, 4H).

Example 66

Reaction of the product of step 2 from example 65 (0.100 g, 0.218 mmol) with 1-bromo-3,5-dichlorobenzene in toluene according to the general coupling procedure of Example 65 afforded 0.044 g (46%) of Example 66 which was recrystallized once from 1-chlorobutane to provide a white solid.

M P 123° C.; TLC (elution with 30% ethyl acetate-hexanes containing 1% acetic acid) $R_f$=0.39; HPLC (elution 0.5% methanol-methylene chloride containing 0.01% TFA) $t_R$=11.0 min; $^1$H NMR (CDCl$_3$, 300 MHz) δ 8.01 (d, J=8.1 Hz, 2H), 7.60 (d, J=8.1 Hz, 2H), 7.46 (br s, 2H), 7.37 (br s, 1H), 7.42 (d, J=8.1 Hz, 2H), 7.15–7.29 (m, 5H), 3.46 (dd, J=8.1, 16.9 Hz, 1H), 3.02–3.14 (m, 2H), 2.65 (brt, J=7.0 Hz, 2H), and 1.66–1.82 (m, 4H); FAB-LCIMS: 442 [M+H]$^+$.

Example 67

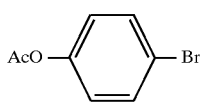

Step 1—Preparation of 1-Acetoxy-4-bromobenzene

A one-necked, 25-mL, round-bottomed flask equipped with an argon inlet adapter was charged with 5 mL pyridine, 4-bromophenol (1.00 g, 5.78 mmol), and acetic anhydride (2.80 g, 27.4 mmol). The resulting mixture was stirred for 12 h at room temperature. A mixture of water (20 mL) and ether (50 mL) was added and the resulting organic phase was washed with a second 20-mL portion of water. The organic phase was dried over MgSO$_4$, filtered, and concentrated to provide a colorless oil:

TLC (10% ethyl acetate-hexanes)$R_f$=0.54; $^1$H NMR (CDCl$_3$, 300 MHz) δ 7.35 (d, J=8.8 Hz, 2H), 6.88 (d, J=8.8 Hz, 2H), and 2.16 (s, 3H).

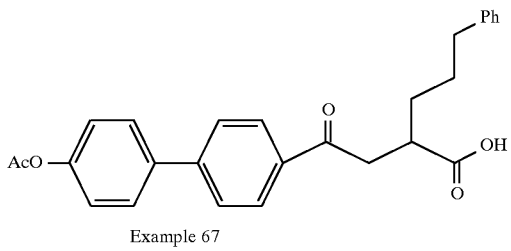

Example 67

Step 2—Preparation of Example 67

Reaction of the product of step 2 from example 65 (0.100 g, 0.218 mmol) with 1-acetoxy-4-bromobenzene in toluene according to the general coupling procedure of Example 65 afforded, after HPLC purification, 0.021 g (22%) of Example 67 as a solid. MP 131° C.; TLC (elution with 5% methanol-methylene chloride) $R_f$=0.35; $^1$H NMR (CDCl$_3$, 300 MHz) δ 8.00 (d, J=8.8 Hz, 2H), 7.63 (d, J=8.8 Hz, 2H), 7.60 (d, J=8.8 Hz, 2H), 7.13–7.29 (m, 7H), 3.46 (dd, J=8.1, 16.9 Hz, 1H), 3.03–3.13 (m, 2H), 2.64 (brt, J=7.0 Hz, 2H), 2.32 (s, 3H), and 1.65–1.78 (m, 4H); FAB-LCIMS: 431 [M+H]$^+$.

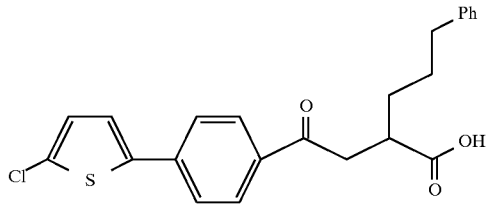

Example 68

Example 68

Reaction of the product of step 2 from example 65 (0.100 g, 0.218 mmol) with 2-bromo-5-chlorothiophene in toluene according to the general coupling procedure of Example 65 afforded, after HPLC purification, 0.016 g (18%) of Example 68 as a solid.

MP 120° C.; TLC (elution with 5% methanol-methylene chloride) $R_f$0.24; $^1$H NMR (CDCl$_3$, 300 MHz) δ 7.93 (d, J=8.5 Hz, 2H), 7.56 (d, J=8.5 Hz, 2H), 7.14–7.28 (m, 6H), 6.92 (d, J=3.7 Hz, 1H), 3.42 (dd, J=8.1, 16.9 Hz, 1H), 3.00–3.13 (m, 2H), 2.64 (brt, J=7.0 Hz, 2H), and 1.680–1.78 (m, 4H); FAB-LCIMS: 413 [M+H]$^+$.

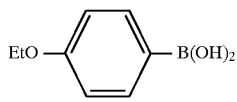

Preparation of 4-Ethoxybenzeneboronic Acid

A one-necked, 25-mL, round-bottomed flask equipped with a reflux condenser fitted with an argon inlet adapter was charged with magnesium powder (0.255 g, 10.5 mmol, −50 mesh), 7 mL THF, and 4-bromophenetol (1.41 g, 1.00 mL, 7.00 mmol). The resulting mixture was heated to reflux for 3 h. A second one-necked, 25-mL, round- bottomed flask equipped with a rubber septum and an argon inlet needle was charged with triisopropyl borate (3.95 g, 4.85 mL, 21.00 mmol) and cooled to −78° C. while the Grignard reagent prepared above was added dropwise via cannula over ca. 5 min. The cooling bath was removed and the reaction mixture was stirred for 3 h at room temperature. A mixture of ether (50 mL) and a 10% HCl solution (59 mL) was added and the resulting organic phase was washed with a 100-mL portion of water. The organic phase was dried over MgSO$_4$, filtered, and concentrated to provide a yellow solid which was recrystallized from ether-hexanes to provide 0.783 g (67%) of a white solid:

$^1$H NMR (CDCl$_3$, 300 MHz) δ 8.14 (d, J=8.5 Hz, 2H), 6.98 (d, J=8.5 Hz, 2H), 4.11 (q, J=7.0 Hz, 2H), and 1.45 (t, J=7.0 Hz, 3H).

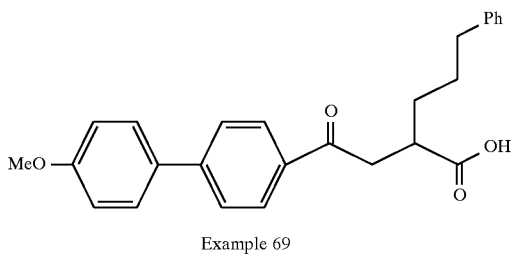

Example 69

Example 69

A one-necked, 100-mL, round-bottomed flask equipped with a reflux condenser fitted with an argon inlet adapter was charged with 30 mL toluene, the product of step 1 of the example 65 preparation (1.00 g, 2.66 mmol), 4-methoxybenzeneboronic acid (1.60 g, 10.5 mmol), sodium carbonate or potassium carbonate (1.60 g, 11.6 mmol) and tetrakis(triphenyl-phoshine)palladium (0.300 g, 0.260 mmol). The resulting mixture was heated at reflux for 12 h. After cooling to room temperature, 5 mL of 30% hydrogen peroxide solution was added and the resulting mixture stirred for 1 h. A mixture of ether (300 mL) and a 10% HCl solution (300 mL) was added and the resulting organic phase was washed with 300 mL of saturated sodium chloride solution. The organic phase was dried over MgSO$_4$, filtered, and concentrated to afford 0.879 g (82%) of Example 69 which was recrystallized once from 1-chlorobutane to provide a white solid.

MP 169° C.; TLC (elution with 2% methanol-methylene chloride) $R_f$=0.19; $^1$H NMR (CDCl$_3$, 300 MHz) δ 8.01 (d, J=8.5 Hz, 2H), 7.65 (d, J=8.5 Hz, 2H), 7.58 (d, J=8.8 Hz, 2H), 7.17–7.33 (m, 5H), 7.01 (d, J=8.8 Hz, 2H), 3.87 (s, 3H), 3.48 (dd, J=8.1, 16.5 Hz, 1H), 3.03–3.16 (m, 2H), 2.67 (brt, J=7.0 Hz, 2H), and 1.71–1.81 (m, 4H); FAB-LCIMS: 403 [M+H]$^+$.

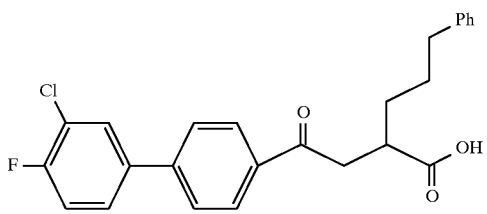

Example 70

Example 70

Reaction of the product of step 1 of the example 65 preparation (0.100 g, 0.266 mmol) with 3-chloro-4-fluorobenzeneboronic acid in toluene according to the general boronic acid coupling procedure of Example 69 afforded 0.036 g (32%) of Example 69 which was recrystallized once from 1-chlorobutane to provide a white solid. MP 141° C.; TLC (elution with 5% methanol-methylene chloride) $R_f$=0.27; HPLC (elution 0.5% methanol-methylene chloride containing 0.01% TFA)$t_R$=12.2 min; $^1$H NMR (CDCl$_3$, 300 MHz) δ 8.00 (d, J=8.1 Hz, 2H), 7.58–7.66 (m, 3H), 7.42–7.48 (m, 1H), 7.15–7.29 (m, 6H), 3.46 (dd, J=8.1, 16.5 Hz, 1H), 3.02–3.14 (m, 2H), 2.65 (brt, J=7.0 Hz, 2H), and 1.64–1.84 (m, 4H); FAB-LCIMS: 425 [M+H]$^+$.

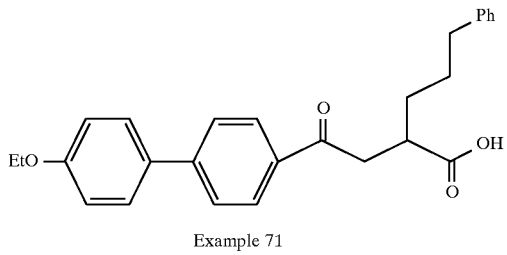

Example 71

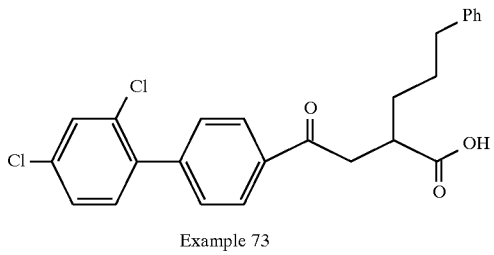

Example 73

Example 71

Reaction of the product of step 1 of the example 65 preparation (0.100 g, 0.266 mmol) with 4-ethoxybenzeneboronic acid in toluene according to the general boronic acid coupling procedure of Example 69 afforded 0.011 g (10%) of Example 71 which was recrystallized once from ethyl acetate-hexanes to provide a white solid.

MP 144° C.; TLC (elution with 5% methanol-methylene chloride) $R_f$=0.26; HPLC (elution 0.5% methanol-methylene chloride containing 0.01% TFA)$t_R$=14.5 min; $^1$H NMR (CDCl$_3$, 300 MHz) δ 7.98 (d, J=8.1 Hz, 2H), 7.62 (d, J=8.1 Hz, 2H), 7.55 (d, J=8.5 Hz, 2H), 7.15–7.26 (m, 5H), 6.99 (d, J=8.5 Hz, 2H), 4.07 (q, J=7.0 Hz, 2H), 3.45 (dd, J=8.1, 16.5 Hz, 1H), 3.06–3.13 (m, 2H), 2.64 (brt, J=7.0 Hz, 2H), 1.69–1.83 (m, 4H), and 1.43 (t, J=7.0 Hz, 3H).

Example 73

Reaction of the product of step 1 of the example 65 preparation (0.100 g, 0.266 mmol) with 2,4-dichlorobenzeneboronic acid in toluene according to the general boronic acid coupling procedure of Example 69 afforded, after HPLC purification, 0.031 g (26%) of Example 73 as a white solid.

MP 138° C.; TLC (elution with 5% methanol-methylene chloride) $R_f$=0.32; $^1$H NMR (CDCl$_3$, 300 MHz) δ 7.97 (d, J=8.8 Hz, 2H), 7.66 (d, J=8.8 Hz, 2H), 7.56–7.59 (m, 1H), 7.41–7.45 (m, 2H), 7.13–7.30 (m, 5H), 3.44 (dd, J=8.1, 16.5 Hz, 1H), 3.04–3.13 (m, 2H), 2.64 (brt, J=7.0 Hz, 2H), and 1.73–1.79 (m, 4H); $^{13}$C NMR (CDCl$_3$, 75 MHz) δ 197.5, 180.6, 143.2, 141.8, 135.7, 132.8, 131.8, 129.9, 129.7, 128.4, 128.1, 127.8, 127.3, 125.6, 40.2, 39.8, 35.6, 31.4, and 28.9; FAB-LCIMS: 441 [M+H]$^+$.

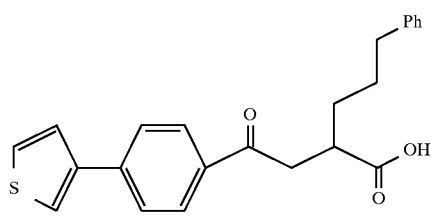

Example 72

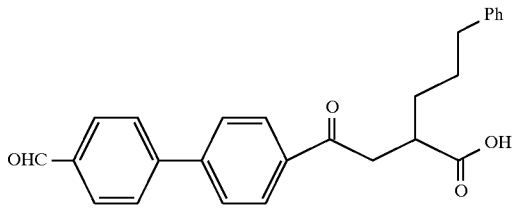

Example 74

Example 72

Reaction of the product of step 1 of the example 65 preparation (0.100 g, 0.266 mmol) with thiophene-3-boronic acid in toluene according to the general boronic acid coupling procedure of Example 69 and bypassing the hydrogen peroxide work-up afforded, after HPLC purification, 0.027 g (27%) of Example 72 as a solid.

MP 145° C.; TLC (elution with 5% methanol-methylene chloride) $R_f$=0.29; HPLC (elution 0.5% methanol-methylene chloride containing 0.01% TFA)$t_R$=13.7 min; $^1$H NMR (CDCl$_3$, 300 MHz) δ 7.97 (d, J=8.8 Hz, 2H), 7.66 (d, J=8.8 Hz, 2H), 7.56–7.59 (m, 1H), 7.41–7.45 (m, 2H), 7.13–7.30 (m, 5H), 3.44 (dd, J=8.1, 16.5 Hz, 1H), 3.04–3.13 (m, 2H), 2.64 (brt, J=7.0 Hz, 2H), and 1.73–1.79 (m, 4H); FAB-LCIMS: 379 [M+H]$^+$.

Example 74

Reaction of the product of step 1 of the example 65 preparation (0.100 g, 0.266 mmol) with 4-formylbenzeneboronic acid in toluene according to the general boronic acid coupling procedure of Example 69 afforded, after HPLC purification, 0.007 g (7%) of Example 74 as a white solid.

MP 174° C.; TLC (elution with 5% methanol-methylene chloride) $R_f$=0.26; $^1$H NMR (CDCl$_3$, 300 MHz) δ 10.06 (s, 1H), 8.05 (d, J=8.5 Hz, 2H), 7.97 (d, J=8.5 Hz, 2H), 7.77 (d, J=8.5 Hz, 2H), 7.71 (d, J=8.5 Hz, 2H), 7.14–7.30 (m, 5H), 3.48 (dd, J=8.1, 16.5 Hz, 1H), 3.07–3.13 (m, 2H), 2.65 (brt, J=7.0 Hz, 2H), and 1.69–1.83 (m, 4H).

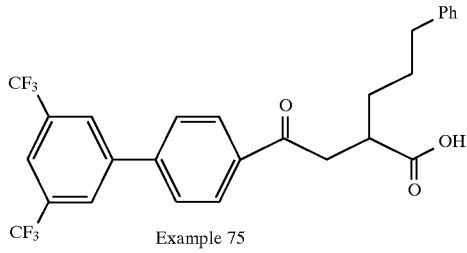

Example 75

Example 75

Reaction of the product of step 1 of the example 65 preparation (0.100 g, 0.266 mmol) with 3,5-bis (trifluoromethyl)benzene-boronic acid in toluene according to the general boronic acid coupling procedure of Example 69 using $Na_2CO_3$ afforded, after HPLC purification, 0.004 g (7%) of Example 75 as a white solid.

MP 145° C.; TLC (elution with 5% methanol-methylene chloride) $R_f$=0.35; HPLC (elution 0.5% methanol-methylene chloride containing 0.01% TFA)$t_R$=13.4 min; $^1$H NMR (CDCl$_3$, 300 MHz) δ 8.07 (d, J=8.8 Hz, 2H), 8.02 (s, 2H), 7.90 (s, 1H), 7.69 (d, J=8.8 Hz, 2H), 7.15–7.29 (m, 5H), 3.48 (dd, J=8.1, 16.5 Hz, 1H), 3.04–3.12 (m, 2H), 2.65 (brt, J=7.0 Hz, 4H), and 1.70–1.78 (m, 2H); FAB-LCIMS: 509 [M+H]$^+$.

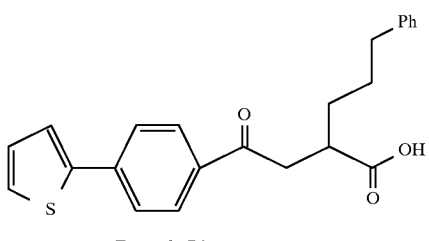

Example 76

Example 76

Reaction of the product of step 1 of the example 65 preparation (0.100 g, 0.266 mmol) with thiophene-2-boronic acid in toluene according to the general boronic acid coupling procedure of Example 69 using $Na_2CO_3$ and bypassing the hydrogen peroxide work-up afforded, after HPLC purification, 0.0015 g (2%) of Example 76 as a solid.

TLC (elution with 5% methanol-methylene chloride) $R_f$=0.27; $^1$H NMR (CDCl$_3$, 300 MHz) δ 7.94 (d, J=8.8 Hz, 2H), 7.67 (d, J=8.8 Hz, 2H), 7.41 (br d, J=3.7 Hz, 1H), 7.36 (br d, J=5.2 Hz, 1H), 7.09–7.28 (m, 6H), 3.43 (dd, J=8.1, 16.5 Hz, 1H), 3.03–3.12 (m, 2H), 2.64 (brt, J=7.0 Hz, 2H), and 1.69–1.78 (m, 4H).

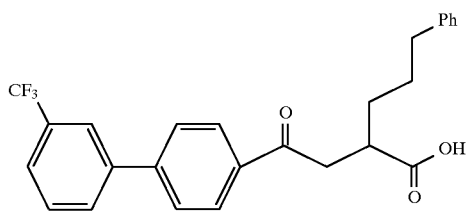

Example 77

Example 77

Reaction of the product of step 1 of the example 65 preparation (0.100 g, 0.266 mmol) with 3-trifluoromethylbenzeneboronic acid in toluene according to the general boronic acid coupling procedure of Example 69 using $Na_2CO_3$ afforded, after HPLC purification, 0.027 g (23%) of Example 77 as a white solid.

MP 118° C.; TLC (elution with 5% methanol-methylene chloride) $R_f$=0.17; HPLC (elution 0.5% methanol-methylene chloride containing 0.1% TFA)$t_R$=7.4 min; $^1$H NMR (CDCl$_3$, 300 MHz) δ 8.04 (d, J=8.5 Hz, 2H), 7.84 (s, 1H), 7.58–7.68 (m, 4H), 7.16–7.29 (m, 5H), 3.47 (dd, J=8.1, 16.5 Hz, 1H), 3.05–3.11 (m, 2H), 2.65 (brt, J=7.0 Hz, 2H), and 1.70–1.79 (m, 4H); FAB-LCIMS: 441 [M+H]$^+$.

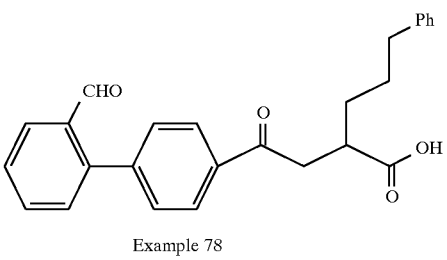

Example 78

Example 78

Reaction of the product of step 1 of the example 65 preparation (0.100 g, 0.266 mmol) with 2-formylbenzeneboronic acid in toluene according to the general boronic acid coupling procedure of Example 69 afforded, after HPLC purification, 0.003 g (3%) of Example 78 as a white solid.

TLC (elution with 5% methanol-methylene chloride) $R_f$=0.23; $^1$H NMR (CDCl$_3$, 300 MHz) δ 9.94 (s, 1H), 8.04 (d, J=8.5 Hz, 2H), 7.49–7.66 (m, 3H), 7.47 (d, J=8.5 Hz, 2H), 7.42 (d, J=8.1 Hz, 1H), 7.14–7.30 (m, 5H), 3.49 (dd, J=8.1, 16.5 Hz, 1H), 3.05–3.13 (m, 2H), 2.66 (brt, J=7.0 Hz, 2H), and 1.71–1.80 (m, 4H).

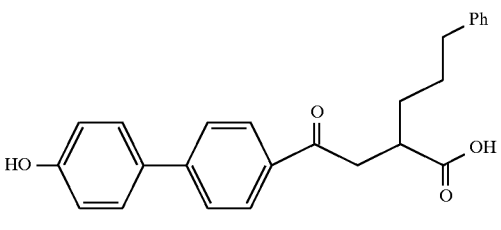

Example 79

Example 79

A one-necked, 100-mL, round-bottomed flask equipped with a reflux condenser was charged with 35 mL acetic acid, Example 69 (0.751 g, 1.86 mmol), and 20 mL 48% hydrobromic acid. The resulting mixture was heated at 90° C. for 12 h. After cooling to room temperature, 100 mL of ethyl acetate was added and the resulting mixture was washed twice with 100 mL of water, and once with 100 mL saturated sodium chloride solution. The organic phase was dried over MgSO$_4$, filtered, and concentrated to afford a brown solid. Column chromatography on 50 g of silica gel (5% methanol-methylene chloride) afforded 0.530 g (73%) of Example 69 as a white solid.

MP 189° C.; TLC (elution with 5% methanol-methylene chloride) $R_f$=0.28; HPLC (elution 0.5% methanol-methylene chloride containing 0.01% TFA)$t_R$=15.2 min; $^1$H NMR (DMSO-d$_6$, 300 MHz) δ 7.99 (d, J=8.5 Hz, 2H), 7.72

(d, J=8.5 Hz, 2H), 7.59 (d, J=8.5 Hz, 2H), 7.16–7.27 (m, 5H), 6.87 (d, J=8.5 Hz, 2H), 3.33 (dd, J=8.1, 16.5 Hz, 1H), 3.03–3.16 (m, 2H), 2.59 (brt, J=7.0 Hz, 2H), and 1.60–1.71 (m, 4H).

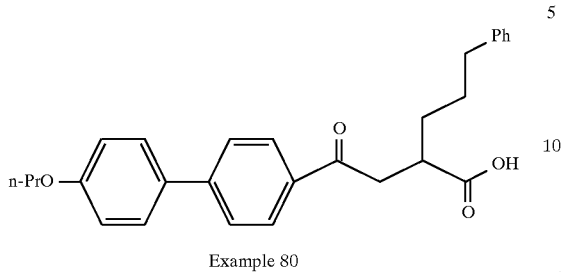

Example 80

Example 80

A one-necked, 10-mL, round-bottomed flask equipped with a rubber septum and an argon needle inlet was charged with 1 mL DMF and Example 79 (0.100 g, 0.257 mmol). Sodium hydride (0.014 g, 0.583 mmol) was added and the reaction mixture stirred 10 min at room temperature. 1-Iodopropane (0.130 g, 0.075 mL, 0.765 mmol) was added and the resulting mixture heated to 60° C. for 12 h. After cooling to room temperature, the reaction mixture was diluted with 50 mL of ethyl acetate, washed twice with 20 mL of water, and washed once with 20 mL saturated sodium chloride solution. The organic phase was dried over $MgSO_4$, filtered, and concentrated to afford an oil. A second, one-necked, 10-mL, round-bottomed flask equipped with a rubber septum and an argon needle inlet was charged with the above oil, 1 mL THF, 1 mL methanol, and 2 mL of a 1M sodium hydroxide solution. The resulting mixture was stirred 10 min at room temperature, dissolved in 20 mL ethyl acetate and washed twice with 20 mL of a 10% HCL solution. The organic phase was dried over $Mg_2SO_4$, filtered, and concentrated to afford, after HPLC purification, 0.014 g (13%) of Example 80 as a white solid.

MP 126° C.; TLC (elution with 5% methanol-methylene chloride) $R_f$=0.31; $^1$H NMR (CDCl$_3$, 300 MHz) δ 7.98 (d, J=8.5 Hz, 2H), 7.62 (d, J=8.5 Hz, 2H), 7.54 (d, J=8.8 Hz, 2H), 7.13–7.29 (m, 5H), 6.97 (d, J=8.8 Hz, 2H), 3.96 (t, J=6.6 Hz, 2H), 3.45 (dd, J=8.1, 16.5 Hz, 1H), 3.03–3.12 (m, 2H), 2.64 (brt, J=7.0 Hz, 2H), 1.67–1.86 (m, 6H), and 1.04 (t, J=7.4 Hz, 3H).

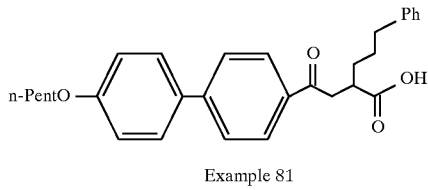

Example 81

Example 81

Reaction of Example 79 (0.100 g, 0.257 mmol) with 1-iodopentane according to the general alkylation procedure of Example 80 afforded, after HPLC purification, 0.024 g (20%) of Example 81 as a white solid:

MP 110° C.; TLC (elution with 5% methanol-methylene chloride) $R_f$=0.32; $^1$H NMR (CDCl$_3$, 300 MHz) δ 7.98 (d, J=8.5 Hz, 2H), 7.61 (d, J=8.5 Hz, 2H), 7.54 (d, J=8.8 Hz, 2H), 7.15–7.28 (m, 5H), 6.97 (d, J=8.8 Hz, 2H), 3.99 (t, J=6.6 Hz, 2H), 3.44 (dd, J=8.1, 16.5 Hz, 1H), 3.04–3.12 (m, 2H), 2.64 (brt, J=7.0 Hz, 2H), 1.69–1.83 (m, 6H), 1.37–1.47 (m, 4H), and 0.93 (t, J=7.0 Hz, 3H); FAB-LCIMS: 459 [M+H]$^+$.

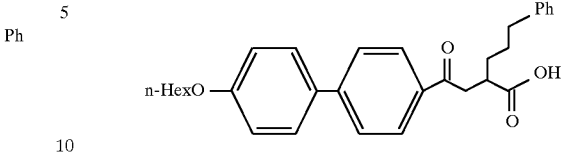

Example 82

Example 82

Reaction of Example 79 (0.079 g, 0.203 mmol) with 1-iodohexane according to the general alkylation procedure afforded, after radial chromatography on silica gel (methanol-methylene chloride), 0.055 g (58%) of Example 82 as a white solid.

MP 110° C.; TLC (elution with 5% methanol-methylene chloride) $R_f$=0.24; HPLC (elution 4% methanol-methylene chloride containing 0.01% TFA)$t_R$=5.4 min; $^1$H NMR (CDCl$_3$, 300 MHz) δ 7.98 (d, J=8.8 Hz, 2H), 7.62 (d, J=8.8 Hz, 2H), 7.54 (d, J=8.8 Hz, 2H), 7.15–7.30 (m, 5H), 6.97 (d, J=8.8 Hz, 2H), 3.99 (t, J=6.6 Hz, 2H), 3.45 (dd, J=8.1, 16.5 Hz, 1H), 3.07–3.13 (m, 2H), 2.65 (brt, J=7.0 Hz, 2H), 1.70–1.84 (m, 6H), 1.32–1.49 (m, 6H), and 0.89 (t, J=7.0 Hz, 3H); FAB-LCIMS: 473 [M+H]$^+$.

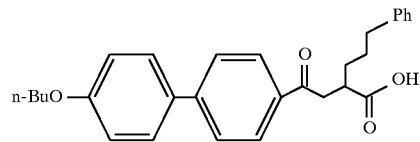

Example 83

Example 83

Reaction of Example 79 (0.100 g, 0.257 mmol) with 1-iodobutane according to the general alkylation procedure afforded, after HPLC purification, 0.054 g (47%) of Example 83 as a white solid.

MP 116° C.; TLC (elution with 30% ethyl acetate-hexanes containing 1% acetic acid) $R_f$=0.56; HPLC (elution 4% methanol-methylene chloride containing 0.01% TFA)$t_R$=6.3 min; $^1$H NMR (CDCl$_3$, 300 MHz) δ 7.98 (d, J=8.5 Hz, 2H), 7.62 (d, J=8.5 Hz, 2H), 7.54 (d, J=8.8 Hz, 2H), 7.15–7.30 (m, 5H), 6.97 (d, J=8.8 Hz, 2H), 4.00 (t, J=6.6 Hz, 2H), 3.44 (dd, J=8.1, 16.5 Hz, 1H), 3.04–3.12 (m, 2H), 2.65 (brt, J=7.0 Hz, 2H), 1.69–1.83 (m, 6H), 1.46–1.53 (m, 2H), and 0.97 (t, J=7.0 Hz, 3H); FAB-LCIMS: 445 [M+H]$^+$.

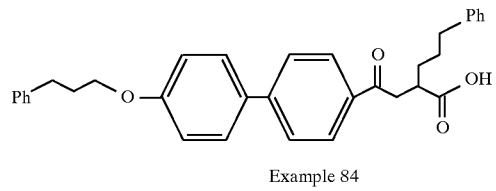

Example 84

Example 84

Reaction of Example 79 (0.102 g, 0.263 mmol) with 1-iodo-3-phenylpropane according to the general alkylation procedure afforded, after radial chromatography on silica gel (methanol-methylene chloride), 0.022 g (17%) of Example 84 as a white solid.

MP 159° C.; TLC (elution with 30% ethyl acetate-hexanes containing 1% acetic acid) $R_f$=0.64; HPLC (elution 4% methanol-methylene chloride containing 0.01% TFA) $t_R$=6.0 min; $^1$H NMR (CDCl$_3$, 300 MHz) δ 7.98 (d, J=8.5 Hz, 2H), 7.62 (d, J=8.5 Hz, 2H), 7.54 (d, J=8.8 Hz, 2H), 7.14–7.37 (m, 10H), 6.96 (d, J=8.8 Hz, 2H), 4.00 (t, J=6.6 Hz, 2H), 3.45 (dd, J=8.1, 16.5 Hz, 1H), 3.06–5 3.15 (m, 2H), 2.82 (brt, J=7.4 Hz, 2H), 2.65 (brt, J=7.0 Hz, 2H), 2.13–2.17 (m, 2H), and 1.69–1.84 (m, 4H); FAB-LCIMS: 507 [M+H]$^+$.

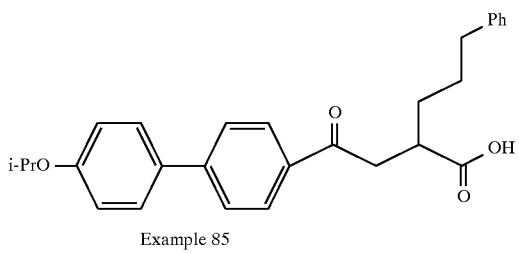

Example 85

Example 85

Reaction of Example 79 (0.104 g, 0.267 mmol) with 2-iodopropane according to the general alkylation procedure afforded, after radial chromatography on silica gel (methanol-methylene chloride), 0.088 g (77%) of Example 85 as a white solid.

M P 122° C.; TLC (elution with 30% ethyl acetate-hexanes containing 1% acetic acid) $R_f$=0.66; HPLC (elution 4% methanol-methylene chloride containing 0.01% TFA) $t_R$=7.1 min; $^1$H NMR (CDCl$_3$, 300 MHz) δ 7.98 (d, J=8.5 Hz, 2H), 7.62 (d, J=8.5 Hz, 2H), 7.54 (d, J=8.8 Hz, 2H), 7.15–7.28 (m, 5H), 6.96 (d, J=8.8 Hz, 2H), 4.59 (sept, J=5.9 Hz, 1H), 3.44 (dd, J=8.1, 16.5 Hz, 1H), 3.04–3.12 (m, 2H), 2.64 (brt, J=7.0 Hz, 2H), 1.69–1.83 (m, 4H), and 1.35 (d, J=5.9 Hz, 6H); FAB-LCIMS: 431 [M+H]$^+$.

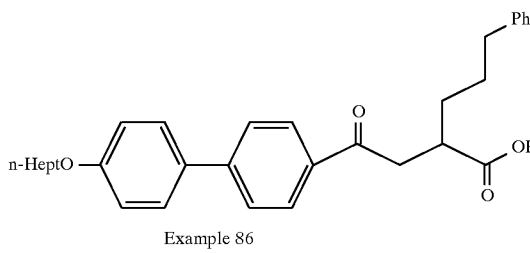

Example 86

Example 86

Reaction of Example 79 (0.102 g, 0.263 mmol) with 1-iodoheptane according to the general alkylation procedure afforded, after radial chromatography on silica gel (methanol-methylene chloride), 0.037 g (29%) of Example 86 as a white solid.

MP 114° C.; TLC (elution with 30% ethyl acetate-hexanes containing 1% acetic acid) $R_f$=0.61; HPLC (elution 4% methanol-methylene chloride containing 0.01% TFA)$t_R$=5.8 min; $^1$H NMR (CDCl$_3$, 300 MHz) δ 7.98 (d, J=8.5 Hz, 2H), 7.62 (d, J=8.5 Hz, 2H), 7.54 (d, J=8.8 Hz, 2H), 7.17–7.30 (m, 5H), 6.97 (d, J=8.8 Hz, 2H), 3.99 (t, J=6.6 Hz, 2H), 3.44 (dd, J=8.1, 16.5 Hz, 1H), 3.04–3.12 (m, 2H), 2.65 (brt, J=7.0 Hz, 2H), 1.69–1.83 (m, 6H), 1.37–1.47 (m, 8H), and 0.89 (t, J=7.0 Hz, 3H); FAB-LCIMS: 487 [M+H]$^+$.

Example 87

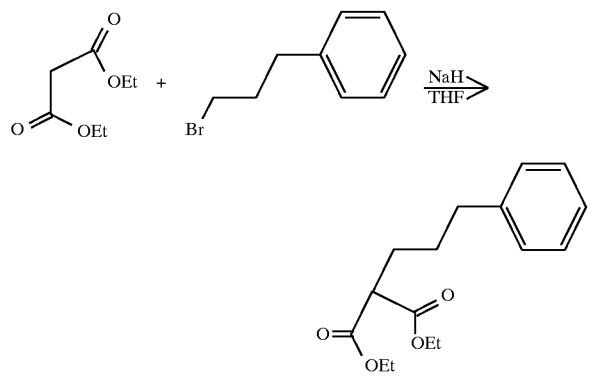

Step 1—Preparation of Ethyl 2-carboethoxy-5-phenyl-pentanoate

A dry 2-L, three-necked, round-bottomed flask was equipped with a stir bar, a pressure equalizing addition funnel, an argon inlet and a thermometer. The flask was charged with a suspension of sodium hydride (8.4 g of 95% NaH; _0.33 mol) in dry THF (700 mL) and was cooled with an ice water bath. Diethyl malonate (48.54 g, 0.30 mol) was added dropwise from the addition funnel over 25 min. Stirring was continued for 1.5 hr before adding 1-bromo-3-phenylpropane (47 mL, _61 g, _0.30 mol) over 10 min via the addition funnel. Rinses of the addition funnel (THF, 2×10 mL) were added to the reaction mixture and stirring was continued for 30 min. The addition funnel and thermometer were replaced with a reflux condenser and stopper, and the reaction was heated at reflux for 19 hr. The mixture was cooled to room temperature and then with an ice water bath. Distilled water (400 mL) was slowly added with stirring. The layers were separated and the aqueous phase was extracted with chloroform (100 mL). The combined organics were washed with 10% HCl (250 mL) and the separated aqueous phase was back-extracted with chloroform (100 mL). The combined organics were washed with saturated NaHCO$_3$ (250 mL) and the separated aqueous phase was back-extracted with chloroform (100 mL). The organics were dried (Na$_2$SO$_4$) and concentrated to yield a yellow oil which was purified by distillation through a Vigreux column at reduced pressure (0.4 torr). The fraction boiling at 124°–138° C. was clean desired product 20 (57.21 g, 0.206 mol; 68% yield).

TLC (hexanes-dichloromethane, 1:1): $R_f$=0.32; $^1$H-NMR (DMSO-d$_6$): δ 1.13 (t, J=7.0 Hz, 6H), 1.50–1.58 (m, 2H), 1.70–1.78 (m, 2H), 2.56 (t, J=7.4 Hz, 2H), 3.46 (t, J=7.4 Hz, 2H), 4.08 (q, J=7.0 Hz, 2H), 7.12–7.16 (m, 3H), 7.22–7.27 (m, 2H).

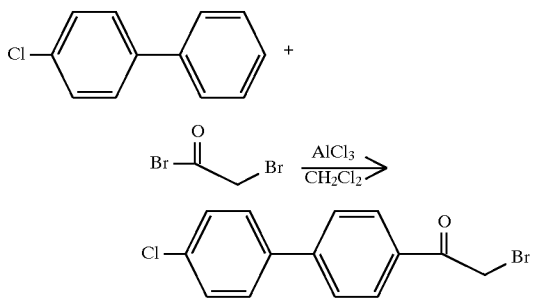

Step 2—Preparation of 1-(2-Bromoethanone)-4-(4-chloro-phenyl)-benzene

A 2-L, three-necked, round-bottomed flask was equipped with a mechanical stirrer, a thermometer and an argon inlet. The flask was charged with a solution of 4-chlorobiphenyl (48.30 g, 0.256 mol) in dichloromethane (500 mL, freshly opened bottle). Bromoacetyl bromide (23 mL, ~53.3 g, ~0.26 mol) was added via syringe and the solution was cooled with an ice water bath to an internal temperature of 3° C. The thermometer was temporarily removed and AlCl$_3$ was added portionwise over 5 min. The internal temperature rose to 10° C. and white gas evolved from the opaque olive green reaction mixture. After 24 h of stirring, the reaction was quenched by cautiously pouring into cold 10% HCl (1 L). The organic layer became cloudy yellow green. Chloroform was added to help dissolve solids, but the organic layer never became transparent. The organics were concentrated on a rotary evaporator and were dried further under high vacuum. The crude product was a pale green solid (~82 g) which recrystallized from hot ethyl acetate to give the desired compound 21 as brown needles (58.16 g). Concentration of the mother liquor followed by addition of hexanes delivered a second crop of crystals (11.06 g) which gave an NMR spectrum identical to that of the first crop. The total yield of the title product was 87%.

TLC (hexanes-dichloromethane, 2:1): R$_f$=0.30; $^1$H-NMR (CDCl$_3$): δ 4.48 (s, 2H), 7.45 (d, J=8.7 Hz, 2H), 7.56 (d, J=8.7 Hz, 2H), 7.67 (d, J=8.5, 2H), 8.06 (d, J=8.7, 2H).

addition funnel over 20 min. The deep orange reaction mixture was stirred under argon overnight while slowly warming to room temperature. The reaction vessel was cooled in an ice water bath while distilled water (300 mL) was added cautiously. The layers were separated and the aqueous phase was extracted with dichloromethane (100 mL). The combined organics were washed sequentially with 10% HCl and saturated sodium bicarbonate (200 mL). The combined aqueous washes were back-extracted with dichloromethane (50 mL). The combined organics were dried (Na$_2$SO$_4$) and concentrated to afford a dark orange oil (84.07 g). This crude material was used in the next step without purification.

A portion of the crude oil (24.09 g, ~47.5 mmol) was taken up in ethanol (400 mL; the sample did not completely dissolve). To this mixture was added NaOH solution (19.0 g of 50 wt. % aqueous NaOH, ~238 mmol) and the reaction was stirred under argon overnight at room temperature. After 20 h of stirring, the reaction showed no diester remaining by TLC. The mixture was brought to pH~1 by adding concentrated HCl (~20 mL) and was then concentrated to dryness. An attempt to partition this material between chloroform (200 mL) and water (100 mL) failed to dissolve all solids. Collection of the undissolved solid followed by drying under high vacuum gave clean desired (12.38 g, 27.46 mmol). Examination of the aqueous and organic phases by TLC

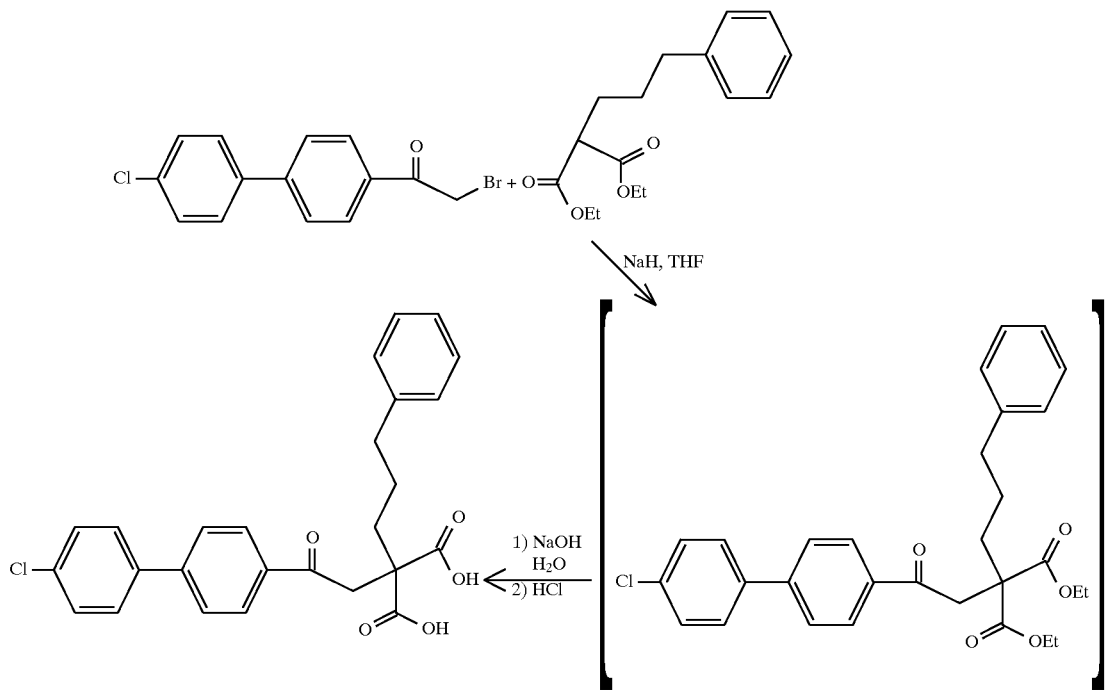

Step 3—Preparation of 2-Carboxy-5-phenyl-2-[2-oxo-2-(4'-chloro-4-biphenyl)ethyl]-pentanoic acid:

A dry 1-L, three-necked, round-bottomed flask was equipped with a magnetic stir bar, a thermometer, an argon inlet and a pressure equalizing addition funnel. The flask was charged with a suspension of sodium hydride (4.7 g of 95% NaH; ~0.185 mol) in dry THF (400 mL), and the addition funnel was charged with the malonate product from step 1 (46.76 g, 0.168 mol). The reaction vessel was cooled with an ice water bath while the malonate was added dropwise over 18 min. After the reaction stirred for 45 min, a solution of the bromomethyl ketone product from step 2 (52.00 g, 0.168 mol) in dry THF (200 mL) was added via the showed a negligible amount of desired. The saponification procedure was repeated on the remaining crude diester (59.47 g, ~117 mol) to deliver additional diacid (28.34 g, 62.85 mmol). The total yield for the alkylation-saponification process to yield the diacid product was 54%.

TLC (chloroform-methanol, 9:1 with trace amount of acetic acid): R$_f$=0.45; $^1$H-NMR (DMSO-d$_6$): δ 1.42–1.63 (m, 2H), 1.92–2.04 (m, 2H), 2.51 (t, J=7.4 Hz, 2H), 3.61 (s, 2H), 7.09–7.23 (m, 5H), 7.55 (d, J=8.5, 2H), 7.77 (d, J=8.8 Hz, 2H), 7.82 (d, J=8.5 Hz, 2H), 8.02 (d, J=8.5, 2H).

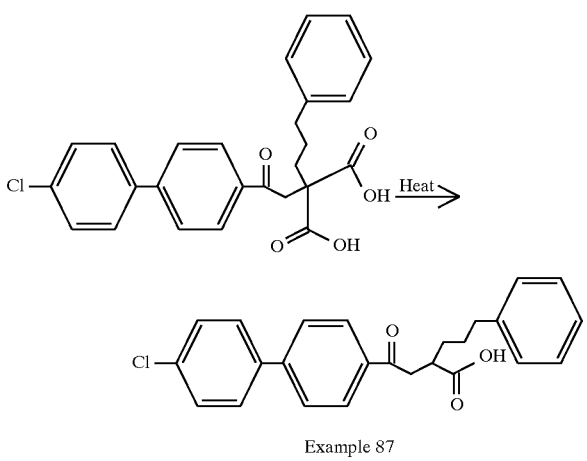

Example 87

Step 4—Preparation of Example 87

The diacid product from step 3 (28.34 g, 62.85 mmol) was dissolved in 1,4-dioxane (1.2 L) and was held at reflux under argon overnight. Concentration gave the crude product as a yellow-white solid (27.60 g) which was recrystallized from toluene to deliver the title compound Example 87 as a tan solid (21.81 g, 53.60 mmol) after overnight drying in a vacuum oven at 100° C. The decarboxylation was repeated on the remaining diacid (12.38 g) from step 3 to give additional recrystallized product (7.60 g, 18.68 mmol). The total yield for the decarboxylation step was 80%. The final product contains 5 mol % toluene even after extensive vacuum oven drying at 100° C.

TLC (chloroform-methanol, 9:1 with trace amount of acetic acid): $R_f$=0.64; $^1$H-NMR (DMSO-$d_6$) δ 1.62–1.71 (m, 4H), 2.54–2.63 (m, 2H), 2.79–2.91 (m, 1H), 3.11 (dd, J=4.1 Hz and 18 Hz, 1H), 3.39 (dd, J=9.6 Hz and 18 Hz, 1H), 7.12–7.28 (m, 5H), 7.54 (d, J=8.8 Hz, 2H), 7.77 (d, J=8.8 Hz, 2H), 7.81 (d, J=8.5 Hz, 2H), 8.04 (d, J=8.5 Hz, 2H); MS (FAB-LSIMS) 407 $[M+H]^+$ ($C_{25}H_{23}O_3Cl$, FW=406.91); Anal. (for $C_{25}H_{23}O_3Cl \cdot 0.05C_7H_8$) C: calcd, 73.99; found, 73.75 . H: calcd, 5.73; found, 5.74.

Resolution of Example 87

Purification of Dehydroabietylamine

A solution of dehydroabietylamine (60%, 100 g, 0.21 mol) in toluene (170 mL) was treated with a second solution of glacial acetic acid (24 mL) in toluene (55 mL) at room temperature. The mixture was stored at room temperature overnight. The crystalline salt was collected by filtration, washed with cold toluene and recrystallized from boiling toluene (152 mL). The crystals were collected by filtration, washed with n-pentane and air-dried to give dehydroabietylamine acetate (47 g, 78%) as a white crystalline solid.

A solution of dehydroabietylamine acetate (47 g, 0.16 mol) in water (175 mL) was gently warmed until the solution became homogeneous. An aqueous solution of NaOH (10% W/V, 61 mL) was carefully added and after cooling to room temperature. The aqueous solution was extracted with diethyl ether, dried over $MgSO_4$, filtered and concentrated to give dehydroabietylamine (35 g, 58%) as a viscous oil which solidified on standing.

Mp 44°–45° C.; $[\alpha]D$ +54° (c 2.3, acetone); $^1$H NMR ($CDCl_3$) δ 7.19 (d, J=8.1 Hz, 1H), 6.99 (dd, $J_1$=8.1 Hz, $J_2$=1.8 Hz, 1H), 6.89 (m, 1 H), 2.78 (m, 3H), 2.62 (d, J=13.2 Hz, 1H), 2.45 (d, J=13.2 Hz, 1 H), 2.30 (dt, $J_1$=12.9 Hz, $J_2$=3 Hz, 1H), 1.73 (m, 3H), 1.51 (m, 4 H), 1.35 (m, 3H), 1.22 (m, 6H), 0.90 (s, 3H); $^{13}$C NMR ($CDCl_3$) δ 147.3, 145.3, 134.5, 126.6, 124.1, 123.6, 53.7, 44.6, 38.4, 37.2, 37.0, 35.0, 33.3, 30.0, 25.1, 23.9, 23.8, 18.6, 18.5, 18.4; MS (FAB) m/$_z$ (relative intensity) 286 ($M^++H$, 100), 173 (40). Anal. Calcd for $C_{20}H_{31}N$: C, 84.15; H, 10.95; N, 4.91. Found C, 83.93; H, 20 10.78; N, 4.84.

Example 88

A solution of Example 87 (45 g, 0.11 mol) and dehydroabietylamine (32 g, 0.11 mol) in an acetone/ethanol/water mixture (50:20:1; 1260 mL) was carefully warmed until the solution became clear (1 h). After cooling to room temperature and standing for 42 h, the solid was removed by filtration.

The solid product from the initial crystallization was diluted with a 10% dichloromethane / ethyl acetate mixture (700 mL) and treated with 10% phosphoric acid (300 mL). After stirring at room temperature for 1 h, the mixture was added to a separatory funnel and diluted with sat. aq. NaCl (200 mL). After the aqueous phase was drained off, the precipitate that remained in the organic layer was removed by filtration and dried to give 9.2 g of near racemic solid with an isomer ratio of 48:52 (Example 89:Example 88). The remaining solution was filtered through a short pad of silica gel and concentrated to give Example 88 (13.3 g, 60% theoretical; isomer ratio 0.8:99.2 (Example 89:Example 88)).

HPLC conditions for Example 87 (Example 88 and Example 89):

column: Chiralcel® OJ analytical column flow rate: 1 mL / min solvent system: 35% (ethanol; 1% water; 0.2% TFA) in hexanes detection: I=288 concentration: 1 mg / mL injection amount: 6 μL 19.8 min. (Example 89); 26.8 min. (Example 88)

Example 88

MP 125°–126° C.; $[\alpha]D$ +25.70° (c 1.4, acetone); $^1$H NMR ($CDCl_3$) δ 8.25 (d, J=8.4 Hz, 2H), 7.65 (d, J=8.7 Hz, 2H), 7.56 (d, J=8.4 Hz, 2H), 7.20 (d, J=8.4 Hz, 2H), 7.28 (t, J=7.8 Hz, 2H), 7.19 (m, 3H), 3.49 (dd, $J_1$=16.8 Hz, $J_2$=8.4 Hz, 1H), 3.14 (dd, $J_1$=12.9 Hz, $J_2$=4.8 Hz, 1H), 3.08 (dd, $J_1$=16.8 Hz, $J_2$=4.2 Hz, 1H), 2.68 (t, J=7.2 Hz, 2H), 1.77, (m, 4H); $^{13}$C NMR ($CDCl_3$) δ 197.4, 180.9, 144.6, 141.8, 138.2, 135.3, 134.5, 129.1, 128.7, 128.5, 128.4, 128.3, 127.1, 125.9, 40.1, 40.0, 35.6, 31.4, 28.9; MS (FAB) m/$_z$ (relative intensity) 407 ($M^++H$, 100), 389 (55), 215 (60). Anal. Calcd for $C_{25}H_{23}O_3Cl$: C, 73.79; H, 5.70; Cl, 8.71. Found C, 74.02; H, 5.79; Cl, 8.82.

Example 89

The filtrate from the initial crystallization was concentrated under reduced pressure. The resulting solid material was processed using the same procedure as described for Example 88. The analogous sequence provided racemate (8.0 g, isomer ratio 57:43) and Example 89 (13.5 g, 60% theoretical; isomer ratio 99.1:0.9).

MP 125°–126° C., $[\alpha]D$ −25.60° (c 1.4, acetone); $^1$H NMR ($CDCl_3$) δ 8.25 (d, J=8.4 Hz, 2H), 7.65 (d, J=8.7 Hz, 2H), 7.56 (d, J=8.4 Hz, 2H), 7.20 (d, J=8.4 Hz, 2H), 7.28 (t, J=7.8 Hz, 2H), 7.19 (m, 3H), 3.49 (dd, $J_1$=16.8 Hz, $J_2$=8.4 Hz, 1H), 3.14 (dd, $J_1$=12.9 Hz, $J_2$=4.8 Hz, 1H), 3.08 (dd, $J_1$=16.8 Hz, $J_2$=4.2 Hz, 1H), 2.68 (t, J=7.2 Hz, 2H), 1.77, (m, 4H); $^{13}$C NMR (CDCl$_3$) δ 197.4, 180.9, 144.6, 141.8, 138.2, 135.3, 134.5, 129.1, 128.7, 128.5, 128.4, 128.3, 127.1, 125.9, 40.1, 40.0, 35.6, 31.4, 28.9; MS (FAB) m/$_z$ (relative intensity) 407 (M$^+$+H, 100), 389 (95), 215 (70). Anal. Calcd for C$_{25}$H$_{23}$O$_3$Clk: C, 73.79; H, 5.70; Cl, 8.71. Found C, 73.45; H, 5.87; Cl, 8.97.

Chiral Synthesis of Example 90

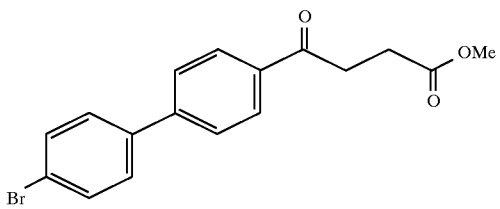

Step 1

4-Bromobiphenyl (11.6 g, 50 mmol) was dissolved in 1,2-dichloroethane (25 mL) and added to a suspension of succinic anhydride (5.0 g, 50 mmol) in 1, 2-dichloroethane (70 mL) and the mixture was cooled to 0° C. Solid aluminum chloride (14.0 g, 105 mmol) was added in six portions resulting in a dark green solution. After 10 min, the reaction was allowed to warm to rt and stirred a further 72 h under Ar. The reaction mixture was poured into a beaker containing 200 mL crushed ice/water. Hexane (200 mL) was added and the mixture stirred for 1 h. The pale orange solid was filtered off to give 16.8 g (100%) of crude acid. A portion of the acid (7.0 g) was then suspended in methanol (25 mL)/ toluene (25 mL) and conc. H$_2$SO$_4$ (2.5 mL) was added dropwise. The mixture stirred 14 h at rt then was heated to 75° C. for 3 h. The solvent was removed in vacuo and the residue dissolved in CH$_2$Cl$_2$ and slowly poured into a mixture of saturated aqueous sodium bicarbonate/ice. The ester was extracted with methylene chloride and dried over MgSO$_4$. Filtration and removal of the solvent in vacuo gave 6.44 g (88%) of pale yellow powder.

$^1$H NMR (300 MHz, CDCl$_3$) δ 2.81 (t, J=6.6 Hz, 2H), 3.36 (t, J=6.6 Hz, 2H), 3.73 (s, 3H), 7.49 (m, 2H), 7.59 (m, 4H), 8.07 (dd, J=1.8, 6.6 Hz, 2H); $^{13}$C NMR (75 MHz, CDCl$_3$) δ 28.0, 33.5, 51.9, 122.7, 127.7, 128.8, 128.9, 132.2, 138.8, 145.7, 173.4, 197.6.

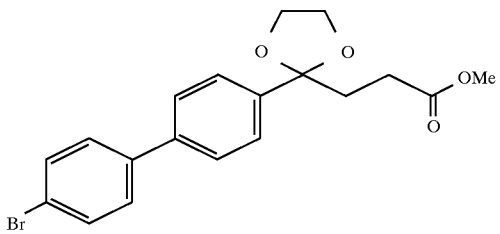

Step 2

A solution of 1,2-bis(trimethylsiloxy)ethane (4.8 mL, 20 mmol) in CH$_2$Cl$_2$ (1 mL) was cooled to −70° C. Catalytic trimethylsilyl trifluoromethanesulfonate (10 μL, 0.05 mmol) and then methyl ester product from step 1 (1.70 g, 5 mmol) dissolved in CH$_2$Cl$_2$ (4 mL) were added resulting in a thick slurry. The ice bath was allowed to warm to rt (over 3 h) and the reaction stirred a further 24 h before water was added. The product was extracted with CH$_2$Cl$_2$ and the organic layers were dried over sodium sulfate. After filtration, the solvent was removed in vacuo and the residue purified by MPLC (15% ethyl acetate/ 85% hexanes) to give 1.71 g (85%) ester as a colorless powder.

$^1$H NMR (300 MHz, CDCl$_3$) δ 2.28 (m, 2H), 2.46 (m, 2H), 3.65 (s, 3 H), 3.81 (m, 2H), 4.04 (m, 2H), 7.45 (dd, J=2.2, 6.6 Hz, 2H), 7.51 (m, 4H), 7.57 (dd, J=2.2, 6.6 Hz, 2H); $^{13}$C NMR (75 MHz, CDCl$_3$) δ 28.7, 35.4, 51.6, 64.8, 109.5, 121.7, 126.3, 126.8, 128.7, 131.9, 139.7, 139.8, 173.9.

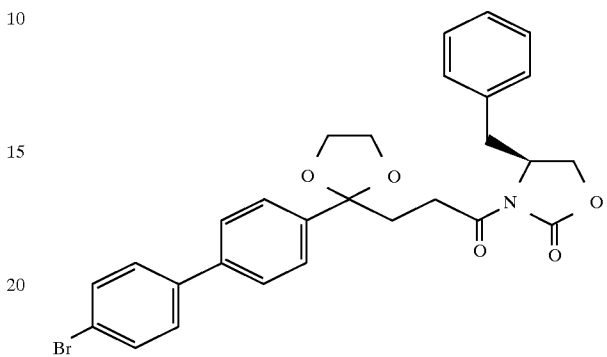

Step 3

The ketal from step 2 (4.61 g, 12 mmol) was dissolved in THF (45 mL) and H$_2$O (15 mL) at rt. NaOH (480 mg, 12 mmol) was added and the reaction stirred at rt for 19 h. Ester was still present by TLC so another portion of NaOH (210 mg) was added. After a further 2 h the reaction was acidified to pH 3 with 4M HCl at 0° C. and the product was extracted with ethyl acetate. Removal of solvent in vacuo gave 4.63 g of a colorless solid that was taken on to the next step crude. A portion of the acid (2.50 g, 6.6 mmol) was dissolved in CH$_2$Cl$_2$ (37 mL). (S)—(—)-4-Benzyl-2-oxazolidinone (1.44 g, 11.1 mmol), 1-(3-dimethylaminopropyl)-3-ethylcarbodiimide hydrochloride (1.56 g, 8.1 mmol), and dimethylaminopyridine (181 mg, 1.5 mmol) respectively were added at rt. A few minutes after the addition of the DMAP, all solid goes into solution. The reaction stirred for 3 d at rt and was then poured into saturated aqueous NH$_4$Cl. The product was extracted with CH$_2$Cl$_2$ and dried over sodium sulfate. After removal of the solvent in vacuo, the residue was purified by MPLC (2% CH$_3$OH/98% CH$_2$Cl$_2$) to give 2.64 g (74%) of the above shown benzyloxazolidinone as a colorless solid.

$^1$H NMR (300 MHz, CDCl$_3$) δ 2.38 (m, 2H), 2.72 (dd, J=9.6, 13.2 Hz, 1H), 3.13 (m, 2H), 3.29 (dd, J=3.3, 13.6 Hz, 1H), 3.82 (m, 2 H), 4.08 (m, 2H), 4.17 (m, 2H), 4.52 (m, 1H), 7.19–7.33 (comp m, 5H), 7.45 (m, 2H), 7.56 (m, 6H); $^{13}$C NMR (75 MHz, CDCl$_3$) δ 30.2, 34.7, 37.9, 55.3, 64.8, 66.2, 109.6, 121.7, 126.4, 126.8, 127.4, 128.8, 129.0, 129.5, 131.9, 135.4, 139.7, 139.8, 141.8, 153.5,

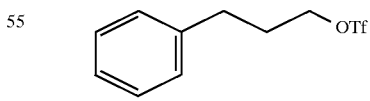

Step 4

A solution of pyridine (0.90 mL, 11 mmol) in CH$_2$Cl$_2$ (33 mL) was cooled to −70° C. Triflic anhydride (1.68 mL, 10 mmol) was added over 6 min resulting in a yellowish, slushy solution. After 5 min, 3-phenyl-1-propanol (1.40 mL, 10 mmol) was added over 4 min. The reaction stirred for 30 min at −70° C. and was then warmed to −20° C. for 75 min. The cold solution was poured through a fritted funnel containing silica gel. The silica was washed with CH₂Cl₂ and the solvent was removed in vacuo to give the above triflate as a pale orange liquid which was kept under vacuum until it was used in the next reaction (approximately 1 h).

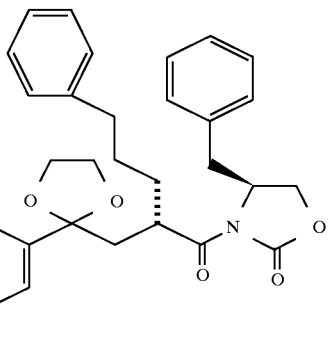

Step 5

Benzyloxazolidinone from step 3 (1.0 g, 1.9 mmol) was dissolved in THF (5 mL) and cooled to −70° C. Sodium bis(trimethylsilyl)amide (1M in THF, 2.0 mL, 2 mmol) was added to the oxazolidinone over 5 min and the reaction stirred a further 30 min. A solution of phenylpropyl triflate from step 4 (2.7 g, 10 mmol) in THF (5 mL) and diisopropylethylamine (1.8 mL, 10 mmol) was added to the sodium anion and the reaction stirred for 2 h at −70° C. The reaction was quenched at −70° C. with saturated aqueous NH₄Cl (100 mL) and then the flask was warmed to rt. The solvent was removed in vacuo and the residue was dissolved in ethyl acetate and washed with saturated aqueous NH₄Cl. The aqueous layer was extracted with ethyl acetate and dried over sodium sulfate. After filtration, the solvent was removed in vacuo and the residue purified by MPLC (20% ethyl acetate/80% hexane to 30% ethyl acetate/70% hexane) to afford 66 mg of recovered starting oxazolidinone, 34 mg of the (R)-diastereomer product and 630 mg of the (S)-diastereomer product as shown above.

¹³C NMR (75 MHz, CDCl₃) δ 28.6, 33.6, 35.8, 38.3, 42.3, 55.6, 64.3, 64.8, 65.9, 109.6, 119.7, 121.8, i25.8, 126.5, 126.7, 127.3, 128.3, 128.5, 128.7, 129.0, 129.5, 132.0, 135.4, 139.7, 141.6, 142.1, 153.3, 177.1

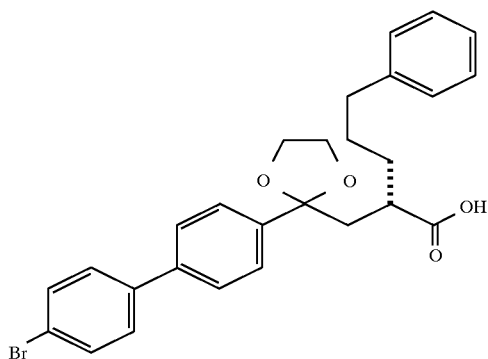

Step 6

The product of step 5 (350 mg, 0.53 mmol) was dissolved in THF (3.75 mL) and H₂O (1.25 mL) and cooled to 0° C. Hydrogen peroxide (30%, 485 mL, 4.2 mmol) then lithium hydroxide monohydrate (90 mg, 2.1 mmol) were added. After 30 min the ice bath was removed and the reaction stirred 6 h at rt. Aqueous sodium bisulfite (10%) was added and the mixture stirred overnight. The aqueous layer was extracted with CH₂Cl₂ and the organic solution was dried over sodium sulfate. After filtration the residue was purified by MPLC (20% ethyl acetate/ 80% hexanes) to give 31 mg of pure acid as shown above and 103 mg of a mixture of starting benzyl oxazolidinone and the product. The mixed fractions were dissolved in 30% ethyl acetate/70% hexanes; crystals formed that were 70% oxazolidinone by HPLC while the mother liquor was pure acid product.

¹³C NMR (75 MHz, CDCl₃) δ 28.9, 32.7, 35.6, 40.3, 42.8, 64.7, 64.8, 109.4, 125.8, 126.2, 126.8, 128.3, 128.3, 128.4, 128.4, 128.8, 132.0, 139.8, 142.0, 142.1, 181.4.

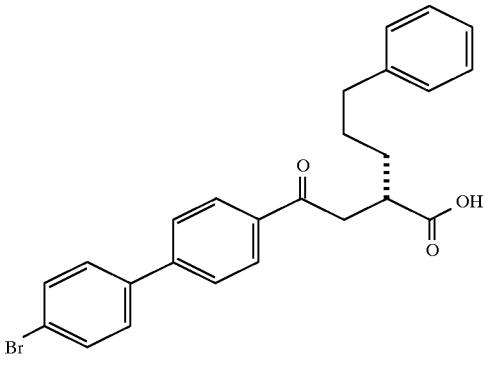

Example 90

Step 7—Preparation of Example 90

The above ketal from step 6 (38 mg, 0.08 mmol) was dissolved in CH₂Cl₂ (475 mL) and cooled to 0° C. A drop of conc. HClO₄ (9.4 mL) was added and the reaction stirred for 3.5 h at 0° C. Saturated sodium bicarbonate was added and the product was extracted with methylene chloride. The combined organic portions were dried over sodium sulfate. Removal of solvent in vacuo gave material (29 mg, 84%) that was pure by analytical HPLC analysis.

[α]D −22.1° (c 1.2, CHCl₃); ¹H NMR (300 MHz, CD₃OD) δ 1.69 (m, 4 H), 2.63 (m, 2H), 2.99 (m 1H), 3.10 (dd, J=4.4, 18.0, 1H), 3.45 (dd, J=9.5, 18.0, 1H), 7.17 (m, 5H), 7.59 (m, 4H), 7.72 (m, 2H), 8.04 (m, 2 H ); ¹³C NMR (75 MHz, CD₃OD) δ 30.2, 32.8, 36.7, 41.6, 48.3, 123.6, 126.8, 129.4, 129.9, 130.0, 133.2, 137.1, 140.2, 143.4, 145.8, 179.3, 200.0.

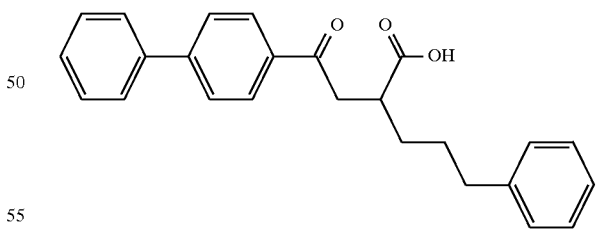

Example 91

Example 91

The title compound was synthesized by a sequence similar to that for producing Example 87 except commercially available 1-(2-bromoethanone)-4-phenyl-benzene was used in the alkylation step 3 instead of the 4'-chlorobiphenyl intermediate. The final product was purified by crystallization from toluene to give a white solid (mp 135.0°–137.0° C.) which retained toluene despite extensive drying in a vacuum oven.

TLC (chloroform-methanol, 9:1 with trace amount of acetic acid): $R_f$ 0.65; $^1$H-NMR (DMSO-$d_6$): δ 1.54–1.67 (m, 4H), 2.55–2.60 (m, 2H), 2.82–2.87 (m, 1H), 3.13 (dd, J=4.0 Hz, 18 Hz, 1H), 3.40 (dd, J=9.6 Hz, 18 Hz, 1H), 7.12–7.28 (m, 5H), 7.38–7.51 (m, 3H), 7.73 (d, J=8.5 Hz, 2H), 7.80 (d, J=8.5 Hz, 2H), 8.04 (d, J=8.5 Hz, 2H), 12.13 (s, 1H); MS (FAB-LSIMS) 373 [M+H]$^+$($C_{25}H_{24}O_3$, FW=372.47); HRMS calcd, 372.1725; found, 372.1735.

Example 92, Example 93, Example 94, Example 95 and Example 96

These compounds were prepared using the general procedure of Example 87 except that the indicated commercial malonates were used instead of ethyl 2-carboethoxy-5-phenylpentanoate.

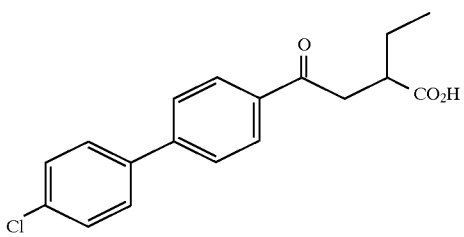

Example 92

Example 92

From diethyl 2-ethylmalonate: MP 151°–152° C.; $^1$H NMR (DMSO) δ 8.03 (d, J=7.6 Hz , 2H).; 7.77 (m, 4H); 7.54 (m, 2H); 3.40 (m, 2H); 3.07 (dd, J=17.9 Hz and 4.1 Hz, 1H); 2.78 (m, 1H); 1.59 (m, 2H); 0.91 (t, J=7.4 Hz, 3H); $^{13}$C NMR (DMSO) δ 199.19, 177.23, 144.24, 138.78, 136.65, 134.42, 130.15, 129.88, 129.77, 127.96, 42.35, 25.68, 12.49; MS (FAB-LSIMS) 317 [M+H]$^+$, ($C_{18}H_{17}Cl O_3$, FW=316.8); Anal C: calcd, 68.25; found, 68.03. H: calcd, 5.41; found, 5.34. Cl: calcd; 11.19, found; 11.19.

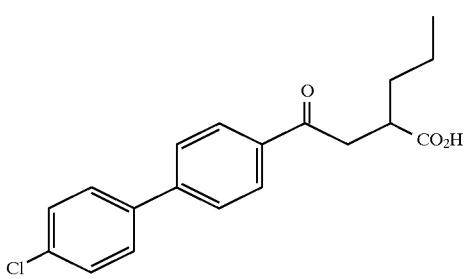

Example 93

Example 93

From diethyl 2-propylmalonate: MP 127°–128° C.; $^1$H NMR (DMSO) δ 8.03 (d, J=8.4 Hz , 2H); 7.76 (m, 4H); 7.53 (d, J=8.4 Hz, 2H); 3.37 (m, 2H); 3.08 (dd, J=17.9 Hz and 4.1 Hz, 1H); 2.83 (m, 1H);2.48 (s, 1H); 1.53 (m, 2H);1.34 (m, 2H); 0.87 (t, J=7.2 Hz, 3H); 13C NMR (DMSO) δ 199.18, 177.40, 144.24, 138.78, 136.63, 134.41, 130.15, 129.88, 129.77, 127.96, 120.25, 34.82, 20.88, 14.99; MS (FAB-LSIMS) 331 [M+H]$^+$, ($Cl_{19}H_{19}Cl O_3$, FW=330.8); Anal C: calcd, 68.99; found, 68.95. H: calcd, 5.79; found, 5.75. Cl: calcd; 10.72, found; 10.77.

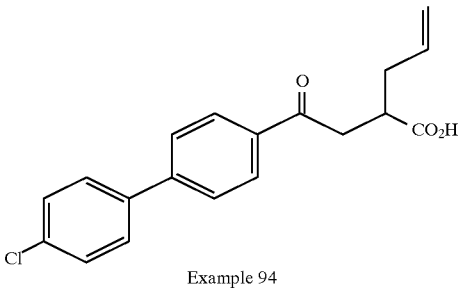

Example 94

Example 94

From diethyl 2-allylmalonate: MP 133°–134° C.; $^1$H NMR (DMSO) δ 8.02 (d, J=8.3 Hz , 2H); 7.76 (m, 4H); 7.53 (d, J=8.3 Hz, 2H); 5.78 (m, 1H); 5.04 (m, 1H); 3.39 (dd, J=18.2 Hz and 9.4 Hz, 2H); 3.07 (dd, J=18.2 Hz and 4.1 Hz, 1H); 2.95 (m, 1H);2.35 (m, 1H); $^{13}$C NMR (DMSO) δ 198.93, 176.61, 144.28, 138.76, 136.59, 134.43, 130.15, 129.88, 129.72, 128.05, 118.33, 36.69; MS (FAB-LSIMS) 329 [M+H]$^+$, ($C_{19}H_{17}Cl O_3$, FW=328.8); Anal C: calcd, 69.41; found, 69.36. H: calcd, 5.21; found, 5.13. Cl: calcd; 10.78, found; 10.67.

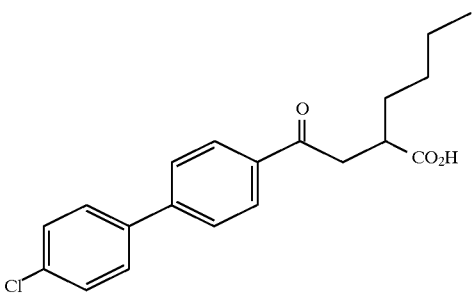

Example 95

Example 95

From diethyl 2-butylmalonate: MP 152°–153° C.; $^1$H NMR (DMSO) δ 8.03 (d, J=8.3 Hz , 2H); 7.75 (m, 4H); 7.53 (d, J=8.3 Hz, 2H); 3.38 (dd, J=18.2 Hz and 9.5 Hz, 2H); 3.08 (dd, J=17.9 Hz and 4.1 Hz, 1H); 2.81 (m, 1H); 1.58 (m, 2H); 1.29 (m, 4H); 0.85 (t, J=6.6 Hz, 3H); $^{13}$C NMR (DMSO) δ 199.16, 177.40, 144.22, 138.78, 136.61, 134.42, 130.15, 129.88, 129.77, 127.96, 32.33, 29.81, 23.20, 14.92; MS (FAB-LSIMS) 345 [M+H]$^+$, ($C_2OH_{21}Cl O_3$, FW=344.8); Anal C: calcd, 69.66; found, 69.60. H: calcd, 6.14; found, 56.06. Cl: calcd; 10.28, found; 10.24.

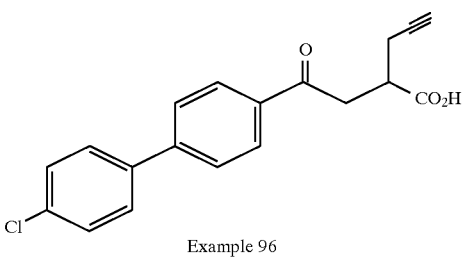

Example 96

Example 96

From diethyl 2-propargylmalonate: MP 130°–132° C.; $^1$H NMR (DMSO) δ 8.00 (d, J=8.3 Hz , 2H); 7.77 (m, 4H); 7.53

(d, J=8.3 Hz, 2H); 3.52 (dd, J=18.2 Hz and 8.3 Hz, 1H); 3.20 (dd, J=18.2 Hz and 4.7 Hz, 1H); 3.03 (m, 1H); 2.90 (t, J=2.5 Hz, 1H) 2.54 (m, 2H); ; $^{13}$C NMR (DMSO) δ 198.58, 175.43, 144.36, 138.75, 136.52, 134.47, 130.17, 129.88, 129.74, 128.04, 120.25, 82.58, 74.29, 21.48,; M S (FAB-LSIMS) 327 [M+H]$^+$, ($C_{19}H_{15}Cl\ O_3$, FW=326.8).

Example 97 and Example 98

These compounds were prepared using the general method of Example 87 except that the indicated alkyl bromides were used in step 1 rather than 1-bromo-3-phenylpropane.

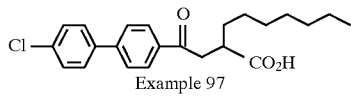

Example 97

Example 97

From 1-bromoheptane: MP 118°–120° C.; $^1$H NMR (CDCl$_3$) δ 8.04 (dd, J=6.6 Hz and 1.6 Hz, 2H); 7.64 (d, J=6.9 Hz, 2H); 7.55 (m, 2H); 7.44 (m, 2H); 3.48 (m, 1H); 3.08 (m, 2H); 1.75 (m, 1H); 1.67 (m, 1H); 1.37 (m, 10H); 0.88 (t, J=6.3 Hz, 3H) $^{13}$C NMR (CDCl$_3$) δ 198.27, 182.09, 145.29, 138.92, 136.16, 135.16, 129.81, 129.43, 129.18, 127.76, 40.83, 40.78, 32.58, 32.46, 30.11, 29.77, 27.81, 23.31, 14.76; MS (FAB-LSIMS) 386.9 [M+H]$^+$, ($C_{23}H_{27}Cl\ O_3$, FW=386.9).

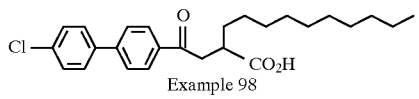

Example 98

Example 98

From 1-bromodecane: MP 108°–110° C.; $^1$H NMR (CDCl$_3$) δ 7.99 (d, J=8.5 Hz, 2H); 7.59 (d, J=8.5 Hz, 2H); 7.50 (m, 2H); 7.39 (m, 2H); 3.43 (dd, J=18.7 Hz and 9.9 Hz, 1H); 3.00 (m, 2H); 1.67 (m, 1H); 1.56 (m, 1H); 1.25 (m, 16H); 0.82 (t, J=6.3 Hz, 3H) $^{13}$C NMR (CDCl$_3$) δ 198.69, 178.51, 144.98, 138.91, 136.39, 134.98, 129.73, 129.36, 129.12, 127.63, 41.04, 40.97, 40.20, 32.71, 32.50, 30.20, 30.07, 29.91, 27.81, 23.27, 14.73; MS (FAB-LSIMS) 429 [M+H]$^+$, ($C_{26}H_{33}Cl\ O_3$, FW=429.00).

Example 99

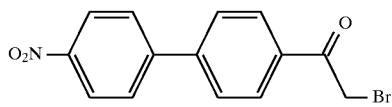

Step 1—Preparation of 1-(2-Bromoethanone)-4-(4-nitrophenyl)-benzene

The title compound was prepared via the procedure outlined for Example 87 (step 2) using commercially available 4-nitrobiphenyl instead of 4-chlorobiphenyl. The final product was recrystallized from ethyl acetate to afford orange crystals (52%).

TLC (hexanes-dichloromethane, 1:1): R$_f$=0.55; $^1$H-NMR (DMSO-d$_6$): δ 4.97 (s, 2H), 7.90–8.40 (m, 8H); MS (FAB-LSIMS) 319, 321 [M+H]$^+$ ($C_{14}H_{10}O_3$NBr, FW=320.15).

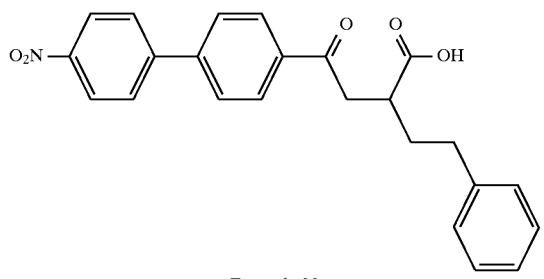

Example 99

Step 2—Preparation of Example 99

The title compound was synthesized by a sequence similar to that for producing Example 87 except that 1-(2-bromoethanone)-4-(4-nitrophenyl)-benzene and commercially available diethyl phenethyl malonate were used in lieu of the 4-chlorobiphenyl and phenylpropyl malonates respectively. The final product was recrystallized from acetone to give orange crystals (MP 193.5°–194.0° C.) which retained acetone despite extensive drying in a vacuum oven.

TLC (chloroform-methanol, 9:1 with trace amount of acetic acid): R$_f$=0.60; $^1$H-NMR (DMSO-d$_6$): δ 1.70–2.00 (m, 2H), 2.55–2.75 (m, 2H), 2.80–2.93 (m, 1H), 3.17–3.25 (m, 1H), 3.48 (dd, J=18.4, 9.6 Hz, 1H), 7.10–7.35 (m, 5H), 7.90–8.35 (m, 8H), 12.24 (s, 1H); $^{13}$C-NMR (DMSO-d$_6$): δ 198.32, 176.28, 147.39, 145.45, 142.25, 141.70, 136.60, 128.96, 128.49, 127.80, 126.05, 124.34, 33.50, 32.76; MS (EI) 403 [M]$^+$ ($C_{24}H_{21}O_5$N, FW=403.44); Anal. C: calcd, 71.45; found, 71.41. H: calcd, 5.25; found, 5.23. N: calcd, 3.47; found, 3.46.

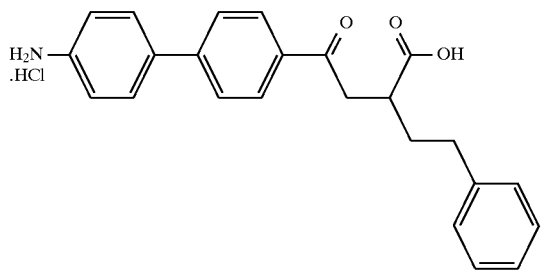

Example 100

Example 100

A 125-mL Parr reaction vessel containing Example 99 (1.15 g, 2.85 mmol), 10% Pd/C (0.06 g), and glacial acetic acid (50 mL) was charged with hydrogen gas at 55 psi and shaken on a Parr apparatus until hydrogen uptake ceased. The Parr reaction vessel was then purged with argon and the reaction mixture was filtered through a pad of Celite, rinsing with acetone. The solution was concentrated to dryness via rotary evaporation using hexane to azeotrope the acetic acid. The solid was dissolved in hot 10% HCl, filtered and concentrated to dryness via rotary evaporation. The crude hydrochloride was then recrystallized from ethanol to afford off-white crystals which when dried in a vacuum oven (80° C., 3 days) became purple (0.18 g, 17%, MP 222.0°–224.0° C).

TLC (dichloromethane-methanol, 24:1): R$_f$=0.55; $^1$H-NMR (DMSO-d$_6$): δ 1.70–2.00 (m, 2H), 2.55–2.75 (m, 2H), 2.80–2.90 (m, 1H), 3.19 (dd, J=18.0, 4.0 Hz, 1H), 3.46 (dd, J=18.0, 9.6 Hz, 1H), 7.10–7.30 (m, 5H), 7.37 (d, J=8.5 Hz, 2H), 7.80 (d, J=8.5 Hz, 4H), 8.05 (d, J=8.1 Hz, 2H), 8.50–11.0 (br s, 4H); $^{13}$C NMR (DMSO-d$_6$): δ 198.19, 176.31, 143.79, 141.73, 136.65, 135.44, 135.11, 128.90, 128.54, 128.49, 128.40, 126.84, 126.05, 122.55, 33.53, 32.79; MS (EI) 373 [M-HCl]$^+$ (C$_{24}$H$_{24}$O$_3$NCl, FW=409.92); Anal. C: calcd, 70.32; found, 70.38. H: calcd, 5.90; found, 5.98. N: calcd, 3.42; found, 3.37.

Example 101

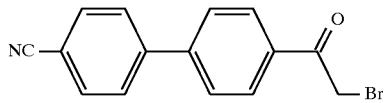

Step 1—Preparation of 1-(2-Bromoethanone)-4-(4-cyanophenyl)-benzene

This material was prepared by a procedure similar to that outlined in the preparation of Example 87 (step 2), using commercially available 4-biphenylcarbonitrile instead of 4-chlorobiphenyl. The final product was recrystallized from ethyl acetate-hexanes to give an off-white solid (63%).

TLC (hexanes-ethyl acetate, 3:1): R$_f$=0.54; $^1$H NMR (CDCl$_3$): δ 4.48 (s, 2H), 7.71–7.80 (m, 6H), 8.11 (d, J=8.5 Hz, 2H); MS (EI) 299, 301 [M]$^+$ (C$_{15}$H$_{10}$ONBr, FW=300.16).

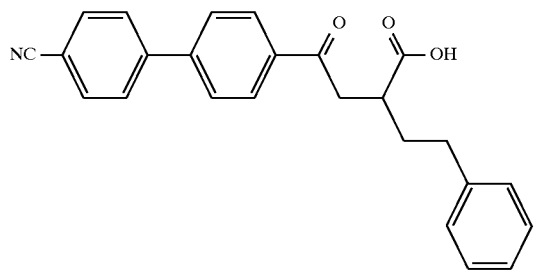

Example 101

Step 2—Preparation of Example 101

The title compound was synthesized by a sequence similar to that for producing Example 87 except that 1-(2-bromoethanone)-4-(4-cyanophenyl)-benzene and commercially available diethyl phenethyl malonate were used in lieu of the 4-chlorobiphenyl and phenylpropyl malonate respectively. The final product was recrystallized from ethanol/hexane to give off-white crystals (mp 181.0°–182.0° C.) which retained ethanol and hexane despite extensive drying in a vacuum oven.

TLC (chloroform-methanol, 19:1 with trace amount of acetic acid): R$_f$=0.53; $^1$H-NMR (DMSO-d$_6$): δ 1.80–1.95 (m, 2H), 2.62–2.68 (m, 2H), 2.82–2.87 (m, 1H), 3.21 (dd, J=18.1, 9.6 Hz, 1H), 7.16–7.30 (m, 5H), 7.90 (d, J=8.5 Hz, 2H), 7.95 (s, 4H), 8.08 (d, J=8.7 Hz, 2H); $^{13}$C NMR (DMSO-d$_6$): δ 198.29, 176.33, 143.53, 142.72, 141.73, 136.41, 133.14, 128.93, 128.56, 128.51, 128.12, 127.60, 126.07, 118.93, 111.11, 40.09, 33.55, 32.82; MS (FAB-LSIMS) 384 [M+H]$^+$ (C$_{25}$H$_{21}$O$_3$N, FW=383.45); HRMS calcd. 383.1521, found 383.1531.

Example 102

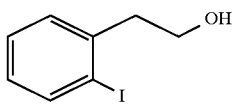

Step 1—Preparation of 2-(2-Iodophenyl)ethanol

A solution of o-iodophenylacetic acid (19.87 g, 75.83 mmol) in dry tetrahydrofuran (110 mL) was added dropwise over 41 min to a solution of borane in tetrahydrofuran (151 mL of 1M solution, ca. 151.0 mmol) which was cooled with an ice-water bath. The reaction was stirred at 0 to 10° C. for 2 hr 15 min. After the reaction mixture was cooled to 0° C., it was quenched by cautious addition (frothing!) of 10 (vol.) % acetic acid in methanol over 20 min. Stirring was continued for 25 min before the reaction was concentrated on a rotary evaporator. The residue was dissolved in ethyl acetate and washed with saturated ammonium chloride followed by saturated sodium bicarbonate. The organics were dried (Na$_2$SO$_4$) and concentrated to a yellow oil (18.07 g) which was used in the next step without purification.

TLC (hexane-ethyl acetate, 1:1): R$_f$=0.71; $^1$H-NMR (DMSO-d$_6$): δ 2.81 (t, J=7.2 Hz, 2H), 3.53 (dt, J=5.1 Hz, 7.5 Hz, 2H), 4.73 (t, J=5.4 Hz, 1H), 6.90–6.95 (m, 1H), 7.29 (dd, J=4.9 Hz, 0.8 Hz, 2H), 7.79 (d, J=7.7 Hz, 1H); MS (EI) 248 [M]$^+$ (C$_8$H$_9$IO, FW=248.07).

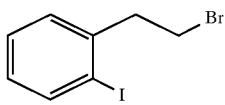

Step 2—Preparation of 2-(2-Iodophenyl)ethyl bromide

Neat 2-(2-iodophenyl)ethanol (17.75 g, 71.55 mmol) was treated dropwise with phosphorous tribromide (3.5 mL, 36.85 mmol) over 6 min while the reaction vessel was placed in a water bath to modulate the exothermic reaction. Stirring was continued for 15 min at room temperature and then for 2 hr while the mixture was heated in an oil bath at 100° C. The reaction was cooled to room temperature, diluted with ether and quenched carefully with water (frothing/exotherm!). The layers were separated, the organics were washed with saturated sodium bicarbonate and dried (Na$_2$SO$_4$). Concentration gave a yellow oil which was purified by Kugelrohr distillation (140° C./700 millitorr) to give a colorless oil (19.50 g, 62.71 mmol; 83% yield for above two steps).

TLC (hexane-ethyl acetate, 20:1): R$_f$=0.79; $^1$H-NMR (DMSO-d$_6$): δ 3.20 (t, J=7.5 Hz, 2H), 3.64 (t, J=7.5 Hz, 2H), 4.73 (t, J=5.4 Hz, 1H), 6.97–7.02 (m, 1H), 7.31–7.39 (m, 2H), 7.81–7.84 (m, 1H); MS (EI) 310, 312 [M]$^+$ (C$_8$H$_8$BrI FW=310.96).

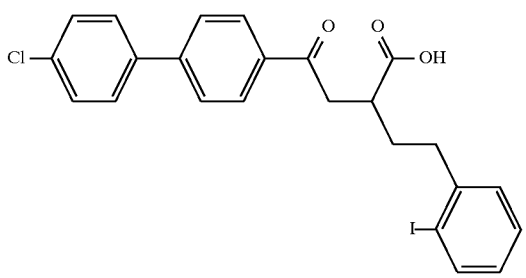

Example 102

Step 3—Preparation of Example 102

The title compound was synthesized by a sequence similar to that for Example 87 except that 2-(2-iodophenyl)ethyl bromide and commercially available diethyl phenethyl malonate were used in lieu of the 4-chlorobiphenyl and phenylpropyl malonate respectively. The final product was recrystallized from chloroform to give a fluffy, white solid (mp: melts/softens over a broad range starting at 50° C.; the bulk of the sample melts at 189°–190° C.).

TLC (chloroform-methanol, 20:1 with a trace of acetic acid): $R_f$=0.49; $^1$H-NMR (DMSO-d$_6$): δ 1.70–1.93 (m, 2H), 2.71–2.77 (m, 2H), 2.87–2.93 (m, 1H), 3.23 (dd, J=4.1 Hz, 18.0 Hz, 1H), 3.49 (dd, J=9.5 Hz, 18.3 Hz, 1H), 6.91–6.97 (m, 1H), 7.32 (d, J=3.9 Hz, 2H), 7.53–7.57 (m, 2H), 7.75–7.84 (m, 5H), 8.06 (d, J=8.5 Hz, 2H), 12.3 (br, 1H); MS (EI) 518 [M]$^+$ (C$_{24}$H$_{20}$ClIO$_3$, FW=518.78); Anal. C: calcd, 55.57; found, 55.34. H: calcd, 3.89; found, 3.79. I: calcd, 24.46; found, 24.76.

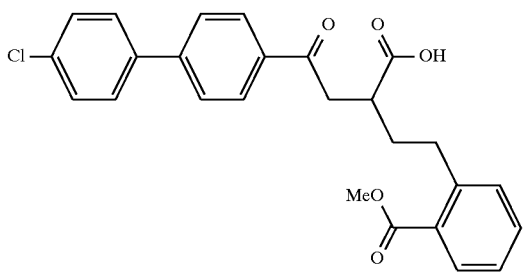

Example 103

Example 103

Acid Example 102 was dissolved in dimethylsulfoxide (1.5 mL) and methanol (1 mL). Triethylamine (0.21 mL, 1.51 mmol) was added followed by palladium(II) acetate (12.8 mg, 0.057 mmol) and 1,3-bis(diphenyl-phosphino) propane (23.0 mg, 0.056 mmol). Carbon monoxide was bubbled through the solution for three minutes. The orange solution was placed under a carbon monoxide atmosphere and was heated in an oil bath at 70°–75° C. The reaction was worked up after 20 hr 45 min of heating. The mixture was cooled to room temperature, diluted with ethyl acetate and washed with 10% HCl followed by water. The organics were dried (Na$_2$SO$_4$) and concentrated to a yellow solid. This material was purified by crystallization from hot hexane/ethyl acetate or from hot toluene/hexane to give the title compound as a tan solid (109.6 mg, 0.243 mmol, 50%).

MP 129°–130° C., TLC (chloroform-methanol, 10:1): $R_f$=0.16; $^1$H-NMR (DMSO-d$_6$): δ 1.70–1.93 (m, 2H), 2.80–3.05 (m, 3H), 3.19 (dd, J=3.9 Hz, 18.0 Hz, 1H), 3.47 (dd, J=9.5 Hz, 18.0 Hz, 1H), 3.80 (s, 3H), 7.28–7.36 (m, 2H), 7.47–7.57 (m, 3H), 7.74–7.84 (m, 5H), 8.05 (d, J=8.5 Hz, 2H), 12.2 (br, 1H); MS (FAB-LSIMS) 451 [M+H]$^+$ (C$_{26}$H$_{23}$ClO$_5$, FW=450.92); Anal. (for C$_{26}$H$_{23}$ClO$_5$·0.3 H$_2$O) C: calcd, 68.44; found, 68.58. H: calcd, 5.21; found, 5.25. Cl: calcd, 7.77; found, 7.91.

Example 104, Example 105 and Example 106

The general methods of Example 87, steps 3 and 4 were used to prepare Example 104, Example 105, and Example 106 using commercially available 2-arylmalonates rather than ethyl 2-carboethoxy-5-phenylpentanoate as indicated below.

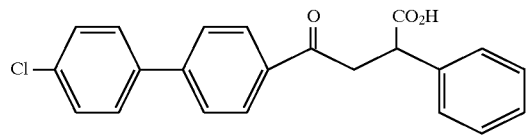

Example 104

Example 104 (Reference With Respect to Composition)

From diethyl phenylmalonate: TLC (3:1 methylene chloride to methanol +2 drops acetic acid) $R_f$=0.77; $^1$H NMR (MeOD) δ 8.03 (d, J=8.8 Hz, 2H), 7.69 (d, J=8.5 Hz, 2H), 7.62 (d, J=8.8 Hz, 2H), 7.43 (d, J=6.6 Hz, 2H), 7.28 (m, 5H), 4.19 (dd, J=10.3, 4.1 Hz, 1 H, CH$_2$CO), 3.91 (dd, J=14.0, 10.3 Hz, 1 H, CH$_2$CO), 3.27 (dd, J=14.0, 4.1 Hz, 2 H, CHCOOH).

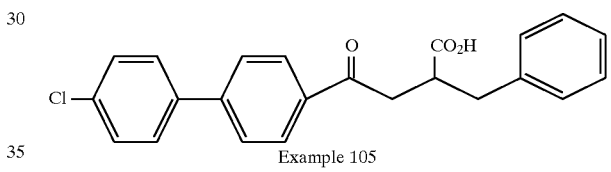

Example 105

Example 105

From diethyl benzylmalonate: MP 167°–171° C.; $^1$H NMR (DMSO-d$_6$) δ 12.28 (bs, 1 H, COOH), 7.98 (d, J=8.5 Hz, 2H), 7.88 (d, J=8.5 Hz, 2H), 7.74 (d, J=8.8 Hz, 2H), 7.53 (d, J=8.8 Hz, 2H), 7.24 (m, 5H), 3.32 (dd, J=17.8, 9.0 Hz, 2 H, CH$_2$CO), 3.14 (m, 1 H, CHCOOH), 2.99 (dd, J=17.7, 4.1 Hz, 2 H, CH$_2$Ph), 2.81 (m, 1 H, CH$_2$CO); $^{13}$C NMR (DMSO-d$_6$) δ 198.87, 176.49, 144.30, 140.05, 138.75, 136.53, 134.43, 130.15, 130.11, 129.88, 129.67, 129.43, 127.99, 127.44, 42.96, 39.76, 38.20; Anal. C: calcd, 72.03; found, 71.87. H: calcd, 5.22; found, 5.01.

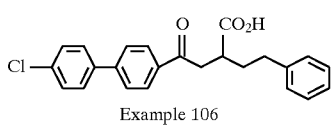

Example 106

Example 106

From diethyl 2-phenethylmalonate. MP 179° C.; $^1$H NMR (DMSO-d$_6$) δ 12.29 (bs, 1 H, COOH), 8.05 (d, J=8.5 Hz, 2H), 7.81 (d, J=8.1 Hz, 2H), 7.76 (d, J=8.5 Hz, 2H), 7.53 (d, J=8.1 Hz, 2H), 7.21 (m, 5H), 3.45 (m, 2 H, CH$_2$CO), 2.85 (m, 1 H, CHCOOH), 2.66 (m, 2 H, CH$_2$Ph), 1.87 (m, 2 H, CH$_2$CH$_2$Ph); $^{13}$C NMR (DMSO-d$_6$) δ 199.13, 177.25, 144.28, 142.64, 138.79, 136.63, 134.45, 130.15, 129.88, 129.80, 129.45, 129.41, 127.96, 126.97, 40.60, 40.55, 34.47, 33.72; Anal. C: calcd, 73.37; found, 73.68. H: calcd, 5.39; found, 5.43.

Example 107

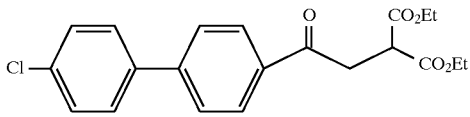

Step 1

Diethylmalonate (2.46 mL, 16.2 mmol) was added dropwise over 20 min to a suspension of sodium hydride (0.43 g, 17.8 mmol) in THF (24 mL) at 0° C. The solution was allowed to stir for 20 min then 4(4'-chlorophenyl)-α-bromoacetophenone (5.0 g, 16.2 mmol) in THF (24 mL) was added over 20 min. The reaction was warmed to rt and stirred a further 12 h then poured into EtOAc (250 mL) and water (250 mL). The phases were separated and the aqueous phase was extracted with EtOAc (2×100 mL). The combined organic phases were washed with 1M phosphoric acid (2×200 mL), saturated sodium bicarbonate (2×200 mL), and brine (100 mL) then dried (MgSO$_4$), filtered, and concentrated in vacuo. The resulting oil was purified by flash chromatography on silica gel using a gradient of ethyl acetate/ hexane (10% to 50% ethyl acetate) as the eluent to afford a crystalline solid which was recrystallized using hexane and ethyl acetate to afford ethyl 2-carboethoxy-4[4'-(4"-chlorophenyl)phenyl]-4-oxobutanoate (1.24 g, 20%).

$^1$H NMR (CDCl$_3$) δ 8.06 (d, J=8.1 Hz, 2H), 7.66 (d, J=8.5 Hz, 2H), 7.56 (d, J=8.5 Hz, 2H), 7.45 (d, J=8.1 Hz, 2H), 4.26 (q, J=7.4 Hz, 4 H, CH$_2$CH$_3$), 4.09 (t, J=7.0 Hz, 1 H, CH(CO$_2$Et)2, 3.66 (d, J=7.0 Hz, 2 H, CH$_2$CO), 1.31 (t, J=7.0 Hz, 6 H, CH$_3$); $^{13}$C NMR (CDCl$_3$) δ 196.72, 169.72, 145.53, 138.87, 135.71, 135.21, 129.83, 129.51, 129.20, 127.81, 62.47, 47.90, 38.49, 14.71.

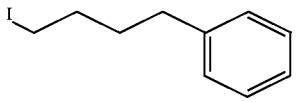

Step 2—Preparation of 4-phenyl-1-iodobutane

Sodium iodide (8.9 g, 59.2 mol) and 4-phenyl-1-chlorobutane (5.0 g, 29.6 mol) were added to acetone (29.6 mL) at rt. The mixture was heated to 70° C. for 12 h. The resulting solution was gravity filtered to remove salts. The solvent was removed under reduced pressure and excess salts were dissolved in water (100 mL). Hexane (100 mL) was added to the aqueous mixture. The phases were separated and the organic phase was washed with saturated sodium bisulfite solution (3×50 mL), treated with decolorizing carbon, and gravity filtered. The organic layer was then dried (MgSO$_4$), filtered, and concentrated in vacuo to afford 4-phenyl-1 -iodobutane (6.94 g, 90%).

The general method of the preparation of 4-phenyl-1-iodobutane was used to prepare 5-phenyl-1-iodopentane, 6-phenyl-1-iodohexane, and 4-(iodomethyl)biphenyl using commercially available 5-phenyl-1 -chloropentane, 6-phenyl-1 -chlorohexane, and 4-(chloromethyl)biphenyl.

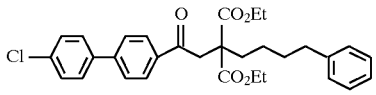

Step 3—Preparation of 1-[4'-(4"-chlorophenyl)phenyl]-3,3-dicarboethoxy-1-oxo-7-phenylheptane Ethyl 2-carboethoxy-4[4'-(4"-chlorophenyl) phenyl]-4-oxobutanoate (0.40 g, 1.02 mmol) was added in one portion at rt to a solution of sodium ethoxide (0.08 g, 1.12 mmol) in DME (1 mL). After 15 min, 4-phenyl-1-iodobutane (0.24 g, 0.93 mmol) in DME (3 mL) was added. The resulting solution was stirred for 18 h. The solvent was concentrated in vacuo and the resulting oil dissolved in CH$_2$Cl$_2$ (100 mL) and washed with water (100 mL). The phases were separated and the aqueous phase was extracted with CH$_2$Cl$_2$ (2×50 mL). The combined organic phases were dried (MgSO$_4$), filtered, and concentrated in vacuo. The resulting oil was purified by flash chromatography on silica gel using a gradient of ethyl acetate/hexane (10% to 25% ethyl acetate) as the eluent to afford a crystalline solid which was recrystallized with hexane and ethyl acetate to afford 1-[4'-(4"-chlorophenyl)phenyl]-3,3-dicarboethoxy-1-oxo-7-phenylheptane (0.272 g, 28%).

MP 67°–69° C.; $^1$H NMR (CDCl$_3$) δ 8.05 (d, J=8.1 Hz, 2H), 7.66 (d, J=8.5 Hz, 2H), 7.57 (d, J=8.5 Hz, 2H), 7.45 (d, J=8.5 Hz, 2H), 7.16 (m, 5H), 4.21 (q, J=7.0 Hz, 4 H, CH$_2$CH$_3$), 3.70 (s, 2 H, CH$_2$CO), 2.58 (t, J=7.7 Hz, 2 H, CH$_2$Ph), 2.16 (t, J=8.5 Hz, 2 H, CH$_2$C), 1.61 (m, 2H), 1.26 (m, 8H); $^{13}$C NMR (CDCl$_3$) δ 196.88, 171.64, 145.37, 142.82, 138.91, 136.26, 135.21, 129.85, 129.41, 129.18, 129.01, 128.89, 127.78, 126.33, 62.20, 56.11, 41.93, 36.02, 33.43, 32.01, 24.83, 14.67; Anal. C: calcd, 71.46; found, 71.00. H: calcd, 6.38; found,

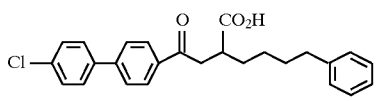

Example 107

Steps 4 and 5—Preparation of Example 107

The diester from step 3 was converted to the monoacid following the general method for Example 40 (steps 4 and 5).

Example 107

MP 127°–130° C.; $^1$H NMR (DMSO-d$_6$) δ 12.12 (bs, 1H, COOH), 8.03 (d, J=7.3 Hz, 2H), 7.81 (d, J=7.3 Hz, 2H), 7.77 (d, J=7.3 Hz; 2H), 7.54 (d, J=7.3 Hz, 2H), 7.20 (m, 5H), 3.35 (dd, J=19.1, 10.3 Hz, 1 H, CH$_2$CO), 3.08 (dd, J=19.1, 4.4 Hz, 1 H, CH$_2$CO), 2.81 (m, 1 H, CHCOOH), 2.55 (t, J=7.3 Hz, 2 H, CH$_2$Ph), 1.56 (m, 4H), 1.35 (m, 2 H, CH$_2$CH$_2$CH); $^{13}$C NMR (DMSO-d$_6$) δ 199.16, 177.34, 144.23, 143.25, 138.77, 136.60, 134.41, 130.17, 129.88, 129.75, 129.36, 129.31, 127.97, 126.73, 40.03, 39.74, 36.07, 32.38, 32.04, 27.26; MS (FAB-LSIMS) 421 (M+H)$^+$ (C$_{26}$H$_{25}$O$_3$Cl, FW=420).

Example 108, Example 109, and Example 110

The general method of Example 107 was improved in Step 1 as shown below to prepare Example 108, Example 109, and Example 110. The other steps were not modified. The indicated aryl halides were used instead of 4-phenyl-1-iodobutane as described below.

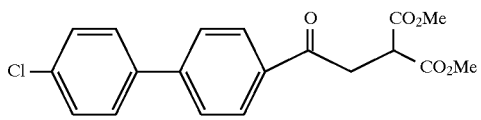

Step 1—Preparation of Methyl 2-carbomethoxy-4[4'-(4"-chloro phenyl)phenyl]-4-oxobutanoate Dimethyl malonate (5.7 mL, 50.0 mmol) was added in one portion to a solution of sodium methoxide (6.6 g, 50.0 mmol) in DME (45 mL) at rt and stirred for 15 min. In a separate reaction vessel, 4(4'-chlorophenyl)-α-bromoacetophenone (14.0 g, 45.0 mmol) was dissolved in DME (136 mL) along with sodium iodide (6.7 g, 45.0 mmol). The NaI solution was allowed to stir for 15 min at rt. The sodium dimethylmalonate solution was cannulated dropwise into the 4(4'-chlorophenyl)-α-bromoacetophenone solution; stirring continued 1 hr at rt. The solvent was removed in vacuo and the resulting oil dissolved in 1:1 methylene chloride:diethyl ether (700 mL). The organic phase was washed with water (250 mL), and saturated sodium chloride solution (250 mL). The organic layer was dried (MgSO$_4$), filtered, and concentrated in vacuo. The resulting oil was recrystallized using 4:1 chloroform:methanol with hexane to precipitate the methyl 2-carbomethoxy-4[4'-(4"-chloro phenyl)phenyl]-4-oxobutanoate (10.43 g, 64%).

$^1$H NMR (DMSO) δ 8.06 (d, J=8.1 Hz, 2H), 7.66 (d, J=8.5 Hz, 2H), 7.56 (d, J=8.5 Hz, 2H), 7.45 (d, J=8.1 Hz, 2H), 3.95 (t, J=7.0 Hz, 1 H, CH(CO$_2$Me)$_2$), 3.70 (s, J=7.0 Hz, 6 H, Me), 3.66 (s, 2 H, CH$_2$CO); $^{13}$C NMR (CDCl$_3$) δ 196.22, 169.03, 143.56, 137.58, 134.75, 133.44, 129.09, 128.84, 128.74, 126.98, 52.60, 46.59, 37.59.

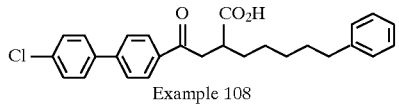

Example 108

Example 108

From 5-phenyl-1-iodopentane and the above Methyl 2-carbomethoxy-4[4'-(4"-chloro phenyl)phenyl]-4-oxobutanoate.

MP 131°–132° C.; $^1$H NMR (DMSO-d$_6$) δ 12.14 (s, 1 H, COOH), 8.06 (d, J=8.1 Hz, 2H), 7.83 (d, J=8.1 Hz, 2H), 7.79 (d, J=8.5 Hz, 2H), 7.57 (d, J=8.5 Hz, 2H), 7.19 (m, 5H), 3.38 (dd, J=18.4, 9.6 Hz, 1 H, CH$_2$CO), 3.14 (dd, J=19.1, 4.4 Hz, 1 H, CH$_2$CO), 2.84 (m, 1 H, CHCOOH), 2.56 (t, J=7.4 Hz, 2 H, CH$_2$Ph), 1.57 (m, 4 H, CH$_2$), 1.33 (m, 4 H, CH$_2$); $^{13}$C NMR (DMSO-d$_6$) δ 198.10, 176.29, 143.14, 137.68, 136.60, 135.53, 133.33, 129.06, 128.79, 128.79, 128.68, 128.26, 128.21, 126.87, 40.32, 40.05, 35.06, 31.42, 30.84, 28.56, 26.29; Anal. C: calcd, 74.56; found, 74.25. H: calcd, 6.26; found, 6.15.

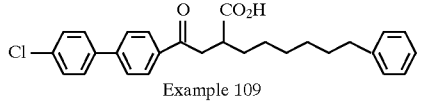

Example 109

Example 109

From 6-phenyl-1-iodohexane and the above Methyl 2-carbomethoxy-4[4'-(4"-chloro phenyl)phenyl]-4-oxobutanoate.

MP 104°–105° C.; $^1$H NMR (DMSO-d$_6$) δ 12.10 (bs, 1 H, COOH), 8.06 (d, J=8.5 Hz, 2H), 7.82 (d, J=8.5 Hz, 2H), 7.78 (d, J=8.5 Hz, 2H), 7.56 (d, J=8.5 Hz, 2H), 7.18 (m, 5H), 3.37 (m, 1 H, CH$_2$CO), 3.13 (dd, J=4.4, 2.2 Hz, 1 H, CH$_2$CO), 2.82 (m, 1 H, CHCOOH), 2.55 (t, J=7.4 Hz, 2 H, CH$_2$Ph), 1.57 (m, 4 H, CH$_2$), 1.24 (m, 6 H, CH$_2$); $^{13}$C NMR (DMSO-d$_6$) δ 198.11, 176.30, 143.14, 142.30, 137.68, 136.60, 135.53, 129.06, 128.79, 128.69, 128.26, 128.21, 126.87, 125.58, 40.32, 40.05, 35.12, 35.06, 30.94, 28.77, 28.50, 26.43; Anal. C: calcd, 74.90; found, 74.77. H: calcd, 6.51; found, 6.41.

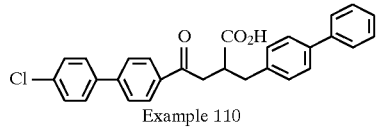

Example 110

Example 110

From 4-(iodomethyl)biphenyl and the above Methyl 2-carbomethoxy-4[4'-(4"-chloro phenyl)phenyl]-4-oxobutanoate.

MP 228°–230° C.; $^1$H NMR (DMSO-d$_6$) δ 12.32 (s, 1 H, COOH), 8.02 (d, J=8.5 Hz, 2H), 7.78 (m, 4H), 7.66 (m, 6H), 7.44 (m, 2H), 7.32 (m, 3H), 3.44 (dd, J=18.0, 9.2 Hz, 1 H, CH$_2$CO), 3.20 (m, 1 H, CHCOOH), 3.07 (m, 2H, CH$_2$; CO, CH$_2$-Biphenyl), 2.90 (m, 1 H, CH$_2$-Biphenyl); $^{13}$C NMR (DMSO-d$_6$) δ 197.80, 175.43, 143.18, 140.94, 139.89, 138.26, 138.18, 137.64, 135.45, 129.63, 129.05, 128.89, 128.77, 128.60, 127.26, 126.88, 126.59, 126.50, 41.86, 38.94, 38.66; Anal. C: calcd, 76.56; found, 76.11. H: calcd, 5.10; found, 4.88.

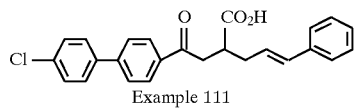

Example 111

Example 111

The general method of Bay 13-6465 was used to prepare Example 111 using commercially available cinnamyl bromide with 0.9 eq of NaI, instead of 5-phenyl-1-iodopentane in Step 3.

MP 171°–172° C.; $^1$H NMR (DMSO-d$_6$) δ 12.25 (s, 1 H, COOH), 8.06 (d, J=8.5 Hz, 2H), 7.82 (d, J=8.5 Hz, 2H), 7.78 (d, J=8.5 Hz, 2H), 7.56 (d, J=8.5 Hz, 2H), 7.40 (d, J=5.9 Hz, 2H), 7.30 (d, J=5.9 Hz, 1H), 7.21 (d, J=5.9 Hz, 2H), 6.47 (d, J=16.2 Hz, 1 H, CHCH$_2$), 6.33 (m, 1 H, CHPh), 3.48 (dd, J=18.4, 8.5 Hz, 1 H, CH$_2$CO), 3.18 (dd, J=18.4, 4.4 Hz, 1 H, CH$_2$CO), 3.05 (m, 1 H, CHCOOH), 2.55 (m, 2 H, CH$_2$); $^{13}$C NMR (DMSO-d$_6$) δ 197.93, 175.51, 143.15, 137.68, 135.51, 133.31, 131.68, 129.05, 128.77, 128.64, 128.50, 127.27, 127.17, 126.87, 126.01, 40.13, 39.11, 34.83; Anal. C: calcd, 73.37; found, 72.94. H: calcd, 5.39; found, 5.08.

Example 112 and Example 113

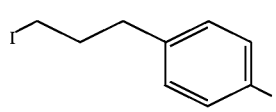

Preparation of 3-(p-methylphenyl)-1-iodopropane

Potassium iodide (0.90 g, 5.4 mmol) and 3-(p-methylphenyl)propan-1-ol (0.4 g, 2.7 mmol) was added to 85% phosphoric acid (5.4 mL) at rt. The solution was heated to 120° C. for 3 h, during which time an oil separated from the acid layer. The mixture was cooled to rt and poured into 150 mL of water and 150 mL of diethyl ether. The organic layer was separated, decolorized with saturated sodium bisulfite solution (100 mL), and washed with saturated sodium chloride solution (100 mL). The organic layer was then dried (MgSO$_4$), filtered, and concentrated in vacuo to afford 3-(4-methylphenyl)-1-iodopropane (0.48 g, 68%).

The general method of the preparation of 3-(4-methylphenyl)-1-iodopropane was used to prepare 3-(4-chlorophenyl)-1-iodopropane using 3-(4-chlorophenyl) propan-1-ol, 3-(4-hydroxyphenyl)-1-iodopropane, 4-hydroxyphenethyl iodide, and 3-hydroxyphenethyl iodide using commercially available 3-(4-hydroxyphenyl)-1-propanol, 4-hydroxyphenethyl alcohol, and 3-hydroxyphenethyl alcohol respectively.

The general method of Example 108 was used to prepare Example 112 and Example 113 using the aryl halides instead of 5-phenyl-1-iodopentane, as indicated below.

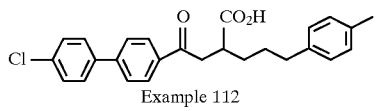

Example 112

Example 112

From 3-(4-methylphenyl)-1-iodopropane: MP 158°–159° C.; $^1$H NMR (DMSO-d$_6$) δ 12.40 (s, 1 H, COOH), 8.30 (d, J=8.1 Hz, 2H), 8.07 (d, J=8.1 Hz, 2H), 8.03 (d, J=8.5 Hz, 2H), 7.81 (d, J=8.5 Hz, 2H), 7.32 (m, 4H), 3.60 (dd, J=13.2, 9.9 Hz, 1 H, CH$_2$CO), 3.39 (dd, J=19.1, 4.1 Hz, 1 H, CH$_2$CO), 3.04 (m, 1 H, CHCOOH), 2.77 (m, 2 H, CH$_2$Ph), 2.50 (s, 3 H, CH$_3$), 1.86 (m, 4 H, CH$_2$); $^{13}$C NMR (DMSO-d$_6$) δ 198.04, 176.24, 143.13, 138.76, 137.67, 135.49, 134.53, 133.31, 129.05, 128.81, 128.78, 128.68, 126.16, 126.84, 40.32, 40.05, 34.59, 31.11, 28.58, 20.61; Anal. C: calcd, 74.19; found, 73.89. H: calcd, 5.99; found, 5.95.

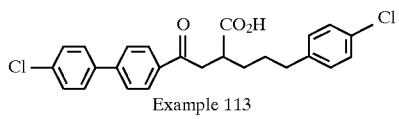

Example 113

Example 113

From 3-4-chlorophenyl-1-iodopropane: MP 148°–149° C.; $^1$H NMR (DMSO-d$_6$) δ 12.16 (s, 1 H, COOH), 8.06 (d, J=8.5 Hz, 2H), 7.80 (d, J=8.1 Hz, 2H), 7.78 (d, J=8.5 Hz, 2H), 7.55 (d, J=8.4 Hz, 2H), 7.32 (d, J=8.1 Hz, 2H), 7.23 (d, J=8.5, 2H), 3.39 (dd, J=18.0, 9.6 Hz, 1 H, CH$_2$CO), 3.13 (dd, J=18.4, 4.4 Hz, 1 H, CH$_2$CO), 2.86 (m, 1 H, CHCOOH), 2.59 (m, 2 H, CH$_2$Ph), 1.61 (m, 4 H, CH$_2$); $^{13}$C NMR (DMSO-d$_6$) δ 198.04, 176.22, 143.13, 140.94, 137.68, 135.48, 133.31, 130.29, 130.18, 129.07, 128.79, 128.68, 128.17, 126.85, 40.32, 34.59, 34.23, 31.00, 28.33; Anal. C: cald, 68.04; found, 67.75. H: cald, 5.02; found, 4.95.

Example 114, Example 115, and Example 116

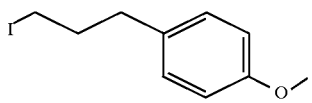

Anhydrous potassium carbonate (4.14 g, 30.0 mmol), iodomethane (3.74 mL, 60.0 mmol), and 3-(4-hydroxyphenyl)-1-iodopropane (1.58 g, 6.0 mmol) were added to acetone (25 mL) at rt. The mixture was heated to 70° C. for 8 h. The resulting solution was gravity filtered to remove salts and the filtrate was concentrated in vacuo to afford 3-(4-methoxyphenyl)-1-iodopropane (1.22 g, 73%).

The general method of the preparation of 3-(4-methoxyphenyl)-1-iodopropane was used to prepare 4-methoxyphenethyl iodide, and 3-methoxyphenethyl iodide from 4-hydroxyphenethyl iodide and 3-hydroxyphenethyl iodide.

The general method of Example 108 was used to prepare Example 114, Example 115, and Example 116 using, as previously stated, 3-(4-methoxyphenyl)-1-iodopropane, 4-methoxyphenethyl iodide, and 3-methoxyphenethyl iodide instead of 5-phenyl-1-Iodopentane, as indicated below.

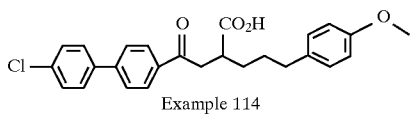

Example 114

Example 114

From 3-(4-methoxyphenyl)-1-iodopropane: MP 125°–126° C.; 1 H NMR (DMSO-d$_6$) δ 12.05 (bs, 1 H, COOH), 8.06 (d, J=8.5 Hz, 2H), 7.80 (m, 4H), 7.56 (d, J=8.5 Hz, 2H), 7.10 (d, J=8.5 Hz, 2H), 6.82 (d, J=8.1, 2H), 3.68 (s, 3 H, CH$_3$), 3.39 (m, 1 H, CH$_2$CO), 3.14 (m, 1 H, CH$_2$CO), 2.80 (m, 1 H, CHCOOH), 2.60 (m, 2 H, CH$_2$Ph), 1.59 (m, 4 H, CH$_2$); $^{13}$C NMR (DMSO-d$_6$) δ 198.06, 176.25, 157.35, 143.14, 135.51, 133.75, 129.19, 129.06, 128.79, 128.69, 128.62, 126.90, 126.85, 113.65, 54.93, 40.34, 38.95, 38.66, 34.14, 28.77; Anal. C: calcd, 71.47; found, 71.27. H: calcd, 5.77; found, 5.55.

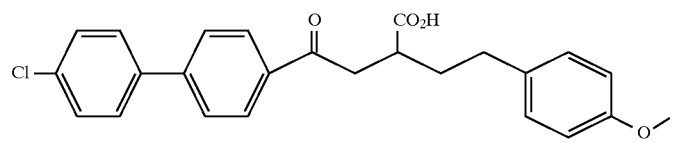

Example 115

Example 115

From 4-methoxyphenethyl iodide: MP 127°–129° C.; $^1$H NMR (DMSO-d$_6$) δ 8.81 (bs, 1 H, COOH), 7.87 (d, J=8.5 Hz, 2H), 7.50 (d, 8.5 Hz, 2H), 7.42 (d, J=8.5 Hz, 2H), 7.29 (d, J=8.5 Hz, 2H), 6.98 (d, J=8.5, 2H), 6.66 (d, J=8.5 Hz, 2H), 3.62 (s, 3 H, CH$_3$), 3.37 (m, 1 H, CHCOOH), 2.93 (m, 2 H, CH$_2$CO), 2.53 (m, 2 H, CH$_2$Ph), 2.05 (m, 1 H, CHCH), 1.90 (m, 1 H, CHCH); $^{13}$C NMR (DMSO-d$_6$) δ 197.43, 176.88, 157.44, 143.99, 137.90, 135.33, 133.21, 128.97, 128.76, 128.36, 128.16, 126.85, 126.66, 113.43, 54.86, 32.14, 29.29, 29.25, 24.40; M S (FAB-LSIMS) 423 (M+H)$^+$ (C$_{25}$H$_{23}$O$_4$Cl, FW=422).

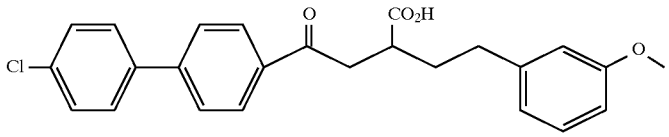

Example 116

Example 116

From 3-methoxyphenethyl iodide. MP 155°–156° C.; $^1$H NMR (DMSO-d$_6$) δ COOH (not seen), 8.08 (d, J=8.1 Hz, 2H), 7.81 (m, 4H), 7.57 (d, 8.5 Hz, 2H), 7.20 (m, 1H), 6.80 (m, 3H), 3.73 (s, 3H, CH3), 3.45 (m, 1 H, CHCOOH), 3.10 (m, 1 H, CH$_2$CO), 2.90 (m, 1 H, CH$_2$CO), 2.65 (m, 2 H, CH$_2$Ph), 1.90 (m, 2 H, CH$_2$); $^{13}$C NMR (DMSO-d$_6$) δ 198.06, 176.12, 159.29, 143.16, 143.11, 137.68, 129.35, 129.07, 128.81, 128.71, 126.87, 120.54, 113.95, 111.29, 54.88, 38.47, 38.31, 33.17, 32.64; MS (FAB-LSIMS) 423 (M+H)$^+$ (C$_{25}$H$_{23}$O$_4$C, FW=422).

Example 117

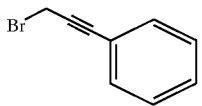

1-phenyl-3-bromo-1-propyn

Phosphorous tribromide (2.62 mL, 27.6 mmol) was added to a solution of 3-phenyl-2-propyn-1-ol (10.0 g, 76 mmol) and pyridine (0.14 mL, 1.77 mmol) in diethyl ether (22 mL) at a rate to maintain reflux. After addition, the mixture was heated at 40° C. for 2 h. The mixture was cooled and poured onto ice. The organic layer was separated and diluted with diethyl ether (100 mL), washed with saturated sodium bicarbonate (2×50 mL) and saturated sodium chloride (50 mL). The organic layer was dried (MgSO$_4$), filtered and concentrated in vacuo to afford 1-phenyl-3-bromo-1-propyn (13.4 g, 90%).

The general method of Example 108 was used to prepare Example 117 using, as stated, 1-phenyl-3-bromo-1-propyn with 0.9 eq of NaI, instead of 5-phenyl-1-iodopentane in Step 3, as indicated below.

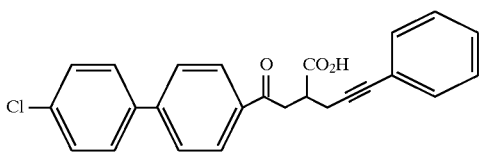

Example 117

Example 117

From 1-phenyl-3-bromo-1-propyn: MP 141°–142° C.; $^1$H NMR (DMSO-d$_6$) δ 12.50 (s, 1 H, COOH), 8.08 (d, J=8.4 Hz, 2H), 7.82 (d, J=8.4 Hz, 2H), 7.78 (d, J=8.4 Hz, 2H), 7.58 (d, J=8.4 Hz, 2H), 7.34 (m, 5H), 3.59 (dd, J=19.0, 10.3 Hz, 1 H, CH$_2$CO), 3.30 (m, 1 H, CH$_2$CO), 3.16 (m, 1 H, CHCOOH), 2.81 (d, J=6.2 Hz, 2 H, CH$_2$CH); $^{13}$C NMR (DMSO-d$_6$) δ 197.59, 174.46, 143.26, 137.65, 135.42, 133.36, 131.29, 129.07, 128.78, 128.70, 128.54, 128.16, 126.95, 122.78, 87.52, 82.25, 40.34, 38.95, 22.40; MS (FAB-HRMS) 403.1101 (M+H)$^+$ (C$_{25}$H$_{20}$O$_3$Cl, FW=403.1112).

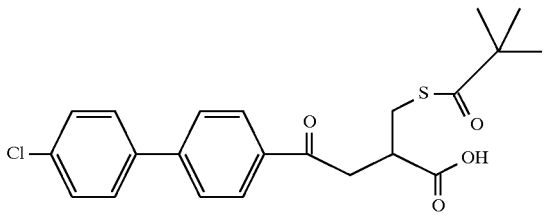

Example 118

Example 118

Methods similar to those of Chem. Pharm. Bull. 36(6), 2050–2060, (1988) were used to prepare Example 118 as follows:

In a 250 mL round bottom flask, 9.84 g (32.77 mmol) of Example 30 was dissolved in 48 mL of DMF. The flask was placed under Ar. Thiopivalic acid (8.4 mL, 66.09 mmol, 2 eq) was added to the flask via syringe followed by addition of 3.2 mL of a 1.93M solution of K$_2$CO$_3$ in H$_2$O. The mixture was then stirred at 25° C. for 23 hours.

The reaction was diluted with 200 mL H2O and acidified with 10% HCl to pH=1. The mixture was extracted with ethyl acetate (100 mL, ×3). The combined organic extracts were washed with water (100 mL, ×4), dried over magnesium sulfate and concentrated in vacuo to yield crude product (13.16 g, 96% crude).

The crude material was dissolved in ethanol, treated with activated carbon, filtered and concentrated in vacuo. The residue was recrystallized from ethyl acetate and hexane to yield 11.2 g (81%) of white crystals. (Example 118).

MP: 119°–120° C.; TLC (methylene chloride-5%methanol) R$_f$ 0.280; $^1$H NMR (CDCl$_3$) δ 8.03 (d, J=8.6 Hz, 2H), 7.65 (d, J=8.84 Hz, 2H), 7.56 (d, J=8.84 Hz, 2H), 7.44 (d, J=8.6 Hz, 2H), 3.51 (m, 1H), 3.28 (m, 4H), 1.24 (s, 9H); 13C NMR (CDCl$_3$) δ 206.75, 197.48, 179.28, 145.42, 138.87, 135.89, 135.18, 129.81, 129.46, 129.17, 127.78, 47.22, 41.15, 39.49, 29.91, 27.97; MS (FAB-LSIMS) 419 [M+H]$^+$ (C$_{22}$H$_{23}$SO$_4$Cl, FW=418.94); Anal. C: calcd, 63.07; found, 62.96 . H: calcd, 5.53; found, 5.47 . Cl: calcd, 8.46; found, 8.50 . S: calcd, 7.65; found 7.37.

Example 119 and Example 120

Example 118 (1.38 g injected in several portions) was separated by chromatography on a Chiralcel® OJ HPLC column (2 cm×25 cm) using 9 ml/min. 85% hexane/15% (0.2% trifluoroacetic acid in ethanol) and peak detection by UV at 320 nM. The best fractions of each isomer were combined and each material was then recrystallized from ethyl acetate/hexane to yield 520 mg of pure Example 119 (first to elute) and 504 mg of pure Example 120 (second to elute).

Example 119

MP 117°–118° C.; [α]D +26.4 (CHCl$_3$); $^1$H NMR essentially identical to that of Example 118.

Example 120

MP 117°–118° C.; [α]D –27.0 (CHCl$_3$); $^1$H NMR essentially identical to that of Example 118.

OTHER THIOMICHAEL PRODUCTS

The following thioMichael material was made by a similar method to that used for Example 118 except that the indicated thiol-containing compounds was used instead of thiopivalic acid.

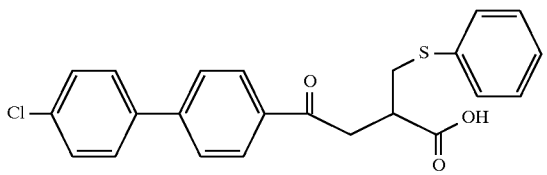

Example 121

Example 121

From thiophenol: MP: 125°–126° C.; TLC (methylene chloride-5%methanol) R$_f$ 0.254; $^1$H NMR (CDCL$_3$) δ 8.01 (d, J=8.84 Hz, 2H), 7.64 (d, J=8.60 Hz, 2H), 7.56 (d, J=8.84 Hz, 2H) 7.43 (m, 4H), 7.25 (m, 3H), 3.52 (m, 3H), 3.33 (m, 1H), 3.19 (m, 1H); $^{13}$C NMR (CDCL$_3$) δ 197.71, 179.25, 145.46, 135.84, 135.48, 135.20, 130.64, 129.83, 129.44, 129.17, 127.78, 127.44, 104.99, 40.83, 39.25, 35.68; MS (FAB-LSIMS) 411 [M+H]$^+$ (C$_{23}$H$_{19}$SO$_3$Cl, FW=410.92); Anal. C: calcd, 67.22; found, 66.94 . H: calcd, 4.66; found, 4.70. Cl: calcd, 8.63; found, 8.81. S: calcd, 7.80; found 7.64

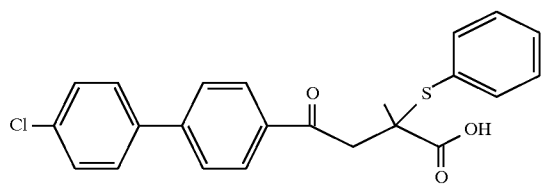

Example 122

Example 122

Mother liquors from crystallization of crude Example 121 were chromatographed on silica gel to yield a purified sample of the isomeric product Example 122.

$^1$H NMR (DMSO-d$_6$) δ 12.5 (bs, 1H), 7.4–8.0 (m, 8H), 3.5 (d, J=2.9Hz, 2H), 1.48 (s, 3H) ; $^{13}$C NMR (CDCl$_3$) δ 197.19, 174.37, 144.46, 138.66, 138.26, 136.40, 134.51, 131.09, 130.90, 130.15, 129.98, 129.86, 129.67, 128.00, 52.46, 47.63, 23.60; MS (FAB-LSIMS) 411[M+H]$^+$ (C$_{23}$H$_{19}$SO$_3$Cl, FW=410.92); Anal. C: calcd, 67.23; found, 66.92. H: calcd, 4.66; found, 4.66. Cl: calcd, 8.63; found, 8.72. S: calcd, 7.80; found 7.69

RESOLUTION OF EXAMPLE 121

Example 123

A solution of Example 121 (24 g, 0.058 mol) and (+)-cinchonine (10 g, 0.034 mol) in acetone (150 mL) was allowed to stand at room temperature for 46 h. The white precipitate was removed by filtration, suspended in ethyl acetate and washed successively with 2N HCl (150 mL) and sat. aq. NaCl (100 mL). The organic layer was dried over MgSO$_4$, filtered and concentrated under reduced pressure to give a white solid (8.4 g, isomer ratio 95.3:4.7 (Example 123:Example 124)). A second iteration (Cinchonine, 6.75 g; acetone, 140 mL) followed by simple crystallization with an ethyl acetate/hexanes mixture (1:2) provided Example 123 (6.67 g, 56% theoretical; isomer ratio 99.3:0.7) as a white crystalline solid.

HPLC conditions for Example 121 (Example 123 and Example 124)

column: Chiralcel® AD analytical column flow rate: 1 mL / min solvent system: 10% (ethanol; 1% water; 0.2% TFA) in hexanes detection: I=288 concentration: 0.5 mg / mL injection amount: 4 μL 39.7 min. (Example 123); 44.6 min. (Example 124)

Example 123

MP 110°–110.5° C., [α]D +84.80 (c 1.5, acetone); $^1$H NMR (CDCl$_3$) δ 8.01 (dt, J$_1$=8.4 Hz, J$_2$=1.8 Hz, 2H), 7.69 (dt, J$_1$=8.4 Hz, J$_2$=1.8 Hz, 2H), 7.56 (dt, J$_1$=8.7 Hz, J$_2$=2.4 Hz, 2H), 7.45 (m, 4H), 7.29 (m, 2H), 7.20 (tt, J$_1$=6.9 Hz, J$_2$=1.5 Hz, 1H), 3.51 (m, 3H), 3.34 (m, 1H), 3.19 (dd, J$_1$=13.5 Hz, J$_2$=8.4 Hz, 1H); $^{13}$C NMR (CDCl$_3$) δ 197.0, 178.7, 144.8, 138.2, 135.2, 134.8, 134.5, 129.9, 129.1, 129.0, 128.7, 128.5, 127.0, 126.7, 40.2, 38.5, 35.0; M S (FAB) m/$_z$ (relative intensity) 411 (M$^+$+H, 100), 393 (40), 215 (40). Anal. Calcd for C$_{23}$ H$_{19}$O$_3$CIS: C, 67.23; H, 4.66; Cl, 8.63; S, 7.80. Found C, 67.00; H, 4.75; Cl, 8.79; S, 7.58.

Example 124

Purified samples of this isomer could be obtained by HPLC on a Chiralpak® AD column (2cm×25 cm) using ethanol/hexane (1:9.+0.15% trifluoroacetic acid added to the ethanol). With these conditions Example 124 eluted second and could be obtained pure only from very small injections. Use of a proprietary chiral stationary phase according to the general procedures of: D. Arit, B. Boemer, R. Grosser and W. Lange, Angew. Chem. Int. Ed. Engl. 30 (1991) No. 12, pages 1662–1664 yielded larger quantities of pure material with isomer ratio <1:>99. The best chromatograpy fractions were freed of solvent by evaporation in vacuo and then the residue (830 mg)was recrystallized from ethyl acetate/hexane mixture to yield pure material (479 mg).

MP 108°–109° C.; [α]D –79.8° (c 1.0, acetone); $^1$H NMR; $^{13}$C NMR and MS essentially identical to that of Example 123; Anal. Calcd for C$_{23}$ H$_{19}$O$_3$CIS: C, 67.23; H, 4.66; Cl, 8.63; S, 7.80; found C, 67.10; H, 4.65; Cl, 8.54; S, 7.72.

Example 125, Example 126, Example 127 and Example 128

A sample of Example 121 was stored for several days as a solution in a mixed solvent containing tetrahydrofuran which also contained significant quantities of peroxides. This resulted in the formation of significant quantities of the isomeric sulfoxides Example 125, Example 126, Example 127 and Example 128 which were separated into pure fractions by chromatography on chiral HPLC stationary phases. These same compounds can also be isolated from aged samples of Example 121 or its isomers Example 123 or Example 124 or samples of the same materials in solution with added hydrogen peroxide. The two sulfoxides Example 127 and Example 128 are often found as contaminants in aged air oxidized samples of Example 123 and therefore must share the C-2 stereochemistry of Example 123, but differ in the stereochemistry at the sulfoxide oxygen. Likewise Example 125 and Example 126 are found in aged samples of Example 124 and therefore share the C-2 stereochemistry of Example 124, but differ in stereochemistry at sulfoxide.

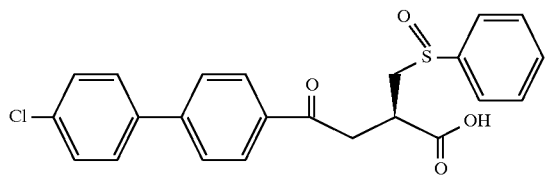

Example 125

MP 151°–152° C.; TLC (methylene chloride-10%methanol) $R_f$ 0.290; [α]D −99.7 (c 0.6, acetone), $^1$H NMR (DMSO-d$_6$) δ 12.68 (bs, 1H), 8.05 (d, J=8.45 Hz, 2H), 7.85 (d, J=8.46 Hz, 2H), 7.79 (d, J=8.82 Hz, 2H), 7.70 (m, 2H), 7.57 (m, 5H), 3.38 (m, 5H); $^{13}$C NMR (DMSO-d$_6$) δ 197.12, 173.88, 143.88, 143.31, 137.61, 135.25, 133.36, 131.02, 129.34, 129.05, 128.79, 128.66, 126.92, 124.01, 57.44, 35.36; MS (FAB-LSIMS) 427[M+H]$^+$ (C$_{23}$H$_{19}$O$_4$SCl, FW=426.92); Anal. C: calcd, 64.71; found, 63.44. H: calcd, 4.49; found, 4.40. Cl: calcd, 8.30; found, 8.17. S: calcd, 7.51; found, 7.35.

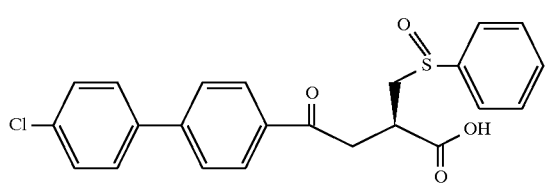

Example 126

MP 146.5°–147.5° C.; TLC (methylene chloride-10%methanol) $R_f$ 0.290; [α]D +100.6 (c 0.6, acetone); $^1$H NMR (DMSO-d$_6$) δ 12.71 (bs, 1H), 7.97. (d, J=8.46 Hz, 2H), 7.78 (m, 4H), 7.68 (m, 2H), 7.54(m, 5H), 3.51 (m, 1H) 3.31 (m, 3H), 2.97 (m, 1H); $^{13}$C NMR (DMSO-d$_6$) δ 196.98, 173.98, 144.70, 143.29, 135.17, 133.36, 130.97, 129.34, 129.05, 128.77, 128.65, 126.88, 123.85, 57.96, 39.63, 35.02; MS (FAB-LSIMS) 427[M+H]$^+$ (C$_{23}$H$_{19}$O$_4$SCl, FW=426.92); Anal. C: calcd, 64.71; found, 64.40. H: calcd, 4.49; found, 4.47. Cl: calcd, 8.30; found, 8.19. S: calcd, 7.51; found, 7.34.

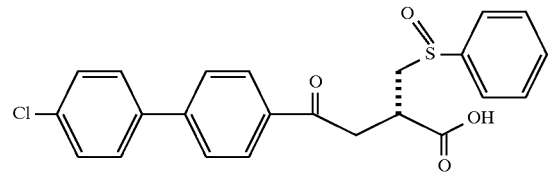

Example 127

Example 127

MP 146°–147° C.; TLC (methylene chloride-10%methanol) $R_f$ 0.303; [α]D −97.4 (c 0.6, acetone); $^1$H NMR (DMSO-d$_6$) δ 12.71 (bs, 1H), 7.98 (d, J=8.46 Hz, 2H), 7.79 (m, 4H), 7.69 (m, 2H), 7.56(m, 5H), 3.50 (m, 1H) 3.33 (m, 3H), 2.98 (m, 1H); $^{13}$C NMR (DMSO-d$_6$) δ 196.97, 173.96, 144.70, 143.29, 137.61, 135.17, 133.36, 130.97, 129.34, 129.05, 128.79, 128.64, 126.88, 123.85, 57.94, 39.63, 35.03; MS (FAB-LSIMS) 427[M+H]$^+$ (C$_{23}$H$_{19}$O$_4$SCl, FW=426.92); Anal. C: calcd, 64.71; found, 64.61. H: calcd, 4.49; found, 4.36. Cl: calcd, 8.30; found, 8.27. S: calcd, 7.51; found, 7.36.

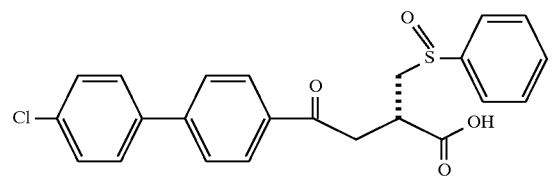

Example 128

Example 128

MP 144°–145° C.; TLC (methylene chloride-10%methanol) $R_f$ 0.303; [α]D +95.6 (c 0.6, acetone); $^1$H NMR (DMSO-d$_6$) δ 12.66 (bs, 1H), 8.04 (d, J=8.82 Hz, 2H), 7.84 (d, J=8.47 Hz, 2H), 7.78 (d, J=8.83 Hz, 2H), 7.69 (m, 2H), 7.56(m, 5H), 3.38 (m, 5H); $^{13}$C NMR (DMSO-d$_6$) δ 197.12, 143.88, 143.31, 135.25, 131.02, 129.34, 129.05, 128.79, 128.66, 126.92, 124.01, 119.14, 57.44, 38.85, 35.36; MS (FAB-LSIMS) 427[M+H]$^+$ (C$_{23}$H$_{19}$O$_4$SCl, FW=426.92); Anal. C: calcd, 64.71; found, 64.32. H: calcd, 4.49; found, 4.35. Cl: calcd, 8.30; found, 8.12. S: calcd, 7.51; found, 7.35.

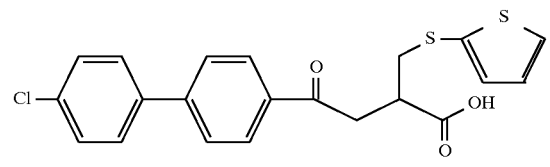

Example 129

Example 129

From 2-mercaptothiophene: MP: 136°–137° C.; TLC (methylene chloride-5%methanol) $R_f$ 0.289; $^1$H NMR (CDCl$_3$) δ 8.03 (d, J=8.6 Hz, 2H), 7.65 (d, J=8.6 Hz, 2H), 7.56 (d, J=8.84 Hz, 2H), 7.44 (d, J=8.84 Hz, 2H), 7.36 (m, 1H), 7.17 (m, 1H), 6.97(m, 1H), 3.54 (m, 2H), 3.31 (m, 2H), 3.06 (m, 1H); $^{13}$C NMR (CDCl$_3$) δ 197.59, 179.71, 145.47, 138.84, 135.85, 135.27, 135.21, 133.38, 130.78, 129.83, 129.47 129.18, 128.43, 127.79, 40.85, 40.44, 39.02; MS (FAB-LSIMS) 417 [M+H]$^+$ (C$_{21}$H$_{17}$S$_2$O$_3$Cl, FW=416.94); Anal. C: calcd, 60.49; found, 60.28. H: calcd, 4.11; found, 4.04. Cl: calcd, 8.50; found, 8.39. S: calcd, 15.37; found 14.98.

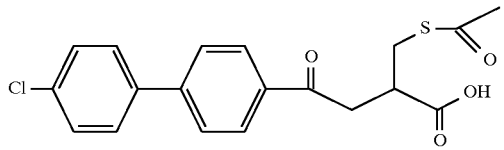

Example 130

Example 130

From thiolacetic acid: MP: 140°–141° C.; TLC (methylene chloride-5%methanol) R$_f$ 0.228; $^1$H NMR (CDCl$_3$) δ 8.03 (d, J=8.6 Hz, 2H), 7.65 (d, J=8.6 Hz, 2H), 7.56 (d, J=8.6 Hz, 2H), 7.45 (d, J=8.6 Hz, 2H), 3.40 (m, 5H), 2.36 (s, 3H); $^{13}$C NMR (CDCl$_3$) δ 197.41, 195.86, 179.23, 145.48, 138.84, 135.81, 135.19, 129.83, 129.47, 129.17, 127.81, 41.07, 39.44, 31.20, 30.44; MS (FAB-LSIMS) 377 [M+H]$^+$ (C$_{19}$H$_{17}$SO$_4$Cl, FW=376.87); Anal. C: calcd, 60.56; found, 60.42. H: calcd, 4.55; found, 4.49. Cl: calcd, 9.41; found, 9.45. S: calcd, 8.51; found 8.27.

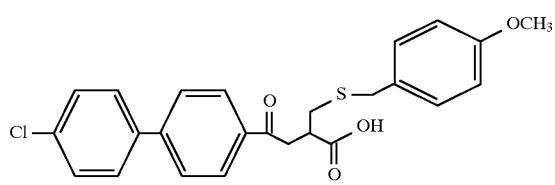

Example 131

Example 131

From 4-methoxybenzylmercaptan: MP 126°–127° C.; T L C (methylene chloride-10%methanol) R$_f$ 0.392; $^1$H NMR (CDCl$_3$) δ 8.02 (d, J=8.45 Hz, 2H), 7.66 (d, J=8.45 Hz, 2H), 7.56 (d, J=8.82 Hz, 2H), 7.45 (d, J=8.82 Hz, 2H), 7.24 (d, J=8.46 Hz, 2H), 6.84 (d, J=8.83 Hz, 2H), 3.78 (s, 3H), 3.71 (s, 2H), 3.44 (m, 2H), 3.31 (m, 1H), 2.93 (m, 1H), 2.69 (m, 1H); $^{13}$C NMR (CDCl$_3$) δ 197.29, 177.55, 158.74, 144.80, 138.19, 135.21, 134.54, 130.02, 129.64, 129.15, 128.81, 128.50, 127.09, 113.99, 55.23, 39.81, 38.99, 35.89, 32.42; M S (FAB-LSIMS) 455 [M+H]$^+$ (C$_{25}$H$_{23}$SO$_4$Cl, FW=454.97); Anal. C: calcd, 65.99; found, 66.04. H: calcd, 5.09; found, 5.04. Cl: calcd, 7.79; found, 7.94. S: calcd, 7.04; found, 6.95

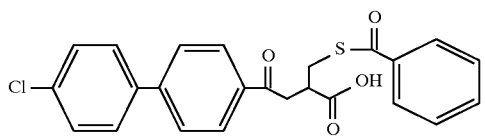

Example 132

Example 132

From thiolbenzoic acid. Treated with decolorizing carbon and recrystallized from Ethyl Acetate and Hexane:

MP 162°–164° C.; TLC (methylene chloride-5%methanol) R$_f$ 0.262; $^1$H NMR (CDCl$_3$) δ 8.00 (m, 4H), 7.54 (m, 8H), 3.52 (m, 5H); $^{13}$C NMR (CDCl$_3$) δ 197.21, 190.64, 174.20, 143.26, 137.65, 136.18, 135.33, 134.03, 133.36, 129.12, 129.07, 128.81, 128.71, 126.89, 29.68; MS (FAB-LSIMS) 439[M+H]$^+$ (C$_{24}$H$_{19}$O$_4$SCl, FW=438.93); Anal. C: calcd, 65.68; found, 65.40. H: calcd, 4.36; found, 4.27. Cl: calcd, 8.07; found, 7.74. S: calcd, 7.30; found, 7.06.

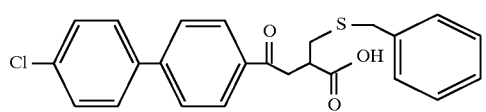

Example 133

Example 133

From benzyl mercaptan. Recrystallized from Ethyl Acetate and Hexane:

MP 155°–157° C.; TLC (methylene chloride-5%methanol) R$_f$ 0.260; $^1$H NMR (CDCl$_3$) δ 8.04 (m, 2H), 7.57 (m, 6H), 7.31 (m, 5H), 3.75 (s, 2H), 3.40 (m, 3H), 2.95 (m, 1H), 2.72 (m, 1H); $^{13}$C NMR (CDCl$_3$) δ 197.12, 178.86, 144.76, 138.19, 137.71, 135.22, 134.51, 129.15, 128.94, 128.81, 128.60, 128.50, 127.19, 127.08, 39.97, 38.94, 36.48, 32.51; MS (FAB-LSIMS) 425[M+H]$^+$ (C$_{24}$H$_{21}$O$_3$SCl, FW=424.95); Anal. C: calcd, 67.84; found, 67.71. H: calcd, 4.98; found, 4.85. Cl: calcd, 8.34; found, 8.32. S: calcd, 7.54; found, 7.64.

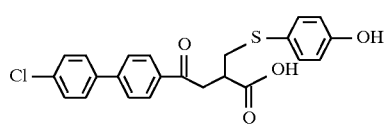

Example 134

Example 134

From 4-hydroxythiophenol. Recrystallized twice from Ethyl Acetate and Hexane:

MP 162°–163° C.; TLC (methylene chloride-10% methanol) R$_f$ 0.429; $^1$H NMR (MeOH-d$_4$) δ 8.00 (d, J=8.46 Hz, 2H), 7.70 (m, 4H), 7.47 (d, J=8.46 Hz, 2H), 7.30 (d, J=8.83 Hz, 2H), 6.72 (d, J=8.83 Hz, 2H), 3.27 (m, 5H); $^{13}$C NMR (MeOH-d$_4$) δ 199.53, 158.61, 145.72, 136.94, 135.31, 130.15, 129.83, 129.73, 128.07, 125.16, 117.17, 42.09, 40.12, 38.73; MS (FAB-LSIMS) 427[M+H]$^+$ (C$_{23}$H$_{19}$O$_4$SCl, FW=426.92); Anal. C: calcd, 64.71; found, 64.63. H: calcd, 4.49; found, 4.65. Cl: calcd, 8.30; found, 8.28. S: calcd, 7.51; found, 7.38.

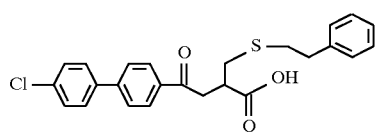

Example 135

Example 135

From 2-phenylethylmercaptan. Chromatographed over silica gel with 2% Methanol and Methylene Chloride and recrystallized from Ethyl Acetate and Hexane:

MP 105°–106° C.; TLC (methylene chloride-10%methanol) R$_f$ 0.574; $^1$H NMR (CDCl$_3$) δ 8.04 (d, J=8.46 Hz, 2H), 7.65 (d, J=8.09 Hz, 2H), 7.55 (d, J=8.08 Hz, 2H), 7.44 (d, J=8.09 Hz, 2H), 7.25 (m, 5H), 3.42 (m, 3H), 2.87 (m, 6H); $^{13}$C NMR (CDCl$_3$) δ 197.14, 178.99, 144.78, 140.11, 138.18, 135.25, 134.53, 129.15, 128.86, 128.81, 128.50, 128.47, 127.11, 126.42, 40.28, 38.82, 35.98, 33.86, 33.35; M S (FAB-LSIMS) 439[M+H]$^+$(C$_{25}$H$_{23}$O$_3$SCl, FW=438.97); Anal. C: calcd, 68.40; found, 67.93. H: calcd, 5.28; found, 5.26. Cl: calcd, 8.08; found, 8.29. S: calcd, 7.30; found, 7.38.

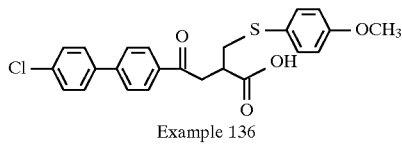

Example 136

From 4-methoxythiophenol. Recrystallized from Ethyl Acetate and Hexane. Note: the second crop of crystals contained the product:

MP 138°–139° C., TLC (methylene chloride-10%methanol) R$_f$ 0.529; $^1$H NMR (CDCl$_3$) δ 8.00 (d, J=8.46 Hz, 2H), 7.64 (d, J=8.46 Hz, 2H), 7.56 (d, J=8.46 Hz, 2H), 7.45 (d, J=8.82 Hz, 2H), 7.38 (d, J=8.82 Hz, 2H), 6.82 (d, J=8.83 Hz, 2H), 3.76 (s, 3H), 3.39 (m, 4H), 3.09 (m, 1H); $^{13}$C NMR (CDCl$_3$) δ 197.06, 178.94, 159.33, 144.72, 138.19, 134.51, 133.77, 129.15, 128.76, 128.49, 127.05, 124.87, 114.79, 55.26, 40.24, 38.45, 37.03; MS (FAB-LSIMS) 441[M+H]$^+$ (C$_{24}$H$_{21}$O$_4$SCl, FW=440.95); Anal. C: calcd, 65.38; found, 65.23. H: calcd, 4.80; found, 4.76. Cl: calcd, 8.04; found, 8.21. S: calcd, 7.27; found, 7.15.

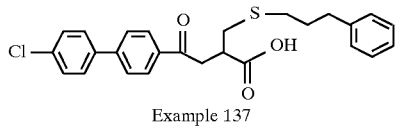

Example 137

From 3-phenylpropane-1-thiol. Purified by HPLC (100% CH$_2$CL$_2$ on silica) then recrystallized from ethyl acetate and hexane, then Purified by reverse phase HPLC (methanol and water) and finally recrystallized from ethyl acetate and hexane:

MP 82°–83° C.; TLC (methylene chloride-10%methanol) R$_f$ 0.50; $^1$H NMR (CDCl$_3$) δ 8.05 (d, J=8.46 Hz, 2H), 7.65 (d, J=8.09 Hz, 2H), 7.56 (d, J=8.46Hz, 2H), 7.45 (d, J=8.46 Hz, 2H), 7.22 (m, 5H), 3.34 (m, 3H), 3.01 (m, 1H), 2.76 (m, 3H), 2.57 (m, 2H), 1.94 (m, 2H); $^{13}$C NMR (CDCl$_3$) δ 197.25, 178.02, 144.81, 141.26, 138.18, 135.25, 134.53, 129.15, 128.79, 128.50, 128.43, 128.39, 127.13, 125.93, 40.15, 38.85, 34.65, 33.23, 31.75, 30.86; MS (FAB-LSIMS) 453[M+H]$^+$ (C$_{26}$H$_{25}$O$_3$SCl, FW=452.00).

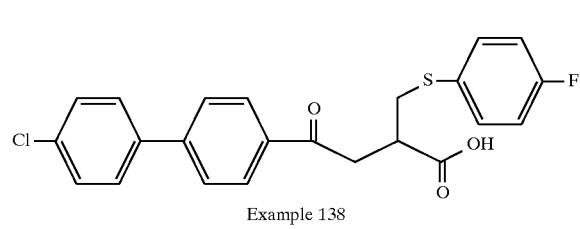

Example 138

From 4-fluorothiophenol. Recrystallized twice from ethyl acetate and hexane then from 1-chlorobutane:

MP 112°–113° C.; TLC (methylene chloride-10% methanol) R$_f$ 0.519; $^1$H NMR (CDCl$_3$) δ 7.99 (d, J=8.46 Hz, 2H), 7.64 (d, J=8.46 Hz, 2H), 7.55 (d, J=8.45 Hz, 2H), 7.42 (m, 4H), 6.98 (m, 2H), 3.36 (m, 5H); $^{13}$C NMR (CDCl$_3$) δ 196.86, 178.58, 163.81, 144.89, 138.16, 134.57, 133.22, 133.10, 129.18, 128.76, 128.50, 127.13, 116.45, 116.16, 40.19, 38.52, 36.32; MS (FAB-LSIMS) 429[M+H]$^+$ (C$_{23}$H$_{18}$O$_3$SFCl, FW=428.91); Anal. C: calcd, 64.41; found, 64.33. H: calcd, 4.23; found, 4.20. Cl: calcd, 8.27; found, 8.58. S: calcd, 7.47; found, 7.54. F: calcd, 4.43; found, 4.50.

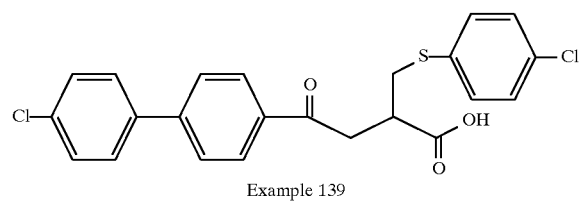

Example 139

From 4-chlorothiophenol. Recrystallized twice from ethyl acetate and hexane then from 1-chlorobutane:

MP 152°–153° C.; TLC (methylene chloride-10% methanol) R$_f$ 0.558; $^1$H NMR (CDCl$_3$) δ 7.98 (d, J=8.09 Hz, 2H), 7.64 (d, J=8.46 Hz, 2H), 7.55 (d, J=8.09 Hz, 2H), 7.44 (d, J=8.45 Hz, 2H), 7.32 (d, J=8.46 Hz, 2H), 7.23 (d, J=8.83 Hz, 2H), 3.38 (m, 5H); $^{13}$C NMR (CDCl$_3$) δ 196.79, 178.44, 144.93, 138.14, 135.06, 134.57, 131.41, 129.28, 129.16, 128.74, 128.52, 127.13, 40.18, 38.48, 35.17; MS (FAB-LSIMS) 445[M+H]$^+$ (C$_{23}$H$_{18}$O$_3$SCl$_2$, FW=445.36); Anal. C: calcd, 62.03; found, 61.83. H: calcd, 4.07; found, 3.86. Cl: calcd, 15.92; found, 15.83. S: calcd, 7.20; found, 7.31.

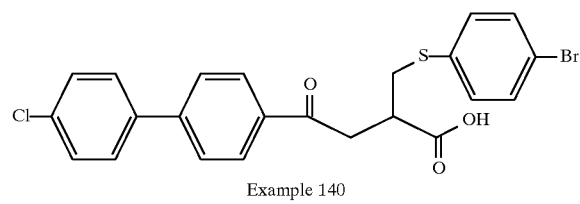

Example 140

From 4-bromothiophenol. Recrystallized from ethyl acetate and hexane:

MP 153°–154° C.; TLC (methylene chloride-10%methanol) R$_f$ 0.519; $^1$H NMR (CDCl$_3$) δ 7.98 (d, J=8.46 Hz, 2H), 7.64 (d, J=8.46 Hz, 2H), 7.56 (d, J=8.46 Hz, 2H), 7.45 (d, J=8.46 Hz, 2H), 7.38 (d, J=8.45 Hz, 2H), .7.25 (d, J=8.46 Hz, 2H), 3.38 (m, 5H); $^{13}$C NMR (CDCl$_3$) δ 196.79, 178.42, 138.14, 135.04, 134.57, 134.15, 132.20, 131.52, 129.16, 128.74, 128.52, 127.13, 120.73, 40.18, 38.48, 34.95; M S (FAB-LSIMS) 491[M+H]$^+$ (C$_{23}$H$_{18}$O$_3$SBrCl, FW=489.82); Anal. C: calcd, 56.40; found, 56.43. H: calcd, 3.70; found, 3.51. Cl: calcd, 7.23 found, 7.23. S: calcd, 6.55; found, 6.68. Br: calcd, 16.31; found, 16.10.

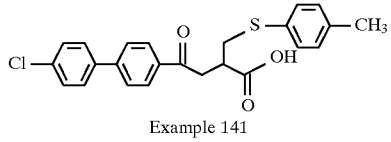

Example 141

Example 141

From 4-methylthiophenol. Recrystallized from ethyl acetate and hexane:

MP 125°–127° C; TLC (methylene chloride-10%methanol) R$_f$ 0.585; $^1$H NMR (CDCl$_3$) δ 7.99 (d J=8.83 Hz, 2H), 7.63 (d, J=8.45 Hz, 2H), 7.55 (d, J=8.83 Hz, 2H), 7.44 (d, J=8.82 Hz, 2H), 7.30 (d, J=8.08 Hz, 2H), 7.08 (d, J=8.09 Hz, 2H), 3.47 (m, 3H), 3.28 (m, 1H), 3.13 (m, 1H), 2.82 (s, 3H); $^{13}$C NMR (CDCl$_3$) δ 197.06, 178.81, 144.73, 138.21, 137.06, 135.20, 134.53, 131.00, 130.83, 129.94, 129.16, 128.78, 128.50, 127.06, 40.21, 38.48, 35.72, 21.02; M S (FAB-LSIMS) 425[M+H]$^+$ (C$_{24}$H$_{21}$O$_3$SCl, FW=424.95); Anal. C: calcd, 67.84; found, 67.75. H: calcd, 4.98; found, 4.89. Cl: calcd, 8.34; found, 8.34. S: calcd, 7.54; found, 7.61.

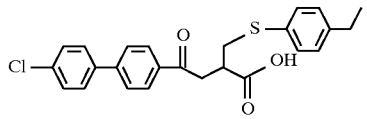

Example 142

Example 142

From 4-ethylthiophenol. Recrystallized twice from ethyl acetate and hexane:

MP 122°–123° C.; TLC (methylene chloride-10% methanol) R$_f$ 0.547; $^1$H NMR (CDCl$_3$) δ 7.99 (d J=8.46 Hz, 2H), 7.63 (d, J=8.45 Hz, 2H), 7.55 (d, J=8.46 Hz, 2H), 7.44 (d, J=8.46 Hz, 2H), 7.33 (d, J=8.46 Hz, 2H), 7.12 (d, J=8.09 Hz, 2H), 3.48 (m, 3H), 3.30 (m, 1H), 3.14 (m, 1H), 2.59 (q, J=7.60 Hz, 2H), 1.19 (t, J=7.71 Hz, 3H); $^{13}$C NMR (CDCl$_3$) δ 197.00, 179.23, 144.70, 143.32, 138.18, 135.19, 134.48, 131.26, 130.71, 129.13, 128.74, 128.47, 127.03, 40.28, 38.47, 35.59, 28.34, 15.37; MS (FAB-LSIMS) 439[M+H]$^+$ (C$_{25}$H$_{23}$O$_3$SCl, FW=438.99); Anal. C: calcd, 68.40; found, 68.33. H: calcd, 5.28; found, 5.17. Cl: calcd, 8.08; found, 7.91. S: calcd, 7.30; found, 7.26.

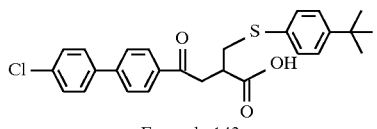

Example 143

Example 143

From 4-tert-butylthiophenol. Recrystallized twice from ethyl acetate and hexane:

MP 135°–136° C.; TLC (methylene chloride-10% methanol) R$_f$ 0.547; $^1$H NMR (CDCl$_3$) δ 7.99 (d J=8.46 Hz, 2H), 7.63 (d, J=8.46 Hz, 2H), 7.54 (d, J=8.45 Hz, 2H), 7.44 (d, J=8.46 Hz, 2H), 7.32 (m, 4H), 3.49 (m, 2H), 3.31 (m, 1H), 3.14 (m, 1H), 1.28 (s, 9H); $^{13}$C NMR (CDCl$_3$) δ 197.04, 179.21, 150.11, 144.73, 138.19, 135.20, 134.51, 131.22, 130.12, 129.15, 128.74, 128.49, 127.06, 126.22, 40.34, 38.53, 35.33, 34.46, 31.20; MS (FAB-LSIMS) 467 [M+H]$^+$ (C$_{27}$H$_{27}$O$_3$SCl, FW=467.03); Anal. C: calcd, 69.44; found, 68.64. H: calcd, 5.83; found, 5.63. Cl: calcd, 7.59; found, 7.44. S: calcd, 6.86; found, 6.99.

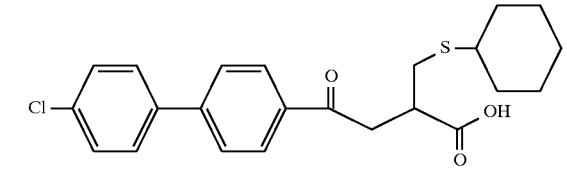

Example 144

Example 144

From cyclohexylmercaptan. Recrystallized from ethyl acetate and hexane, and the filtrate was purified by. reverse phase HPLC (75% Methanol, 25% Water, and 0.05% TFA).

TLC (methylene chloride-10%methanol) R$_f$ 0.640; $^1$H NMR (CDCl$_3$) δ 8.05 (d J=8.45 Hz, 2H), 7.65 (d, J=8.09 Hz, 2H), 7.55 (d, J=8.82 Hz, 2H), 7.44 (d, J=8.46 Hz, 2H), 3.40 (m, 3H), 3.06 (m, 1H), 2.75 (m, 2H), 1.80 (m, 5H), 1.33 (m, 5H); MS (FAB-LSIMS) 417[M+H]$^+$ (C$_{23}$H$_{25}$O$_3$SCl, FW=416.97);

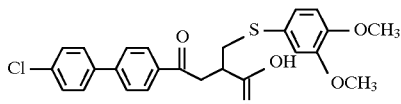

Example 145

Example 145

From 3,4-dimethoxythiophenol. Recrystallized twice from 1-chlorobutane:

MP 144°–145° C.; TLC (methylene chloride-10% methanol) R$_f$ 0.467; $^1$H NMR (CDCl$_3$) δ 7.99 (d, J=8.46 Hz, 2H), 7.63 (d, J=8.45 Hz, 2H), 7.55 (d, J=8.45 Hz, 2H), 7.44 (d, J=8.82 Hz, 2H), 6.99 (m, 2H), 6.75 (d, J=8.09 Hz, 1H), 3.86 (s, 3H), 3.81 (s, 3H), 3.41 (m, 4H), 3.13 (m, 1H); $^{13}$C NMR (CDCl$_3$) δ 197.04, 178.55, 149.21, 144.79, 134.55, 129.16, 128.73, 128.50, 127.06, 125.30, 124.67, 114.98, 111.63, 55.94. 55.87, 40.31, 38.48, 36.72; MS (FAB-LSIMS) 471[M+H]$^+$ (C$_{25}$H$_{23}$SO$_5$Cl, FW=470.98); Anal. C: calcd, 63.75; found, 63.74. H: calcd, 4.92; found, 4.84. Cl: calcd, 7.53; found, 7.47. S: calcd, 6.81; found 6.81

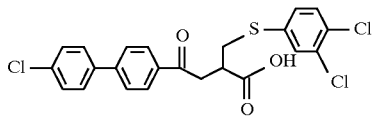

Example 146

Example 146

From 3,4-dichlorothiophenol. Recrystallized from 1-chlorobutane then ethyl acetate and hexane:

MP 156°–157° C.; TLC (methylene chloride-10%methanol) R$_f$ 0.545; $^1$H NMR (CDCl$_3$) δ 7.99 (d J=8.46

Hz, 2H), 7.65(d, J=8.46 Hz, 2H), 7.56 (d, J=8.83 Hz, 2H), 7.45 (m, 3H), 7.32 (m, 1H), 7.22 (m, 1H), 3.41 (m, 5H); $^{13}$C NMR (CDCl$_3$) δ 196.59, 178.66, 144.99, 138.13, 135.43, 134.93, 134.59, 133.07, 131.13, 130.79, 129.18, 128.86, 128.71, 128.53, 127.15, 40.23, 38.40, 34.74; MS (FAB-LSIMS) 479[M+H]$^+$ (C$_{23}$H$_{17}$O$_3$SCl$_3$, FW=479.81); Anal. C: calcd, 57.58; found, 57.49. H: calcd, 3.57; found, 3.49. Cl: calcd, 22.17; found, 21.91. S: calcd, 6.68; found, 6.79.

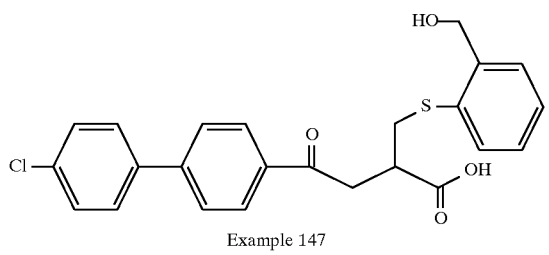

Example 147

Example 147

From 2-mercaptobenzyl alcohol. Recrystallized from 1-chlorobutane then ethyl acetate and hexane, then 1-chlorobutane:

MP 111°–112° C.; TLC (methylene chloride-10% methanol) R$_f$ 0.457; $^1$H NMR (CDCl$_3$) δ 7.98 (d, J=8.46 Hz, 2H), 7.63(d, J=8.46 Hz, 2H), 7.54 (d, J=8.82 Hz, 2H), 7.44 (m, 4H), 7.25 (m, 2H), 5.40 (bs, 1H), 4.80(m, 2H). 3.42 (m, 5H); $^{13}$C NMR (CDCl$_3$) δ 196.96, 177.82, 144.86, 141.31, 138.11 135.08, 134.56, 133.38, 131.25, 129.15, 128.95, 128.78, 128.63, 128.49, 127.52, 127.11, 63.52, 40.31, 38.90, 35.87; MS (FAB-LSIMS) 441[M+H]$^+$ (C$_{24}$H$_{21}$SO$_4$Cl, FW=440.95); Anal. C: calcd, 65.38; found, 65.22. H: calcd, 4.80; found, 4.68. Cl: calcd, 8.04; found, 8.16. S: calcd, 7.27 found 7.22.

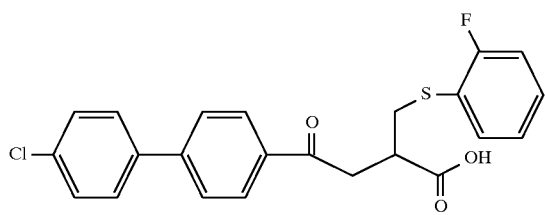

Example 148

Example 148

From 2-fluorothiophenol. Recrystallized from ethyl acetate and hexane.

MP 131°–132° C.; TLC (methylene chloride-10% methanol) R$_f$ 0.491; $^1$H NMR (CDCl$_3$) δ 8.02 (d, J=8.45 Hz, 2H), 7.64 (d, J=8.09 Hz, 2H), 7.55 (d, J=8.45 Hz, 2H), 7.44 (m, 3H), 7.15 (m, 3H), 3.49 (m, 3H), 3.21 (m, 2H); $^{13}$C NMR (CDCl$_3$) δ 231.29, 197.00, 177.97, 144.85, 135.16, 133.15, 129.44, 129.34, 129.16, 128.79, 128.50, 127.11, 124.74, 124.69, 116.08. 115.79, 40.18, 38.52, 34.74; MS (FAB-LSIMS) 429[M+H]$^+$ (C$_{23}$H$_{18}$SO$_3$ClF, FW=428.91); Anal. C: calcd, 64.41; found, 64.48. H: calcd, 4.23; found, 4.20. Cl: calcd, 8.27; found, 8.11. S: calcd, 7.47; found 7.30.

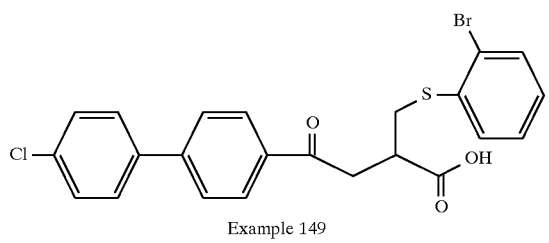

Example 149

Example 149

From 2-bromothiophenol. Recrystallize from ethyl acetate and hexane:

MP 159°–160° C.; TLC (methylene chloride-10% methanol) R$_f$ 0.477; $^1$H NMR (CDCl$_3$) δ 8.05 (d, J=8.46 Hz, 2H), 7.66 (d, J=8.46 Hz, 2H), 7.57 (m, 3H), 7.45 (m, 3H), 7.31 (m, 1H), 7.07 (m, 1H), 3.56 (m, 3H), 3.37 (m, 1H), 3.25 (m, 1H); $^{13}$C NMR (CDCl$_3$) δ 196.95, 178.60, 144.87, 138.16, 136.24, 135.11, 133.24, 129.34, 129.17, 128.81, 128.50, 128.07, 127.52, 127.13, 124.48, 39.80, 38.71, 34.22; M S (FAB-LSIMS) 490[M+H]$^+$ (C$_{23}$H$_{18}$SO$_3$ClBr, FW=489.92); Anal. C: calcd, 56.40; found, 56.34. H: calcd, 3.70; found, 3.65. Br: calcd, 16.31; found, 16.22. Cl: calcd, 7.23; found, 7.11. S: calcd, 6.54; found 6.33.

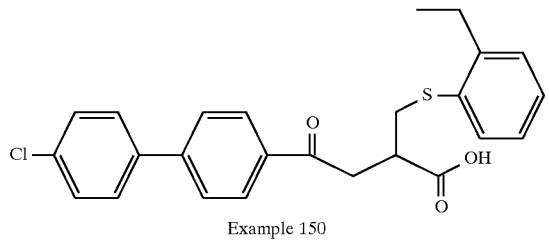

Example 150

Example 150

From 2-ethylthiophenol. Recrystallized from ethyl acetate and hexane:

MP 134°–135° C.; TLC (methylene chloride-10% methanol) R$_f$ 0.504; $^1$H NMR (CDCl$_3$) δ 8.00 (d, J=8.45 Hz, 2H), 7.64 (d, J=8.82 Hz, 2H), 7.55 (d J=8.82 Hz, 2H), 7.42 (m 3H), 7.16 (m, 3H), 3.44 (m, 4H), 3.17 (m, 1H), 2.77 (q, J=7.47 Hz, 2H), 1.20 (t, J=7.54 Hz, 3H); $^{13}$C NMR (CDCl$_3$) δ 197.04, 178.37, 138.19, 135.20, 134.54, 133.57, 129.47, 129.16, 128.77, 128.50, 127.11, 126.82, 126.68, 119.59, 40.09, 38.73, 34.85, 26.94, 14.79; MS (FAB-LSIMS) 439 [M+H]$^+$ (C$_{25}$H$_{23}$SO$_3$Cl, FW=438.97); Anal. C: calcd, 68.40 found, 68.37. H: calcd, 5.28; found, 5.21. Cl: calcd, 8.08; found, 7.90. S: calcd, 7.30; found 7.58.

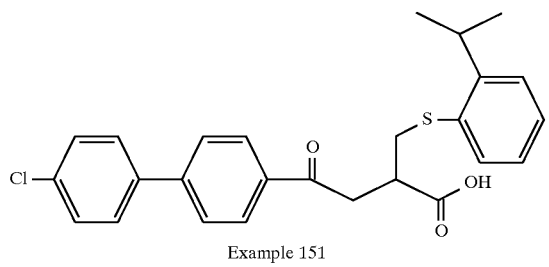

Example 151

Example 151

From 2-isopropylthiophenol. Recrystallized from ethyl acetate and hexane:

MP 149°–150° C.; TLC (methylene chloride-10%methanol) R$_f$ 0.531; $^1$H NMR (CDCl$_3$) δ 8.01 (d, J=8.09 Hz, 2H), 7.64 (d, J=8.09 Hz, 2H), 7.55 (d, J=8.46 Hz, 2H), 7.42 (m, 3H), 7.19 (m, 3H), 3.43 (m, 5H), 3.16 (m, 1H), 1.21 (d, J=6.62 Hz, 6H); $^{13}$C NMR (CDCl$_3$) δ 197.00, 178.62, 148.98, 144.79, 138.19, 135.21, 134.53, 132.93, 130.05, 129.15, 128.77, 128.50, 127.19, 127.09, 126.50, 125.81, 40.08, 38.69, 35.38, 30.26, 23.51, 23.39; MS (FAB-LSIMS) 453[M+H]$^+$ (C$_{26}$H$_{25}$SO$_3$Cl, FW=453.00); Anal. C: calcd, 68.93; found, 68.94. H: calcd, 5.56; found, 5.54. Cl: calcd, 7.82; found, 7.82. S: calcd, 7.07; found 6.90.

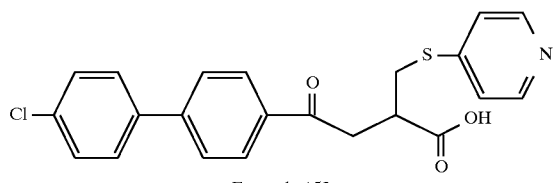

Example 152

Example 152

From 4-mercaptopyridine. Prepared in a manner similar to Example 121 but it was the aqueous layer that was neutralized with 1N NaOH to pH=4 and, the solid that formed was collected and recrystallized from ethyl acetate.

MP 190°–191° C.; TLC (methylene chloride-20% methanol) R$_f$ 0.613; $^1$H NMR (DMSO-d$_6$) δ 12.69 (bs, 1H), 8.38 (d, J=6.25 Hz, 2H), 8.04 (d, J=8.45 Hz, 2H), 7.81 (m, 4H), 7.56 (d, J=8.82 Hz, 2H), 7.33 (d, J=6.25 Hz, 2H), 3.56 (m, 1H), 3.36 (m, 3H), 3.18 (m, 1H); $^{13}$C NMR (DMSO-d$_6$) δ 197.33, 174.14, 149.29, 147.77, 143.33, 137.61, 135.25, 133.38, 129.07, 128.79, 128.71, 126.92, 120.64, 39.71, 39.40, 31.25; MS (FAB-LSIMS) 412[M+H]$^+$ (C$_{22}$H$_{18}$SNO$_3$Cl, FW=411.91); Anal. C: calcd, 64.15; found, 63.49. H: calcd, 4.40; found, 4.45. N: calcd, 3.40; found, 3.29. Cl: calcd, 8.61; found, 8.67. S: calcd, 7.78; found 7.86.

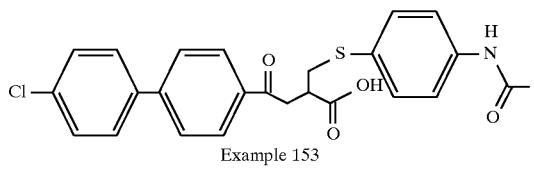

Example 153

Example 153

From N-acetyl-4-mercaptoaniline. Recrystallized from ethyl acetate and hexane then 1-chlorobutane, what did not dissolve in the 1-chlorobutane was filtered and this was the product.

MP 165°–166° C. then 203°–204° C.; TLC (methylene chloride-10% methanol) R$_f$ 0.370; $^1$H NMR (DMSO-d$_6$) δ 12.50 (bs, 1H), 9.97 (bs, 1H), 7.99 (d, J=8.08 Hz, 2H), 7.79 (m, 4H), 7.55 (m, 4H), 7.33 (d, J=8.46 Hz, 2H), 3.35 (m, 3H), 3.11 (m, 2H), 2.00 (s, 3H); $^{13}$C NMR (DMSO-d$_6$) δ 197.48, 174.37, 168.28, 143.23, 138.16, 133.35, 130.63, 129.07, 128.79, 128.65, 126.87, 119.60, 23.96; MS (FAB-LSIMS) 468[M+H]$^+$ (C$_{25}$H$_{22}$SNO$_4$Cl, FW=467.98); Anal. C: calcd, 64.16; found, 63.97. H: calcd, 4.74; found, 4.64. N: calcd, 2.99; found, 2.98. Cl: calcd, 7.58; found, 7.42. S: calcd, 6.85; found 6.92.

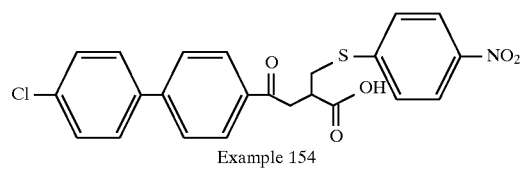

Example 154

Example 154

From 4-nitrothiophenol. Recrystallized from Ethyl Acetate and Hexane:

MP 211°–212° C.; TLC (methylene chloride-10% methanol) R$_f$ 0.550; $^1$H NMR (DMSO-d$_6$) δ 12.69 (bs, 1H), 8.13 (d, J=8.83 Hz, 2H), 8.03 (d, J=8.46 Hz, 2H), 7.80 (m, 4H), 7.56 (m, 4H), 3.37 (m, 5H) ; $^{13}$C NMR (DMSO-d$_6$) δ 197.25, 174.09, 146.72, 144.62, 143,33, 137.59, 135.20, 133.38, 129.05, 128.77, 128.69, 126.88, 126.66, 123.96, 39.69, 32.56; MS (FAB-LSIMS) 456[M+H]$^+$ (C$_{23}$H$_{18}$SNO$_5$Cl, FW=455.92); Anal. C: calcd, 60.59; found, 60.26. H: calcd, 3.98; found, 3.86. N: calcd, 3.07; found, 2.98. Cl: calcd, 7.77; found, 7.61. S: calcd, 7.03; found 6.90.

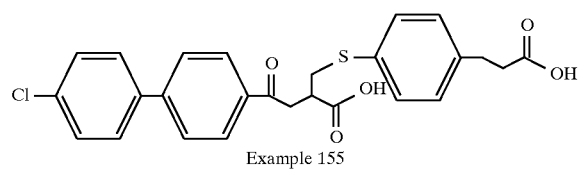

Example 155

Example 155

From 3-(4-mercaptophenyl)propionic acid. Recrystallized from 1-chlorobutane:

MP 172°–173° C.; TLC (methylene chloride-10% methanol) R$_f$ 0.30; $^1$H NMR (DMSO-d$_6$) δ 12.32 (s, 1H), 7.99 (d, J=8.46 Hz, 2H), 7.79 (m, 4H), 7.55 (d, J=8.45 Hz, 2H), 7.29 (d, J=8.45 Hz, 2H), 7.18 (d, J=8.09 Hz, 2H), 3.49 (m, 1H), 3.31 (m, 4H), 3.11 (m, 2H), 3.76 (m, 2H); $^{13}$C NMR (DMSO-d$_6$) δ 197.48, 174.35, 173.71, 143.26, 139.13, 137.64, 135.32, 133.36, 132.59, 129.11, 129.07, 128.81, 128.66, 126.90, 40.15, 39.06, 35.01, 34.62, 29.78; MS (FAB-LSIMS) 483[M+H]$^+$ (C$_{26}$H$_{23}$SO$_5$Cl, FW=482.99; Anal. C: calcd, 64.66; found, 64.46. H: calcd, 4.80 found, 4.65. Cl: calcd, 7.34; found, 7.11. S: calcd, 6.63; found 6.55.

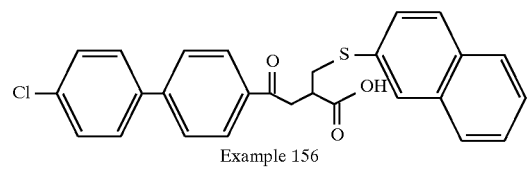

Example 156

Example 156

From 2-mercaptonaphthaline. Recrystallized from ethyl acetate and hexane, then 1-chlorobutane:

MP 155°–156° C.; TLC (methylene chloride-10% methanol) R$_f$ 0.489; $^1$H NMR (CDCl$_3$) δ 7.93 (d, J=8.45 Hz, 2H), 7.83 (m, 1H), 7.73 (m, 2H), 7.49 (m, 10H), 3.55 (m ,3H), 3.33 (m, 2H); $^{13}$C NMR ((CDCl$_3$) δ 197.11, 178.62, 144.87, 138.32, 135.21, 134.67, 132.14, 129.29, 128.95, 128.84, 128.65, 128.28, 127.82, 127.71, 127.37, 127.15, 126.77, 126.11, 40.45, 38.65, 34.84; MS (FAB-LSIMS) 461[M+H]⁺ ($C_{27}H_{21}SO_3Cl$, FW=460.98); Anal. C: calcd, 70.35; found, 70.17. H: calcd, 4.59; found, 4.46. Cl: calcd, 7.69; found, 7.71. S: calcd, 6.95; found 6.80.

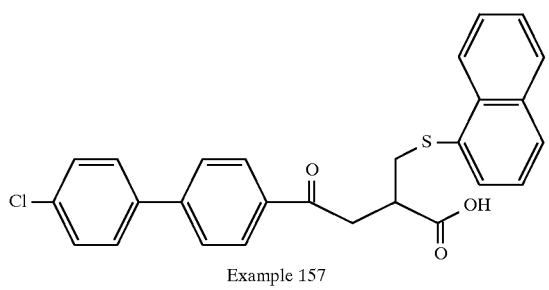

Example 157

From 1-mercaptonaphthaline. Recrystallized from ethyl acetate and hexane, then 1-chlorobutane.

MP 168°–169° C.; TLC (methylene chloride-10% methanol) $R_f$ 0.50; ¹H NMR (CDCl₃) δ 8.41 (m, 1H), 7.65 (m 14H), 3.51 (m, 3H), 3.30 (m, 2H); ¹³C NMR (CDCl₃) δ 178.18, 150.54, 144.72, 138.18, 135.09, 134.51, 134.03, 133.08, 132.04, 129.59, 129.15, 128.71, 128.68, 128.48, 128.11, 127.03, 126.69, 126.31, 125.61, 124.93, 40.25, 38.62, 35.66; MS (FAB-LSIMS) 461[M+H]⁺ ($C_{27}H_{21}SO_3Cl$, FW=460.98); Anal. C: calcd, 70.35; found, 70.31. H: calcd, 4.59; found, 4.43. Cl: calcd, 7.69; found, 7.63. S: calcd, 6.95; found 6.86.

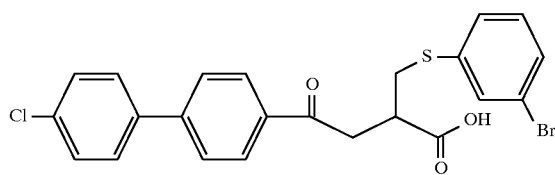

Example 158

From 3-bromothiophenol. Recrystallized from ethyl acetate and hexane:

MP 167°–168° C.; TLC (methylene chloride-10% methanol) $R_f$ 0.450; ¹H NMR (DMSO-d₆) δ 12.61 (bs 1H), 8.02 (d, J=8.46 Hz, 2H), 7.79 (m, 4H), 7.55 (m, 3H), 7.37 (m, 2H), 7.26 (m, 1H), 3.33 (m, 5H); ¹³C NMR (DMSO-d₆) δ 197.33, 174.21, 138.63, 137.61, 135.24, 133.35, 130.94, 129.92, 129.05, 128.78, 128.66, 126.98, 126.87, 122.28, 39.95, 33.72; MS (FAB-LSIMS) 491[M+H]⁺ ($C_{23}H_{18}SO_3ClBr$, FW=489.92); Anal. C: calcd, 56.40; found, 56.35. H: calcd, 3.70; found, 3.67. Cl: calcd, 7.24; found, 7.39. S: calcd, 6.55; found, 6.39. Br: calcd, 16.31; found, 16.38.

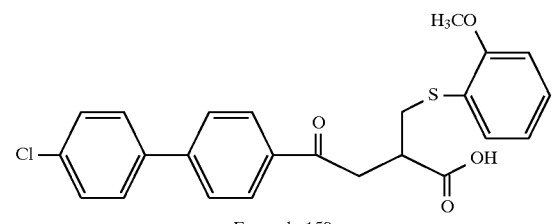

Example 159

From 2-methoxythiophenol. Recrystallized from ethyl acetate and hexane, then 1-chlorobutane:

MP 115°–116° C.; TLC (methylene chloride-10% methanol) $R_f$ 0.452 ¹H NMR (CDCl₃) δ 7.99 (d, J=8.09, 2H), 7.54 (m, 6H), 7.19 (m, 1H), 6.96 (m, 2H), 6.72 (m, 1H), 3.77 (s, 3H), 3.47 (m, 4H), 3.22 (m 1H); ¹³C NMR (CDCl₃) δ 196.94, 179.02, 159.93, 144.75, 138.18, 136.16, 135.15, 134.51, 129.97, 129.15, 128.76, 128.47, 127.06, 121.75, 114.82, 112.53, 55.26, 40.26, 38.53, 34.64; M S (FAB-LSIMS) 441[M+H]⁺ ($C_{24}H_{21}SO_4Cl$, FW=440.95); Anal. C: calcd, 65.38; found, 65.19. H: calcd, 4.80; found, 4.81. Cl: calcd, 8.04; found, 8.02. S: calcd, 7.27; found 7.02.

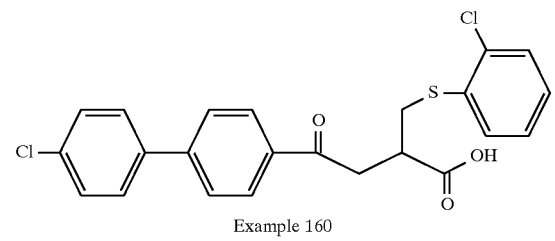

Example 160

From 2-chlorothiophenol. Recrystallized from ethyl acetate and hexane:

MP 153°–154° C.; TLC (methylene chloride-10% methanol) $R_f$ 0.533; ¹H NMR (CDCl₃) δ 8.03 (m, 2H), 7.65 (m, 2H), 7.55 (m, 2H) 7.44 (m, 3H), 7.37 (m, 1H), 7.24 (m, 1H) 7.14 (m, 1H), 3.53 (m, 3H), 3.33 (m, 1H), 3.21 (m, 1H); ¹³C NMR (CDCl₃) δ 196.99, 178.19, 138.18, 135.12, 134.57, 134.41, 129.97, 129.77, 129.18, 128.83, 128.52, 127.50, 127.45, 127.15, 39.84, 38.71, 33.83; MS (FAB-LSIMS) 445[M+H]⁺ ($C_{23}H_{18}SO_3Cl_2$, FW=445.36); Anal. C: calcd, 62.03; found, 61.87. H: calcd, 4.07; found, 4.16. Cl: calcd, 15.92; found, 16.21. S: calcd, 7.19; found 7.12.

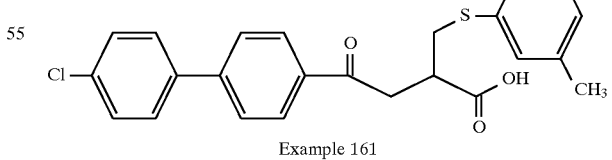

Example 161

From 3-methylthiophenol. Recrystallized from ethyl acetate and hexane:

MP 137°–138° C.; TLC (methylene chloride-10% methanol) $R_f$ 0.525; ¹H NMR (CDCl₃) δ 7.99 (d, J=8.83 Hz, 2H), 7.63 (d, J=8.45 Hz, 2H), 7.55 (d, J=8.82 Hz, 2H), 7.44 (d, J=8.83 Hz, 2H), 7.18 (m, 3H), 6.98 (m, 1H) 3.49 (m, 4H), 3.18 (m, 1H), 2.29 (m, 3H); $^{13}$C NMR (CDCl$_3$) δ 196.99, 179.09, 144.75, 138.97, 138.19, 135.19, 134.59, 134.51, 130.49, 129.15, 128.99, 128.76, 128.49, 127.58, 127.06, 126.87, 40.26, 38.52, 34.89, 21.28; MS (FAB-LSIMS) 425 [M+H]$^+$ (C$_{24}$H$_{21}$SO$_3$Cl, FW=424.95); Anal. C: calcd, 67.84; found, 67.76. H: calcd, 4.98; found, 4.81. Cl: calcd, 8.34; found, 8.48. S: calcd, 7.54; found 7.40.

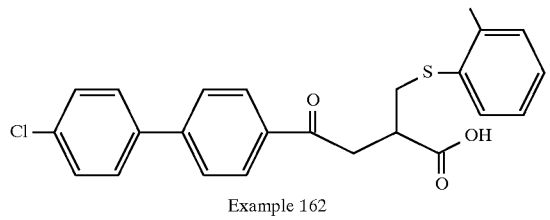

Example 162

From 2-methylthiophenol. Recrystallized from ethyl acetate and hexane:

MP 130°–131° C.; TLC (methylene chloride-10% methanol) R$_f$ 0.551; $^1$H NMR (CDCl$_3$) δ 8.01 (d, J=8.46 Hz, 2H), 7.64 (d, J=8.46 Hz, 2H), 7.55 (d, J=8.82 Hz, 2H), 7.44 (d, J=8.83 Hz, 2H), 7.37 (m, 1H), 7.14 (m, 3H), 3.47 (m, 4H), 3.16 (m, 1H), 2.39 (s, 3H) ; $^{13}$C NMR (CDCl$_3$) δ 196.99, 178.60, 144.78, 138.24, 138.18, 135.19, 134.09, 130.38, 129.15 129.07, 128.76, 128.49, 127.09, 126.66, 126.55, 40.06, 38.69, 34.28, 20.44; MS (FAB-LSIMS) 425 [M+H]$^+$ (C$_{24}$H$_{21}$SO$_3$Cl, FW=424.95); Anal. C: calcd, 67.84; found, 67.56. H: calcd, 4.98; found, 5.06. Cl: calcd, 8.34; found, 8.45. S: calcd, 7.54; found 7.40.

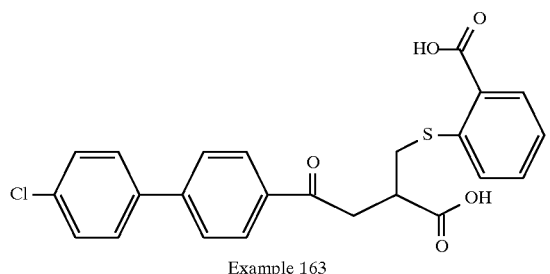

Example 163

From 2-mercaptobenzoic acid. Recrystallized from ethyl acetate and hexane:

MP 221°–222° C.; TLC (methylene chloride-15% methanol+0.5% acetic acid) R$_f$ 0.441; $^1$H NMR (DMSO-d$_6$) δ 12.75 (bs, 1.5H), 8.062 (d, J=7.36 Hz, 2H), 7.84 (m, 5H), 7.55 (m, 4H), 7.25 (m, 1H), 3.59, (m, 1H), 3.29 (m, 4H); $^{13}$C NMR (DMSO-d$_6$) δ 197.47, 174.39, 167.45, 143.28, 139.86, 137.64, 135.32, 133.36, 132.41, 130.97, 129.06, 128.79, 128.71, 128.66, 126.91, 125.67, 124.22, 39.40, 32.79; MS (FAB-LSIMS) 455[M+H]$^+$ (C$_{24}$H$_{19}$SO$_5$Cl, FW=454.92); Anal. C: calcd, 63.37; found, 63.39. H: calcd, 4.21; found, 4.04. Cl: calcd, 7.79; found, 7.81. S: calcd, 7.05; found 7.06.

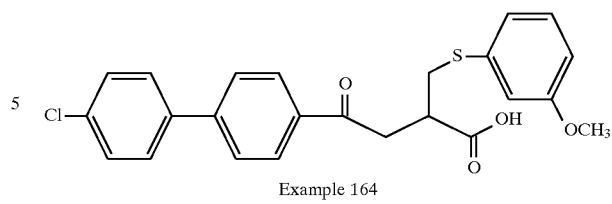

Example 164

From 3-methoxythiophenol. Recrystallized from ethyl acetate and hexane, then 1-chlorobutane the ethyl acetate and hexane.

MP 143°–144° C.; TLC (methylene chloride-10% methanol) R$_f$ 0.828; $^1$H NMR (DMSO-d$_6$) δ 12.51 (bs, 1H), 8.02 (d, J=8.46 Hz, 2H), 7.80 (m, 4H), 7.56 (d, J=8.83 Hz, 2H), 7.33 (m, 1H), 7.20 (m, 2H), 3.78 (s, 3H), 3.37 (m, 5H); $^{13}$C NMR (CDCl$_3$) δ 197.30, 178.32, 158.18, 144.76, 135.29, 134.54, 131.75, 129.18, 128.83, 128.62, 128.53, 127.11, 122.25, 121.25, 110.87, 55.80, 40.11, 38.74, 33.83; MS (FAB-LSIMS) 441[M+H]$^+$ (C$_{24}$H$_{21}$SO$_4$Cl, FW=440.95); Anal. C: calcd, 65.38; found, 65.22. H: calcd, 4.80; found, 4.61. Cl: calcd, 8.04 found, 7.78. S: calcd, 7.27; found 7.43.

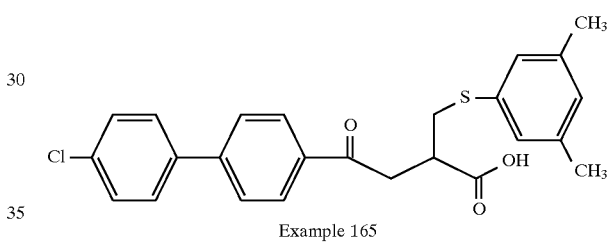

Example 165

From 3,5-dimethylthiophenol. Recrystallized from ethyl acetate and hexane:

MP 175°–176° C.; TLC (methylene chloride-10% methanol) R$_f$ 0.482; $^1$H NMR (DMSO-d$_6$) δ 12.53 (bs, 1H), 8.01 (d, J=8.46 Hz, 2H), 7.79 (m, 4H), 7.55 (d, J=8.46 Hz, 2H), 6.97 (bs, 2H), 6.79 (bs, 1H), 3.51 (m, 1H), 3.32 (m, 2H), 3.14 (m, 2H), 2.21 (bs, 6H); $^{13}$C NMR (DMSO-d$_6$) δ 196.41, 173.31, 142.25, 137.24, 136.61, 134.27, 134.12, 132.35, 128.05, 127.78, 127.63, 126.63, 125.85, 124.97, 39.13, 38.05, 32.96, 19.75; MS (FAB-LSIMS) 439[M+H]$^+$ (C$_{25}$H$_{23}$O$_3$SCl, FW=438.97); Anal. C: calcd, 68.40; found, 68.32. H: calcd, 5.28; found, 5.16. Cl: calcd, 8.08; found, 8.26. S: calcd, 7.30; found, 7.08.

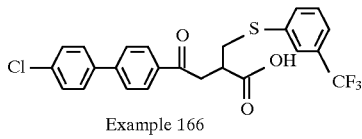

Example 166

From 3-trifluoromethythiophenol. Recrystallized from ethyl acetate and hexane.

MP 114°–115° C.; TLC (methylene chloride-10% methanol) R$_f$ 0.517; $^1$H NMR (DMSO-d$_6$) δ 12.60 (bs, 1H), 8.00 (d, J=8.46 Hz, 2H), 7.79 (m, 4H), 7.68 (m, 2H), 7.54

(m, 4H), 3.41 (m, 4H), 3.10 (m, 1H); $^{13}$C NMR (DMSO-d$_6$) δ 197.31, 174.20, 143.31, 137.88, 137.63, 135.25, 133.36, 131.81, 130.08, 129.07, 128.79, 128.68, 126.89, 124.05, 124.00, 122.45, 39.94, 33.58; MS (FAB-LSIMS) 479[M+H]$^+$ (C$_{24}$H$_{18}$O$_3$SClF$_3$, FW=478.92); Anal. C: calcd, 60.19; found, 60.36. H: calcd, 3.79; found, 3.95. Cl: calcd, 7.40; found, 7.57. S: calcd, 6.69; found, 6.97. F: calcd, 11.90; found, 11.90.

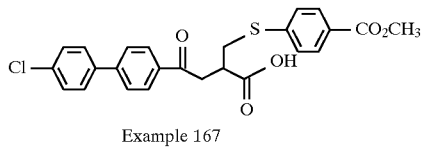

Example 167

From 4-carbomethoxythiophenol. Chromatographed on silica gel using methanol/methylene chloride mixtures and then recrystallized from ethyl acetate and hexane:

MP 152°–153° C.; TLC (methylene chloride-10% methanol) R$_f$ 0.462; $^1$H NMR (CDCl$_3$) δ 8.00 (d, J=8.46 Hz, 2H), 7.93 (d, J=8.46 Hz, 2H), 7.64 (d, J=8.46 Hz, 2H), 7.56 (d, J=8.83 Hz, 2H), 7.45 (d, J=8.46 Hz, 2H), 7.39 (d, J=8.46 Hz, 2H), 3.87 (s, 3H), 3.46 (m, 5H); $^{13}$C NMR (CDCl$_3$) δ 196.73, 177.84, 166.58, 144.91, 142.07, 138.09, 135.01, 134.59, 130.17, 129.16, 128.76, 128.50, 127.57, 127.39, 127.11, 52.08, 40.02, 38.59, 33.25; MS (FAB-LSIMS) 469 [M+H]$^+$ (C$_{25}$H$_{21}$O$_5$SCl, FW=468.96); Anal. C: calcd, 64.03; found, 62.16. H: calcd, 4.51; found, 4.65. Cl: calcd, 7.56; found, 8.19. S: calcd, 6.84; found, 6.21.

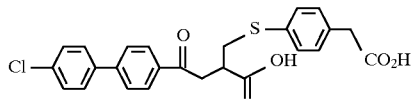

Example 168

Example 168

From 2-(4-mercaptophenyl)acetic acid. Recrystallized from ethyl acetate and hexane:

MP 162°–163° C.; TLC (methylene chloride-20% methanol) R$_f$ 0.618; $^1$H NMR (DMSO-d$_6$) δ 12.43 (bs, 1H), 7.99 (d, J=8.83 Hz, 2H), 7.78 (m, 4H), 7.54 (d, J=8.82 Hz, 2H), 7.32 (d, J=8.09 Hz, 2H), 7.20 (d, J=8.09 Hz, 2H), 3.52 (m 3H), 3.31 (m, 2H), 3.12 (m, 2H); $^{13}$C NMR (DMSO-d$_6$) δ 197.46, 174.33, 172.57, 143.28, 137.66, 133.51, 133.36, 133.12, 130.25, 129.08, 128.81, 128.71, 128.68, 126.92, 40.13, 39.58, 39.13, 38.68; MS (FAB-LSIMS) 469[M+H]$^+$ (C$_{25}$H$_{21}$O$_5$SCl, FW=468.96); Anal. C: calcd, 64.03; found, 63.94. H: calcd, 4.51; found, 4.37. Cl: calcd, 7.56; found, 7.34. S: calcd, 6.84; found, 6.67.

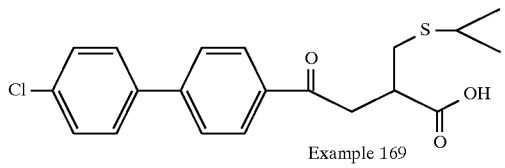

Example 169

Example 169

From isopropylthiol. Purified by reverse phase HPLC using MeOH (75%)/ H$_2$O (35%) and TFA (0.05%). The final product was recrystallized from ethyl acetate and hexane.

MP 110°–111° C.; TLC (methylene chloride-10% methanol) R$_f$ 0.561; $^1$H NMR (CDCl$_3$) δ 8.07 (d, J=8.82 Hz, 2H), 7.67 (d, J=8.46 Hz, 2H), 7.56 (d, J=8.46 Hz, 2H), 7.45 (d, J=8.46 Hz, 2H), 3.43 (m, 3H), 3.00 (m, 2H), 2.83 (m, 1H), 1.29 (m, 6H); $^{13}$C NMR (CDCl$_3$) δ 197.38, 177.66, 144.80, 138.21, 135.29, 134.54, 129.17, 128.83, 128.52, 127.12, 40.35, 38.97, 35.30, 31.74, 23.26; MS (FAB-LSIMS) 377[M+H]$^+$ (C$_{20}$H$_{21}$O$_3$SCl, FW=376.90).

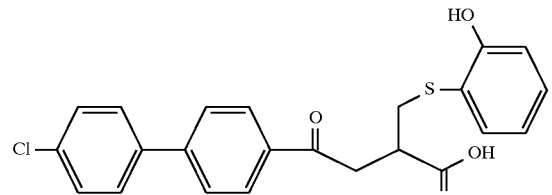

Example 170

Example 170

From 2-hydroxythiophenol. Recrystallized from ethyl acetate and hexane:

MP 148°–149° C.; TLC (methylene chloride-10% methanol) R$_f$ 0.448; $^1$H NMR (CDCl$_3$) δ 7.99 (d, J=8.83 Hz, 2H), 7.64 (d, J=8.46 Hz, 2H), 7.55 (d, J=8.46 Hz, 2H), 7.46 (m, 3H), 7.26 (m, 1H), 6.98 (m, 1H), 6.86 (m, 1H), 6.75 (bs, 1H), 3.55 (m, 1H), 3.20 (m, 4H); $^{13}$C NMR (CDCl$_3$) δ 196.56, 178.21, 156.93, 144.93, 138.11, 135.93, 134.99, 134.57, 131.52, .129.16, 128.78, 128.49, 127.13, 121.04, 117.96, 115.39, 40.39, 38.84, 37.60; MS (FAB-LSIMS) 427[M+H]$^+$ (C$_{23}$H$_{19}$O$_4$SCl, FW=426.92); Anal. C: calcd, 64.71; found, 64.47. H: calcd, 4.49; found, 4.60. S: calcd, 7.51; found, 7.57. Cl: calcd, 8.30; found, 8.31.

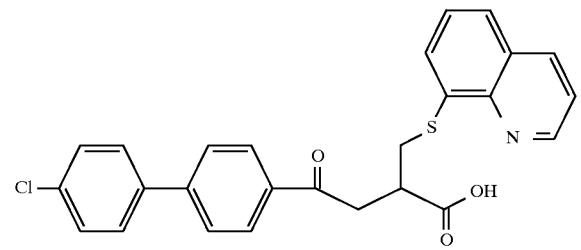

Example 171

Example 171

From 8-mercaptoquinoline. Recrystallized from ethyl acetate and hexane:

MP 172°–173° C.; TLC (methylene chloride-10% methanol) R$_f$ 0.518; $^1$H NMR (CDCl$_3$) δ 8.99 (m, 1H), 8.22 (m, 1H), 7.99 (d, J=8.83 Hz, 2H), 7.86 (m, 1H), 7.72 (m, 1H), 7.50 (m, 8H), 3.69 (m, 1H), 3.41 (m, 4H); $^{13}$C NMR (CDCl$_3$) δ 197.11, 177.45, 149.53, 146.19, 144.59, 138.14, 137.45, 135.29, 135.17, 134.41, 129.92, 129.07, 128.74, 128.44, 127.08, 126.98, 126.55, 121.83, 40.34, 39.55, 34.56; M S (FAB-LSIMS) 462[M+H]$^+$ (C$_{26}$H$_{20}$NO$_3$SCl, FW=461.97); Anal. C: calcd, 67.60; found, 67.40. H: calcd, 4.36; found, 4.39. N: calcd, 3.03; found, 3.03. S: calcd, 6.94; found, 7.04. Cl: calcd, 7.67; found, 7.35.

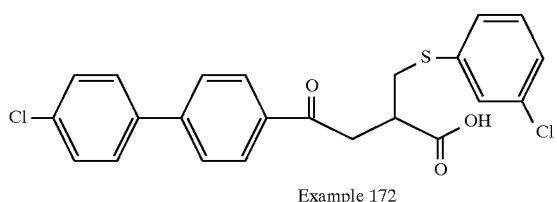

Example 172

Example 172

From 3-chlorothiophenol. Recrystallized from ethyl acetate and hexane:

MP 164°–165° C.; TLC (methylene chloride-10% methanol) $R_f$ 0.450; $^1$H NMR (DMSO-d$_6$) δ 12.58 (bs, 1H), 8.01 (d, J=8.45 Hz, 2H), 7.79 (m, 4H), 7.54 (d, J=8.83 Hz, 2H), 7.43 (m, 1H), 7.32 (m, 2H), 7.23 (m, 5H), 3.30 (m, 5H); $^{13}$C NMR (DMSO-d$_6$) δ 197.36, 174.22, 143.30, 138.39, 137.63, 135.27, 133.36, 130.70, 129.07, 128.79, 128.68, 127.15, 126.90, 126.60, 125.77, 33.67; MS (FAB-LSIMS) 445[M+H]$^+$ (C$_{23}$H$_{18}$O$_3$SCl$_2$, FW=445.36); Anal. C: calcd, 62.03; found, 62.22. H: calcd, 4.07; found, 3.93. S: calcd, 7.19; found, 7.03. Cl: calcd, 15.92; found, 15.54.

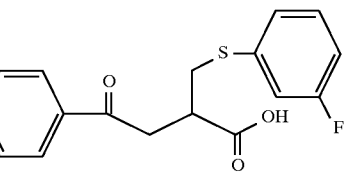

Example 173

Example 173

From 3-fluorothiophenol. Recrystallized from ethyl acetate and hexane:

MP 135°–136° C.; TLC (methylene chloride-10% methanol) $R_f$ 0.420; $^1$H NMR (CDCl$_3$) δ 8.01 (d, J=8.82 Hz, 2H), 7.65 (d, J=8.83 Hz, 2H), 7.56 (d, J=8.45 Hz, 2H), 7.45 (d, J=8.83 Hz, 2H), 7.18 (m, 3H), 6.88 (m, 1H), 3.36 (m, 5H); $^{13}$C NMR (CDCl$_3$) δ 196.77, 178.84, 135.08, 134.56, 130.49, 130.38, 129.16, 128.74, 128.49, 127.11, 124.79, 124.74, 116.26, 115.95, 113.66, 113.37, 40.13, 38.56, 34.41; M S (FAB-LSIMS) 429[M+H]$^+$ (C$_{23}$H$_{18}$O$_3$SFCl, FW=428.91); Anal. C: calcd, 64.41; found, 64.48. H: calcd, 4.23; found, 4.17. S: calcd, 7.47; found, 7.53. Cl: calcd, 8.27; found, 8.15. F: calcd, 4.43; found, 4.53.

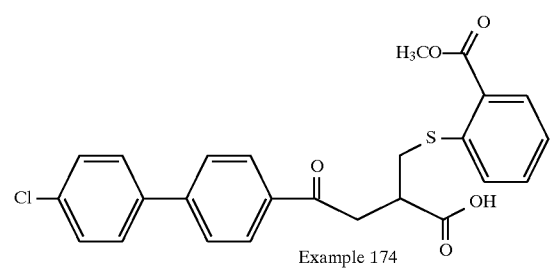

Example 174

Example 174

From methyl 2-mercaptobenzoate. Recrystallized from ethyl acetate and hexane:

MP 167°–168° C.; TLC (methylene chloride-10% methanol) $R_f$ 0.510; $^1$H NMR (DMSO-d$_6$) δ 12.62 (bs, 1H), 8.05 (d, J=8.46 Hz, 2H), 7.83 (m, 5H), 7.58 (m, 4H), 7.27 (m, 1H), 3.81 (s, 3H), 3.55 (m, 1H), 3.37 (m, 2H), 3.21 (m, 2H); $^{13}$C NMR (DMSO-d$_6$) δ 197.38, 174.30, 166.09, 143.26, 139.61, 137.61, 135.28, 133.35, 132.75, 130.73, 129.05, 128.78, 128.68, 127.87, 126.89, 126.18, 124.51, 52.09, 39.37, 32.9; MS (FAB-LSIMS) 469[M+H]$^+$ (C$_{25}$H$_{21}$SO$_5$Cl, FW=468.96); Anal. C: calcd, 64.03; found, 64.07. H: calcd, 4.51; found, 4.44. Cl: calcd, 7.56; found, 7.52. S: calcd, 6.84; found 6.54.

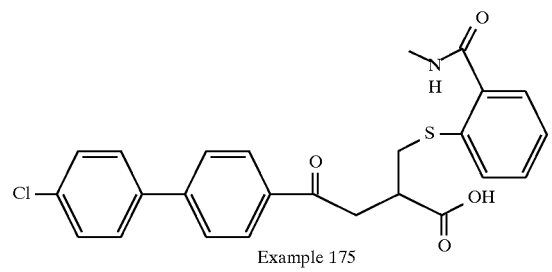

Example 175

Example 175

A solution of Example 174 (20.9 mg, 0.0445 mmol) in THF (1.5 mL) was cooled in a dry ice/ acetone bath. The reaction vessel was sealed with a rubber septum and methylamine gas was bubbled through for approximately 1 minute. The reaction was allowed to warm to room temperature and stirred for several hours. Concentration under reduced pressure and recrystallization from ethyl acetate and hexane provided Example 175 as white crystals.

MP 185°–186° C.; TLC (methylene chloride-10% methanol) $R_f$ 0.288; $^1$H NMR (DMSO-d$_6$) δ 12.51 (bs, 1H), 8.22 (m, 1H), 8.03 (d, J=8.46 Hz, 2H), 7.80 (m, 4H), 7.46 (m, 5H), 7.24 (m, 1H), 3.51 (m, 1H), 3.34 (m, 2H), 3.10 (m, 2H), 2.69 (d, J=4.41 Hz, 3H); $^{13}$C NMR (DMSO-d$_6$) δ 198.61, 175.52, 169.19, 144.37, 138.76, 138.58, 136.45, 135.68, 134.47, 131.12, 130.19, 129.91, 129.78, 129.06, 128.73, 128.02, 126.42, 35.19, 27.10; MS (FAB-LSIMS) 468[M+H]$^+$ (C$_{25}$H$_{22}$O$_4$SNCl, FW=467.98); Anal. C: calcd, 64.17; found, 64.04. H: calcd, 4.74; found, 4.92. N: calcd, 2.99; found, 2.88. S: calcd, 6.85; found, 6.75. Cl: calcd,7.58; found, 7.84.

Example 176

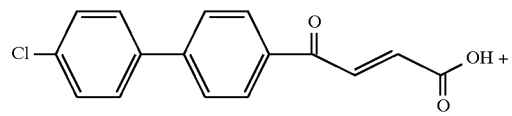

Example 34

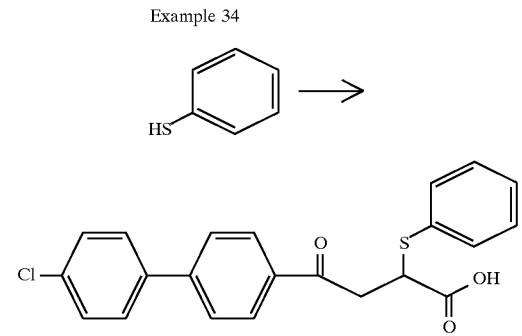

Example 176

Example 176

In a 25 mL round bottom flask, 209.8 mg (0.732 mmol) of Example 34 was dissolved in 5 mL of 1,4-Dioxane. The flask was placed under Ar. Thiophenol, 0.1 mL (0.934 mmol, 1.33 eq) was added to the flask via syringe. The mixture was then stirred at 25° C. At 102 hours an additional 0.1 mL of thiophenol was added via syringe. The mixture stirred for a total of 125 hours. The reaction was then concentrated in vacuo and the residue was recrystallized from ethyl acetate and hexane to yield 93.0 mg (32%) of white crystals (mp=168°–169° C.). (Ref. Chem. Pharm. Bull. 36(6), 2050–2060 (1988).

TLC (methylene chloride-10% methanol) $R_f$ 0.377; $^1$H NMR (CDCl$_3$) δ 8.01 (d, J=8.46 Hz, 2H), 7.51 (m, 11H), 4.26 (m, 1H), 3.69 (m, 1H), 3.45 (m, 1H); $^{13}$C NMR (DMSO-d$_6$) δ 196.07, 176.09, 144.99, 138.11, 134.85, 134.57, 133.73, 132.01, 129.19, 129.16, 128.79, 128.48, 127.16, 45.10, 40.87; MS (FAB-LSIMS) 397[M+H]$^+$ (C$_{22}$H$_{17}$O$_3$SCl, FW=396.89); Anal. C: calcd, 66.58; found, 66.37. H: calcd, 4.32; found, 4.33. Cl: calcd, 8.93; found, 9.07. S: calcd, 8.08; found, 8.18.

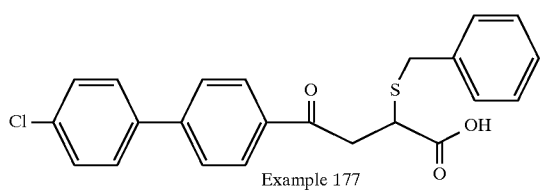

Example 177

Example 177

Made in a manner similar to Example 176 but the crude yellow crystals were dissolved in ethanol, treated with decolorizing carbon, filtered and concentrated in vacuo. The residue was recrystallized from ethyl acetate and hexane to yield 148 mg (40%) of white crystals (mp=162°–164° C.).

TLC (methylene chloride-10% methanol) $R_f$ 0.435; $^1$H NMR (CDCl$_3$) δ 7.96 (d, J=8.09 Hz, 2H), 7.49 (m, 11H), 3.85 (m, 4H), 3.20 (m, 1H); $^{13}$C NMR (CDCl$_3$) 67 195.99, 177.39, 144.93, 138.13, 137.14, 134.77, 134.57, 129.21, 129.15, 128.78, 128.65, 128.50, 127.42, 127.13, 40.53, 40.02, 36.39; MS (FAB-LSIMS) 411[M+H]$^+$ (C$_{23}$H$_{19}$O$_3$SCl, FW=410.92); Anal. C: calcd, 67.23; found, 67.07. H: calcd, 4.66; found, 4.70. Cl: calcd, 8.63; found, 8.73. S: calcd, 7.80; found, 7.82.

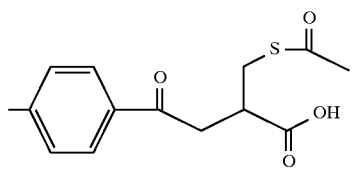

Example 178

Example 178 (Reference)

This compound was prepared using a method similar to that used for Example 118 except that thiolacetic acid was used instead of thiopivalic acid and Example 31 was used instead of Example 30.

MP: 94.0°–95.0° C. $^1$H NMR (DMSO-d$_6$) δ 12.5 (bs, 1H), 7.8 (d, J=7 Hz, 2H), 7.3 (d, J=7 Hz, 2H), 3.4–3.0 (m, 5H), 2.35 (s, 3H), 2.30 (s, 3H); $^{13}$C NMR (DMSO-d$_6$) δ 198.19, 195.96, 175.32, 144.82, 134.93, 130.38, 129.10, 120.27, 31.59, 30.85, 22.26; MS (FAB-LSIMS) 281[M+H]$^+$ (C$_{14}$H$_{16}$O$_4$S, FW=280.27); Anal. C: calcd, 59.98; found, 59.93. H: calcd, 5.75; found, 5.76; S: calcd, 8.51; found, 8.31. S: calcd, 11.44; found, 11.53.

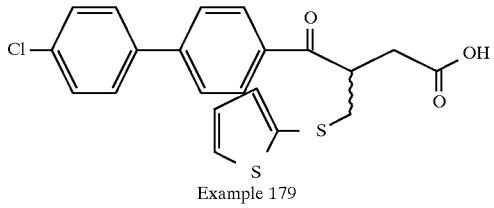

Example 179

Example 179

195.3 mg (0.650 mmole) of Example 25 and 120.9 mg 2-mercaptothiophene were dissolved in 3 ml of distilled THF. The reaction was purged with argon and stirred at ambient temperature overnight. The volatile components were removed in vacuo to give a crude solid that was recrystallized (EtOAc-hexane) to give 140.0 mg (52%) of Example 179.

MP: 160.0°–161.0° C. $^1$H NMR (CDCl$_3$) δ 7.77 (d, J=9Hz, 2H), 7.7–7.4 (m, 6H), 7.20 (dd, J=1.5 Hz, J=3.5 Hz, 1H), 7.06 (dd, J=3.6 Hz, J=5 Hz, 2H), 4.07 (m, 1H), 3.21 (dd, J=4 Hz, J=13 Hz, 1H), 3.11–2.91 (m, 2H), 2.70 9dd, J=9 Hz, J=13 Hz, 1H); $^{13}$C NMR (CDCl$_3$) δ 199.90, 177.65, 145.48, 138.81, 135.94, 135.24, 135.06, 133.32, 131.24, 129.86, 129.83, 129.17, 128.59, 127.86, 42.54, 41.54, 41.15, 34.66; MS (FAB-LSIMS) 417[M+H]$^+$ (C$_{21}$H$_{17}$O$_3$S$_2$Cl, FW=416.94); Anal. C: calcd, 60.50; found, 60.41. H: calcd, 4.11; found, 4.03. S: calcd, 15.38; found, 15.28. Cl: calcd, 8.50; found, 8.57.

Example 180, Example 181, and Example 182

These compounds were similarly prepared from Example 25 and the mercapto-compounds described below (recrystallized from EtOAc-hexane)

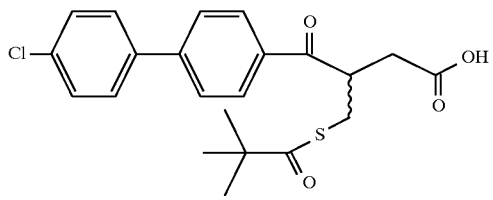

Example 180

Example 180

From thiopivalic acid. MP: 106.0°–107.5° C.; $^1$H NMR (CDCl$_3$) δ 8.17 (d, J=8 Hz, 2H), 7.69 (d, J=8 Hz, 2H), 7.57 (d, J=8 Hz, 2H), 7.45 (d, J=8 Hz, 2H), .4.11 (m, 1H), 3.33 (dd, J=6 Hz, J=14 Hz, 1H), 3.03 (dd, J=10 Hz, J=17 Hz, 1H), 2.82 (dd, J=9 Hz, 14 Hz, 1H), 2.7 (dd, J=17 Hz,J=4 Hz); $^{13}$C NMR (CDCl$_3$) δ 206.21, 199.72, 177.42, 144.80, 138.26, 134.78, 134.46, 129.47, 129.13, 128.50, 127.23, 46.57, 41.86, 34.82, 30.44, 27.28; MS (FAB-LSIMS) 419[M+H]$^+$ (C$_{22}$H$_{23}$O$_4$SCl, FW=418.90); Anal. C: calcd, 63.08; found, 63.05. H: calcd, 5.53; found, 5.46. S: calcd, 7.65; found, 7.27. Cl: calcd, 8.46; found, 8.53.

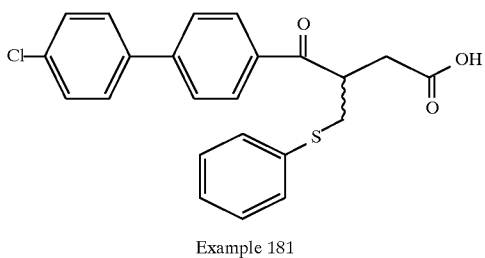

Example 181

Example 181

From thiophenol. MP: 135.0°–136.0° C.; $^1$H NMR (CDCl$_3$) δ 7.85 (d, J=8 Hz, 2H), 7.60–7.25 (m, 11H), 4.05 (m, 1H); $^{13}$C NMR (CDCl$_3$) δ 200.34, 178.36, 145.46, 138.81, 135.32, 135.27, 135.22, 131.75, 129.86, 129.83, 129.17, 127.93, 127.83, 42.41, 37.13,35.37; M S (FAB-LSIMS) 411[M+H]$^+$(C$_{23}$H$_{19}$O$_3$SCl, FW=410.88); Anal. C: calcd, 67.23; found, 66.87. H: calcd, 4.66 found, 4.67. S: calcd, 7.80; found, 7.57. Cl: calcd, 8.63; found, 8.81.

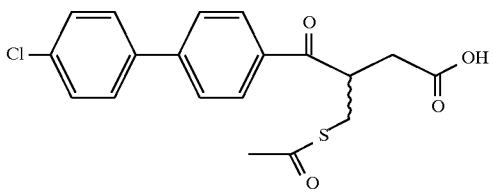

Example 182

Example 182 (Reference With Respect to Composition)

From thioacetic acid. MP: 118.0°–119.0° C.; $^1$H NMR (CDCl$_3$) δ 8.2 (d, J=9 Hz, 2H), 7.7 (d, J=9 Hz, 2H), 7.6 (d, J=9 Hz, 2H), 7.5 (d, J=9 Hz, 2H), 4.1 (m, 1H), 3.4 (dd, J=5 Hz, J=14 Hz, 1H), 3.0 (dd, J=9 Hz, J=17 Hz, 1H), 2.8 (dd, J=9 Hz, J=14 Hz, 1H), 2.7 (dd, J=4 Hz, J=17 Hz, 1H), 2.35 (s, 3H); $^{13}$C NMR (CDCl$_3$) δ 200.03, 196.03, 178.05, 145.59, 138.87, 135.21, 130.14, 129.83, 129.18, 127.94, 42.65, 35.37, 31.58, 31.20; MS (FAB-LSIMS) 377[M+H]$^+$ (C$_{19}$H$_{17}$O$_4$SCl, FW=376.83); Anal. C: calcd, 60.56; found, 60.63. H: calcd, 4.55 found, 4.53; S: calcd, 8.51; found, 8.31. Cl: calcd, 9.41; found, 9.45.

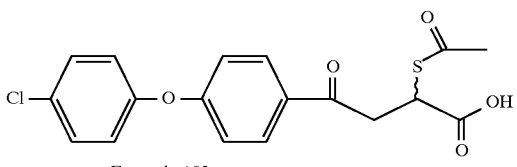

Example 183

Example 183 (Reference)

This compound was prepared by a method similar to that used for Example 118 except that thiolacetic acid was used instead of thiopivalic acid and Example 35 was used instead of Example 30.

Example 183

MP: 91.0°–92.0° C.; $^1$H NMR (DMSO-d$_6$) δ 7.94 (d, J=9 Hz, 2H), 7.36 (d, J=9 Hz, 2H), 7.05–6.95 (m, 4H), 4.75 (m, 1H), 3.5–3.7 (m, 2H), 2.4 (s, 3H); MS (FAB-LSIMS) 378 [M+H]$^+$ (C$_{18}$H$_{15}$O$_5$SCl, FW=378.80).

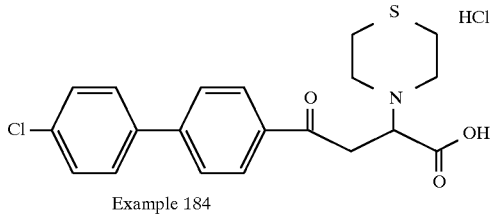

Example 184

Example 184

Example 34 (0.36 mmoles) was dissolved in 10 ml of 1,4-dioxane under argon at ambient temperature. 1.06 EQ of thiomorpholine was added to the solution and within 5 minutes a precipitate began to form. Some additional 1,4-dioxane was added to make the mixture easier to stir. Stirring continued overnight. The solid was removed by filtration and dried in vacuo to yield 129 mg of the free base form of Example 184 as a solid product.

The hydrochloride salt of the product was formed by suspending the initial solid in EtOH and bubbling HCl gas into the suspension until clear. Et$_2$O was used to precipitate the salt which was collected by filtration to give final product Example 184.

MS (FAB-LSIMS) 390 [M+H]$^+$ (C$_{20}$H$_{21}$O$_3$NSCl$_2$, FW=426.41).

Example 185 and Example 186

These compounds were prepared in the same way as Example 184 except that the indicated amine was added instead of thiomorpholine. In each case the initial products were converted to hydrochlorides as above before assay as inhibitors of MMPs.

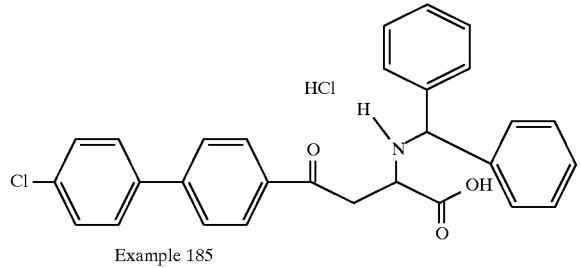

Example 185

Example 185

From aminodiphenylmethane (benzhydrylamine). $^1$H NMR (DMSO-d$_6$) δ 7.3–8.1 (m, 18H), 5.76 (m, 1H), 4.22 (m, 1 H0, 3.78 (m, 2H); MS (FAB-LSIMS) 470 [M+H]$^+$ (C$_{29}$H$_{25}$O$_3$NCl$_2$, FW=506.49).

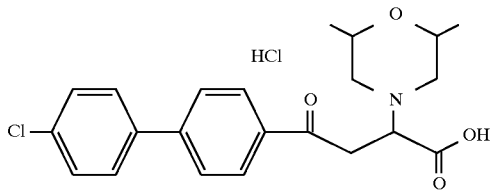

Example 186

Example 186

From 2,6-dimethylmorpholine: $^1$H NMR (DMSO-d$_6$) δ 11.4 (bs, 1H), 8.10 (d, J=9 Hz, 2H), 7.88 (d, J=9 Hz, 2H), 7.78 (d, J=9 Hz, 2H), 7.56 (d, J=9 Hz, 2H), 4.64 (m, 1H), 4.1–2.7 (m, 8H), 1.14 (d, J=6 Hz, 6H); MS (FAB-LSIMS) 402 [M+H]+($C_{22}H_{25}O_4NCl_2$, FW=423.32).

Example 187

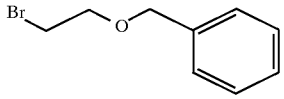

Step 1

A solution of triphenyl phosphine (2.1 g, 7.9 mmol) in dry methylene chloride (16 mL) was added dropwise over 10 min to a stirred mixture of N-bromosuccinimide (1.4 g, 7.9 mmol) in dry methylene chloride (23 mL) at −78° C. The reaction was kept in the dark and stirring was continued until all the N-bromosuccinimide had dissolved (10 min). A solution of 2-(benzyloxy)ethanol in dry methylene chloride (10 mL) was added dropwise. The cooling bath was removed and stirring was continued for 12 h at rt. The organic layer was then concentrated in vacuo and passed through a silica plug with 1:1 hexane:methylene chloride to afford 2-(benzyloxy)bromoethane (1.20 g, 85%).

Step 2

The general method of the preparation of 4-phenyl-1-iodobutane (see Example 107 preparation—step 2) was used to prepare 2-(benzyloxy)iodoethane using 2-(benzyloxy)bromoethane rather than 4-phenyl-1-chlorobutane.

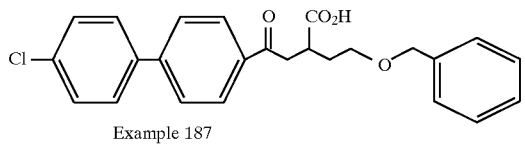

Example 187

Step 3—Preparation of Example 187

The general method of Example 108 was used to prepare Example 187 using 2-(benzyloxy)iodoethane instead of 5-phenyl-1-iodopentane.

Example 187

MP 99°–100° C.; $^1$H NMR (CDCl$_3$) δ COOH (not seen), 8.05 (d, J=8.5 Hz, 2H), 7.63 (d, J=8.5 Hz, 2H), 7.56 (d, J=8.5 Hz, 2H), 7.11 (d, J=8.5 Hz, 2H), 7.33 (m, 5H), 4.53 (s, 2 H, CH$_2$Ph), 3.66 (t, J=5.9 Hz, 2 H, CH$_2$CO), 3.50 (dd, J=16.9, 7.0 Hz, 1 H, CH$_2$CO), 3.25 (m, 2 H, CHCOOH, CH$_2$CO), 2.13 (m, 1 H, CH$_2$CH), 1.98 (m, 1 H, CH$_2$CH); $^{13}$C NMR (CDCl$_3$) δ 197.56, 178.68, 144.65, 138.24, 137.80, 135.40, 134.50, 129.15, 128.76, 128.50, 128.45, 127.77, 127.74, 127.08, 73.17, 68.12, 40.20, 37.85, 31.38; MS (FAB-HRMS) 423.1363 (M+H)+ ($C_{25}H_{24}O_4Cl$, FW=423.1366).

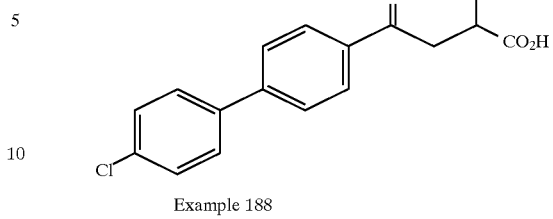

Example 188

Example 188

This compound were prepared using the general procedure of Example 87 except that the indicated commercial malonate was used instead of ethyl 2-carboethoxy-5-phenylpentanoate. From diethyl 2-trimethylsilylmethylmalonate:

MP 134°–136° C.; $^1$H NMR (CDCl$_3$) δ 8.02 (dd, J=6.6 Hz and 1.9 Hz, 2H); 7.65 (d, J=6.6 Hz, 2H); 7.56 (d, J=6.6 Hz, 2H); 7.45 (dd, J=6.6 Hz and 1.9 Hz, 2H); 3.50 (m, 1H); 3.10 (m, 3H); 1.08 (dd, J=14.8 Hz and 7.2 Hz, 1H); 0.80 (dd, J=14.6 Hz and 7.2 Hz, 1H); 0.09 (s, 9H); $^{13}$C NMR (CDCl$_3$) δ 198.13, 183.06, 145.27, 138.92, 136.11, 135.14, 129.81, 129.38, 129.17, 127.78, 43.75, 37.00, 20.56, −0.40; MS (FAB-LSIMS) 375 [M+H]+, ($C_{20}H_{23}Cl\ O_3Si$, FW=374.9); Anal. C: calcd, 64.07; found, 64.12. H: calcd, 6.18; found, 6.14. Cl: calcd; 9.46, found; 9.47.

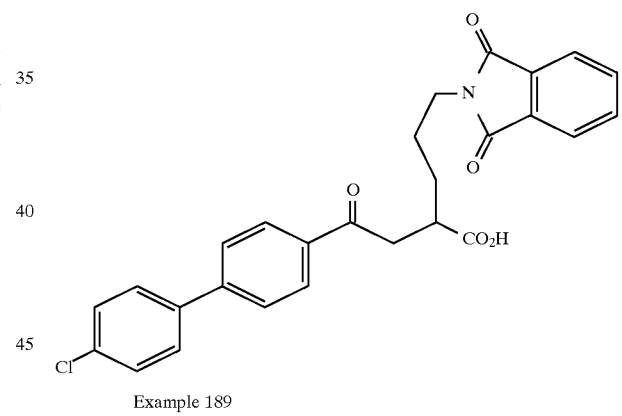

Example 189

Example 189

This compound was prepared using the general procedure of Example 87 except that commercial dimethyl 2-(3-N-phthalimidopropyl)malonate was used instead of ethyl 2-carboethoxy-5-phenylpentanoate . Also the following procedures were used instead of the treatment of the crude oil with NaOH in ethanol/water and successive steps. The substituted diester (product from steps 1,2, and the first half of 3) was dissolved in a 1:4 solution of concentrated hydrochloric acid : glacial acetic acid in a sealed vessel and heated to 110° C. for 18h. After cooling, solvent was removed under reduce pressure. The resultant was concentrated from hexanes (2×25 mL) and toluene (2×25 mL) affording a solid which was chromatographed on silica gel with 3% acetic acid/ethyl acetate.

MP 191°–192° C.; $^1$H NMR (CDCl$_3$/DMSO) δ 7.73 (d, J=8.5 Hz , 2H); 7.56 (m, 2H); 7.46 (m, 2H); 7.37 (d, J=8.3

Hz, 2H); 7.29 (m, 2H); 7.17 ( d, J=8.8 Hz, 2H); 3.44 (m, 2H); 3.21 (dd, J=18.7 Hz and 9.3 Hz, 1H); 2.76 (m, 2H); 1.48 (m, 4H); $^{13}$C NMR (DMSO) δ 199.8, 177.20, 168.70, 144.70, 138.68, 136.08, 134.69, 134.51, 132.45, 129.56, 129.15, 129.01, 127.47, 123.61, 29.65, 26.78; MS (FAB-LSIMS) 475 [M+H]$^+$, (C$_{27}$H$_{22}$NCl O$_5$, FW=475.9).

Example 190

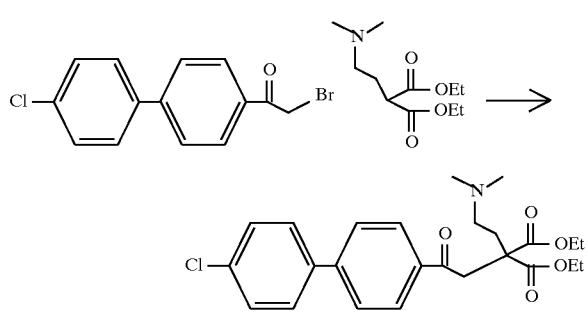

Step 1

The bromomethylketone product from step 2 of the Example 87 preparation was recrystallized from ethyl acetate. In a 50 mL round bottom flask, 1.22 g (3.94 mmol) of this purified material was dissolved in 12 mL of dimethoxyethane (DME). Sodium iodide, 618.9 mg (4.13 mmol, 1.05 eq) was added to the flask to yield solution 1.

In a separate flask, 1.00 g (4.34 mmol, 1.1 eq) of commercial diethyl (2-dimethylaminoethyl)malonate was dissolved in 4 mL of DME. Sodium ethoxide, 336 mg (4.69 mmol) was added to the flask to yield solution 2.

Solution 1 was added to solution 2 and the mixture stirred at 25° C. for 1.5 hours. The reaction was concentrated in vacuo and the residue dissolved in chloroform. The chloroform was washed twice with a 10% solution of potassium carbonate and once with a solution of sodium bisulfite. The organic layer was dried over magnesium sulfate, filtered and concentrated in vacuo.

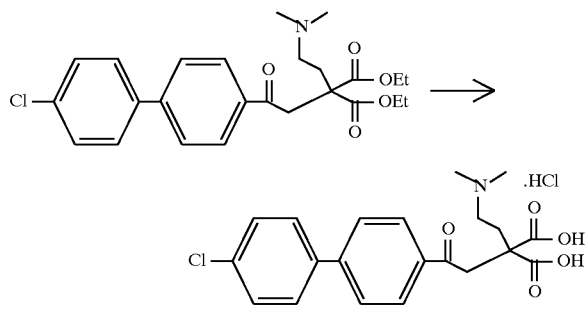

Step 2

The residue from step 1 was dissolved in 20 mL of a 1:1:1 mixture of ethanol/water/tetrahydrofuran and 6 mL of 1.0N NaOH was added. The mixture was refluxed for several days, diluted with water, acidified with 10% HCl to pH=3 and condensed.

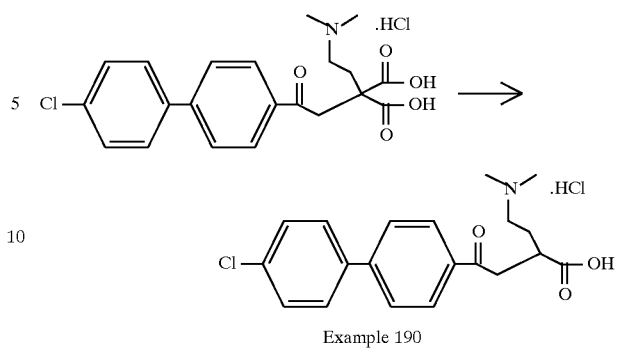

Example 190

Step 3—Preparation of Example 190

The resultant solid was mixed with 100 mL of 1N HCl and refluxed for 8 hours. The mixture was filtered and the solid was washed with hot ethanol. The ethanol washes were concentrated and crystals were collected. The filtrate was concentrated to dryness and recrystallized from ethyl acetate to produce 15.6 mg (3.7%) of white crystals of Example 190.

MP 207°–208° C.; $^1$H NMR (DMSO-d$_6$) δ 8.06 (d, J=8.46 Hz, 2H), 7.82 (m, 4H), 7.56 (d, J=8.46 Hz, 2H); the rest of the signals are buried under the DMSO and H$_2$O peaks; MS (FAB-LSIMS) 360[M+H]$^+$ (C$_{20}$H$_{22}$NO$_3$Cl.HCl, FW=359.86+HCl);. Anal. C: calcd, 60.61; found, 59.81. H: calcd, 5.85; found, 5.75. N: calcd, 3.53; found, 3.30. Cl: calcd, 17.89; found, 17.48.

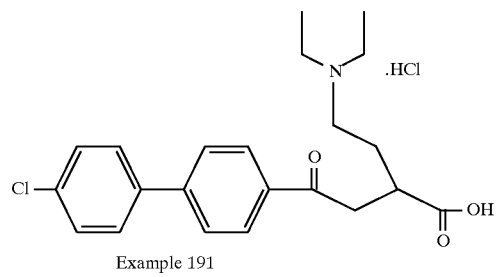

Example 191

Example 191

Example 191 was made in a manner similar to Example 190 except that diethyl 2-(2-diethylaminoethyl)malonate was used instead of diethyl (2-dimethylaminoethyl) malonate. The final product was first crystallized from acetone and hexane and then from acetone to yield pure Example 191.

MP 185°–186° C.; $^1$H NMR (DMSO-d$_6$) δ 12.75 (bs, 1H), 10.25 (bs, 1H), 8.07 (d, J=8.46 Hz, 2H), 7.85 (d, J=8.46 Hz, 2H), 7.79 (d, J=8.83 Hz, 2H), 7.56 (d, J=8.46 Hz, 2H), 3.23 (m, 9H), 1.99 (m, 2H), 1.20 (t, J=7.17 Hz, 6H); $^{13}$C NMR (DMSO-d$_6$) δ 197.59, 175.23, 143.29, 137.63, 135.35, 133.39, 129.07, 128.81, 128.73, 126.89, 48.52, 46.14, 37.51, 24.76, 8.45; MS (FAB-LSIMS) 388[M+H]$^+$ (C$_{22}$H$_{26}$NO$_3$Cl.HCl FW=387.91+HCl); Anal. C: calcd, 62.27; found, 62.28. H: calcd, 6.41; found, 6.32. N: calcd, 3.30; found, 3.20. Cl: calcd, 16.71; found, 16.84.

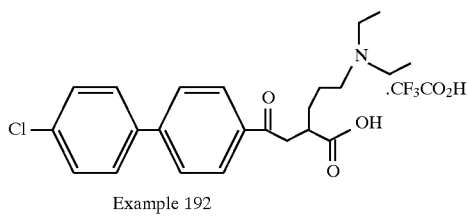

Example 192

Example 192

Example 192 was prepared in a manner similar to Example 190 except that diethyl 2-(3-diethylaminopropyl)malonate was used instead of diethyl (2-dimethylaminoethyl)malonate. The solid that precipitated after the acidification with HCl was chromatographed by reverse phase HPLC using MeOH(65%)/H$_2$O (35%) and TFA (0.05%).

$^1$H NMR (CDCl$_3$) δ 11.13 (bs, 1H), 8.01 (d, J=8.09 Hz, 2H), 7.62 (d, J=8.09 Hz, 2H), 7.54 (d, J=8.46 Hz, 2H), 7.44 (d, J=8.45 Hz, 2H), 4.33 (m, 4H), 3.50 (m, 1H), 3.16 (m, 8H), 1.83 (m, 4H), 1.34 (m, 6H); MS (FAB-LSIMS) 402 [M+H]$^+$ (C$_{23}$H$_{28}$NO$_3$Cl.TFA, FW=401.93 +TFA).

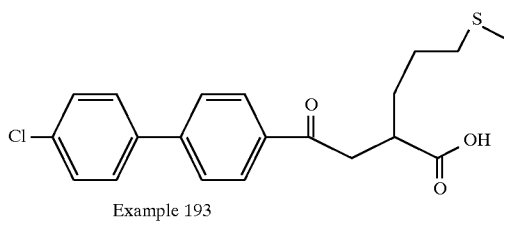

Example 193

Example 193

Example 193 was prepared in a manner similar to Example 190 except that diethyl 2-(3-methylthiopropyl)malonate was used instead of diethyl (2-dimethylaminoethyl)malonate. The crude diester intermediate was not washed with base. It was chromatographed over silica gel using Hexane and ethyl acetate. After the final acidification the product was extracted into ethyl acetate and concentrated. The residue was dissolved in 1,4-dioxane and refluxed to decarboxylate. The crude product was then chromatographed over silica gel using ethyl acetate and acetic acid. The product was recrystallized from ethyl acetate and hexane.

MP 134°–135° C.; TLC (methylene chloride-5%methanol) R$_f$ 0.274; $^1$H NMR (CDCl$_3$) δ 8.04 (d, J=8.43 Hz, 2H), 7.66 (d, J=8.43 Hz, 2H), 7.56 (d, J=8.43 Hz, 2H), 7.45 (d, J=8.80 Hz, 2H), 3.51 (m, 1H), 3.13 (m, 2H), 2.55 (m, 2H), 2.11 (s, 3H), 1.80 (m, 4H); $^{13}$C NMR (CDCl$_3$) δ 197.35, 179.83, 144.75, 135.32, 134.53, 129.15, 128.76, 128.50, 127.13, 40.29, 39.63, 33.82, 30.83, 26.58, 15.49; MS (FAB-LSIMS) 377[M+H]$^+$ (C$_{20}$H$_{21}$O$_3$SCl, FW=376.90); Anal. C: calcd, 63.74; found, 63.54. H: calcd, 5.62; found, 5.56. S: calcd, 8.51; found, 8.34. Cl: calcd, 9.41; found, 9.59.

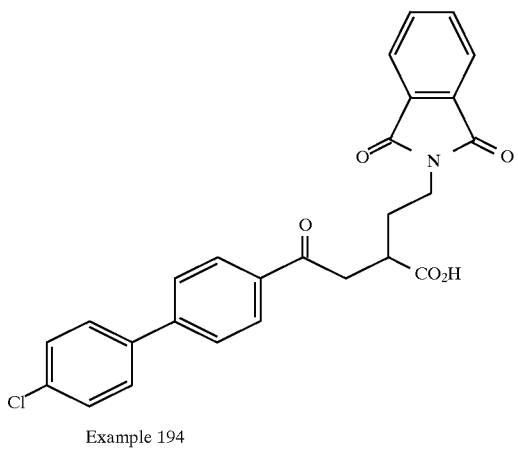

Example 194

Example 194

This compound was prepared using the general methods of Example 107 except that commercial N-(2-bromoethyl) phthalimide was used instead of 4-phenyl-1-iodobutane in step 3. Also the alternative hydrolysis and decarboxylation procedure given for Example 189 was used instead of treatment with NaOH and then acid followed by heating.

MP 209°–210° C.; $^1$H NMR (CDCl$_3$/DMSO) δ 7.75 (d, J=8.5 Hz , 2H); 7.54 (m, 2H); 7.46 (m, 2H); 7.37 (d, J=6.5 Hz, 2H); 7.30 (m, 2H); 7.16 ( d, J=8.5 Hz, 2H); 3.55 (m, 2H); 3.26 (dd, J=17.8 Hz and 8.3 Hz, 1H); 2.94 (dd, J=17.6 Hz and 5.0 Hz, 1H); 2.76 (m, 1H); 1.87 (m, 1H); 1.70 (m, 1H); $^{13}$C NMR (DMSO) δ 197.76, 176.68, 168.59, 144.72, 138.66, 136.06, 134.69, 134.50, 132.46, 129.56, 129.18, 128.99, 127.47, 123.63, 38.40, 36.32, 30.67, 27.86 ; MS (FAB-LSIMS) 462 [M+H]$^+$, (C$_{26}$H$_{19}$NCl O$_5$, FW=461.9).

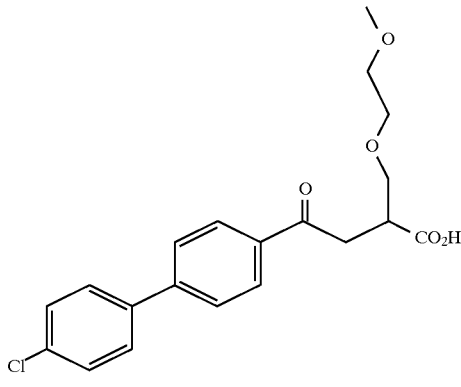

Example 195

Example 195

This compound was made using the general methods of Example 107 except that 2-methoxyethoxymethyl chloride was used instead of 4-phenyl-1-iodobutane in step 3.

MP 95°–97° C.; $^1$H NMR (DMSO) δ 8.02 (d, J=8.5 Hz , 2H); 7.77 (m, 4H); 7.54 (d, J=8.5 Hz, 2H); 3.64 (m, 2H); 3.46 (m, 5H); 3.20 (s, 3H); 3.16 (m, 2H); $^{13}$C NMR (DMSO) δ 198.82, 175.24, 144.27, 138.76, 136.63, 134.43, 130.17, 129.88, 129.75, 128.01, 72.22, 71.93, 70.82, 59.19, 42.04, 38.18; MS (FAB-LSIMS) 377 [M+H]$^+$, (C$_{20}$H$_{21}$Cl O$_5$, FW=376.8).

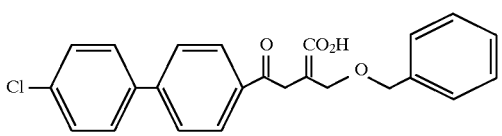

Example 196

Example 196

The general method of Example 108 was used to prepare Example 196 using commercially available benzylchloromethyl ether with 0.9 eq of NaI, instead of 5-phenyl-1-iodopentane in Step 3.

$^1$H NMR (DMSO-d$_6$) δ 12.33 (s, 1 H, COOH), 8.05 (d, J=7.3 Hz, 2H), 7.84 (d, J=7.3 Hz, 2H), 7.79 (d, J=8.8 Hz, 2H), 7.57 (d, J=8.8 Hz, 2H), 7.30 (m, 5H), 4.49 (s, 2 H, CH$_2$Ph), 3.69 (m, 2 H, CH$_2$CO), 3.51 (m, 1 H, CHCOOH), 3.18 (d, 2 H, CH$_2$CH); $^{13}$C NMR (DMSO-d$_6$) δ 197.70, 174.20, 143.18, 138.25, 137.70, 135.53, 133.36, 129.10, 128.81, 128.71, 128.24, 127.44, 127.08, 126.92, 72.07, 70.18, 40.92, 38.67; MS (FAB-LSIMS) 409 (M+H)$^+$ (C$_{24}$H$_{21}$O$_4$Cl, FW=408); Anal. C: calcd, 70.50; found, 70.73. H: calcd, 5.18; found, 5.14.

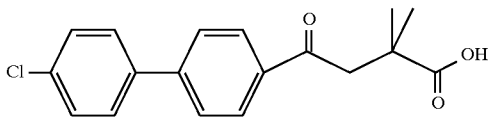

Example 197

Example 197

This compound was prepared by a similar method to that used for Example 30, except thatthe indicated anhydride was used instead of itaconic anhydride. From 2,2-dimethylsuccinic anhydride:

MP 179°–180° C.; TLC (methylene chloride-10%methanol) R$_f$ 0.571; $^1$H NMR (CDCL$_3$) δ 8.03 (d, J=8.8 Hz, 2H), 7.65 (d, J=8.07 Hz, 2H), 7.55 (d, J=8.07 Hz, 2H), 7.45 (d, J=8.07 Hz, 2H), 3.35 (s, 2H), 1.4 (s, 1H); $^{13}$C NMR (CDCL$_3$) δ 197.64, 183.80, 145.17,138.92, 136.42, 135.11, 129.80, 129.33, 129.17, 127.71, 48.95, 40.62, 26.29; MS (FAB-LSIMS) 317 [M+H]$^+$ (C$_{18}$H$_{17}$O$_3$Cl, FW=316.79); Anal. C: calcd, 68.25; found, 68.03. H: calcd, 5.41; found, 5.42. Cl: calcd, 11.19; found, 11.18.

Example 198

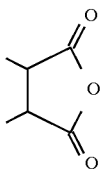

Step 1—Preparation of 2,3-Dimethyl succinic anhydride

To the 2,3-dimethyl succinic acid (5.13 g, 35.1 mmol), was added acetyl chloride (8.27 g, 7.49 mL, 105 mmol) at room temperature. The reaction mixture was refluxed at about 65° C. for 2 hrs. Workup consisted of concentration in vacuo, and drying in high vacuo. The desired product ( 4.95 g, with a little impurity of acetic acid) was obtained as a white solid.

$^1$H-NMR (CDCl$_3$) δ isomer #1:1.25 (d, 6H), 3.18–3.23 (m, 2H); isomer #2:1.36 (d, 6H), 2.71–2.77 (m, 2H).

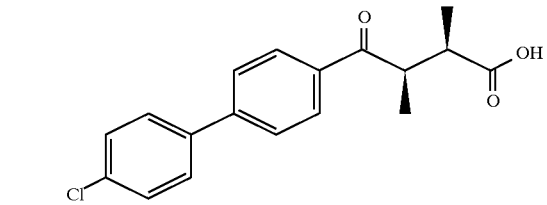

Example 198 (racemate)

Step 2—Preparation of Example 198

Produced using the general method of Example 1 except that 1,2-dichloroethane was used as solvent and the anhydride from step 1 was used instead of dihydro-3-(2-methylpropyl)-2,5-furandione.

MP 157°–159° C.; TLC (1/1 (v/v) EtOAc/hexane) R$_f$=0.21; $^1$H-NMR (CDCl$_3$) δ 8.04 (d, J=8.09 Hz, 2H), 7.62 (d, J=8.09 Hz, 2H), 7.55 (d, J=8.45 Hz, 2H), 7.44 (d, J=8.45 Hz, 2H), 3.81–3.71 (m, 1H), 3.07–2.97 (m, 1H), 1.28 (d, J=7.35 Hz, 3H), 1.21 (d, J=7.36 Hz, 3H); MS (FAB-LSIMS) 317 [M+H]$^+$ (C$_{18}$H$_{17}$ClO$_3$, FW=316.77); Anal. C: calcd, 68.25; found, 68.22.1 H: calcd, 5.41,; found, 5.24.

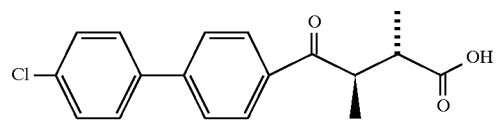

Example 199 (racemate)

Example 199

This compound was prepared in a similar manner to Example 1, except that the indicated anhydride was used instead of dihydro-3-(2-methylpropyl)-2,5-furandione. From meso-2,3-dimethylsuccinic anhydride:

MP 165.0°–167.0° C.; TLC (1/1 (v/v) EtOAc/hexane) R$_f$=0.17; $^1$H NMR (CDCl$_3$) δ 8.07 (d, J=8.46 Hz, 2H), 7.68 (d, J=8.09 Hz, 2H), 7.57 (d, J=8.46, 2H), 7.45 (d, J=8.82, 2H), 3.77 (dq, J=7.35 Hz, J=8.09 Hz, 1H), 3.02 (dq, J=6.98 Hz, J=8.08 Hz, 1H), 1.30 (d, J=7.35 Hz, 3H), 1.24 (d, J=6.98 Hz, 1H); IR (nujol) 1708.7, 1679.7, 1604.5 cm$^{-1}$;

MS (FAB-LSIMS) 317 [M+H]$^+$ (C$_{18}$H$_{17}$ClO$_3$, FW=316.77); Anal. C: calcd, 68.25; found, 68.23. H: calcd, 5.41; found, 5.26.

Example 200, Example 201, and Example 202

These compounds were prepared in a similar manner to Example 1, except that the indicated anhydrides were used instead of dihydro-3-(2-methylpropyl)-2,5-furandione:

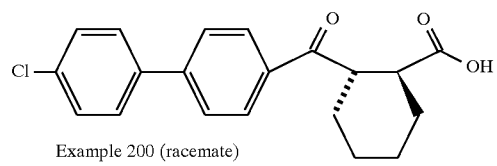

Example 200 (racemate)

Example 200

From trans-cyclohexane-1,2-dicarboxylic acid anhydride: MP 187°–188° C.; TLC (methylene chloride-5%methanol) R$_f$ 0.236; 1 H NMR (DMSO-d$_6$) δ 12.17 (bs, 0.7H), 8.06 (d, J=8.8 Hz, 2H), 7.81 (d, J=8.8 Hz, 2H), 7.76 (d, J=8.8 Hz, 2H), 7.55 (d, J=8.8 Hz, 2H), 3.61 (m, 1 H), 2.66 (m, 1H), 2.07 (bd, 1H), 1.90 (bd, 1H), 1.73 (m, 2H), 1.39 (m, 3H), 1.09 (m, 1H); $^{13}$C NMR (DMSO-d$_6$) δ 203.13, 177.18, 144.21, 138.87, 135.79, 134.40, 130.16, 130.09, 129.91, 128.12, 46.98, 45.37, 30.61, 29.80, 26.34, 26.03; MS (FAB-LSIMS) 343 [M+H]$^+$ (C$_{20}$H$_{19}$O$_3$Cl, FW=342); Anal. C: calcd, 70.07; found, 69.61. H: calcd, 5.59; found, 5.61. Cl: calcd, 10.34; found, 10.10.

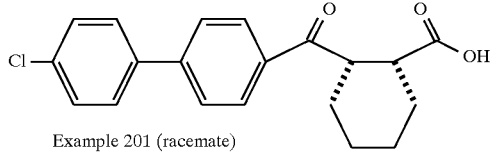

Example 201 (racemate)

Example 201

From cis-cyclohexane-1,2-dicarboxylic acid anhydride: MP 180°–181° C.; TLC (methylene chloride-5%methanol) R$_f$ 0.267; $^1$H NMR (DMSO-d$_6$) δ 12.02 (bs, 0.6H), 7.94 (d, J=8.07 Hz, 2H), 7.76 (t, J=8.8 Hz, 4H), 7.53 (d, J=8.06 Hz, 2H), 3.94 (m, 1H), 2.68 (m, 1 H), 2.03 (m, 1H), 1.79 (m, 3H), 1.59 (m, 1H), 1.26 (m, 3H); $^{13}$C NMR (DMSO-d$_6$) δ 202.92, 176.06, 143.66, 138.92, 136.68, 134.32, 130.24, 130.14, 129.86, 127.98, 44.32, 43.37, 27.86, 26.39, 25.07, 23.29; MS (FAB-LSIMS) [M+H]$^+$ (C$_{20}$H$_{19}$O$_3$Cl, FW=342); Anal. C: calcd, 70.07; found, 69.77. H: calcd, 5.59; found, 5.58. Cl: calcd, 10.34; found, 10.27.

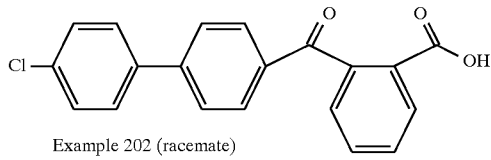

Example 202 (racemate)

Example 202

From phthalic anhydride: MP >230° C.; TLC (methylene chloride-5%methanol) R$_f$ 0.138; $^1$H NMR (DMSO-d$_6$) δ 13.17 (bs), 7.71 (m); $^{13}$C NMR (DMSO-d$_6$) δ 205.89, 130.93, 130.68, 130.63, 130.17, 129.89, 128.02, 41.08, 40.99, 40.71, 40.68, 40.50, 40.42, 40.16, 40.13, 39.96; MS (FAB-LSIMS) 337 [M+H]$^+$ (C$_2$OH$_{13}$O$_3$Cl, FW=336.78); Anal. C: calcd, 71.33; found,,69.94. H: calcd, 3.89; found, 3.92. Cl: calcd, 10.53; found, 11.09.

Example 203

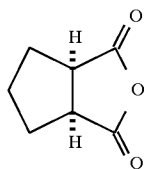

Step 1—Preparation of cis-Cyclopentane-1,2-dicarboxylic anhydride

To the trans-cyclopentane-1,2-dicarboxylic acid (1.16 g, 7.33 mmol) at room temperature, was added Acetic anhydride (10 mL, ex). The reaction mixture was refluxed at about 165° C. for 14 hrs. Workup consisted of concentration in vacuo and co-evaporation with toluene three times. The crude product (1.0 g, ~100%, with a little impurity of Acetic anhydride) was given as a brown oily solid.

$^1$H-NMR (CDCl$_3$) δ 3.55–3.35 (m, 2H), 2.4–2.2 (m, 2H), 2.15–1.75 (m, 5H), 1.55–1.35 (m, 1H).

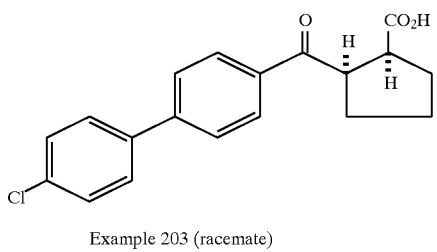

Example 203 (racemate)

Step 2—Preparation of Example 203

Produced using the general method of Example 1 except that 1,2-dichloroethane was used as solvent and the anhydride made in step 1 was used instead of dihydro-3-(2-methylpropyl)-2,5-furandione. The product (1.0 g, 43%) purified by chromatography on silica gel to yield a residue containing both cis and trans isomers. The cis isomer Example 203 (160 mg) was isolated by several recrystallizations.

MP 176°–178° C.; TLC (1/1 (v/v) EtOAc/hexane) R$_f$=0.37; $^1$H-NMR (CDCl$_3$) δ 11.89 (bs, 1H), 8.02 (d, J=8.46 Hz, 2H), 7.81 (d, J=8.46 Hz, 2H), 7.77 (d, J=8.82 Hz, 2H), 7.55 (d, J=8.46 Hz, 2H), 4.15–4.11 (m, 1H), 3.14–3.11 (m, 1H), 2.03–1.61 (m, 6H); IR (nujol) 2983.4, 1708.7, 1679.7 cm$^{-1}$; MS (FAB-LSIMS) 329 [M+H]$^+$ (C$_{19}$H$_{17}$ClO$_3$, FW=328.79); Anal. C: calcd, 69.40; found, 69.36. H: calcd, 5.21; found, 5.37.

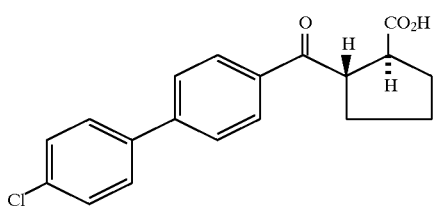

Example 204 (racemate)

Example 204

To the trans isomer containing mother liquid of Example 203 (110 mg, 0.334 mmol) in THF (5 mL), was added 1,8-Diazabicyclo [5.4.0] undec-7-ene (75 μL, 0.502 mmol) at room temperature. The reaction mixture was stirred under argon for 48 hrs. Workup consisted of dilution with CH$_2$Cl$_2$ (15 mL), addition of 1N HCl (15 mL), separation, extraction of the aqueous with CH$_2$Cl$_2$ (15 mL×3), drying the combined organic layers over MgSO$_4$, filtration and concentration in vacuo. The crude product (98 mg, 89%) was purified by HPLC, to provide pure trans compound Example 204 as a white solid.

Example 204

MP 169°–172° C.; TLC (1/1 (v/v) EtOAc/hexane) R$_f$=0.37; $^1$H-NMR (CDCl$_3$) δ 8.05 (d, J=8.46, 2H), 7.63 (d, J=8.83 Hz, 2H), 7.53 (d, J=8.82 Hz, 2H), 7.41 (d, J=8.83 Hz, 2H), 4.16–4.08 (m, 1H), 3.48–3.41 (m, 1H), 2.21–1.73 (m, 6H); IR (nujol) 1700.9, 1672.0 cm$^{-1}$; MS (FAB-LSIMS) 329 [M+H]$^+$ (C$_{19}$H$_{17}$ClO$_3$, FW=328.79); Anal. C: calcd, 69.40; found, 69.14. H: calcd, 5.21; found, 5.13.

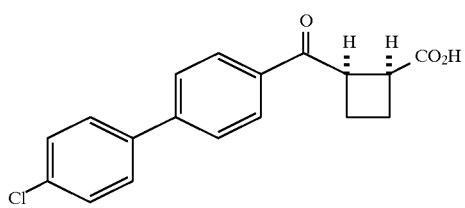

Example 205 (racemate)

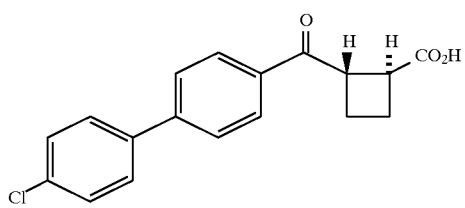

Example 206 (racemate)

Example 205 and Example 206

These compounds were produced using the general method of Example 1 except that 1,2-dichloroethane was used as solvent and cyclobutanedicarboxylic anhydride was used instead of dihydro-3-(2-methylpropyl)-2,5-furandione. The crude product (0.72 g, 30%) contained a mixture of cis and trans isomers (cis: trans =2/1): MS (FAB-LSIMS) 315 [M+H]$^+$ (C$_{18}$H$_{15}$ClO$_3$, FW=314.84).

Example 205

The crude product was purified by chromatography on silica gel to provide 40 mg of the cis isomer as a white solid.

MP 154°–156° C.; TLC (¹/₁₀ (v/v) IPA/hexane) R$_f$=0.15; $^1$H-NMR (DMSO-d$_6$) δ 7.93 (d, J=8.46 Hz, 2H), 7.79 (d, J=7.72 Hz, 2H), 7.77 (d, J=8.46 Hz, 2 H0, 7.55 (d, J=8.83 Hz, 2H), 4.37–4.34 (m, 1H), 3.58–3.61 (m, 1H), 2.42–2.04 (m, 4H); IR (nujol) 3079.8, 1699.0, 1681.7 cm$^{-1}$; MS (El) 315 [M+H]$^+$ (C$_{18}$H$_{15}$ClO$_3$, FW=314.84); Anal. C: calcd, 68.66; found, 68.27. H: calcd, 4.80; found, 4.43.

Example 206

To the suspension of the crude two component product (14.5 g, 46.06 mmol) in MeOH (250 mL) at room temperature, was added K$_2$CO$_3$ (ex). The reaction mixture was stirred at room temperature for 48 hrs. Workup consisted of addition of 2N HCl (500 mL), extraction of the aqueous layer with CH$_2$Cl$_2$ (7×400 mL), washing the combined organic layers with sat. NaCl (1200 mL), drying over MgSO$_4$, filtration and concentration in vacuo. The crude product (13.2 g, 91%) was given as off-white solid with 84% de favour trans isomer. The recrystallization was carried out to provide 9.1 g of pure trans material as white crystals.

MP 184°–186° C.; TLC (¹/₁₀ (v/v) IPA/hexane) R$_f$=0.15; $^1$H-NMR (DMSO-d$_6$) δ 12.3 (bs, 1H), 8.01 (d, J=8.45 Hz, 2H), 7.82 (d, J=8.46 Hz, 2H), 7.77 (d, J=8.82 Hz, 2H), 7.55 (d, J=8.46 Hz, 2H), 4.35–4.27 (m, 1H), 3.47–3.38 (m, 1H), 2.32–1.98 (m, 4H); $^{13}$C-NMR (DMSO-d$_6$) δ 199.39, 176.08, 144.46, 134.92, 134.47, 130.14, 129.91, 128.13, 44.75, 39.18, 23.71, 22.37; IR (nujol) 3035.5, 1693.2, 1670.1 cm$^{-1}$; MS (El) 315 [M+H]$^+$ (C$_{18}$H$_{15}$ClO$_3$, FW=314.84); Anal. C: calcd, 68.66; found, 68.81. H: calcd, 4.80; found, 4.59.

Example 207

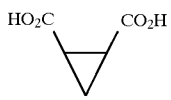

Step 1—Preparation of Cyclopropane-1,2-dicarboxylic acid

To the solution of 1,2-cis-dimethylcyclopropane dicarboxylate ester (4.71 g, 29.8 mmol) in THF (100 mL) at room temperature, was added 1N NaOH (150 mL). The reaction mixture was stirred under argon for 14 hrs. Workup consisted of separation of THF layer from the aqueous, washing the aqueous with diethyl ether, acidification the aqueous with 2N HCl, concentration to dryness, dilution with EtOAc, filtration and concentration in vacuo. The desired product (3.5 g, 90%) was given as a white solid.

$^1$H-NMR (DMSO-d$_6$) δ 4.21 (bs, 2H), 1.29–1.24 (m, 1H), 0.71–0.65 (m, 1H).

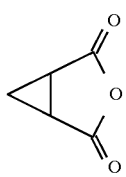

Step 2—Preparation of cis-Cyclopropane-1,2-dicarboxylic anhydride

To the cyclopropane-1,2-dicarboxylic acid (3.24 g, 24.9 mmol) at room temperature, was added acetic anhydride (30 mL, ex). The reaction mixture was refluxed for 4 hrs. Workup consisted of concentration in vacuo to provide the desired product.

$^1$H-NMR (DMSO-d$_6$) δ 2.00 (dd, J=4.04, J'=8.08, 2H), 0.90–0.83 (m, 2H).

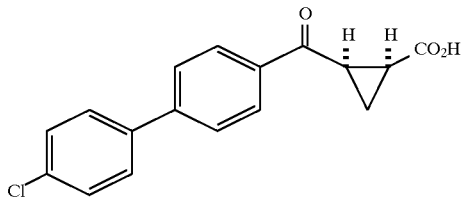

Example 207 (racemate)

Step 3—Preparation of Example 207 (Reference With Respect to Composition)

Produced using the general method of Example 1 except that 1,2-dichloroethane was used as solvent and the anhydride of step 2 above was used instead of dihydro-3-(2-methylpropyl)-2,5-furandione.

MP 175°–176° C.; $^1$H-NMR (DMSO-d$_6$) δ 12.16 (s, 1H), 8.08 (d, J=8.46 Hz, 2H), 7.84 (d, J=8.45 Hz, 2H), 7.78 (d, J=8.46 Hz, 2H), 7.56 (d, J=8.46 Hz, 2H), 3.05–2.97 (m, 1H), 2.33–2.25 (m, 1H), 1.57–1.51 (m, 1H), 1.33–1.26 (m, 1H); $^{13}$C-NMR (DMSO-d6) δ 194.85, 144.25, 138.83, 136.98, 134.42, 130.15, 129.91, 127.97, 27.33, 23.76, 12.07; IR (nujol) 1689.4, 1673.9, 1604.5 cm$^{-1}$; MS (FAB-LSIMS) 301 [M+H]$^+$ (C$_{17}$H$_{13}$ClO$_3$, FW=300.7); Anal. C: calcd, 67.89; found, 68.06. H: calcd, 4.36; found, 4.15.

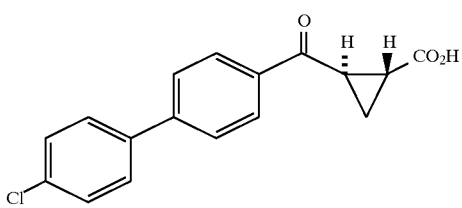

Example 208 (racemate)

Example 208 (Reference With Respect to Composition)

To the solution of Example 207 (50 mg, 0.166 mmol) in MeOH (20 mL) at room temperature, was added $K_2CO_3$ (ex). The reaction mixture was stirred at room temperature for 48 hrs. Workup consisted of addition of 1N HCl (25 mL), extraction of the aqueous layer with $CH_2Cl_2$ (4×25 mL), washing the combined organic layers with sat. NaCl (50 mL), drying over $MgSO_4$, filtration and concentration in vacuo. The product (50 mg, 100%) was given as a white solid with >99% de favour trans isomer.

MP 181°–183° C.; $^1$H-NMR (DMSO-d6) δ 12.65 (s, 1H), 8.13 (d, J=8.46 Hz, 2H), 7.86 (d, J=8.46 Hz, 2H), 7.79 (d, J=8.46 Hz, 2H), 7.56 (d, J=8.45 Hz, 2H), 3.28–3.22 (m, 1H), 2.14–2.08 (m, 1H), 1.52–1.45 (m, 2H); MS (FAB-LSIMS) 301 [M+H]$^+$ ($C_{17}H_{13}ClO_3$, FW=300.7); Anal. C: calcd, 67.89; found, 67.95. H: calcd, 4.36; found, 4.34.

Example 209 and Example 210

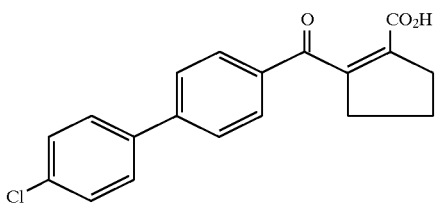

Step 1

Using the general method of Example 1 except that the solvent was 1,2-dichloroethane and 1-Cyclopentene-1,2-dicarboxylic anhydride was used instead of dihydro-3-(2-methylpropyl)-2,5-furandione, the above compound (27.7 g) was obtained as white crystals in 91% yield.

MP 226°–227° C.; $^1$H NMR (DMSO-d6) δ 7.90 (d, J=8.46 Hz, 2H), 7.62 (d, J=8.46 Hz, 2H), 7.54 (d, J=8.83 Hz, 2H), 7.44 (d, J=8.82 Hz, 2H), 2.89–2.78 (m, 2H), 2.16–2.06 (m, 2H); $^{13}$C NMR (DMSO-d6) δ 196.77, 166.07, 153.31, 144.77, 138.81, 135.60, 135.43, 134.53, 130.36, 130.20, 129.96, 128.25, 38.23, 33.97, 23.35.

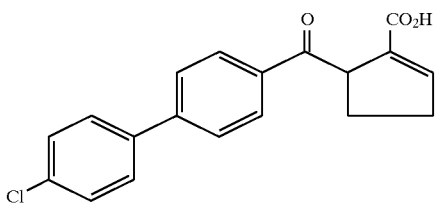

Step 2

To the solution of diisopropylamine (19 mL, 130 mmol) in THF (60 mL) at −78 ° C., was added n-Butyl lithium (78 mL, 125 mmol). The formed LDA was stirred for 30 min at −78° C. and then treated with a solution. of the product from step 1 (10.2 g, 31.2 mmol) in THF (100 ML). The reaction mixture was stirred under argon at −78° C. for 1.5 hrs, and quenched with AcOH (21 mL, 375 mmol). The resulting mixture was allowed to warm to room temperature during a period of 2 hrs. Workup consisted of addition of 1N HCl (100 mL), extraction of the aqueous with $CH_2C_{12}$ (3×150 mL), and concentration in vacuo. The crude product was recrystallized from EtOAc to provide 6.22 g of the above compound as off-white crystals.

MP 202°–204° C.; $^1$H NMR (DMSO-d6) δ 8.06 (d, J=8.46 Hz, 2H), 7.64 (d, J=8.09 Hz, 2H), 7.54 (d, J=8.46 Hz, 2H), 7.43 (d, J=8.45 Hz, 2H), 7.14 (m, 1H), 4.80–4.75 (m, 1H), 2.75–2.44 (m, 3H), 2.11–2.00 (m, 1H); $^{13}$C NMR (DMSO-d6) δ 201.25, 166.39, 146.46, 144.35, 138.81, 137.79, 136.11, 134.47, 130.36, 130.18, 129.94, 128.10, 52.20, 33.50, 29.83.

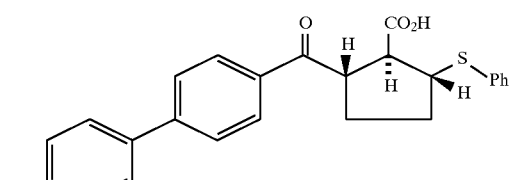

Example 209 (racemate)

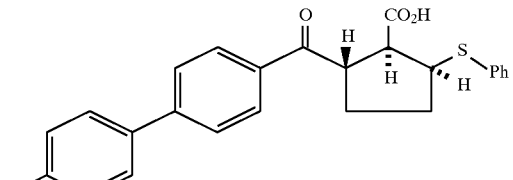

Example 210 (racemate)

Step 3—Preparation of Example 209 and Example 210

To a solution of the product from step 2 (919 mg, 2.81 mmol) in DMF (6 mL) at room temperature under argon, was added thiophenol (433 μL, 4.22 mmol) and $K_2CO_3$ in $H_2O$ (2 M, 141 μL, 0.281 mmol). The reaction mixture was stirred under argon at room temperature for 18 hrs. Workup consisted of dilution with $CH_2Cl_2$ (15 mL), acidification with 2N HCl, addition of $H_2O$ (20 mL), washing the organic layer with $H_2O$ (3×40 mL), sat. NaCl (30 mL), drying over $MgSO_4$, filtration and concentration in vacuo. The crude product was purified by chromatography on silica gel to provide two separated diastereomers, trans-trans Example 209 and trans-cis Example 210 in a total yield of 46%.

Example 209

MP 177°–178° C; $^1$H NMR (CDCl$_3$) δ 8.01 (d, J=8.46 Hz, 2H), 7.64 (d, J=8.82 Hz, 2H), 7.54 (d, J=8.83 Hz, 2H), 7.47–7.41 (m, 4H), 7.30–7.25 (m, 3H), 4.13–4.08 (m, 1H), 3.91–3.88 (m, 1H), 3.60–3.55 (m, 1H), 2.28–2.19 (m, 2H), 2.01–1.83 (m, 2H); IR (nujol) 3075.9, 110.6, 1675.9 cm$^{-1}$; MS (FAB-LSIMS) 337 [M+H]$^+$ ($C_{25}H_{21}Cl$ $O_3S$, FW=436.94); Anal. C: calcd, 68.72; found, 68.61. H: calcd, 4.85; found, 4.76.

Example 210

MP 184°–185° C.; $^1$H NMR (CDCl$_3$) δ 8.07 (d, J=8.45 Hz, 2H), 7.66 (d, J=8.45 Hz, 2H), 7.56 (d, J=8.86 Hz, 2H), 7.47–7.43 (m, 4H), 7.29–7.25 (m, 3H), 4.43–4.34 (m, 1H), 4.11–4.05 (m, 1H), 3.95–3.90 (m, 1H), 2.57–2.49 (m, 1H), 2.22–2.13 (m, 1H), 2.11–2.02 (m, 1H), 1.83–1.73 (m, 1H); IR (nujol) 3074.0, 1708.6, 1673.9, 1604.5 cm$^{-1}$; MS (FAB-LSIMS) 337 [M+H]$^+$ ($C_{25}H_{21}Cl\ O_3S$, FW=436.94); Anal. C: calcd, 68.72; found, 68.52. H: calcd, 4.85; found, 4.81.

Example 211 and Example 212

Enantiomeric separation of Example 209 was carried out by using a Diacel® AD semi-prep column (2 cm×25 cm) with 15% IPA (with 1% $H_2O$ and 0.1% TFA) in hexane to provide enantiomer Example 211 with >98% ee, and enantiomer Example 212 with >97% ee.

Example 211

(+)-enantiomer; MP 165°–167° C.; Anal. C: calcd, 6 8.72; found, 68.59. H: calcd, 4.85; found, 4.64.

Example 212

(−)-enantiomer; MP 168°–169° C.; Anal. C: calcd, 68.72; found, 68.39. H: calcd, 4.85; found, 4.67.

Example 213, Example 214, Example 215, Example 216, Example 217, Example 218, Example 219, Example 220, Example 221, Example 222, AND Example 223

Example 213, Example 214, Example 215, Example 216, Example 217, Example 218, Example 219, Example 220, Example 221, Example 222 and Example 223 were made in a similar method to that used for Example 209 except that the indicated thiol-containing compounds were used instead of thiophenol.

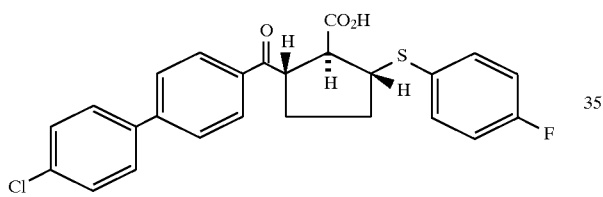

Example 213 (racemate)

Example 213

From 4-florothiophenol: MP 164°–166° C.; $^1$H NMR (CDCl$_3$) δ 7.90 (m, 2H), 7.52 (m, 2H), 7.43 (m, 2H), 7.39–7.29 (m, 4H), 6.88 (m, 2H), 4.03 (m, 1H), 3.74 (m, 1H), 3.32 (m, 1H), 2.05 (m, 2H), 1.84 (m, 1H), 1.67 (m, 1H); MS (FAB-LSIMS) 455 [M+H]$^+$ ($C_{25}H_{20}ClFO_3S$, FW=454.95); Anal. C: calcd, 66.00; found, 65.90. H: calcd, 4.43; found, 4.51.

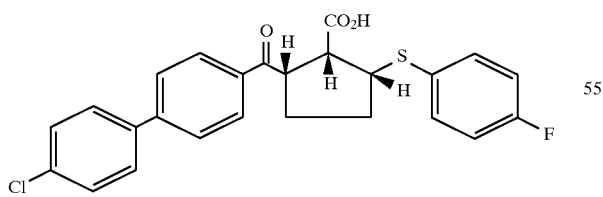

Example 214 (racemate)

Example 214

From 4-florothiophenol: $^1$H NMR (CDCl$_3$) δ 7.98 (d, J=8.46 Hz, 2H), 7.60 (d, J=8.45 Hz, 2H), 7.54 (d, J=8.46 Hz, 2H), 7.44 (d, J=8.82 Hz, 2H), 7.30–7.29 (m, 2H), 6.88 (m, 2H), 4.23 (m, 1H), 3.79 (m, 1H), 3.46 (m, 1H), 2.32–2.08 (m, 3H), 1.86 (m, 1H); MS (FAB-LSIMS) 455 [M+H]$^+$ ($C_{25}H_{20}ClFO_3S$, FW=454.95).

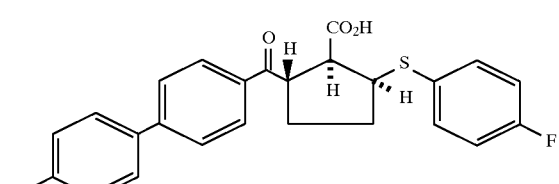

Example 215 (racemate)

Example 215

From 4-florothiophenol: MP 211°–212° C.; $^1$H NMR (CDCl$_3$) δ 7.89 (d, J=8.09 Hz, 2H), 7.49 (d, J=8.45 Hz, 2H), 7.40 (d, J=8.45 Hz, 2H), 7.30–7.25 (m, 2H), 6.84 (m, 2H), 4.19 (m, 1H), 3.78 (m, 1H), 3.62 (m, 1H), 2.32 (m, 1H), 1.97–1.78 (m, 2H), 1.58 (m, 1H); MS (FAB-LSIMS) 455 [M+H]$^+$ ($C_{25}H_{20}ClFO_3S$, FW=454.95); Anal. C: calcd, 66.00; found, 65.98. H: calcd, 4.43; found, 4.48.

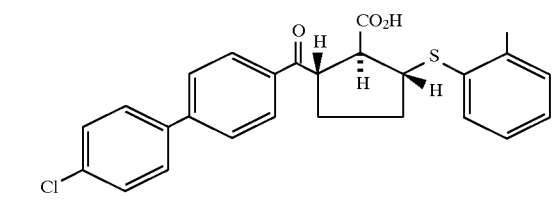

Example 216 (racemate)

Example 216

From o-thiocresol: MP 175°–176° C.; $^1$H NMR (CDCl$_3$) δ 8.02 (d, J=8.46 Hz, 2H), 7.64 (d, J=8.83 Hz, 2H), 7.54 (d, J=8.82 Hz, 2H), 7.43 (d, J=8.46 Hz, 2H), 7.47–7.41 (m, 1H), 7.14–7.13 (m, 3H), 4.12 (m, 1H), 3.91 (m, 1H), 3.62 (m, 1H), 2.24 (m, 2H), 2.02 (m, 1H), 1.85 (m, 1H); IR (nujol) 3074.0, 1708.6, 1673.9, 1604.5 cm$^{-1}$; M S (FAB-LSIMS) 451 [M+H]$^+$ ($C_{26}H_{23}ClO_3S$, FW=450.99); Anal. C: calcd, 69.24; found, 69.20. H: calcd, 5.14; found, 5.07.

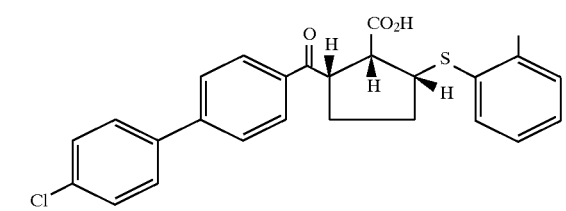

Example 217 (racemate)

Example 217

From o-thiocresol: $^1$H NMR (CDCl$_3$) δ 8.01 (d, J=8.46 Hz, 2H), 7.59 (d, J=8.83 Hz, 2H), 7.54 (d, J=8.45 Hz, 2H), 7.43 (d, J=8.82 Hz, 2H), 7.29(m, 1H), 7.12–7.02 (m, 3H), 4.26 (m, 1H), 3.82 (m, 1H), 3.55 (m, 1H), 2.37–2.07 (m, 3H), 1.94–1.83 (m, 1H); MS (FAB-LSIMS) 451 [M+H]$^+$ ($C_{26}H_{23}ClO_3S$, FW=450.99).

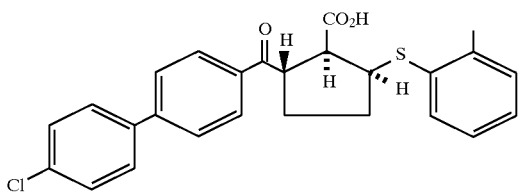

Example 218 (racemate)

Example 218

From o-thiocresol: MP 196°–197° C.; ¹H NMR (CDCl$_3$) δ 8.09 (d, J=8.46 Hz, 2H), 7.67 (d, J=8.45 Hz, 2H), 7.56 (d, J=8.83 Hz, 2H), 7.44 (d, J=8.83 Hz, 2H), 7.45 (m, 1H), 7.16 (m, 3H), 4.12 (m, 1H), 4.06 (m, 1H), 3.96 (m, 1H), 2.58 (m, 1H), 2.14 (m, 1H), 2.05 (m, 1H), 1.81 (m, 1H); MS (FAB-LSIMS) 451 [M+H]$^+$ (C$_{26}$H$_{23}$ClO$_3$S, FW=450.99); Anal. C: calcd, 69.24; found, 69.27. H: calcd, 5.14; found, 5.20.

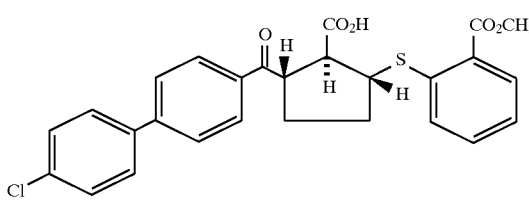

Example 219 (racemate)

Example 219

From o-methylthiosalicylate: 1H NMR (CDCl$_3$) δ 8.03 (d, J=8.83 Hz, 2H), 7.90 (m, 1H), 7.64 (d, J=8.82 Hz, 2H), 7.54 (d, J=8.82 Hz, 2H), 7.46–7.42 (m, 4H), 7.19 (m, 1H), 4.17–4.04 (m, 2H), 3.70 (m, 1H), 2.64–2.24 (m, 2H), 2.10–1.90 (m, 2H); MS (FAB-LSIMS) 495 [M+H]$^+$ (C$_{27}$H$_{23}$ClO$_5$S, FW=494.99).

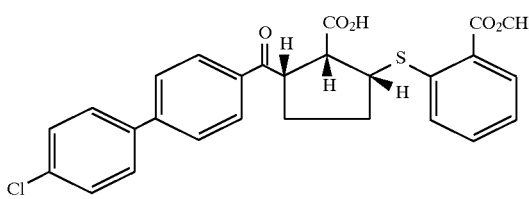

Example 220 (racemate)

Example 220

From o-methylthiosalicylate: ¹H NMR (CDCl$_3$) δ 8.10 (d, J=8.82 Hz, 2H), 7.86 (m, 1H), 7.60 (d, J=8.83 Hz, 2H), 7.52 (d, J=8.82 Hz, 2H), 7.41 (d, J=9.83 Hz, 2H), 7.28 (m, 2H), 7.11 (m, 1H), 4.30 (m, 1H), 4.03 (m, 1H), 3.50 (m, 1H), 2.37–2.23 (m, 3H), 2.00–1.93 (m, 1H); MS (FAB-LSIMS) 495 [M+H]$^+$(C$_{27}$H$_{23}$ClO$_5$S, FW=494.99).

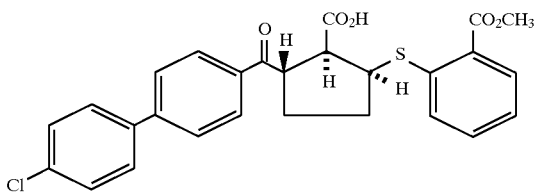

Example 221 (racemate)

Example 221

From o-methylthiosalicylate: MP 227°–228° C.; ¹H NMR (CDCl$_3$) δ 7.90 (m, 2H), 7.72 (m, 1H), 7.50 (m, 2H), 7.40 (m, 2H), 7.35–7.25 (m, 4H), 7.02 (m, 1H), 4.26 (m, 1H), 3.90 (m, 1H), 3.76 (m, 1H), 2.35 (m, 1H), 2.08 (m, 1H), 1.94 (m, 1H), 1.62 (m, 1H); MS (FAB-LSIMS) 495 [M+H]$^+$ (C$_{27}$H$_{23}$ClO$_5$S, FW=494.99); Anal. C: calcd, 65.51; found, 65.17. H: calcd, 4.68; found, 4.73.

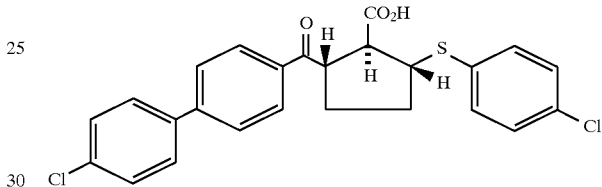

Example 222 (racemate)

Example 222

From 4-chlorothiophenol: MP 213°–214° C.; ¹H NMR (CDCl$_3$) δ 7.99 (d, J=8.46 Hz, 2H), 7.60 (d, J=8.46 Hz, 2H), 7.51 (d, J=8.82 Hz, 2H), 7.40 (d, J=8.46 Hz, 2H), 7.37 (d, J=8.09 Hz, 2H), 7.22 (d, J=8.46 Hz, 2H), 4.12 (m, 1H), 3.91 (m, 1H), 3.44 (m, 1H), 2.17 (m, 2H), 1.94 (m, 1H), 1.78 (m, 1H); MS (FAB-LSIMS) 471 [M+H]$^+$ (C$_{25}$H$_{20}$Cl$_2$O$_3$S, FW=470); Anal. C: calcd, 63.69; found, 63.68. H: calcd, 4.28; found, 4.28.

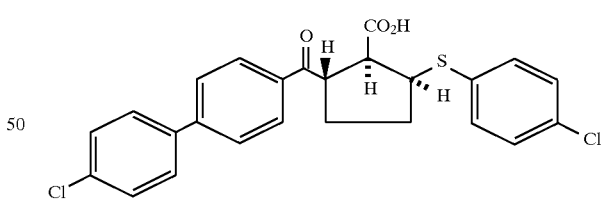

Example 223 (racemate)

Example 223

From 4-chlorothiophenot: MP 210°–211° C.; ¹H NMR (CDCl$_3$) δ 8.06 (d, J=8.46 Hz, 2H), 7.67 (d, J=8.09 Hz, 2H), 7.56 (d, J=8.83 Hz, 2H), 7.44 (d, J=8.46 Hz, 2H), 7.39 (d, J=8.46 Hz, 2H), 7.28 (m, 2H), 4.37 (m, 1H), 4.04 (m, 1H), 3.94 (m, 1H), 2.52 (m, 1H), 2.19 (m, 1H), 2.05 (m, 1H), 1.81 (m, 1H); MS (FAB-LSIMS) 471 [M+H]$^+$ (C$_{25}$H$_{20}$Cl$_2$O$_3$S, FW=470); Anal. C: calcd, 63.69; found, 63.58. H: calcd, 4.28; found, 4.31.

Example 224 and Example 225

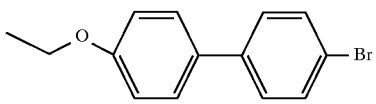

Step 1—Preparation of Ethyl 4-(4-bromophenyl) phenyl ether

To a solution of 4-(4-bromophenyl)-phenol (4.06 g, 16.3 mmol) in acetone (30 mL) at room temperature, was added 4.5 eq $K_2CO_3$ (4.0 M, 18 mL, 73.3 mmol) in water and 4.0 eq Iodoethane (5.26 mL, 65.2 mmol). The reaction mixture was stirred overnight, and heated to reflux for 6 hrs. The product was crystallized out of the solution, and filtered. The crude product was recrystallized from hexane to provide ethyl 4-(4-bromophenyl) phenyl ether (4.1 g, 91%) as an white crystal.

$^1$H NMR (CDCl$_3$) δ 7.53 (d, J=8.83 Hz, 2H), 7.47 (d, J=6.62 Hz, 2H), 7.41 (d, J=8.46 Hz, 2H), 6.96 (d, J=8.82 Hz, 2H), 4.07 (q, J=6.99 Hz, 2H), 1.44 (t, J=6.99 Hz, 3H).

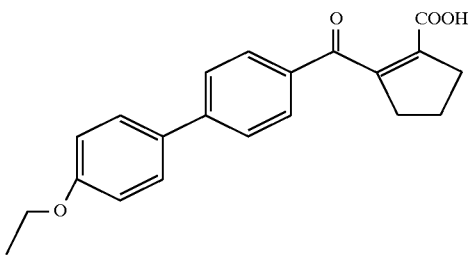

Step 2

To the solution of ethyl 4-(4-bromophenyl) phenyl ether (12.87 g, 46.43 mmol) in THF (90 mL), was added t-BuLi (1.7M, 54.6 mL, 92.87 mmol) at −78° C. The reaction mixture was stirred under argon at −78° C. for 3 hrs, and treated with 1-cyclopentene-1,2-dicarboxylic anhydride (6.73 g, 48.75 mmol). The resulting mixture was stirred at −78° C. for 2 hrs, and then warmed to room temperature. Workup consisted of addition of 1N HCl (150 mL), extraction with EtOAc (4×200 mL), and concentration in vacuo. The crude product (18 g) was recrystallized from EtOAc to provide the intermediate acylacrylic acid (6.8 g, 43%) as an off-white solid.

$^1$H NMR (CDCl$_3$) δ 7.88 (d, J=8.09 Hz, 2H), 7.63 (d, J=8.45 Hz, 2H), 7.56 (d, J=8.82 Hz, 2H), 6.98 (d, J=9.19 Hz, 2H), 4.09 (q, J=6.99 Hz, 2H), 2.84 (m, 4H), 2.10 (m, 2H), 1.45 (t, J=6.99 Hz, 3H).

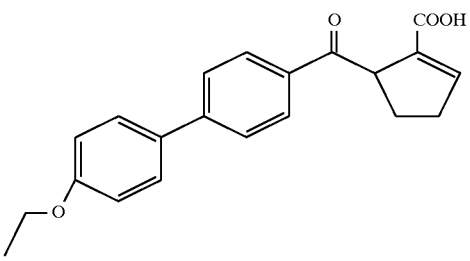

Step 3

To the solution of intermediate from step 2 (3.45 g, 10.25 mmol) in THF (100 mL) at −78° C., was added 4.0 eq LiN(TMS)$_2$ (1M, 41.03 mL, 41.03 mmol). The resulting yellow mixture was stirred under argon at −78° C. for 18 hrs, quenched with AcOH (10 mL), and then allowed to warm to room temperature. Workup consisted of addition of 1N HCl (120 mL), extraction with EtOAc (4×130 mL), washing the combined organic layers with sat. NaCl (250 mL), drying over MgSO$_4$, filtration and concentration in vacuo. The crude product was purified by recrystallization from EtOAc to provide a rearranged acrylic acid intermediate (2.40 g, 70%) as an off-white solid.

$^1$H NMR (CDCl$_3$) δ 7.89 (d, J=8.64 Hz, 2H), 7.50 (d, J=8.09 Hz, 2H), 7.42 (d, J=8.83 Hz, 2H), 6.85 (s, 1H), 6.83 (d, J=8.83 Hz, 2H), 4.64 (m, 1H), 3.94 (q, J=6.99 Hz, 2H), 2.47 (m, 2H), 2.35 (m, 1H), 1.85 (m, 1H), 1.29 (t, J=6.99 Hz, 3H).

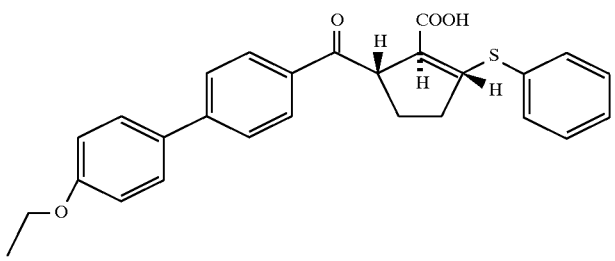

Example 224 (racemate)

-continued

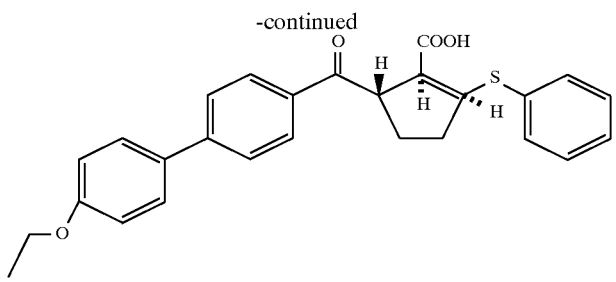

Example 225 (racemate)

Step 4—Preparation of Example 224 and Example 225

To the solution of intermediate from step 3 (510 mg, 1.52 mmol) in DMF (2 mL) at room temperature under argon, was added thiophenol (311 μL, 3.03 mmol) and freshly made $K_2CO_3$ in $H_2O$ (2M, 75 μL, 0.15 mmol). The homogeneous solution was stirred at room temperature overnight. Workup consisted of acidification with 2N HCl (1 mL), addition of $H_2O$ (10 mL), extraction with $CH_2Cl_2$ (2×15 mL), filtration through silica, and concentration in vacuo. The crude product was purified by HPLC (0–8% EtOAc/$CH_2Cl_2$) to provide two separated diastereomers, trans-trans isomer Example 224 and trans-cis isomer Example 225.

Example 224

$^1$H NMR (CDCl$_3$) δ 7.99 (d, J=8.82 Hz, 2H), 7.63 (d, J=8.46 Hz, 2H), 7.55 (d, J=8.83 Hz, 2H), 7.48 (m, 2H), 7.29–7.20 (m, 3H), 6.98 (d, J=9.19 Hz, 2H), 4.10 (m, 1H), 4.08 (q, J=6.99 Hz, 2H), 3.90 (m, 1H), 3.58 (m, 1H), 2.35 (m, 2H), 1.95 (m, 1H), 1.85 (m, 1H), 1.44 (t, J=6.99 Hz, 3H); MS (FAB-LSIMS) 447 [M+H]$^+$ ($C_{27}H_{26}O_4S$, FW=446.54); Anal. C: calcd, 72.62; found, 72.74; H: calcd, 5.87; found, 5.84.

Example 225

$^1$H NMR (CDCl$_3$) δ 8.03 (d, J=8.45 Hz, 2H), 7.64 (d, J=8.46 Hz, 2H), 7.55 (d, J=8.46 Hz, 2H), 7.44 (m, 2H), 7.29–7.15 (m, 3H), 6.97 (d, J=8.82 Hz, 2H), 4.36 (m, 1H), 4.07 (q, J=6.99 Hz, 2H), 4.07 (m, 1H), 3.90 (m, 1H), 2.50 (m, 1H), 2.15 (m, 1H), 2.05 (m, 1H), 1.75 (m, 1H), 1.43 (t, J=6.99 Hz, 3H); MS (FAB-LSIMS) 447 [M+H]$^+$ ($C_{27}H_{26}O_4S$, FW=446.54); Anal. C: calcd, 72.62; found, 72.39; H: calcd, 5.87; found, 5.87.

Example 226

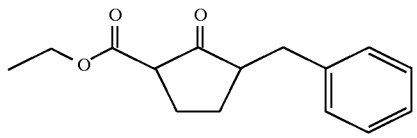

Step 1

To the solution of diisopropylamine (30.8 mL, 220 mmol) in THF (100 mL) at −78° C., was added n-BuLi (2M, 100 mL, 200 mmol). The LDA solution was stirred at −78° C. for 30 min., and followed by addition of ethyl-2-oxocyclopentanecarboxylate (15.6 g, 14.8 mL, 100 mmol). The reaction mixture was allowed to warm to 0° C. for 30 min. After cooling down to −78° C., the reaction mixture was treated with benzyl chloride (12.66 g, 11.51 mL, 100 mmol). The resulting mixture was warmed to 0° C. for 3 hrs.

Workup consisted of acidification with 2N HCl (100 mL), extraction with EtOAc (4×100 mL), drying over MgSO$_4$, filtration and concentration in vacuo. The crude product was purified by MPLC (5–15% EtOAc/hexane) to provide the indicated intermediate (7.1 g, 29%) as a clear oil.

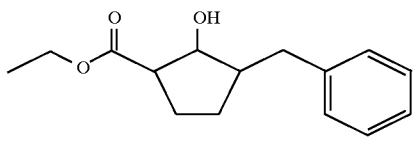

Step 2

To the solution of intermediate from step 1 (7.28 g, 29.56 mmol) in EtOH (50 mL) at 0° C., was added NaBH$_4$ (1.12 g, 29.56 mmol). The reaction mixture was stirred at room temperature for 3 hrs under argon, and then quenched by sat. NH$_4$Cl (100 mL). Workup consisted of extraction with EtOAc (4×100 mL), drying over MgSO$_4$, filtration and concentration in vacuo. The crude product was given as an yellow oil.

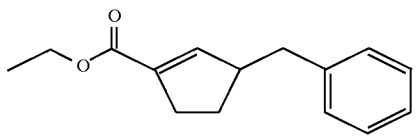

Step 3

To the solution of triphenylphosphine (14.64 g, 55.8 mmol) and DEAD (7.99 mL, 50.74 mmol) in THF (100 mL) at room temperature, was added the solution of intermediate from step 2 (6.30 g, 25.37 mmol) in THF (_50 mL). The reaction mixture was refluxed overnight under argon. Workup consisted of concentration in vacuo. The crude product was purified by MPLC twice (2% EtOAc/hexane) to provide the above intermediate (2.85 g, 49%).

$^1$H NMR (CDCl$_3$) δ 7.35–7.15 (m, 5H), 6.68 (bs, 1H), 4.20 (q, 2H), 3.15 (m, 1H), 2.80–2.45 (m, 4H), 2.10 (m, 1H), 1.65 (m, 1H), 1.29 (t,

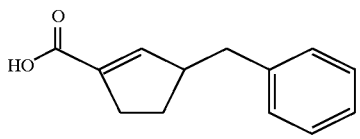

Step 4

To the solution of intermediate from step 3 (2.8 g, 12.16 mmol) in DME (35 mL) at room temperature, was added LiOH.H$_2$O (5.1 g, 121.6 mmol) in H$_2$O (_35 mL). The resulting mixture was heated to reflux for 3 hrs. Workup consisted of acidification with 2N HCl (_100 mL), extraction with EtOAc (4×100 mL), washing the combined organic layers with sat. NaCl, drying over MgSO$_4$, filtration, concentration and co-evaporation with toluene (3×50 mL). The desired intermediate as shown above (2.35 g, 96%) was given as a white solid.

$^1$H NMR (CDCl$_3$) δ 7.35–7.15 (m, 5H), 3.15 (m, 1H), 2.80–2.65 (m, 2H), 2.65–2.45 (m, 2H), 2.15 (m, 1H), 1.70 t(m, 1H).

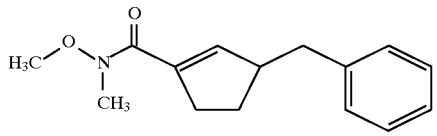

Step 5

To the solution of intermediate from step 4 (2.3 g, 11.34 mmol) in THF (80 mL) at 0° C., was added DCC (2.82 g, 13.65 mmol), and HOBT (1.84 g, 13.65 mmol). The resulting mixture was stirred for about 1 hr, and followed by addition of N,O-dimethyl-hydroxylamine hydrochloride (2.22 g, 22.74 mmol) and Et$_3$N (3.96 mL, 28.43 mmol). The reaction mixture was allowed to warm to room temperature and stirred overnight. Workup consisted of filtration, washing the filter cake with EtOAc, concentration in vacuo. The crude product was purified by HPLC (elution: 7–15% EtOAc/CH$_2$Cl$_2$) to provide intermediate as shown above (2.56 g, 92%) as light yellow oil. $^1$H NMR (CDCl$_3$) δ 7.25 (m, 2H), 7.15 (m, 3H), 6.38 (m, 1H), 3.55 (s, 3H), 3.20 (s, 3H), 3.10 (m, 1H), 2.65 (m, 4H), 2.05 (m, 1H), 1.60 (m, 1H).

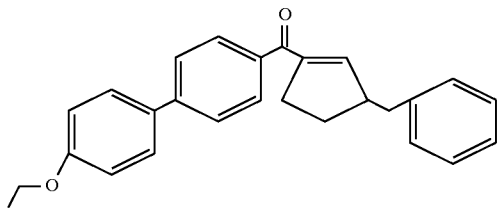

Step 6

To the solution of ethyl 4-(4-bromophenyl) phenyl ether (830 mg, 2.99 mmol) in THF (6 mL), was added t-BuLi (1.7M, 3.52 mL, 5.99 mmol) at −78° C. The reaction mixture was stirred under argon at −78° C. for 1 hrs, and treated with intermediate from step 5 (770 mg, 3.14 mmol). The resulting mixture was stirred at −78° C. for 30 min., 0° C. for 30 min., and room temperature for 30 min. Workup consisted of addition of 1N HCl (25 mL), extraction with EtOAc (4×20 mL), filtration through silica, and concentration in vacuo. The crude product was purified by HPLC (elution: 5–20% EtOAc/hexane) to provide the intermediate as shown above (400 mg, 35%) as an off- white solid.

$^1$H NMR (CDCl$_3$) δ 7.80 (d, J=8.46 Hz, 2H), 7.62 (d, J=8.46 Hz, 2H), 7.57 (d, J=8.83 Hz, 2H), 7.29 (m, 2H), 7.21 (m, 3H), 7.00 (d, J=8.82, 2H), 6.46 (bs, 1H), 4.10 (q, J=6.99 Hz, 2H), 3.30 (m, 1H), 2.84 (m, 4H), 2.20 (m, 1H), 1.75 (m, 1H), 1.46 (t, J=6.99 Hz, 3H).

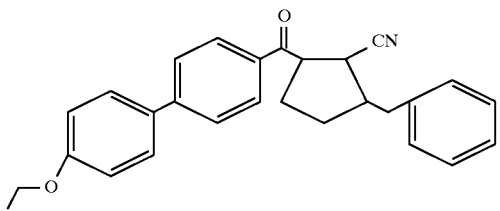

Step 7

To the solution of intermediate from step 6 (205 mg, 0.53 mmol) in toluene (5 mL) at 0° C., was added diethylaluminum cyanide (1N, 2.1 mL, 2.1 mmol) in toluene. The reaction mixture was stirred at room temperature for 2 hrs under argon. Workup consisted of addition of 1N HCl (20 mL), extraction with EtOAc (4×20 mL), washing the combined organic layers with sat. NaCl, drying over MgSO$_4$, filtration and concentration in vacuo. The crude product was carried to the next step.

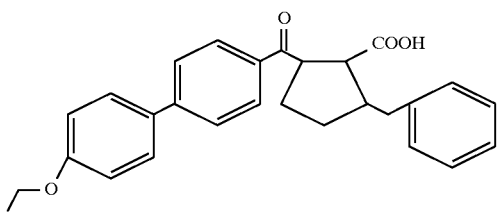

Step 8

To the solution of the crude intermediate from step 7 in dioxane (5 mL) at room temperature, was added 50% H$_2$SO$_4$ (5 mL). The reaction mixture was refluxed for 18 hrs. Workup consisted of addition of EtOAc (25 mL), washing the organic layer with H$_2$O (3× 15 mL), drying over MgSO$_4$, filtration and concentration in vacuo. The crude product was carried to the next step.

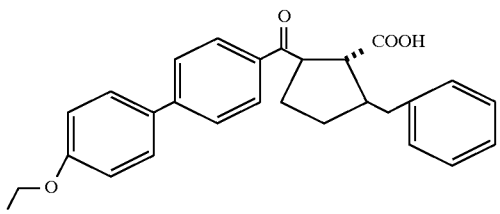

Example 226 (racemate)

Step 9—Preparation of Example 226

To the solution of crude intermediate from step 8 in THF (5 mL) at room temperature, was added DBU (ex). The reaction mixture was stirred overnight. Workup consisted of dilution with EtOAc (30 mL), washing with 2N HCl (2×10 mL), filtration through silica and concentration in vacuo. The crude product was purified by HPLC and recrystallization from EtOAc to provide Example 226 as off-white solid.

MP: 138°–139° C.; $^1$H NMR (DMSO-d6) δ 8.02 (d, J=8.45 Hz, 2H), 7.77 (d, J=8.82 Hz, 2H), 7.69 (d, J=8.83 Hz, 2H), 7.27 (m, 2H), 7.20 (m, 3H), 7.03 (d, J=8.82 Hz, 2H), 4.15 (m, 1H), 4.06 (q, J=6.99 Hz, 2H), 2.95 (m, 2H), 2.55 (m, 1H), 2.45 (m, 1H), 2.10 (m, 1H), 1.70 (m, 2H), 1.35 (m, 1H), 1.32 (t, J=6.99 Hz, 3H). MS (FAB-LSIMS) 429

[M+H]⁺ (C₂₈H₂₈O₄, FW=428.50); Anal. C: calcd, 78.48; found, 78.21; H: calcd, 6.59; found, 6.38.

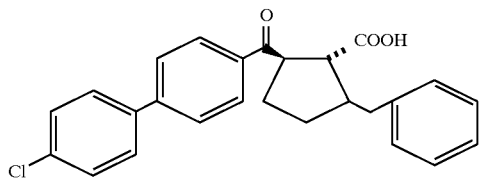

Example 227 (racemate)

Example 227

Example 227 was obtained through the same synthetic sequence preparing Example 226, by using 4-bromo-4'-chloro biphenyl in the place of ethyl 4-(4-bromophenyl) phenyl ether at step 6.

MP: 170°–171° C.; ¹H NMR (DMSO-d6) δ 12.35 (s, 1H), 8.06 (d, J=8.46 Hz, 2H), 7.83 (d, J=8.46 Hz, 2H), 7.78 (d, J=8.46 Hz, 2H), 7.55 (d, J=8.83 Hz, 2H), 7.26 (m, 2H), 7.19 (m, 3H), 4.15 (m, 1H), 2.97 (m, 2H), 2.55 (m, 1H), 2.45 (m, 1H), 2.10 (m, 1H), 1.70 (m, 2H), 1.40 (m, 1H). MS (FAB-LSIMS) 419 [M+H]⁺ (C₂₆H₂₃ClO₃, FW=418.89); Anal. C: calcd, 74.54; found, 74.27; H: calcd, 5.53; found, 5.35.

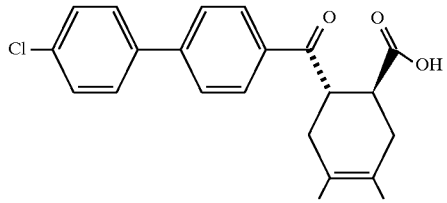

Example 228 (racemate)

Example 228

To the suspension of 4-Oxo-4-(4'-chloro-4-biphenyl)but-2-enoic acid, Example 34 (0.941 g, 3.28 mmol) in MeOH (5 mL) at room temperature, was added 2,3-dimethyl-1,3-butadiene (2.69 g, 3.71 mL, 32.8 mmol). The reaction mixture was refluxed under argon for a total of 2.5 hours. Workup consisted of concentration in vacuo. The crude product was purified by recrystallization from MeOH to yield 950 mg Example 228 as a white solid.

MP 217.0°–220.0° C.; TLC (1/1 (v/v) EtOAc/hexane) R_f=0.23; ¹H NMR (DMSO-d6) δ 12.22 (s, 1H), 8.07 (d, J=8.45 Hz, 2H), 7.81 (d, J=8.09 Hz, 2H), 7.76 (d, J=8.46, 2H), 7.54 (d, J=8.46, 2H), 3.79 (m, 1H), 2.81 (m, 1H), 2.23 (m, 3H), 1.87 (m, 1H), 1.62 (s, 3H), 1.56 (s, 3H); IR (nujol) 1706.7, 1673.9, 1604.5 cm⁻¹; MS (FAB-LSIMS) 369 [M+H]⁺ (C₂₂H₂₁ClO₃, FW=368.91); Anal. C: calcd, 71.62; found, 71.49. H: calcd, 5.74; found, 5.50.

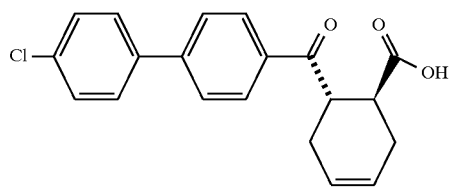

Example 229 (racemate)

Example 229

To the suspension of 4-Oxo-4-(4'-chloro-4-biphenyl)but-2-enoic acid, Example 34 (1.01 g, 3.53 mmol) in MeOH (5 mL) at −78° C., was added butadiene (ex) for 30 min, and followed by addition of DMF (5 mL). The reaction mixture was refluxed under argon for a total of 72 hours. Workup consisted of dilution with EtOAc (15 mL), addition of water (15 mL), and extraction of the aqueous layer with EtOAc (3×15 mL). The combined organic layers were washed with sat. NaCl, dried over MgSO₄, and concentrated in vacuo. The crude product was purified by chromatography (EtOAc/hexane) to yield 140 mg Example 229 as a white solid.

MP 185.0°–186.0° C.; TLC (1/1 (v/v) EtOAc/hexane) R_f=0.23; ¹H NMR (CDCl₃) δ 8.05 (d, J=8.46 Hz, 2H), 7.64 (d, J=8.46 Hz, 2H), 7.55 (d, J=8.82, 2H), 7.44 (d, J=8.82, 2H), 5.76 (m, 2H), 3.82 (m, 1H), 3.14 (m, 1H), 2.6–1.9 (m, 4H); IR (nujol) 1702.9, 1677.8, 1604.5 cm⁻¹; MS (FAB-LSIMS) 341 [M+H]⁺ (C₂₀H₁₇ClO₃, FW=340.85); Anal. C: calcd, 70.47; found, 70.38. H: calcd, 5.03; found, 4.93.

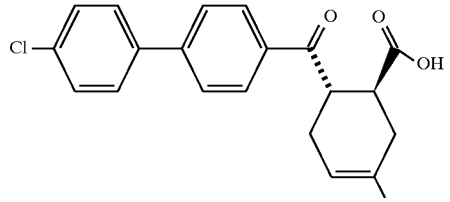

Example 230 (racemate)

Example 230

To the suspension of 4-Oxo-4-(4'-chloro-4-biphenyl)but-2-enoic acid, Example 34 (1.208 g, 4.21 mmol) in MeOH (5 mL) at room temperature, was added isoprene (2.87 g, 4.21 mL, 42.1 mmol). The reaction mixture was refluxed under argon overnight. Workup consisted of concentration in vacuo. The crude product was purified by chromatography (EtOAc/hexane) and recrystallization (three times) to yield 20 mg Example 230 as a white solid.

MP 174.0°–177.0° C.; TLC (1/1 (v/v) EtOAc/hexane) R_f=0.20; ¹H NMR (CDCL₃) δ 8.05 (d, J=6.99 Hz, 2H), 7.66 (d, J=8.09 Hz, 2H), 7.57 (d, J=8.46 Hz, 2H), 7.46 (d, J=8.46 Hz, 2H), 5.44 (m, 1H), 3.78 (m, 1H), 3.20 (m, 1H), 2.5–2.0 (m, 4H), 1.75 (s, 1H); IR (nujol) 1702.9, 1675.9, 1604.5 cm⁻¹; MS (FAB-LSIMS) 355 [M+H]⁺ (C₂₁H₁₉ClO₃, FW=354.8); Anal. C: calcd, 71.07; found, 70.85. H: calcd, 5.40; found, 5.62.

163

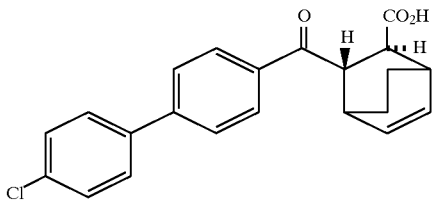

Example 231 (racemate)

Example 231

To the solution of 4-Oxo-4-(4'-chloro-4-biphenyl)but-2-enoic acid, Example 34 (1.123 g, 3.915 mmol) in THF (7 mL) at room temperature, was added 5 eq. 1,3-cyclohexadiene (1.87 mL, 19.577 mmol). The reaction mixture was stirred under refluxed for 18 hrs. Workup consisted of concentration in vacuo. The crude product was purified by HPLC to provide the desired product Example 231 (570 mg, 40%) as a white solid containing two isomers.

MP 174°–176° C.; TLC (1/20 (v/v) MeOH/CH$_2$Cl$_2$) R$_f$=0.27; $^1$H NMR (DMSO-d6) consistent with structure; IR (nujol) 1704.8, 1677.8, 1602.6 cm$^{-1}$; MS (FAB-LSIMS) 367 [M+H]$^+$ (C$_{22}$H$_{19}$ClO$_3$, FW=366.88); Anal. C: calcd, 72.03; found, 72.03. H: calcd, 5.22; found, 5.08.

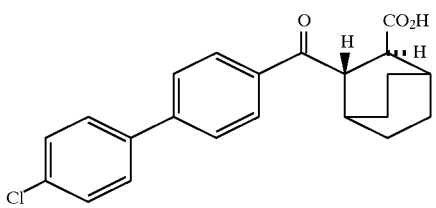

Example 231 (racemate)

Example 232

The mixture of Example 231 (299 mg, 0.815 mmol) and p Toluene-sulfono hydrazide (1.5 g, 8.15 mmol) was dissolved in dimethoxyethane (20 mL), and allowed to warm to reflux. The solution of Sodium acetate (1.0 g, 12.2 mmol) in water (16 mL) was added over a period of 4 hrs. The reaction mixture was cooled to room temperature, poured into water (120 mL), and extracted with CH$_2$Cl$_2$ (4×70 mL). The combined organic layers were washed with 150 mL water, dried over MgSO$_4$ and concentrated in vacuo. The crude product was purified by HPLC to provide the desired product Example 232 (85 mg, 28%).

MP 191°–193° C.; $^1$H NMR (DMSO-d6) δ 12.33 (s, 1H), 8.07 (d, J=8.45 Hz, 2H), 7.83 (d, J=8.09 Hz, 2H), 7.77 (d, J=8.46 Hz, 2H), 7.56 (d, J=8.46 Hz, 2H), 4.00 (d, J=7.35 Hz, 1H), 3.22 (d, J=7.35 Hz, 1H), 2.10 (bs, 1H), 1.87 (bs, 2H), 1.55–1.45 (m, 5H), 1.26–1.23 (m, 2H); IR (nujol) 1704.8, 1664.3, 1604.5 cm$^{-1}$; MS (FAB-LSIMS) 369 [M+H]$^+$ (C$_{22}$H$_{21}$ClO$_3$, FW=368.89); Anal. C: calcd, 71.63; found, 71.92. H: calcd, 5.74; found, 5.67.

164

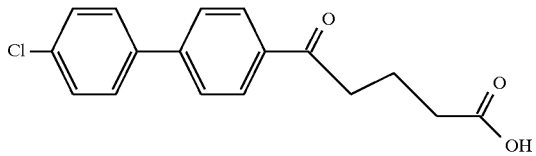

Example 223

Example 233 (Reference With Respect to Composition)

This compound was prepared by a similar method to that used for Example 30, except that the indicated anhydride was used instead of itaconic anhydride. From glutaric anhydride:

MP: 174°–176° C.; TLC (methylene chloride-5% methanol) R$_f$ 0.183; $^1$H NMR (CDCL$_3$) δ 8.05 (d, J=8.8 Hz, 2H), 7.66 (d, J=8.07 Hz, 2H), 7.56 (d, J=8.06 Hz, 2H), 7.45 (d, J=8.07 Hz, 2H), 3.13 (t, J=6.97 Hz, 2H), 2.54 (d, J=6.97 Hz, 2H), 2.13 (quintet, J=7.15 Hz, 2H); $^{13}$C NMR (CDCL$_3$) δ 199.46, 151.96, 145.20, 138.96, 136.32,135.13, 129.81, 129.39, 129.16, 127.77, 38.01, 33.52, 19.68; MS (FAB-LSIMS) 303 [M+H]$^+$ (C$_{17}$H$_{15}$O$_3$Cl, FW=302.76); Anal. C: calcd, 67.44; found, 67.21. H: calcd, 4.99; found, 4.96. Cl: calcd, 11.71; found, 11.74.

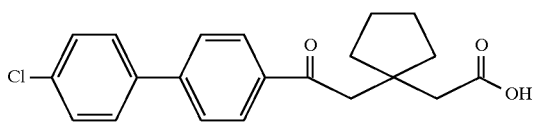

Example 234

Example 234

This compound was prepared in a similar manner to Example 1, except that the indicated anhydride was used instead of dihydro-3-(2-methylpropyl)-2,5-furandione. From 3,3-tetramethyleneglutaric anhydride:

MP 139°–140° C.; TLC (methylene chloride-5%methanol) R$_f$ 0.403; $^1$H NMR (CDCl$_3$) δ 8.03 (d, J=8.36 Hz, 2H), 7.63 (d, J=8.36 Hz, 2H), 7.55 (d, J=8.36 Hz, 2H), 7.44 (d, J=8.60 Hz, 2H), 3.28 (s, 2H), 2.70 (s, 2H), 1.69 (m, 8H); $^{13}$C NMR (CDCl$_3$) δ 200.59, 178.51, 145.09, 138.91, 137.37, 135.11, 129.79, 129.44, 129.15, 127.71, 45.79, 43.91, 42.41, 39.26, 24.61; MS (FAB-LSIMS) 357 [M+H]$^+$ (C$_{21}$H$_{21}$O$_3$Cl, FW=356.85); Anal. C: calcd, 70.68; found, 70.73. H: calcd, 5.93; found, 5.89. Cl: calcd, 9.93; found, 10.08.

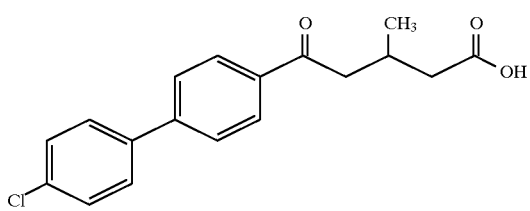

Example 235 (Reference With Respect to Composition)

A dry dichloromethane (10 mL) solution of 4-chlorobiphenyl (0.76 g, 4 mmol) and 3-methylglutaric anhydride (0.52 g, 4 mmol) in a 50-mL flask was chilled using an ice bath. Solid aluminum chloride (1.1 g, 8 mmol) was cautiously added over several minutes. The reaction mixture was stirred for 20 hours while warming to room temperature. After 20 hours, the reaction mixture was re-cooled with an ice bath and quenched with 10% HCl (10 mL). The layers were separated and the aqueous phase was back-extracted with dichloromethane (2×10 mL). The combined organic portions were washed with brine (25 mL), dried ($Na_2SO_4$), and concentrated in vacuo. The resulting yellow-white solid was recrystallized (ethyl acetate-hexane) to afford white microcrystals of Example 235: (0.7 g, 56 %, mp 140.5°–142.5° C.).

TLC (chloroform-methanol, 9:1 with trace amount of acetic acid): $R_f$ 0.49; $^1$H-NMR (DMSO-$d_6$) δ 0.93 (d, J=6.3 Hz, 3H), 2.10–2.45 (m, 3H), 2.85–3.15 (m, 2H), 7.50–8.10 (m, 8H), 12.09 (s, 1H); MS (FAB-LSIMS) 317 [M+H]$^+$ ($C_{18}H_{17}O_3Cl$, FW =316.79); Anal. C: calcd, 68.25; found, 68.17. H: calcd, 5.41; found, 5.44.

Example 236, Example 237, Example 238, Example 239 AND Example 240

The syntheses of Example 236, Example 237, Example 238, Example 239, and Example 240 were effected in a manner similar to the method used for Example 235 except that the indicated anhydrides were used instead of 3-methylglutaric anhydride. The anhydrides were either commercially available or synthesized by the routes described below.

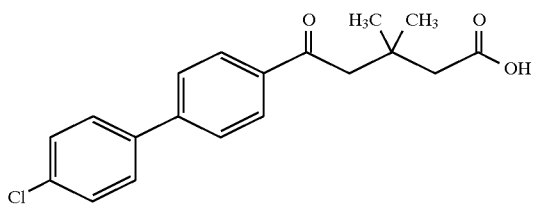

Example 236

Example 236

From 3,3-dimethylglutaric anhydride. The crude product was purified by recrystallization (ethyl acetate-hexane) to afford white microcrystals of Example 236 (49 %, mp 152.0°–154.5° C.):

TLC (chloroform-methanol, 9:1 with trace amount of acetic acid): $R_f$ 0.56; $^1$H NMR (DMSO-$d_6$) δ 1.08 (s, 6H), 2.39 (s, 2H), 3.13 (s, 2H), 7.50–8.10 (m, 8H), 11.97 (s, 1H); MS (FAB-LSIMS) 331 [M+H]$^+$ ($C_{19}H_{19}O_3Cl$, FW =330.81); Anal. C: calcd, 68.98; found, 68.89. H: calcd, 5.79; found, 5.84.

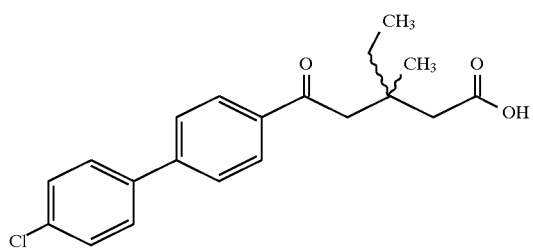

Example 237

Example 237

From 3-ethyl-3-methylglutaric anhydride. The crude product was purified by recrystallization (ethyl acetate-hexane) to afford white microcrystals of Example 237 (65 %, mp 130.0°–131.0° C.):

TLC (chloroform-methanol, 9:1 with trace amount of acetic acid): $R_f$ 0.42; $^1$H NMR (DMSO-$d_6$) δ 0.79 (t, J =7.4 Hz, 3H), 1.03 (s, 3H), 1.50 (m, 2H), 2.39 (m, 2H), 3.12 (m, 2H), 7.50–8.10 (m, 8H), 11.95 (s, 1H); MS (FAB-LSIMS) 345 [M+H]$^+$ ($C_{20}H_{21}O_3Cl$, FW =344.84); Anal. C: calcd, 69.66; found, 69.62. H: calcd, 6.14; found, 6.11.

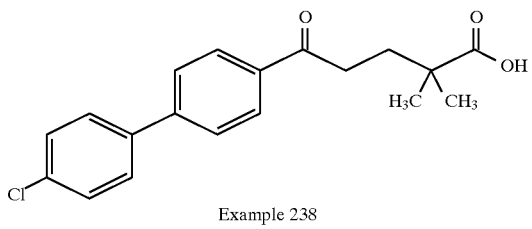

Example 238

Example 238

From 2,2-dimethylglutaric anhydride. The crude product was purified via flash column chromatography (gradient elution, dichloromethane to dichloromethane-methanol (99.5:0.5)) followed by recrystallization (ethyl acetate-hexane) to provide white microcrystals of Example 238 (8%, mp 163.5°–164.0° C.):

TLC (chloroform-methanol, 9:1 with trace amount of acetic acid): $R_f$ 0.67; $^1$H-NMR (DMSO-$d_6$) δ 1.14 (s, 6H), 1.81 (m, 2H), 2.98 (m, 2H), 7.50–8.10 (m, 8H), 12.21 (s, 1H); MS (FAB-LSIMS) 331 [M+H]$^+$ ($C_{19}H_{19}O_3Cl$, FW =330.81); Anal. C: calcd, 68.98; found, 68.92. H: calcd, 5.79; found, 5.73.

Example 9

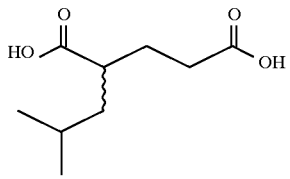

Step 1—Preparation of 2-Isobutylglutaric acid

To a 25-mL round-bottomed flask was added diethyl isobutyl malonate (2.82 g, 13 mmol), t-butanol (8.6 mL), and 30% methanolic KOH solution (0.25 mL, 1.3 mmol). Acrylonitrile (0.86 mL, 13 mmol) was added via syringe and the reaction mixture was heated to 33° C. using an oil bath. After stirring for 3 hours under inert atmosphere the reaction mixture was quenched with 2M HCl (1 mL) and diluted with distilled water (15 mL) and ether (20 mL). The separated aqueous phase was back-extracted with ether (2×20 mL). The combined organic portiqns were dried ($Na_2SO_4$) and concentrated in vacuo to afford an oil with solid precipitate (3.42 g). This crude material was used in the next step without purification. A portion of the crude oil and solid (1.5 g) was dissolved in 48% HBr (6 mL). The solution was held at reflux under inert atmosphere for 24.5 hours after which the solution was concentrated almost to dryness. The residue was partitioned between distilled water (20 mL) and ether (20 mL). The separated aqueous layer was back-extracted with ether (2×20 mL). The combined organic portions were then dried and concentrated in vacuo to yield an oily residue (1.5 g). $^1$H-N M R indicated reaction completion, so the remaining crude nitrile diester (1.9 g) was subjected to the above hydrolytic conditions to provide an additional amount of the crude substituted glutaric acid (1.5 g). The crude lots were combined (3.0 g total) and purified via flash column chromatography [gradient elution, dichloromethane to dichloromethane-methanol (98:2)] to afford the title compound as a white solid (1.64 g, 69%)I.

$^1$H NMR (DMSO-d$_6$) δ 0.83 (dd, J=6.6 Hz, 2.9 Hz, 6H), 1.16 (m, 1H), 1.36–1.56 (m, 2H), 1.61 (q, J=7.4 Hz, 2H), 2.17 (m, 2H), 2.28 (m, 1H), 12.11 (s, 2H).

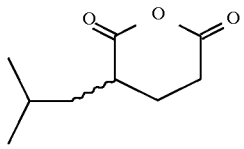

Step 2—Preparation of 2-Isobutylglutaric anhydride

To a 100-mL round-bottomed flask was added the product of step 1 (compound 23, 1.62 g, 8.6 mmol) and acetic anhydride (10 mL). The reaction mixture was held at reflux for 2 hours, and then cooled to room temperature. Volatiles were removed via vacuum distillation (0.1 Torr, 20°–60° C.). The crude product was dried under vacuum (0.1 Torr) at 80° C. for 14 hours to yield the title compound as a brown oil which was used without further purification (1.15 g, 79%).

$^1$H NMR (DMSO-d$_6$) δ 0.86 (m, 6H), 1.30 (m, 1H), 1.60–1.95 (m, 4H), 2.65–2.90 (m, 3H); IR (neat) 1805, 1762 cm$^{-1}$.

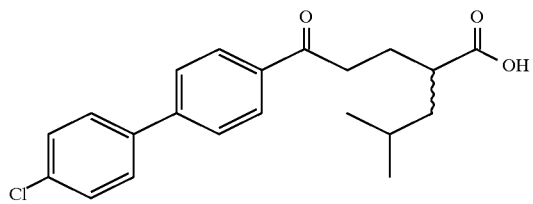

Example 239

Step 3—Preparation of Example 239

From 2-isobutylglutaric anhydride rather than 3-methylglutaric anhydride and using the general procedure of Example 235. The crude product was purified via flash column chromatography [gradient elution, dichloromethane to dichloromethane-methanol (98.5:1.5)] followed by recrystallization (ethyl acetate-hexane) to provide white microcrystals of Example 239 (10 %, mp 129.0°–130.5° C.).

TLC (chloroform-methanol, 9:1 with trace amount of acetic acid): R$_f$ 0.54; $^1$H-NMR (DMSO-d$_6$) δ 0.85 (dd, J=6.3 Hz, 2.6 Hz, 6H), 1.24 (m, 1H), 1.50 (m, 2H), 1.77 (m, 2H), 2.38 (m, 1H), 3.03 (m, 2H), 7.50–8.10 (m, 8H), 12.17 (s, 1H); MS (FAB-LSIMS) 359 [M+H]$^+$ (C$_{21}$ H$_{23}$O$_3$Cl, FW =358.87); Anal. C: calcd, 70.29; found, 70.33. H: calcd, 6.46; found, 6.41.

Example 240

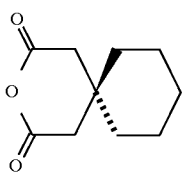

Step 1—Preparation of 3,3-Pentamethyleneglutaric an hydride

To a 100-mL round-bottomed flask was added 1,1-cyclohexanediacetic acid (2.03 g, 9.99 mmol) and acetic anhydride (11.6 mL). The reaction mixture was held at reflux for 2 hours, and then cooled to room temperature. Volatiles were removed via vacuum distillation (0.1 Torr, 20°–60° C.). The resulting crude product was dried under vacuum (0.1 Torr) at 80° C. for 14 hours to yield the title compound as a white solid which was used without further purification (1.75 g, 96 %).

$^1$H NMR (DMSO-d$_6$) δ 1.20–1.50 (m, 1 0H), 2.73 (s, 4H); IR (neat) 1813, 1770 cm$^{-1}$.

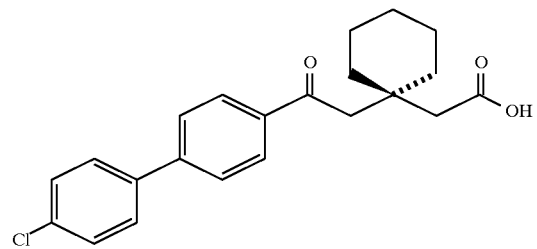

Example 240

Step 2—Preparation of Example 240

From 3,3-pentamethyleneglutaric anhydride rather than 3-methylglutaric anhydride and using the general procedure of Example 235. The crude product was purified via flash column chromatography (gradient elution, dichloromethane to dichloromethane-methanol (97:3)) followed by recrystallization (ethyl acetate-hexane) to provide white microcrystals of Example 240 (13 %, mp 129.0°–131.5° C.).

TLC (chloroform-methanol, 9:1 with trace amount of acetic acid): R$_f$ 0.55; $^1$H-NMR (DMSO-d$_6$) δ 1.20–1.60 (m, 10H), 2.50 (s, 2H), 3.20 (s, 2H), 7.50–8.00 (m, 8H), 11.92 (s, 1H); $^{13}$C-NMR (DMSO-d$_6$) δ 199.45, 173.52, 143.01, 137.92, 137.34, 133.45, 129.23, 128.96, 128.77, 126.97, 43.87, 35.71, 35.39, 25.80, 21.24; M S (FAB-LSIMS) 371 [M+H]$^+$ (C$_{22}$H$_{23}$O$_3$Cl, FW =370.88); Anal. C: calcd, 71.25; found, 71.06. H: calcd, 6.25; found, 6.21.

Example 241

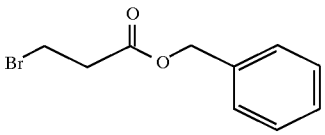

Step 1—Preparation of Benzyl-3-bromopropionate

A spatula tip full of p-toluenesulfonic acid monohydrate was added to a solution of 3-bromopropionic acid (20.49 g, 0.134 mol) and benzyl alcohol (15 mL, 15.7 g, 0.145 mol) in benzene (150 mL). A Dean-Stark trap was fitted to the reaction vessel and the solution was held at reflux with overnight stirring. After 16 hr at reflux, the reaction was cooled, washed with saturated sodium bicarbonate, dried ($Na_2SO_4$), and concentrated to an oil (28.78 g). Fractional distillation at reduced pressure (0.18 torr) gave the desired product as a colorless liquid (18.49 g, 56%) boiling in the range 99°–109° C.

TLC (hexane-ethyl acetate, 3:1): $R_f$ 0.72; $^1$H NMR ($CDCl_3$): δ 2.98 (t, J=6.9 Hz, 2H), 3.61 (t, J=6.9 Hz, 2H), 5.18 (s, 2H), 7.38 (s, 5H).

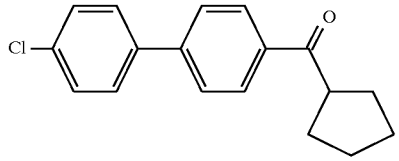

Step 2—Preparation of (4'-chlorobiphenyl)cyclopentyl ketone

A dry dichloromethane (50 mL) solution of 4-chlorobiphenyl (3.57 g, 18.9 mmol) and cyclopentanecarbonyl chloride (2.6 g, 18.9 mmol) in a 100-mL flask was chilled using an ice bath. Solid aluminum chloride (5 g, 37.7 mmol) was cautiously added over several minutes. The reaction mixture was stirred for 6 hours while warming to room temperature. After 6 hours, the reaction mixture was re-cooled with an ice bath and quenched with 10% HCl (50 mL). The layers were separated and the aqueous phase was back-extracted with dichloromethane (2×50 mL). The combined organic portions were washed with brine (100 mL), dried ($Na_2SO_4$), and concentrated in vacuo. The resulting yellow solid was used without further purification (5.5 g, 100 %).

TLC (hexane-ethyl acetate, 3:1): $R_f$ 0.22; $^1$H NMR (DMSO-$d_6$) δ 1.50–2.00 (m, 8H), 3.83 (m, 1H), 7.50–8.10 (m, 8H).

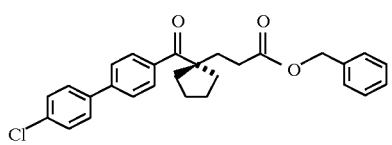

Step 3—Preparation of the Benzyl Ester of Example 241 n-Butyl lithium (2.64M in hexanes, 0.8 mL, 2.16 mmol) was added dropwise to freshly distilled diisopropylamine (0.3 mL, 0.22 g, 2.16 mmol) in anhydrous tetrahydrofuran (4 mL) at 0° C. and under an argon atmosphere. The solution was stirred for 30 minutes and then cooled to −70° C. A solution of the product from step 2 (0.59 g, 2.06 mmol) in tetrahydrofuran (1 mL, with 0.5 mL rinse) was added via syringe over 20 minutes. Stirring was continued for 75 minutes at −70° C. A solution of benzyl-3-bromopropionate from step 1 (0.50 g, 2.06 mmol) in tetrahydrofuran (1 mL, with 0.5 mL rinse) was added via syringe over 20 minutes. The reaction stirred at −70° C. for 1 hour and was then warmed slowly to room temperature overnight. After 14.25 hours of stirring under inert atmosphere, the reaction mixture was quenched with 10% HCl (10 mL) after dilution with ether (25 mL) and dichloromethane (15 mL). The separated organics were then washed sequentially with 10% HCl (10 mL), saturated sodium bicarbonate (2×10 mL), and brine (2×10 mL). The combined aqueous washes were then back-extracted with dichloromethane (10 mL). The combined organic phases were dried ($Na_2SO_4$) and concentrated in vacuo to yield an orange-yellow residue which was purified via flash column chromatography [gradient elution, hexane-dichloromethane (1:1) to hexane-dichloromethane (2:3)] to afford the desired product as an off-white solid (0.18 g, 20 %).

TLC (hexane-dichloromethane, 1:1): $R_f$ 0.45; $^1$H NMR (DMSO-$d_6$) δ 1.40–2.30 (m, 12H), 4.95 (s, 2H), 7.20–8.00 (m, 13H).

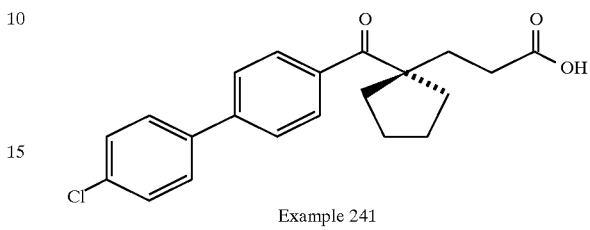

Example 241

Step 4—Preparation of Example 241

To a solution of the benzyl ester from step 3 (0.14 g, 0.31 mmol) in absolute ethanol (0.62 mL) was added a solution of aqueous sodium hydroxide (1M, 0.46 mL, 0.46 mmol). After stirring for three hours, the reaction mixture was diluted with ethyl acetate (10 mL) and distilled water (10 mL). The separated aqueous layer was acidified to pH _1 with concentrated HCl and was extracted with ethyl acetate (2×10 mL). Extractions were combined, dried ($Na_2SO_4$), and concentrated in vacuo to provide the product (0.08 g, 73 %, mp 161.0°–164.0° C.).

TLC (chloroform-methanol, 9:1 with trace amount of acetic acid): $R_f$ 0.57; $^1$H NMR (DMSO-$d_6$) δ 1.40–1.80 (m, 6H), 1.90–2.30 (m, 6H), 7.50–8.00 (m, 8H), 12.04 (br s, 1H); MS (FAB-LSIMS) 357 [M+H]$^+$ ($C_{21}H_{21}O_3Cl$, FW =356.85); HRMS calcd, 356.1179; found, 356.1165.

Example 242

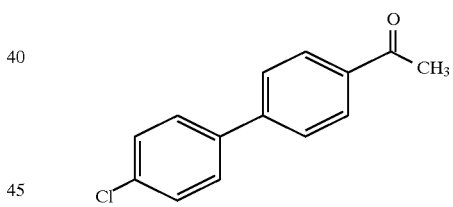

Step 1—Preparation of 4-(4'-chlorobiphenyl) methylketone

A dry 1,2-dichloroethane (300 mL) solution of 4-chlorobiphenyl (22.64 g, 120 mmol) and acetyl chloride (9.6 g, 120 mmol) in a 500-mL flask was chilled using an ice bath. Solid aluminum chloride (17.8 g, 132 mmol) was cautiously added over ten minutes. The reaction mixture was stirred for 20 hours while warming to room temperature. After 20 hours, the reaction mixture was quenched by slowly adding it to a stirred chilled solution of 10% HCl (300 mL). Ethyl acetate (200 mL) was added to help dissolve solids. The layers were separated and the aqueous phase was back-extracted with ethyl acetate (200 mL). The combined organic portions were washed with brine (300 mL), dried ($Na_2SO_4$), and concentrated in vacuo. The resulting yellow-white solid was recrystallized (ethyl acetate-hexane) to provide multiple, crystalline crops of the desired ketone (25.66 g, 93 %).

TLC (hexane-dichloromethane, 2:1): $R_f$ 0.61; $^1$H NMR (DMSO-$d_6$) δ 2.59 (s, 3H), 7.50–8.10 (m, 8H).

TLC (chloroform-methanol, 9:1 with trace amount of acetic acid): $R_f$ 0.49; $^1$H NMR (DMSO-$d_6$) δ 7.50–8.05 (m, 8H), 13.00 (1 H, s); $^{13}$C NMR (DMSO-$d_6$) δ 167.25, 143.11, 138.00, 133.42, 130.19, 129.23, 128.96, 126.99; MS (EI) 232 [M]$^+$ ($C_{13}H_9O_2Cl$, FW =232.67); Anal. C: calcd, 67.11; found, 66.86. H: calcd, 3.90; found, 3.82.

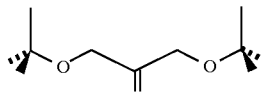

Step 2—Preparation of Di-tert-butyl methylenemalonate

This compound was prepared and purified according to literature precedent (Roberts, et.al., *J. Org. Chem*, 1983, 48, 3603.) to provide a clear oil (41 %).

$^1$H NMR (DMSO-$d_6$) δ 1.43 (s, 18H), 6.19 (s, 2H).

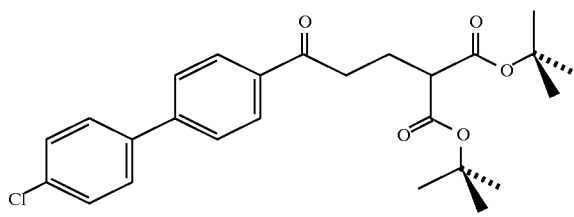

Step 3

A dry 100-mL round-bottomed flask was charged with a suspension of sodium hydride (0.24 g of 95% NaH, 9.1 mmol) in dry N,N-dimethylformamide (43 mL) and was cooled to 0° C. A solution of 4-(4"-chlorobiphenyl) methylketone from step 1 (2.0 g, 8.67 mmol) in N,N-dimethylformamide (7 mL) was then added via syringe over 15 minutes and stirring was continued for one hour at 0° C. under inert atmosphere. A solution of di-tert-butyl methylenemalonate from above step 2 (1.98 g, 8.67 mmol) in N,N-dimethylformamide (5 mL) was added via syringe over 15 minutes. After stirring for 15.5 hours with gradual warming to room temperature, the reaction mixture was diluted with ether (350 mL) and quenched with 10% HCl (550 mL). The separated aqueous layer was then back-extracted with ether (100 mL). The combined organics were washed with brine (2×500 mL). Again, the combined aqueous phases were back-extracted with ether (100 mL). The combined organic phases were dried (Na$_2$SO$_4$) and concentrated in vacuo to yield an orange solid which was purified initially via recrystallization (hexane) to give white fluffy crystals of the desired product (1.64 g). A significant amount of the desired compound remained in the mother liquors and was purified via flash column chromatography [gradient elution, hexane-dichloromethane (1:1) to dichloromethane-methanol (98:2)] to provide additional desired material as an off-white solid (0.47 g, total 2.11 g, 53 %).

TLC (hexane-ethyl acetate, 9:1): $R_f$ 0.43; $^1$H NMR (DMSO-$d_6$) δ 1.38 (s, 18H), 2.00 (m, 2H), 3.06 (t, J =7.4 Hz, 2H), 3.30 (m, 1H), 7.50–8.10 (m, 8H).

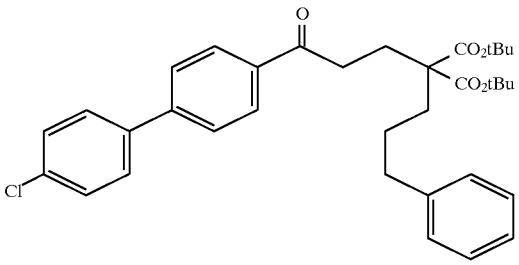

Step 4

A dry 25-mL round-bottomed flask was charged with a suspension of sodium methoxide (0.26 g of 95 % NaOMe, 4.75 mmol) and the pure product from step 3 (2.0 g, 4.36 mmol) in dry dimethoxyethane (4.7 mL). Simultaneously, a dry dimethoxyethane (13.5 mL) suspension of 1-bromo-3-phenylpropane (0.67 mL, 0.87 g, 4.36 mmol) and sodium iodide (0.66 g, 4.36 mmol) was formed in a 50-mL round-bottomed flask. After stirring 40 minutes under inert atmosphere, the orange enolate suspension was added via syringe over 10 minutes to the yellow bromide-iodide suspension. After 40 hours of stirring, the reaction was not complete as judged by TLC. Additional sodium methoxide (0.13 g, 2.38 mmol) and 1-bromo-3-phenylpropane (0.33 mL, 0.44 g, 2.18 mmol) were added. After 24 hours of stirring, the reaction mixture was concentrated to dryness. The residue was dissolved in ethyl acetate (50 mL) and quenched with 10% HCl (50 mL). The separated organics were washed with 10% HCl (50 mL). Combined aqueous phases were back-extracted with dichloromethane (50 mL). Combined organic phases were dried (Na$_2$SO$_4$) and concentrated in vacuo to yield an orange oil which was purified via flash column chromatography [gradient elution, hexane to hexane-ethyl acetate (19:1)] to afford the desired product as an off-white solid (1.66 g, 66 %).

TLC (hexane-ethyl acetate, 9:1); $R_f$ 0.47; $^1$H NMR (DMSO-$d_6$) δ 1.25–1.50 (m, 20H), 1.74 (m, 2H), 2.04 (m, 2H), 2.57 (t, J=7.0 Hz, 2H), 2.81 (m, 2H) 7.10–8.00 (m, 13H); MS (FAB-LSIMS) 577 [M+H]$^+$ ($C_{35}H_{41}O_5Cl$, FW =577.17).

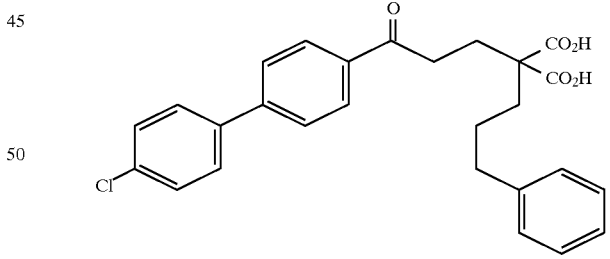

Step 5

A dichloromethane (10 mL) solution of the product from step 4 (1.66 g, 2.88 mmol), anisole (7.81 mL, 7.77 g, 71.90 mmol), and trifluoroacetic acid (2.22 mL, 3.28 g, 28.76 mmol) was stirred for 55 hours in a 50-mL round-bottomed flask. The reaction mixture was partitioned between ether (50 mL) and brine (50 mL). Some distilled water was added to solubilize precipitating salts. The organic phase was separated, dried (Na$_2$SO$_4$), and concentrated in vacuo to yield a white-pink solid which was purified via flash column chromatography [gradient elution, ethyl acetate-hexane-acetic acid (25:74:1) to ethyl acetate-hexane-acetic acid (49:50:1)] to afford the desired product as an off-white solid (0.53 g, 39%, mp 168.5°–170.0° C.).

TLC (chloroform-methanol, 9:1 with trace amount of acetic acid): $R_f$ 0.28; $^1$H NMR (DMSO-$d_6$) δ 1.44 (m, 2H), 1.80 (m, 2H), 2.09 (m, 2H), 2.57 (m, 2H), 2.84 (m, 2H), 7.10–8.00 (m, 13H), 12.78 (br s, 2H); $^{13}$C NMR (DMSO-$d_6$) δ 198.74, 173.07, 143.32, 142.03, 137.88, 135.71, 133.55, 129.28, 129.01, 128.81, 128.48, 127.12, 125.97, 56.14, 35.40, 33.50, 31.63, 26.39, 25.84; MS (FAB-LSIMS) 465 [M+H]$^+$ ($C_{27}H_{25}O_5Cl$, FW =464.95); Anal. C: calcd, 69.75; found, 69.66. H: calcd, 5.42; found, 5.38.

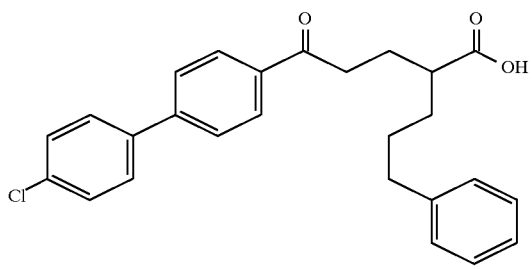

Step 6—Preparation of Example 242

A 1,4-dioxane (7.5 mL) solution of the diacid from step 5 (0.4 g, 0.86 mmol) was held at reflux for 44 hours with stirring under inert atmosphere. The reaction mixture was then concentrated to dryness and purified via flash column chromatography [ethyl acetate-hexane-acetic acid (24:75:1)] to afford the title compound as a white solid (0.25 g, 69 %, mp 97.0°–98.5° C.).

TLC (chloroform-methanol, 9:1 with trace amount of acetic acid): $R_f$ 0.60; $^1$H-NMR (DMSO-$d_6$) δ 1.40–1.60 (m, 4H), 1.78 (m, 2H), 2.35 (m, 1H), 2.55 (m, 2H), 3.01 (m, 2H), 7.10–8.05 (m, 13H), 12.19 (s, 1H); $^{13}$C-NMR (DMSO-$d_6$) δ 199.13, 176.88, 143.25, 142.15, 137.89, 135.79, 133.50, 129.25, 128.98, 128.81, 128.44, 127.09, 125.88, 44.04, 36.03, 35.16, 31.48, 28.99, 26.18; MS (EI) 420 [M]$^+$ ($C_{26}H_{25}O_3Cl$, FW =420.94); Anal. C: calcd, 74.19; found, 74.08. H: calcd, 5.99; found, 5.88.

Example 243

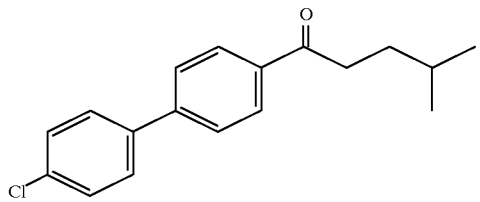

Step 1

A dry dichloromethane (93.5 mL) solution of 4-chlorobiphenyl (7.06 g, 37.4 mmol) and γ-methylvaleroyl chloride (5.0 g, 37.4 mmol) in a 250-mL flask was chilled using an ice bath. Solid aluminum chloride (9.97 g, 74.8 mmol) was cautiously added over ten minutes. Stirring was continued for 23 hours while warming slowly to room temperature. The reaction mixture was quenched by slowly adding it to a stirred chilled solution of 10% HCl (100 mL). The layers were separated and the aqueous phase was back-extracted with dichloromethane (2×50 mL). The combined organic portions (cloudy) were washed with brine (50 mL), dried (Na$_2$SO$_4$), and filtered. Dilution with dichloromethane (100 mL) and finally ethyl acetate (100 mL) clarified the solution which was re-dried (Na$_2$SO$_4$) and concentrated in vacuo to produce a yellow solid (10.33 g). A portion of this crude product (2.97 g) was purified via flash column chromatography [dichloromethane-hexane (2:3)] to yield the desired product as a pale-yellow solid (2.54 g, 82%).

TLC (hexane-ethyl acetate, 9:1): $R_f$ 0.54; $^1$H NMR (DMSO-$d_6$) δ 0.85–0.95 (m, 6H), 1.40–1.70 (m, 3H), 3.01, (m, 2H), 7.50–8.10 (m, 8H).

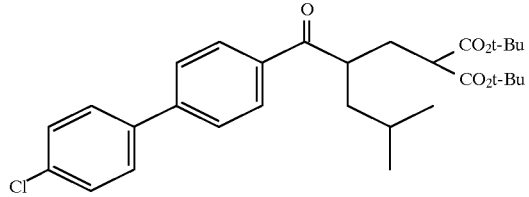

Step 2

A dry 25-mL round-bottomed flask was charged with a suspension of sodium hydride (0.044 g of 95% NaH, 1.74 mmol) in dry N,N-dimethylformamide (7.9 mL) and was cooled to 0° C. Solid ketone from step 1 (0.5 g, 1.74 mmol) was cautiously added to the suspension and stirring was continued for one hour at 0° C. under inert atmosphere. A solution of di-tert-butyl methylenemalonate from Example 242 step 2 (0.4 g, 1.74 mmol) in N,N-dimethylformamide (3 mL) was added via syringe over 15 minutes. After stirring for 19 hours with gradual warming to room temperature, the reaction mixture was diluted with ether (70 mL) and quenched with 10% HCl (120 mL). The separated organic phase was washed with brine (2×100 mL), dried (Na$_2$SO$_4$), and concentrated in vacuo to yield a yellow oil. The crude product was purified via flash column chromatography (gradient elution, hexane-dichloromethane (3:1) to hexane-dichloromethane (1:2)) to afford the desired compound in two fractions, the first slightly contaminated with high $R_f$ spots (0.36 g, 40%), and the second pure by TLC (0.22 g, 24% (total 64 %)).

TLC (hexane-dichloromethane, 1:2): $R_f$ 0.20; $^1$H NMR (DMSO-$d_6$) δ 0.83 (dd, J=13.2 Hz, 5.9 Hz, 6H), 1.30–1.60 (m, 21H), 1.80–2.15 (m, 2H), 3.12 (dd, J=8.5 Hz, 6.6 Hz, 1H), 3.45–3.65 (m, 1H), 7.50–8.10 (m, 8H).

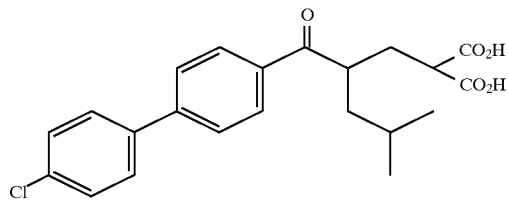

Step 3

The two fractions of product from step 2 were reacted separately in this step. The order of parenthetical notations of stoichiometry refer to the first fraction and the second fraction respectively. Dichloromethane (4.6 mL and 2.9 mL) solutions of each fraction of the product from step 2 (0.36 g, 0.7 mmol and 0.22 g, 0.43 mmol ), anisole (1.9 mL, 1.9 g, 17.5 mmol and 1.17 mL, 1.16 g, 10.75 mmol), and trifluoroacetic acid (0.54 mL, 0.8 g, 7.0 mmol and 0.33 mL, 0.49g, 4.3 mmol) were formed in separate 25-mL round-bottomed flasks. After stirring under inert atmosphere for 22 hours, both reaction mixtures were separately partitioned between ethyl acetate (20 mL) and brine (20 mL). Some distilled water was added to solubilize precipitated salts. Each organic phase was separated, then the two fractions were combined, washed with distilled water, (2×15 mL), dried (Na$_2$SO$_4$), and concentrated in vacuo to yield a faint pink oil which was purified via flash column chromatography [gradient elution, ethyl acetate-hexane-acetic acid (25:74:1) to ethyl acetate-hexane-acetic acid (49:50:1)] to yield fractions whose $^1$H-NMRs indicated that. the reaction had not gone to completion. The fractions were recombined and resubjected to the reaction conditions for 16 hours. When the reaction was complete as indicated by TLC, the reaction mixture was worked-up and chromatographed using the same conditions described above to afford the desired diacid as an off-white solid (0.2 g, 44 %).

TLC (chloroform-methanol, 9:1 with trace amount of acetic acid): R$_f$ 0.17; $^1$H-NMR (DMSO-d$_6$) δ 0.70–0.90 (m, 6H), 1.20–1.60 (m, 3H), 1.80–2.20 (m, 2H), 3.16 (dd, J=8.5 Hz, 6.6 Hz, 1H), 3.60 (m, 1H), 7.50–8.10 (m, 8H), 12.83 (br s, 2H).

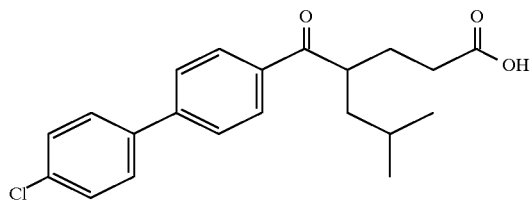

Example 243

Step 4—Preparation of Example 243

A 1,4-dioxane (9.1 mL) solution of diacid from step 3 (0.2 g, 0.5 mmol) was held at reflux for 15 hours with stirring under inert atmosphere. The reaction mixture was then concentrated to dryness and purified via flash column chromatography (dichloromethane-methanol (99:1)) to afford the title compound as a white solid (0.11 g, 61 %, mp 102.0–103.0° C.).

TLC (chloroform-methanol, 9:1 with trace amount of acetic acid): R$_f$ 0.48; $^1$H-NMR (DMSO-d$_6$) δ 0.75–0.90 (m, 6H), 1.20–1.90 (m, 5H), 2.18 (m, 2H), 3.67 (m, 1H), 7.50–8.10 (m, 8H), 12.08 (s, 1H); MS (FAB-LSIMS) 359 [M+H]$^+$ (C$_{21}$H$_{23}$O$_3$Cl, FW =358.87); Anal. C: calcd, 70.29; found, 70.23. H: calcd, 6.46; found, 6.46.

Example 244

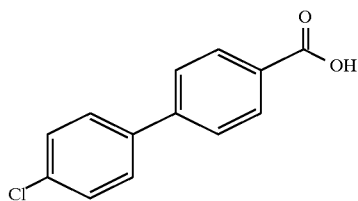

Step 1—Preparation of 4-(4'-Chlorobiphenyl)carboxylic acid

Bromine (5.6 mL, 17.3 g, 108.35 mmol) was added to a solution of sodium hydroxide (15.2 g, 379 mmol) in distilled water (75.8 mL) at 0° C. and was stirred for 15 minutes. To this reagent mixture was added a solution of 4-(4'-chlorobiphenyl)methylketone from the Example 242 preparation step 1 (5.0 g, 21.67 mmol) in 1,4-dioxane (54.2 mL). The reaction mixture was heated for 18 hours at 40° C. using an oil bath and was cooled to room temperature. A solution of sodium thiosulfate pentahydrate (21.5 g, 86.68 mmol) in distilled water (60 mL) was added to the reaction mixture to quench the remaining bromoform. The mixture was acidified to pH ~1 with concentrated HCl (~25 mL) causing foaming. The solids which precipitated were isolated via filtration and recrystallized (ethyl acetate) to provide multiple, crystalline crops of the title compound (4.44 g, 88 %, mp 286.0°–288.0° C.).

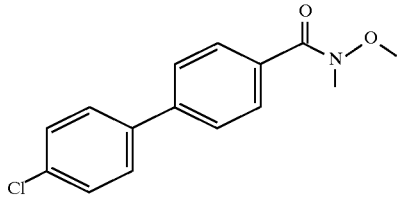

Step 2

A dry dichloromethane (66 mL) solution of 4-(4'-chlorobiphenyl)carboxylic acid from step 1 (3.7 g, 15.9 mmol), N,O-dimethylhydroxylamine hydrochloride (2.34 g, 23.85 mmol), and 1-hydroxybenzotriazole (2.36 g, 17.49 mmol) in a 100-mL round-bottomed flask was chilled using an ice bath and stirred for a few minutes. N-methylmorpholine (2.62 mL, 2.41 g, 23.85 mmol) was added quickly via syringe followed by solid 1-ethyl-3-(3-dimethylaminopropyl)carbodiimide (3.36 g, 17.49 mmol). The reaction mixture was stirred for several hours at 0° C. under inert atmosphere. Stirring was continued while warming to room temperature overnight. After a total of 23 hours of stirring, the reaction was incomplete as judged by TLC. Dry N,N-dimethylformamide (2 mL) was added at 0° C. to clarify the reaction mixture. TLC after 1 hour showed no further conversion, so additional reagents were added [N,O-dimethylhydroxylamine hydrochloride (0.46 g), 1-hydroxybenzotriazole (0.47 g), N-methylmorpholine (0.52 mL), and 1-ethyl-3-(3-dimethylaminopropyl) carbodiimide (0.66 g)] at 0° C. TLC after 3 more hours indicated complete conversion so the reaction mixture was diluted with dichloromethane (200 mL) and washed sequentially with saturated sodium bicarbonate (2×100 mL), 10% HCl (100 mL), and saturated sodium bicarbonate (100 mL). The combined aqueous portions were back-extracted with ether (50 mL). The combined organic phases were dried (Na$_2$SO$_4$) and concentrated in vacuo to yield an orange solid which was purified via flash column chromatography (gradient elution, dichloromethane to dichloromethane-methanol (99.5:0.5)) to afford the desired product as a white solid (3.89 g, 89 %).

TLC (dichloromethane): R$_f$ 0.27; $^1$H NMR (DMSO-d$_6$) δ 3.26 (s, 3H), 3.55 (s, 3H), 7.50–7.80 (m, 8H); MS (FAB-LSIMS) 276 [M+H]$^+$ (C$_{15}$H$_{14}$O$_2$NCl, FW =275.74).

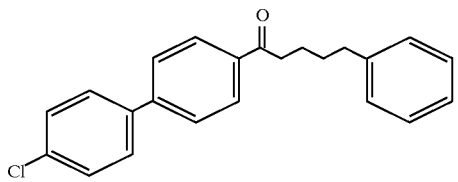

Step 3 n-Butyl lithium (2.64M in hexanes, 10.2 mL, 26.98 mmol) was added dropwise to freshly distilled diisopropylamine (3.78 mL, 2.73 g, 26.98 mmol) in anhydrous tetrahydrofuran (50 mL) at −40° C. and under an argon atmosphere. The solution was stirred for 25 minutes with warming to −20° C. and then cooled to −40° C. A solution of 5-phenylvaleric acid (2.40 g, 13.49 mmol) in tetrahydrofuran (4 mL, with 1 mL rinse) was added via syringe over 7 minutes causing precipitation of a solid. The stirred solution was heated at 50° C. for 2 hours and was then re-cooled to −40° C. A solution of the product from step 2 (3.1 g, 11.24 mmol) in tetrahydrofuran (4 mL, with 1 mL rinse) was added via syringe over 8 minutes. The reaction stirred at −40° C. for 3 hours and was then quenched by cautious decanting into 10% HCl (50 mL). The mixture was extracted with ether (150 mL). The separated aqueous phase was back-extracted with ethyl acetate (2×50 mL). The combined organic phases were washed with brine (75 mL), dried ($Na_2SO_4$), and concentrated in vacuo to provide an orange solid which was then purified via flash column chromatography (gradient elution, hexane-dichloromethane (3:1) to hexane-dichloromethane (3:2)) to afford the desired product as a yellow-white solid (1.80 g, 46 %):.

TLC (hexane-dichloromethane, 1:2): $R_f$ 0.75; $^1$H NMR (DMSO-$d_6$) δ 1.62 (m, 4H), 2.60 (m, 2H), 3.05 (m, 2H), 7.10–8.10 (m, 13H); MS (FAB-LSIMS) 349 [M+H]$^+$ ($C_{23}H_{21}O_3Cl$, FW =348.88).

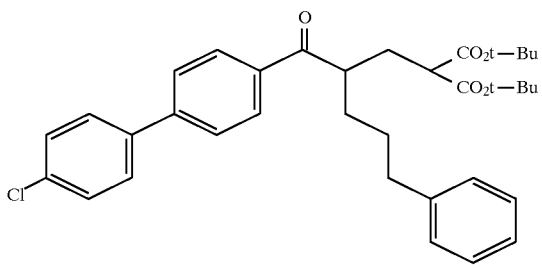

Step 4

A dry 50-mL round-bottomed flask was charged with a suspension of sodium hydride (0.15 g of 95 % NaH, ~5.8 mmol) in dry N,N-dimethylformamide (20 mL) and was cooled to 0° C. A solution of the ketone product from step 3 (1.93 g, 5.53 mmol) in N,N-dimethylformamide (10 mL) was added via syringe over 10 minutes. Stirring was continued for one hour at 0° C. under inert atmosphere. A solution of the di-tert-butyl methylenemalonate from the Example 242 preparation step 2 (1.26 g, 5.53 mmol) in N,N-dimethyl-formamide formamide (3 mL) was added via syringe over 4 minutes to the dark orange reaction mixture. After stirring for 15 hours with gradual warming to room temperature, the reaction mixture was diluted with ether (300 mL) and quenched with 10% HCl (500 mL). The separated organic phase was washed with brine (2×500 mL), dried ($Na_2SO_4$), and concentrated in vacuo to yield a yellow oil which was purified via flash column chromatography [gradient elution, hexane-dichloromethane (4:1) to hexane-dichloromethane (1:1)] to yield the desired material as an off-white solid (2.13 g, 67 %).

TLC (hexane-dichloromethane, 1:2): $R_f$ 0.64; $^1$H NMR (DMSO-$d_6$) δ 1.32 (d, J =5.9 Hz, 18H), 1.35–1.70 (m, 4H), 1.80–2.15 (m, 2H), 2.51 (m, 2H), 3.05–3.15 (m, 1H), 3.45–3.60 (m, 1H) 7.00–8.00 (m, 13H); MS (FAB-LSIMS) 577 [M+H]$^+$ ($C_{35}H_{41}O_5Cl$, FW =577.17).

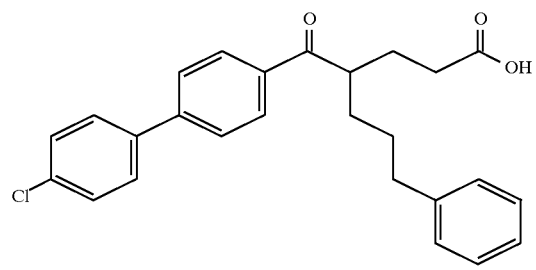

Example 244

Step 5—Preparation of Example 244

A dichloromethane (15 mL) solution of the product from step 4 (2.1 g, 3.64 mmol), anisole (9.9 mL, 91 mmol), and trifluoroacetic acid (2.8 mL, 36.4 mmol) was stirred in a 50-mL round-bottomed flask. After 72 hours, the reaction had not gone to completion. Additional trifluoroacetic acid (5 mL, 65 mmol) was added. After stirring for an additional 4.5 hours the reaction mixture was partitioned between ethyl acetate (75 mL) and brine (75 mL). Some distilled water was added to solubilize precipitated salts. The organic phase was separated, dried ($Na_2SO_4$), and concentrated in vacuo to yield an orange-brown oil which was purified via flash column chromatography [gradient elution, ethyl acetate-hexane-acetic acid (25:74:1) to ethyl acetate-hexane-acetic acid (49:50:1)] to afford the desired diacid plusf decarboxylated compound (after vacuum oven drying) as a white solid (1.35 g, ~80 %, mp 45.0°–51.0 C. (dec.)): TLC (chloroform-methanol, 9:1 with trace amount of acetic acid): $R_f$ 0.34. A 1,4-dioxane (18 mL) solution of a portion of the partially converted diacid (1.0 g, ~2.15 mmol) was held at reflux for 20 hours with stirring under inert atmosphere The reaction mixture was then concentrated to dryness and purified via flash column chromatography (ethyl acetate-hexane-acetic acid (19:80:1))to afford the title compound as a clear gum (0.75 g, 83 %).

TLC (chloroform-methanol, 9:1 with trace amount of acetic acid): $R_f$ 0.62; $^1$H NMR (DMSO-$d_6$) δ 1.40–2.20 (m, 8H), 2.52 (m, 2H), 3.64 (m, 1H), .7.00–8.10 (m, 13H), 12.09 (br s, 1H); $^{13}$C NMR (DMSO-$d_6$) δ 203.24, 174.29, 143.47, 141.99, 137.86, 136.08, 133.56, 129.26, 129.04, 128.42, 127.29, 125.89, 44.16, 35.27, 31.56, 28.83, 26.97; MS (FAB-LSIMS) 421 [M+H]$^+$ ($C_{26}H_{25}O_3Cl$, FW=420.94); Anal. C: calcd, 74.19; found, 73.95. H: calcd, 5.99; found, 5.82.

Example 245

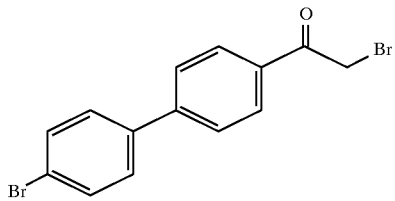

Step 1

A solution of p-bromobiphenyl (20.0 g, 0.0858 mol) and α-bromoacetyl bromide (7.5 mL, 0.0858 mol, 1.0 equiv.) in $CH_2Cl_2$ (400 mL) under argon was cooled to 0° C. and $AlCl_3$ (24.0 g, 0.180 mol, 2.1 equiv) was added in four parts. The resulting dark green solution was allowed to slowly warm to room temperature, then stirred for 14 h. The reaction was then cooled to 0° C. and quenched with a 10% HCl solution (200 mL). The resulting aqueous layer was separated and extracted with CH$_2$Cl$_2$ (3×100 mL). The combined organic layers were washed with a saturated NaCl solution (150 mL), dried (anh. MgSO$_4$) and concentrated under reduced pressure to afford a brown solid (29.3 g, 96%) which was used in the next step without further purification

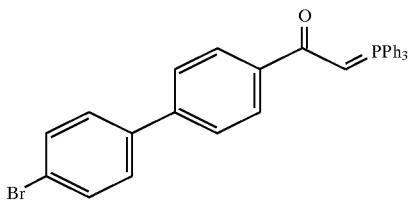

Step 2

A slurry of the intermediate from step 1 (29.3 g, 0.0827 mol) and PPh$_3$ (23.9 g, 0.0910 mol, 1.1 equiv.) in dry THF (400 mL) way heated at the reflux temperature for 14 h. The resulting solids were removed by filtration and washed with diethyl ether to give the phosphonium bromide (46.7 g, 92%). A mixture of the bromide (7.60 g, 1.23 mmol), CH$_2$Cl$_2$ (50 mL) and a 10% NaOH solution (20 mL) was vigorously stirred for 30 min. The aqueous layer was extracted with CH$_2$Cl$_2$ (30 mL) and the combined organics were washed with H$_2$O (30 mL) and dried (anh. MgSO$_4$). The resulting solids were triturated with EtOAc to give the desired ylid as a light brown powder (5.17 g, 78%) which was used in the next step: TLC R$_f$ (EtOAc) 0.55.

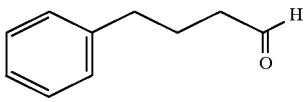

Step 3

To a solution of N-methylmorpholine oxide (11.4 g, 0.0973 mol, 1.40 equiv.) in CH$_2$Cl$_2$ (200 mL) was added 4-phenylbutanol (10.2 mL, 0.0696 mol) and powdered 4A seives (2.0 g). After stirring for 10 min., tetrapropylammonium perruthenate (0.218 g, 6.20 mmol. 9 mol %), and the resulting mixture was allowed to stir for 48 h. The reaction mixture was filtered through Florisil® with the aid of CH$_2$Cl$_2$ (200 mL) and the resulting solution was washed with a saturated Na$_2$SO$_3$ solution (200 mL), a saturated NaCl solution (200 mL), a 1M CuSO$_4$ solution (200 mL) and dried (anh. MgSO$_4$). Concentration under reduced, pressure followed by bulb-to-bulb distillation afforded the desired aldehyde as a colorless oil (9.3 g, 90%), which slowly oxidized on exposure to air.

TLC R$_f$ (25% EtOAc/hexane) 0.60; $^1$H NMR (CDCl$_3$) δ 1.98 (pent, J=7.44 Hz, 2H), 2.46 (td, J=7.35, 2.46 Hz, 2H), 2.67 (t, J=7.54 Hz, 2H), 7.17–7.33 (m, 5H), 89.77 (t, J=1.66 Hz, 1H).

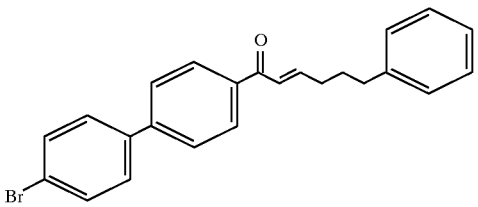

Step 4

A mixture of compound from step 2 (12.5 g, 0.0233 mol) and compound from step 3 (4.13 g, 0.0280 mol, 1.5 equiv.) in dry THF (230 mL) were heated at the reflux temperature for 80 h. The resulting mixture was concentrated under reduced pressure, dissolved in acetone (250 mL), cooled to 0° C. and treated dropwise with Jones reagent until all starting aldehyde was consumed as shown by TLC analysis. The acetone mixture was concentrated under reduced pressure, dissolved in EtOAc (250 mL), washed with a saturated NaHCO$_3$ solution (150 mL), and dried (anh. MgSO$_4$). The resulting solution was concentrated under reduced pressure, dissolved in CH$_2$Cl$_2$, and filtered through a small pad of SiO$_2$ with the aid of 25% EtOAc/hexane to remove remaining 4-phenylbutyric acid and Ph$_3$P O to afford the desired enone as a single diastereomer (3.85 g, 41%).

TLC R$_f$ (25% EtOAc/hexane) 0.68. Anal. Calcd for C$_{24}$H$_{21}$BrO: C, 71.05; H, 5.22; O, Br; 19.71. Found: C, 70.77; H, 5.23; O, 19.56.

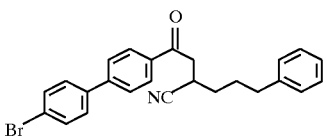

Step 5

To a solution of the product from step 4 (0.405 g, 1.00 mmol) and acetic acid (0.060 mL, 1.0 mmol, 1.0 equiv) in abs. EtOH (15 mL) at 35° C. was slowly added a solution of KCN (0.130 g, 2.00 mmol, 2.0 equiv.) in H$_2$O (1.2 mL). The mixture was stirred at 35° C. for 14 h and the resulting slurry was separated between CHCl$_3$ (50 mL) and H$_2$O (50 mL). The aqueous layer was extracted with CHCl$_3$ (2×20 mL), and the combined organics were washed with H$_2$O (3×40 mL), dried (anh. MgSO$_4$) and concentrated under reduced pressure. The resulting solids were recrystallized using EtOAc/hexane to afford the cyano product as a white powder (0.252 g, 58%).

MP 139°–141° C.; TLC R$_f$(25% EtOAC/hexane) 0.46; $^1$H NMR (CDCl$_3$) δ 1.74 (tt, J=6.98, 6.98 Hz, 2H), 1.84–2.01 (m, 2H), 2.67–2.74 (m, 2H), 3.23 (dd, J=16.54, 6.26 Hz, 1H), 3.33 (dddd, J=6.25, 6.25, 6.25, 6.25 Hz, 1H), 3.43 (dd, J=16.55,6.25 Hz, 1H), 7.19–7.39 (m, 3H), 7.31–7.33 (m, 2H), 7.50 (app d, J=8.46 Hz, 2H), 7.61 (app d, J=8.82 Hz, 2H), 7.67 (app d, J=8.46 Hz, 2H), 8.01 (app d, J=8.83 Hz, 2H); $^{13}$C NMR (CDCl$_3$) δ 26.3, 28.8, 31.4, 35.1, 40.8, 121.7, 122.9, 126.0, 127.2 (2 C), 128.4 (2 C), 128.5 (2 C), 128.7 (2 C), 128.8 (2 C), 132.2 (2 C), 134.8, 138.4, 141.2, 145.2, 194.7; MS (FAB-LSIMS; rel abund.) 432 (40%, [M($^{79}$Br) +H]$^+$), 434 (40%, [M($^{81}$Br)+H]$^+$). HRMS (FAB) Calcd for C$_{25}$H$_{23}$$^{79}$BrNO M+H]$^+$: 432.09630. Found: 432.09552. Anal. Calcd for C$_{25}$H$_{22}$BrNO: C, 69.44; H, 5.13; Br, 18.48; N, 3.24. Found: C, 69.18; H, 5.26; Br, 18.51; N, 3.03.

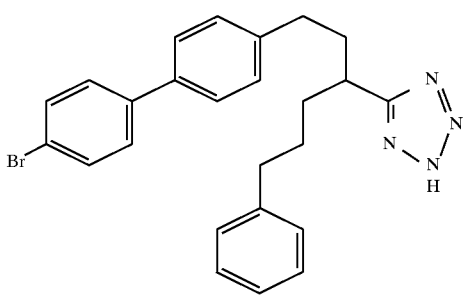

Example 245

Step 6—Preparation of Example 245

A mixture of the product of step 5 and trimethyltin azide (0.180 g, 0.874 mmol, 2.00 equiv.) in toluene (25 mL) was heated at 105° C. for 60 h, after which volatiles were removed at 105° C. to afford the trimethylstannyl tetrazole as a single compound. The foamy brown solids were redissolved in toluene (10 mL) and treated with HCl (4.0M in dioxane, 0.33 mL, 1.32 mmol, 3.02 equiv.). The resulting mixture was stirred at room temperature for 14 h, then separated between EtOAc (50 mL) and $H_2O$ (50 mL). The organic phase was washed with $H_2O$ (2×50 mL) and a saturated NaCl solution (2×50 mL) and concentrated to give the desired tetrazole as a yellow solid (0.211 g, 100%).

MP 175°–180° C. (dec); $^1$H NMR (CD$_3$OD) δ 1.35–1.55 (m, 2H), 1.75–1.80 (m, 2H), 2.30 (br s, 1H), 2.30–2.60 (m, 2H), 3.45–3.80 (m, 3H), 7.10–7.2 (m, 2H), 7.72 (br s, 4H), 7.81, D, J=8.85 Hz, 2H), 8.02 (d, J=8.84 Hz, 2H) (the $^1$H NMR also shows a minor amount of a second tetrazole N—H diastereomer); $^{13}$C NMR (CD$_3$OD) δ 28.4, 30.0, 33.5, 34.8, 41.8, 122.1, 125.8, 126.9 (2 C), 128.3 (4 C), 128.8 (2 C), 129.1 (2 C), 132.0 (2 C), 135.4, 138.0, 141.8, 143.4, 167.4, 197.4; M S (FAB-LSIMS; rel abund.) 475 (10%, [M($^{79}$Br)+H]$^+$), 477(9%, [M($^{81}$Br)+H]$^+$). HRMS (FAB) Calcd for $C_{25}H_{24}^{79}BrN_4O$ M+H]$^+$: 475.1132. Found: 475.1120.

Example 246

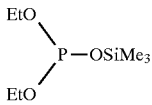

Step 1

To a mixture of diethyl phosphite (2.8 mL, 0.0217 mol) and triethylamine (9. mL, 0.065 mol, 3.0 equiv.) in dry diethyl ether (250 mL) at 0° C. was slowly added freshly distilled trimethylsilyl chloride (3.3 mL, 0.0260 mol, 1.2 equiv.) via syringe. The resulting slurry was allowed to slowly warm to room temperature, and was then warmed to 45° C. for 14 h. Volatiles were removed by distillation using a 55° C. oil bath. The resulting mixture was diluted with pentane (150 mL), filtered to remove triethylammonium salts, and concentrated at atmospheric pressure using a 55° C. oil bath. Distillation of the resulting oil gave diethyl trimethylsilyl phosphite as a colorless oil (3.64 g, 80%).

BP 60° C. (5 mmHg); $^{31}$P NMR (CDCl$_3$) δ 8.27 (s).

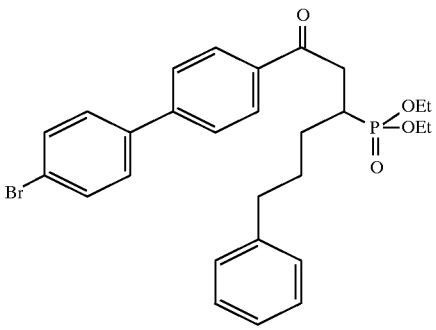

Step 2

A slurry of product from step 4 of the Example 245 preparation (0.200 g, 0.490 mmol) and diethyl trimethylsilyl phosphite (0.105 g, 0.490 mmol, 1.0 equiv.) in a dry NMR tube under argon was dissolved using a 50° C. sonicator bath, then heated at 50° C. for 14 h. This was concentrated under reduced pressure and treated with an additional portion of diethyl trimethylsilyl phosphite (0.5 mL) and heated at 50° C. for 24 h. The reaction mixture was concentrated under reduced pressure, dissolved in CDCl$_3$ (which apparently cleaved the silyl enol ether), concentrated under 1 mmHg at 50° C. for 3 h to afford the above diethyl ester as a viscous, slightly yellow oil (0.23 g, 95%).

$^1$H NMR (CDCl$_3$) δ; MS (FAB-LSIMS; rel abund.) 543 (92%, [M($^{79}$Br)+H]$^+$), 545(100%, [M($^{81}$Br)+H]$^+$). Anal. Calcd for $C_{28}H_{32}BrO_4P$: C, 61.83; H, 5.94. Found: C, 62.05; H, 6.11.

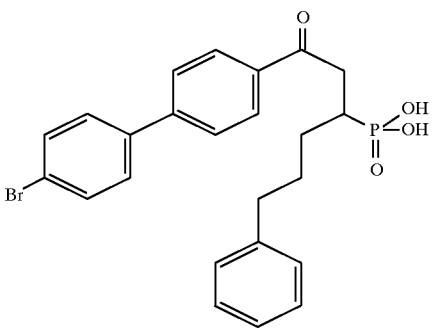

Example 246

Step 3—Preparation of Example 246

To a solution of the product from step 2 (0.243 g, 0.490 mmol) in dry $CH_2Cl_2$ (15 mL) was added trimethylsilyl bromide (0.48 mL, 3.64 mmol, 7.4 equiv.) via syringe. This was allowed to stir at room temperature for 14 h. The resulting solution was then concentrated to approximately 8 mL under reduced pressure then treated with MeOH (10 mL). This concentration/dilution regimen was repeated five more times, after which the reaction mixture was concentrated under reduced pressure. The resulting solids were triturated with hexanes to afford the desired phosphonic acid (0.150 g, 63%).

MP 150°–152° C.; $^1$H NMR (CD$_3$OD) δ 1.50–1.65 (m, 1H), 1.65–1.85 (m, 2H), 1.85–1.97 (m, 1H), 2.15–2.35 (m, 2H), 2.72–2.84 (m, 1H), 10 3.15–3.32 (m, 1H), 7.08–7.11 (m, 3H), 7.19 (app d, j=6.99 Hz, 2H), 7.44 (app d, J=8.45 Hz, 2H), 7.55 (app d, J=8.46 Hz, 2H), 7.63 (app d, J=8.45

Hz, 2H), 8.01, (app d, J=8.09 Hz, 2H); $^{13}$C NMR (CD$_3$OD) δ 28.9 (d, J=2.44 Hz, 1 C), 29.9 (d, J=9.76 Hz, 1 C), 31.4 (d, J=142.83 Hz, 1 C), 37.0 (d, J=33.07 Hz, 1 C), 50.9, 120.3, 123.5,. 126.6, 127.9 (2 C), 129.0 (4 C), 129.5 (2 C), 129.7 (2 C), 132.8 (2 C), 135.6, 139.0, 142.2, 145.9, 198.9 (d, J=11.0 Hz, 1 C); $^{31}$p NMR (CDCl$_3$) δ 35.5 (s); MS (FAB-LSIMS; rel abund.) 487 (100%, [M($^{79}$Br)+H]$^+$), 489 (92%, [M($^{81}$Br)+H]$^+$). Anal. Calcd for C$_{24}$H$_{24}$BrO$_4$P.H$_2$O: C, 57.04; H, 5.19; Br, 15.81; P, 6.13. Found: C, 56.69; H, 5.98; Br, 15.98; P, 6.16.

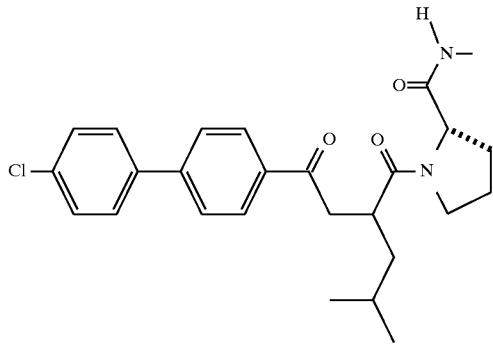

Example 247

Example 247

A dry dichloromethane (3 mL) solution of Example 1 (0.25 g, 0.725 mmol), proline N-methyl amide hydrochloride (0.48 g, 2.90 mmol), and 1-hydroxybenzotriazole (0.10 g, 0.725 mmol) in a 10-mL round-bottomed flask was chilled using an ice bath and stirred for a few minutes. N-methylmorpholine (0.32 mL, 0.29 g, 2.90 mmol) was added quickly via syringe followed by solid 1-ethyl-3-(3-dimethylaminopropyl)carbodiimide (0.146 g, 0.76 mmol). The reaction mixture was stirred under argon for several hours at 0° C. and was then warmed to room temperature overnight. The reaction mixture was then diluted with chloroform (30 mL) and washed with 10% HCl (10 mL). The separated aqueous layer was back-extracted with chloroform (5 mL). The combined organic portions were washed with saturated NaHCO$_3$ (10 mL), dried (Na$_2$SO$_4$), and concentrated in vacuo. The crude oil was purified via flash column chromatography [dichloromethane-methanol (98:2)] to provide the title compound as a white solid (0.26 g, 79%, mp 75.5°–78.0°C.).

TLC (dichloromethane-methanol, 94:6): R$_f$ 0.73; $^1$H NMR (DMSO-d$_6$) δ 0.60–1.00 (m, 6H), 1.20–2.00 (m, 7H), 2.50–2.60 (m, 3H), 2.60–5.00 1 0 (m, 6H), 7.00–8.20 (m, 9H); MS (FAB-LSIMS) 455 [M+H]$^+$ (C$_{26}$H$_{31}$O$_3$N$_2$Cl, FW=455.00); HRMS calcd, 454.2023; found, 454.203C.

Example 248

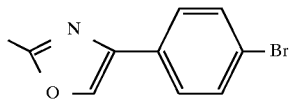

Step 1

A solution of 2,4'-dibromoacetophenone (0.62 g, 2.19 mmoles) and acetamide (0.20 g, 3.32 mmoles) in 6 mL of toluene was refluxed for 3 days. The solvent was removed at reduced pressure and the residue was chromatographed with 0–30% ethyl acetate in hexanes to afford 0.20 mg (38%) of product as a white solid.

TLC (methylene chloride) R$_f$ 0.42; $^1$H NMR (CDCl$_3$) δ 7.81 (s, 1H), 7.59 (d, J =8.6 Hz, 2H), 7.52 (d, J =8.9 Hz, 2H), 2.52 (s, 3H); $^{13}$C NMR (CDCl$_3$) δ 162.01, 139.71, 133.33, 131.81, 130.07, 126.90, 121.64, 13.94.

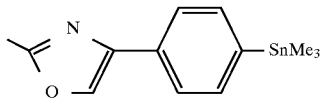

Step 2

A solution of trimethyltin chloride (0.81 g, 4.06. mmoles) in DME (1.5 mL) was added to a stirred suspension of small cubes of metallic sodium (0.3 g, 13.05 mmoles) in DME (2.5 mL) under a stream of argon in an ice cold round bottom flask. The mixture was stirred in the ice bath for 3.5 hrs when the mixture turned green. The mixture was syringed into a cooled round bottom flask and treated with a solution of the product of step 1 (0.8 g, 3.36 mmoles) in DME (4 mL). The reaction mixture was then allowed to warm and stir at room temperature overnight. At this time, it was diluted with ethyl acetate, washed with water, brine, and dried over MgSO$_4$. The crude product was chromatographed with 3–20% ethyl acetate in hexanes to afford 0.76 g (70%) of product as an oil.

TLC (hexanes—20% ethyl acetate) R$_f$ 0.37; $^1$H NMR (CDCl$_3$) δ 7.80 (s, 1H), 7.66 (d, J=8.05 Hz, 2H), 7.51 (d, J=8.05, 2H), 2.50 (s, 3H), 0.28 (s, 9H).

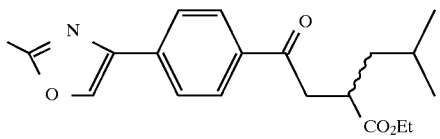

Step 3

A solution of the product of step 2 (0.21 g, 0.65 mmole), the acid chloride from step 3 of the Example 61 preparation (0.16 g, 0.74 mmole), and PdCl$_2$(PPh$_3$)2 (0.078 g, 0.14 mmole) in 1,2-dichloroethane (1.5 mL) was refluxed overnight. The reaction mixture was diluted with ethyl acetate and filtered. The filtrate was concentrated at reduced pressure and chromatographed with 3-50% ethyl acetate in hexanes to afford 66 mg of product as a solid.

TLC (hexanes—20% ethyl acetate) R$_f$ 0.17; $^1$H NMR (CDCl$_3$) δ 7.98 (d, J=8.9 Hz, 2H), 7.90 (s, 1H), 7.78 (d, J=8.6 Hz, 2H), 4.14 (q, J=6.6 Hz, 2H), 3.42 (q, J =8.3 Hz, 1H), 3.12–2.99 (m, 2H), 2.53 (s, 3H), 1.67–1.58 (m, 2H), 1.45–1.34 (m, 1H), 1.24 (t, J=7.5 Hz, 3.H), 0.96 (d, J=6.3 Hz, 3H), 0.90 (d, J=6.3 Hz, 3H); $^{13}$C NMR (CDCl$_3$) δ 197.66, 175.98, 162.30, 139.73, 135.88, 135.61, 134.59, 128.63, 125.34, 60.46, 41.50, 40.89, 38.66, 25.93, 22.64, 22.29, 14.19, 13.95; MS (FAB-LSIMS) 344 [M+H]$^+$; HRMS (FAB) calcd. for C$_{20}$H$_{26}$NO$_4$ [M+H]$^+$344.18618, Found 344.18600 .

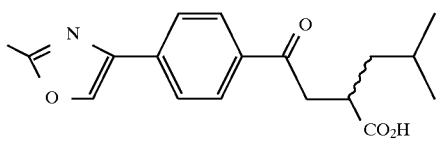

Step 4—Preparation of Example 248

The product of step 3 (56 mg, 0.16 mmole) was suspended in ethanol (1.3 mL) and treated with 4N NaOH (0.4 mL). The mixture was stirred at room temperature overnight. The reaction mixture was then quenched with 2N HCl, diluted with ethyl acetate, and the layers were separated. The organic layer was washed with brine and dried over $MgSO_4$. The product was chromatographed with 0–12% methanol in methylene chloride to afford 40 mg (78%) of Example 248 as a solid.

MP 120° C.; TLC (methylene chloride—10% methanol) Rf 0.32; $^1$H NMR (CDCl$_3$) δ 8.00 (d, J=8.2 Hz, 2H), 7.91 (s, 1H), 7.79 (d, J=8.2 Hz, 2H), 3.43 (dd, J$_1$=17.1 Hz, J$_2$=7.9 Hz, 1H), 3.17–3.04 (m, 2H), 2.55 (s, 3H), 1.75–1.65 (m,2H), 1.44–1.39 (m,1H), 0.98 (d, J=6.2 Hz, 3H), 0.93 (d, J=6.2 Hz, 3H); $^{13}$C NMR (CDCl$_3$) δ 197.43, 180.62, 162.38, 139.71, 135.72, 135.69, 134.64, 128.66, 125.39, 41.13, 40.65, 38.26, 25.89, 22.53, 22.30, 13.92; MS (FAB-LSIMS) 316 [M+H]$^+$; HRMS (FAB) calcd. for $C_{18}H_{22}NO_4$ [M+H]$^+$316.15488, Found 316.15424; Elemental Analysis: calcd. C 68.55, H 6.71, N 4.44; found C 68.35, H 6.70, N 4.31.

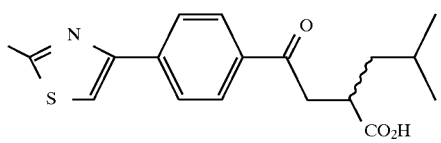

Example 249

Example 249

The procedure was analogous to that of Example 248 except thioacetamide was used instead of acetamide.

TLC (methylene chloride—10% methanol) R$_f$ 0.44; $^1$H NMR (CDCl$_3$) δ 7.92 (broad s, 4H), 7.39 (broad s, 1H), 3.35 (m, 1H), 3.00 (m, 2H), 2.72 (s, 3H), 1.64 (m, 2H), 1.35 (m, 1H), 0.91 (broad s, 3H), 0.86 (broad s, 3H); $^{13}$C NMR (CDCl$_3$) δ 197.53, 180.49, 166.58, 153.74, 138.69, 135.64, 128.66, 126.34, 114.60, 41.12, 40.69, 38.22, 25.87, 22.53, 22.28, 19.25; MS (FAB-LSIMS) 332 [M+H]$^+$; HRMS (FAB) calcd. for $C_{18}H_{22}NO_3S$ [M+H]$^+$332.13204, Found 332.13287.

Example 250

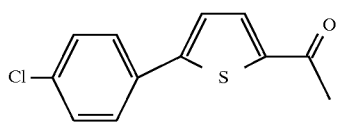

Step 1

A solution of 2-acetyl-5-bromothiophene (0.55 g, 2.64 mmoles) in toluene (5 mL) was treated with Pd(PPh$_3$)4 and allowed to stir at room temperature for 30 min. at which time 4-chlorobenzeneboronic acid (0.46 g, 2.91 mmoles) and NaOMe in MeOH (1.21 mL, 25 % wt, 5.29 mmoles) were added. The reaction mixture was then refluxed for 4 hrs. The mixture was cooled to room temperature and 2N NaOH (3 mL) was added and stirring was continued for another 2 hrs. The mixture was then diluted with methylene chloride, washed with brine and dried over MgSO$_4$. The crude product was chromatographed with 0–30% ethyl acetate in hexanes to afford 0.51 g (82%) of product.

TLC (hexanes—10% ethyl acetate) R$_f$ 0.24; $^1$H NMR (CDCl$_3$) δ 7.66 (d, J=3.6 Hz, 1H), 7.59 (d, J=8.6 Hz, 2H), 7.40 (d, J=8.9 Hz, 2H), 7.30 (d , J=3.9 Hz, 1H), 2.58 (s, 3H); $^{13}$C NMR (CDCl$_3$) δ 190.55, 151.24, 143.46, 134.96, 133.41, 131.83, 129.33, 127.45, 124.19, 26.56.

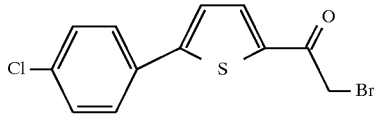

Step 2

The product of step 1 (0.51 g, 2.17 mmoles) was dissolved in THF (10 mL), cooled to 0° C., and treated with phenyltrimethyl-ammonium tribromide (0.84 g, 2.17 mmoles). The reaction mixture was then stirred at room temperature for 5 hrs. The mixture was quenched with H$_2$O and extracted with ethyl acetate (2×15 mL). The extracts were washed with brine and dried over MgSO$_4$ to afford 0.62 g (91%) crystallized from ether / hexanes.

TLC (hexanes-10% ethyl acetate) R$_f$ 0.27; $^1$H NMR (CDCl$_3$) δ 7.77 (d, J=3.9 Hz, 1H), 7.59 (d, J=8.3 Hz, 2H), 7.41 (d, J=8.3 Hz, 2H), 7.33 (d , J=3.8 Hz, 1H), 4.36 (s, 2H); $^{13}$C NMR (CDCl$_3$) δ 184.20, 152.82, 139.60, 135.41, 134.56, 131.46, 129.42, 127.57, 124.43, 30.12.

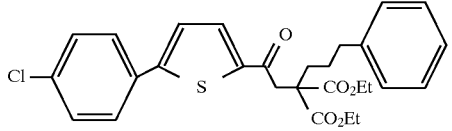

Step 3

A solution of 3-phenyl-propyl diethyl malonate (0.85 g, 3.05 mmoles) in THF (10 mL) was treated with NaH (0.068 g, 2.81 mmoles) under a stream of argon. The solution was stirred at room temperature for 30 min. At this time, a solution of the product of step 2 (0.62 g, 1.98 mmoles) in THF (14 mL) was added dropwise. After the addition, the reaction mixture was stirred at room temperature for 15 min when it was quenched with H$_2$O, diluted with ethyl acetate, and the layers were separated. The organic layer was washed with brine, dried over MgSO$_4$. The residue was then chromatographed with 0–10% ethyl acetate in hexanes to afford 0.63 g of product.

TLC (hexanes-20% ethyl acetate) R$_f$ 0.39; $^1$H NMR (CDCl$_3$) δ 7.70 (d, J=4.2 Hz, 1H), 7.58 (d, J=8.6 Hz, 2H), 7.40 (d, J=8.3 Hz, 2H), 7.30 (d , J=3.9 Hz, 1H), 7.25–7.11 (m, 5H), 4.20 (q, J=6.9 Hz, 4H), 3.59 (s, 2H), 2.61 (t, J=7.5 Hz, 2H), 2.20–2.13 (m, 2H), 1.65–1.55 (m, 2H), 1.23 (t, J=6.8 Hz, 6H).

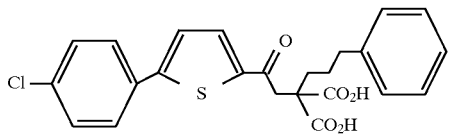

Step 4

A solution of the product of step 3 (0.63 g, 1.23 mmoles) in ethanol (5 mL) was treated with sodium hydoxide (0.24 g, 6.16 mmoles) in H$_2$O (0.5 mL) and the mixture was stirred at room temperature for 2 hrs. At this time, the reaction mixture was acidified with 2N HCl, diluted with ethyl acetate, and the layers were separated. The organic layer was washed with brine and dried over MgSO$_4$ to afford 0.54 g of the diacid product after decolorizing with activated carbon.

TLC (methylene chloride-10% methanol) $R_f$ 0.13; $^1$H NMR (CDCl$_3$/DMSO-d$_6$) δ 7.63 (d, J=3.9 Hz, 1H), 7.50 (d, J=8.6 Hz, 2H), 7.32 (d, J=8.3 Hz, 2H), 7.23 (d , J=4.2 Hz, 1H), 7.20–7.06 (m, 5H), 3.63 (s, 2H), 2.59–2.50 (m, 2H), 1.97–1.91 (m, 2H), 1.69–1.61 (m, 2H).

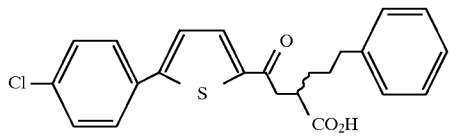

Example 250

Step 5—Preparation of Example 250

The product of step 4 (50 mg, 0.11 mmoles) was dissolved in dry acetonitrile (1.5 mL) and treated with copper oxide (2 mg, 0.014 mmole). The mixture was refluxed for 36 hrs under a stream of argon. At this time, it was diluted with ethyl acetate and quenched with 2N HCl. The layers were separated, and the organic was washed with brine and dried over MgSO$_4$ to afford 34 mg of Example 250 crystallized from ether/hexanes.

Example 250

MP 149° C.; TLC (methylene chloride-10% methanol) $R_f$ 0.40; $^1$H NMR (CDCl$_3$) δ 7.69 (d, J=3.6 Hz, 1H), 7.58 (d, J=8.6 Hz, 2H), 7.39 (d, J=8.6 Hz, 2H), 7.30–7.16 (m, 6H), 3.37 (dd, J$_1$=16.7 Hz, J$_2$=8.3 Hz, 1H), 3.16–3.11 (m, 1H), 3.00 (dd, J$_1$=16.7 Hz, J$_2$=4.5 Hz, 1H), 2.69–2.63 (m, 2H), 1.84–1.66 (m, 4H); $^{13}$C NMR (CDCl$_3$) δ 190.61, 179.33, 151.40, 142.42, 141.73, 135.04, 133.09, 131.75, 129.34, 128.36, 127.48, 125.89, 124.24, 40.23, 39.89, 35.58, 31.35, 28.81; MS (FAB-LSIMS) 413 [M+H]$^+$; Elemental Analysis calcd. for C$_{23}$H$_{21}$ClO$_3$S C 66.90, H 5.13, Cl 8.59, S 7.76; Elemental Analysis found. C 67.00, H 5.28, Cl 8.40, S 7.85.

Example 251

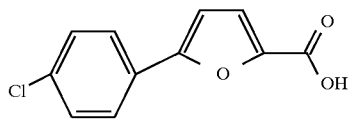

Step 1

The methyl ester of 5-bromofuroic acid (204 mg, 0.99 mmole) was dissolved in DME (3.5 mL) followed by the addition of Pd(OAc)2 (24 mg, 0.11 mmole), P(o-tolyl)$_2$ (60 mg, 0.20 mmole), 4-chlorobenzeneboronic acid (168 mg, 1.07 mmoles), and sodium carbonate (1.0 mL, 2N in H$_2$O, 2 mmoles). The reaction mixture was refluxed for 1 hr when thin layer chromatography showed complete reaction. The mixture was cooled to room temperature, diluted with water, and extracted with methylene chloride (2×15 mL). The combined extracts were washed with brine, dried over MgSO$_4$, and the solvent removed at reduced pressure to afford 170 mg (72%) of product as the methyl ester. The methyl ester was then suspended in 2 mL of ethanol, treated with 5 eq of aqueous NaOH and the mixture was stirred at room temperature for 1 hr. At this time, the reaction mixture was quenched with 2N HCl, diluted with ethyl acetate, and the layers were separated. The aqueous layer was extracted with ethyl acetate, and the combined extracts were washed with brine, dried over MgSO$_4$, and the solvent removed at reduced pressure to afford 140 mg of product.

TLC (methylene chloride-10% methanol) $R_f$ 0.17; $^1$H NMR (CDCl$_3$/CD$_3$OD) δ 7.65 (d, J=8.3 Hz, 2H), 7.31 (d, J=8.6 Hz, 2H), 7.18(d, J=3.6 Hz, 1H), 6.68 (d , J=3.6 Hz, 1H).

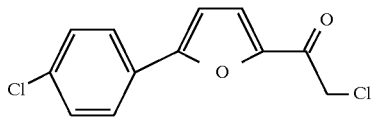

Step 2

A suspension of the product of step 1 (1.42 g, 6.38 mmoles) in methylene chloride was treated with oxalyl chloride (3.5 mL, 2M in CH$_2$Cl$_2$, 7.00 mmoles) and one drop of DMF. The mixture was refluxed for 1 hr under argon. At this time, the mixture was cooled to 0° C. and cannulated into an ice cold solution of diazomethane (50 mL, 0.6M in Et$_2$O, 30 mmoles). The reaction mixture was allowed to stir at 0° C. for 1 hr before it was quenched with HCl (30 mL, 1N in Et$_2$O, 30 mmoles). The mixture was then stirred at room temperature for 1.5 hr, transferred to a separatory funnel with ethyl acetate, washed with saturated sodium bicarbonate solution, brine, and dried over MgSO$_4$. The crude product was chromatographed with 0–30% ethyl acetate in hexanes to afford 1.28 g (79%) of product.

TLC (hexanes-10% ethyl acetate) $R_f$ 0.13; $^1$H NMR (CDCl$_3$) δ 7.73 (d, J=8.6 Hz, 2H), 7.46–7.40 (m, 3H), 6.83 (d, J=3.6 Hz, 1H), 4.60 (s, 2H); $^{13}$C NMR (CDCl$_3$) δ 179.73, 157.43, 149.64, 135.64, 129.31, 127.39, 126.32, 121.12, 108.15, 44.88.

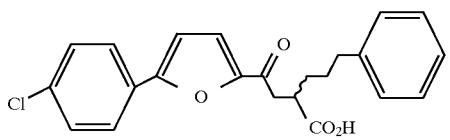

Example 251

Step 3—Preparation of Example 251

The procedure was analogous to that of Example 250 except the product of step 2 was used instead of the corresponding product from the Example 250 preparation.

Example 251

MP 129°–130° C.; TLC (methylene chloride-10% methanol) $R_f$ 0.47; $^1$H NMR (CDCl$_3$) δ 7.72 (d, J=8.6 Hz, 2H), 7.42 (d, J=8.3 Hz, 2H), 7.30–7.16 (m, 6H), 6.77 (d, J=3.6 Hz, 1H), 3.34 (dd, J=16.7 Hz, J$_2$=8.3 Hz, 1H), 3.17–3.08 (m, 1H), 2.98 (dd, J$_1$=17.3 Hz, J$_2$=4.8 Hz, 1H), 2.66 (t, J=6.9 Hz, 2H), 1.85–1.65 (m, 4H); MS (FAB-LSIMS) 397 [M+H]$^+$; Elemental Analysis calcd. for C$_{23}$H$_{21}$ClO$_4$ C 69.61, H 5.33, Cl 8.93; Elemental Analysis found. C 69.47, H 5.43, Cl 8.71.

BIOLOGICAL PROTOCOLS AND IN VITRO TEST DATA

Preparation of Gelatinase-B (92 kDa, MMP-9):

MMP-9 was isolated modifying the previously described procedures of Hibbs et al (J. Biol. Chem., 260, 2493–2500, 1984) and Wilhelm et al (J. Biol. Chem., 264, 17213–17221, 1989). Briefly, polymorphonuclear leukocytes (PMN) preparations were isolated as described above from 3 or more units of freshly drawn whole blood obtained from the New York Blood Center (N.Y., N.Y.). Cells were resuspended in phosphate buffered saline (PBS) containing 100 ng/ml phorbol myristate acetate (PMA) in the presence of 50 mM di-isopropylfluorophospate (DFP), 1 μg/ml leupeptin and aprotinin, and 1 mg/ml catalase for 1 hr at 37° C. Supernatants were collected by centrifugation (300×g) and the samples were frozen at −70° C. All chromatographic methods were performed at 4° C. Thawed samples were concentrated 5-fold using an Amicon chamber equipped with a YM-10 membrane. The concentrate was pressure dialyzed against 0.02M Tris-HCl, 0.1M NaCl, 1 mM $CaCl_2$, 1 μM $ZnCl_2$, 0.001% Brij-35, 0.02% sodium azide ($NaN_3$), pH 7.5 and applied to DEAE ion exchange chromatography resin which was previously equilibrated with the same buffer at a flow rate of 0.4 ml/min. The column was extensively washed with the same buffer and gelatinase was eluted as 4 ml fractions from the column with 0.02M Tris-HCl, 0.5M NaCl, 1 mM $CaCl_2$, 1 μM $ZnCl_2$, 0.001% Brij-35, 0.02% $NaN_3$, pH 7.5. Gelatinase containing fractions were observed by gelatin zymography (see below), loaded onto a gelatin agarose affinity resin and washed with the same buffer. Gelatinase activity was eluted at a flow rate of 1 ml/min from the column as 1 ml fractions with 0.02M Tris-HCl, 1M NaCl, 1 mM $CaCl_2$, 1 μM $ZnCl_2$, 0.001% Brij-35, 0.02% $NaN_3$, pH 7.5 containing 10% dimethyl sulfoxide (DMSO). The fractions containing gelatinase activity were pooled and dialyzed against 0.005M Tris-HCl, 5mM NaCl, 0.5 mM $CaCl_2$, 0.1 μM $ZnCl_2$, 0.001% Brij-35, pH 7.4. The protein content associated with material was determined with a micro-BCA assay (Pierce, Rockford, Ill.), lyophilized and reconstituted to a desired working concentration (100 μg/ml).

Thiopeptilide MMP-9 Inhibition Assay

Progelatinase (10 μg/ml) isolated from human PMNs (described above) was activated with 1 mM 4-aminophenylmercuric acetate (APMA) in 50 mM Tris-HCl, 200 mM NaCl, 5 mM $CaCl_2$, 0.001% Brij-35, pH 7.6 at 37° C. for 16 hr. The activated enzyme was dialyzed against the above buffer to remove APMA. The thiopeptolide spectrophotometric ( Weingarten, H., Feder, J., Anal. Biochem., 147, 437–440, 1985) substrate hydrolysis assay was modified to a micro-assay format. Spectrophotometric analysis of MMP-9 activity required a 1000-fold dilution of activated MMP-9 (10 ng/ml, 0.14 nM) in assay buffer comprised of 50 mM 4-(2-hydroxyethyl)1-piperazine ethane sulfonic acid (HEPES), 0.15M NaCl, 10 mM $CaCl_2$, 0.001% Brij-35, pH 6.5 between 100 and 1000-fold for enzyme assays. Reaction mixtures for inhibitor studies contained 1 mM Ac-Pro-Leu-Gly-S-Leu-Leu-Gly-o-ethyl thiopeptolide substrate dissolved in HEPES assay buffer pH 6.5, along with 0.5 mM 5,5'-dithio-bis-(nitrobenzoic acid), drug concentrations ranging from 0.5 nM to 5 μM and activated enzyme (10–100 ng) in a total volume of 130 μl. The hydrolysis of substrate was monitored at 405 nm using an automated plate reader (Molecular Devices, Menlo Park, Calif.). Enzyme mediated substrate hydrolysis was corrected for non-enzymatic hydrolysis of the substrate by the subtraction of values from control samples incubated in the absence of enzyme. Drug efficacy was reported as the percent inhibition of enzyme activity calculated as:

(Control Values−Treated Values)/Control Values×100

Active compounds with a demonstrated 30% inhibition of enzyme activity or greater were tested further at varying concentrations (0.5 nM—5 μM) and linear regression analysis of percent inhibition versus log drug concentration was used to obtain $IC_{50}$ values. Two way analysis of variance was used to determine significance between individual test groups.

Expression and Purification of Recombinant Truncated Prostromelysin (MMP-3)

Truncated Prostromelysin-257 was expressed in a soluble form in E.coli as described by Marcy et al., Biochemistry, 30, 6476–6483, 1991. Soluble truncated prostromelysin was purified by a modification of the monoclonal antibody affinity chromatography method described by Housley et al., J. Biol. Chem., 268, 4481–87, 1993.

Primary Thiopeptilide MMP-3 Inhibition Assay

Enzyme: recombinant stromelysin expressed in E.coli and purified as described above. Truncated stromelysin was heat activated as described by Kokalitis et al., Biochem. J., 276, 217–221, 1991. The protocols for the assay of compounds as stromelysin inhibitors was the same as that used for MMP-9 except that the assay buffer was 50 mM MES, pH 6.5 containing 150 mM NaCl, 10 mM $CaCl_2$, .005% Brij, and 1% DMSO. The enzyme concentration was 13 nM stromelysin. The substrate concentration was 658 micromolar (μM) and our drug concentrations were the same as with the MMP-9 assay.

Secondary P218 Quenched fluorescence Assay for MMP-3 Inhibition

This assay was originally described by Knight et al., FEBS Letters, 296, 263–266, 1992, for a related substrate. The assay is run continuously in a 3.0 ml cuvette using a Perkin-Elmer LS 50 B Spectrofluorimeter at 25° C. in a final volume of 2.0 mls. P218 substrate (10 mM) in 100% DMSO is diluted to a final concentration of 2.0 micromolar (μM) into assay buffer: 50 mM MES, pH 6.5 containing 150 mM NaCl, 10 mM $CaCl_2$, 0.005% Brij-35, and 1%(v/v) DMSO. Test compounds(10 mM) in DMSO are diluted in assay buffer at an initial concentration of 10 to 100 micromolar. These are diluted to a final concentration in the assay from 10 nM to 1 μM depending upon their potency previously determined in primary thiopeptilide assay described above. The reaction is initiated by the addition of recombinant stromelysin (MMP-3) at a final concentration of 1.0 nM. Upon peptide cleavage, the fluorescent MCA group was detected using an excitation wavelength of 328 nanometers and an emission wavelength of 393 nanometers. The assay is linear from 0.2 to 5 nM MMP-3 concentration and percent inhibition is calculated as described above for the primary thiopeptilide assay and $IC_{50}$ values are determined by a linear regression analysis of percent inhibition versus log drug concentration. The peptide sequence of the MCA substrate, hereinafter designated P218, is shown below:

P218

For MMP-3, this substrate has a $K_m$ of 16 μM at pH 6.5 and a $kcat/K_m$ value of 56,000 $M^{-1}$ $sec^{-1}$.

Secondary P218 Quenched fluorescence Assay for MMP-2 Inhibition

Gelatinase A (MMP-2) was prepared using a vaccinia expression system according to the method of R. Fridman, et al J. Biol. Chem., 267, 15398 (1992). Inhibition assays with MMP-2 were carried out as described for MMP-3 above using 0.2 nM final enzyme concentration and the P218 substrate. MMP-2 has a turnover number of 400,000 in this assay. Initial velocities (nM/sec.) never exceeded 5% of the total substrate in these experiments.

BIARYL MATRIX METALLOPROTEASE INHIBITORS

Assay Data for the Invention and Reference Compounds

All IC$_{50}$ values are expressed as nM. When "I=x%" is shown, x represents the % inhibition at 5 μM. When "x (n)" is shown, x is the average IC$_{50}$ value of n separate determinations.

| EX. # | MMP-3 Thiopeptilide IC$_{50}$ | MMP-3 Fluorogenic IC$_{50}$ | MMP-9: Thiopeptilide IC$_{50}$ | MMP-2 Fluorogenic IC$_{50}$ |
|---|---|---|---|---|
| fenbufen |  | Inactive | I = 2% | 1,000 |
| 1 | 486 (7) | 805 (2) | 1,000 |  |
| 2 | 270 |  | 2,200 |  |
| 3 | I = 13% |  | I = 0% |  |
| 4 | 379 | 480 | 2,700 |  |
| 5 | I = 11% |  | I = 19% |  |
| 6 | 2,100 |  | I = 38% |  |
| 7 | 690 |  | 2,100 |  |
| 8 | I = 26% |  | I = 0% |  |
| 9 | I = 0% |  | I = 3% |  |
| 10 | I = 1% |  | I = 0% |  |
| 11 | I = 14% |  | I = 0% |  |
| 12 | I = 17% |  | I = 0% |  |
| 13 | I = 27% |  | I = 3% |  |
| 14 | 440 | 570 | 1,200 |  |
| 15 | 2,000 |  | I = 0% |  |
| 16 | 620 |  | 3,100 |  |
| 17 | I = 35% |  | I = 0% |  |
| 18 | I = 0.3% |  | I = 9% |  |
| 19 | 550 |  | 1,200 |  |
| 20 | I = 32% |  | I = 34% |  |
| 21 | 750 |  | 1,200 |  |
| 22 | I = 11% |  | I = 15% |  |
| 23 | 790 |  | 1,200 |  |
| 24 | I = 56% |  | I = 29% |  |
| 25 | I = 58% |  | 6,000 |  |
| 26 | 2,600 |  | 2,400 |  |
| 27 | 5,000 |  |  |  |
| 28 | I = 0% |  |  |  |
| 29 | I = 0% |  | I = 0% |  |
| 30 | I = 24% |  | I = 0% |  |
| 31 | I = 14% |  | I = 0% |  |
| 32 | I = 40% |  | I = 0% |  |
| 33 | 950 |  | I = 43% |  |
| 34 | I = 28% |  | I = 44% |  |
| 35 | I = 8% |  | I = 25% |  |
| 36 | 620 | 240 | 4,300 |  |
| 37 | I = 9% |  | I = 0% |  |
| 38 | 10,000 |  | I = 10% |  |
| 39 | I = 16% |  | I = 4% |  |
| 40 | 121 (4) |  | 50 |  |
| 41 | 118 (3) | 260 | 500 |  |
| 42 |  | 48 |  | 21 |
| 43 |  |  |  |  |
| 44 |  | 1,970 |  | 1,150 |
| 45 |  | I = 43% |  | I = 56% |
| 46 | 700 |  | 4,000 |  |
| 47 | 560 |  | I = 22% |  |
| 48 | I = 53% |  | I = 15% |  |
| 49 | 750 |  | I = 13% |  |
| 50 | 630 |  | 800 |  |
| 51 | 170 |  | 100 |  |
| 52 | 76 (2) |  | 37 |  |
| 53 | 950 |  | 800 |  |
| 54 | 190 |  | 700 |  |
| 55 | 170 |  | 110 |  |
| 56 | 310 |  | 700 |  |
| 57 | I = 16% |  | I = 22% |  |
| 58 | 1,200 |  | 1,500 |  |
| 59 | I = 33% |  | 2,000 |  |
| 60 | 600 |  | 180 |  |
| 61 | I = 35% |  | I = 22% |  |
| 62 | 400 |  | 4,500 |  |
| 63 | 980 |  | 500 |  |
| 64 | 300 |  | I = 29% |  |
| 65 | 840 |  | I = 47% |  |
| 66 | I = 7% |  | I = 11% |  |
| 67 | 150 |  | 780 |  |
| 68 | 280 |  | 300 |  |
| 69 | 220 |  | 600 |  |
| 70 | 2,300 |  | I = 38% |  |
| 71 | 78 |  | 82 (2) |  |
| 72 | 1,000 |  | 1,800 |  |
| 73 | I = 24% |  | I = 7% |  |
| 74 | 310 |  | 1,200 |  |
| 75 | I = 12% |  | I = 9% |  |
| 76 | 470 |  | 800 |  |
| 77 | I = 30% |  | I = 12% |  |
| 78 | I = 23% |  | I = 9% |  |
| 79 | 720 |  | 1,400 |  |
| 80 | 150 |  | 100 (2) |  |
| 81 | 37 |  | I = 44% (3) |  |
| 82 | 168 (4) |  | I = 30% |  |
| 83 | 111 (4) |  | 480 |  |
| 84 | I = 36% |  | I = 11% |  |
| 85 | 174 |  | 700 |  |
| 86 | I = 60% |  | I = 26% |  |
| 87 | 244 (11) | 120 (3) | 285 (2) | 25 (2) |
| 88 | I = 39% |  | I = 31% |  |
| 89 | 145 (4) | 80 (2) | 190 | 28 (2) |
| 90 | 150 |  | 240 |  |
| 91 | 2,800 (2) |  | 2,800 |  |
| 92 | 590 |  | 3,800 |  |
| 93 | 440 |  | 2,200 |  |
| 94 | 760 |  | 1,800 |  |
| 95 | 380 |  | I = 60% |  |
| 96 | 1,000 |  | I = 45% |  |
| 97 | 403 (2) |  |  |  |
| 98 | I = 43% |  |  |  |
| 99 | 180 (2) |  | I = 28% |  |
| 100 | 1,600 |  | I = 50% (2) |  |
| 101 | 105 (2) |  | 1,800 |  |
| 102 | 600 (2) |  |  |  |
| 103 | 310 (2) |  |  |  |
| 104 | 230 | 1,200 | 2,900 |  |
| 105 | 310 (2) |  | 900 |  |
| 106 | 112 (4) |  | 2,600 (2) |  |
| 107 | 160 (2) |  | 200 |  |
| 108 | 270 |  | 360 |  |
| 109 | 330 |  | 290 |  |
| 110 | I = 7% |  | I = 17% |  |
| 111 | 270 |  | 710 |  |
| 112 | 280 |  | I = 41% |  |
| 113 | 220 |  | I = 31% |  |
| 114 | 170 |  | 383 (3) |  |
| 115 | 757 |  | 1,500 |  |
| 116 | 151 |  | 1,300 |  |
| 117 | 530 |  | 600 |  |
| 118 | 153 (3) | 150 (2) | 2,450 (2) | 40 (2) |
| 119 | 115 (2) | 62 | 750 |  |
| 120 | I = 31% |  | I = 20% |  |
| 121 | 236 (12) | 180 (2) | 438 (5) | 20 (2) |
| 122 | I = 55% |  |  |  |
| 123 | 117 (2) | 92 | 197 (3) | 26 (2) |
| 124 | I = 23% |  | I = 21% |  |
| 125 | I = 14% |  |  |  |
| 126 | I = 17% |  |  |  |
| 127 | 830 |  |  |  |
| 128 | 1,600 |  |  |  |
| 129 | 170 |  | 200 |  |
| 130 | 640 |  | 2,300 |  |
| 131 | 340 |  | 800 |  |
| 132 | 250 |  | 500 |  |
| 133 | 247 (3) |  | 1,200 |  |
| 134 | 213 (3) |  | 215 (2) |  |
| 135 | 87 (3) |  | 170 |  |
| 136 | 950 (2) |  | 417 (3) |  |
| 137 | 180 (2) |  | 290 (3) |  |
| 138 | 140 (2) |  | 1,050 (2) |  |
| 139 | 340 |  | 390 (2) |  |
| 140 | 500 |  | 205 (2) |  |
| 141 | 440 |  | 280 |  |
| 142 | 650 |  | 390 (2) |  |
| 143 | 2,500 |  | I = 41% |  |
| 144 | 170 |  | 2,200 |  |
| 145 | 1,300 |  | 1,200 |  |
| 146 | 770 |  | 590 |  |

| EX. # | MMP-3 Thiopeptilide $IC_{50}$ | MMP-3 Fluorogenic $IC_{50}$ | MMP-9: Thiopeptilide $IC_{50}$ | MMP-2 Fluorogenic $IC_{50}$ |
|---|---|---|---|---|
| 147 | 83 | | 245 (2) | |
| 148 | 170 | | 435 (2) | |
| 149 | 260 | | 600 | |
| 150 | 190 | | 950 | |
| 151 | 240 | | 2,400 | |
| 152 | 610 | | 1,800 | |
| 153 | 930 | | 580 | |
| 154 | 680 | | 550 | |
| 155 | 310 | | 550 | |
| 156 | 720 | | 255 (2) | |
| 157 | 220 | | 360 (2) | |
| 158 | 360 | | 800 | |
| 159 | 300 | | 900 | |
| 160 | 250 | | 550 | |
| 161 | 280 | | 820 | |
| 162 | 150 | | 200 (2) | |
| 163 | 339 (2) | | 4,800 | |
| 164 | 144 (2) | | 600 | |
| 165 | 1,600 | | | |
| 166 | 2,000 | | | |
| 167 | 2,000 | | | |
| 168 | 920 | | | |
| 169 | 490 | | I = 53% | |
| 170 | 96 (2) | | 300 (2) | |
| 171 | 195 (2) | | 340 (2) | |
| 172 | 490 | | 1,300 | |
| 173 | 360 | | 850 | |
| 174 | 79 (4) | 27 (1) | 600 | 7 (1) |
| 175 | 125 (2) | | 800 | |
| 176 | 640 (3) | | 7,500 | |
| 177 | 293 (3) | | 2,900 | |
| 178 | I = 0% | | I = 21% | |
| 179 | 950 | | 2,000 | |
| 180 | 600 | | 3,000 | |
| 181 | 800 | | 2,100 | |
| 182 | 820 | | 2,100 | |
| 183 | I = 10% | | I = 27% | |
| 184 | I = 19% | | | |
| 185 | 520 | | I = 16% | |
| 186 | 900 | | I = 20% | |
| 187 | 227 | | 215 (2) | |
| 188 | 640 | | 10,000 | |
| 189 | 95 (2) | | 76 (2) | |
| 190 | I = 33% | | I = 21% | |
| 191 | I = 48% | | I = 31% | |
| 192 | 2,900 | | I = 42% | |
| 193 | 250 | | 650 | |
| 194 | 38 (3) | | 1.8 (2) | |
| 195 | 330 | | I = 62% | |
| 196 | 140 | | 510 | |
| 197 | I = 2% | | I = 0% | |
| 198 | 2,400 | | 7,000 | |
| 199 | I = 10% | | I = 1% | |
| 200 | 2,500 | | I = 21% | |
| 201 | I = 19% | | I = 0% | |
| 202 | I = 26% | | I = 3% | |
| 203 | I = 40% | | I = 46% | |
| 204 | 348 (4) | | 910 (2) | |
| 205 | I = 35% | | I = 15% | |
| 206 | 437 (3) | | 2,700 (3) | |
| 207 | I = 21% | | I = 12% | |
| 208 | I = 16% | | I = 0% | |
| 209 | 47 (8) | 14 (4) | 56 (5) | 4 (2) |
| 210 | 99 | | 600 | |
| 211 | 26 (10) | 12 (2) | 25 (4) | |
| 212 | | | 640 (3) | |
| 213 | 73 | | 62 (2) | |
| 214 | | | | |
| 215 | 310 | | 1,400 | |
| 216 | 55 | | 42 (2) | |
| 217 | 470 | | 1,800 | |
| 218 | 150 | | 550 | |
| 219 | 33 | | 108 (2) | |
| 220 | | | | |
| 221 | 50 | | 850 | |
| 222 | 80 | | 32 (2) | |
| 223 | 340 | | 700 | |
| 224 | 36 (4) | | | |
| 225 | 66 (4) | | | |
| 226 | 98 (2) | | | |
| 227 | 140 (2) | | | |
| 228 | I = 55% | | 12,000 | |
| 229 | I = 49% | | I = 45% | |
| 230 | I = 58% | | 8,000 | |
| 231 | I = 9% | | I = 16% | |
| 232 | I = 15% | | I = 18% | |
| 233 | I = 62% (2) | | I = 25% | |
| 234 | 1,400 | | 600 | |
| 235 | I = 37% | | I = 41% | |
| 236 | I = 42% | | 6,000 | |
| 237 | I = 55% | | 6,000 | |
| 238 | I = 20% | | I = 2% | |
| 239 | I = 24% | | I = 32% | |
| 240 | 1,700 | | 1,500 | |
| 241 | I = 14% | | I = 21% | |
| 242 | 2,400 | | 3,800 | |
| 243 | 360 | | 700 | |
| 244 | 500 | | 680 | |
| 245 | I = 11% | | I = 14% | |
| 246 | 5,000 | | I = 30% | |
| 247 | 6,000 | | I = 34% | |
| 248 | I = 12% | | I = 0% | |
| 249 | I = 31% | | I = 36% | |
| 250 | 550 | | 330 | |
| 251 | I = 4% | | I = 20% | |

It should be noted in the above table that a biaryl portion is necessary for significant MMP inhibitory activity—see, for example, biphenyl example 1 in comparison to reference phenyl example 22 or biphenyl example 130 in comparison to reference phenyl example 178. It is also noted that reference phenoxyphenyl example 183 is only of very low potency. It is also demonstrated that, while a 4-substituent on ring A is not essential for potency, it does lead to significant improved potency—see low potency unsubstituted examples 13 and 91 in comparison to chlorine substituted examples 1 and 87. It is also clear that increased size of substituent $R^6$ on portion E leads to increased activity—see unsubstituted example 6 compared to methyl substituted example 33 compared to ethyl substituted example 92. This is also shown in a comparison of example 208 in which E represents a cyclopropane ring in comparison to much more active example 206 with a cyclobutane ring. Only minor activity, at best, is observed when the compound is neither substituted on biphenyl nor on portion E such as in reference compound Fenbufen (first entry of the table).

EXAMPLE

Compound

Number: Chemical Abstracts (CA) Index Name

1: [1,1'-Biphenyl]-4-butanoic acid, 4'-chloro-α-(2-methylpropyl)-γ-oxo-

2: [1,1'-Biphenyl]-4-butanoic acid, 4'-chloro-α-(2-methylpropyl)-γ-oxo-, (S)—

3: [1,1'-Biphenyl]-4-butanoic acid, 4'-chloro-α-(2-methylpropyl)-γ-oxo-, (R)—

4: [1,1'-Biphenyl]-4-butanoic acid, 4'-chloro-β-(2-methylpropyl)-γ-oxo-, (S)—

5: [1,1'-Biphenyl]-4-butanoic acid, 4'-chloro-β-(2-methylpropyl)-γ-oxo-, (R)—

6: [1,1'-Biphenyl]-4-butanoic acid, 4'-chloro-γ-oxo-

7: [1,1'-Biphenyl]-4-butanoic acid, 4'-bromo-γ-oxo-
8: [1,1'-Biphenyl]-4-butanoic acid, 4'-fluoro-γ-oxo-
9: [1,1'-Biphenyl]-4-butanoic acid, 2'-fluoro-γ-oxo-
10: [1,1'-Biphenyl]-4-butanoic acid, 2'-chloro-γ-oxo-
11: [1,1'-Biphenyl]-4-butanoic acid, 2',4'-difluoro-γ-oxo-
12: [1,1'-Biphenyl]-4-butanoic acid, 3'-chloro-γ-oxo-
13: [1,1'-Biphenyl]-4-butanoic acid, α-(2-methylpropyl)-γ-oxo-
14: [1,1'-Biphenyl]-4-butanoic acid, 4'-bromo-α-(2-methylpropyl)-γ-oxo-
15: [1,1'-Biphenyl]-4-butanoic acid, 4'-fluoro-α-(2-methylpropyl)-γ-oxo-
16: [1,1'-Biphenyl]-4-butanoic acid, 4'-ethyl-α-(2-methylpropyl)-γ-oxo-
17: [1,1'-Biphenyl]-4-butanoic acid, 2'-fluoro-α-(2-methylpropyl)-γ-oxo-
18: [1,1'-Biphenyl]-4-butanoic acid, 2'-chloro-α-(2-methylpropyl)-γ-oxo-
19: [1,1'-Biphenyl]-4-butanoic acid, 4'-methoxy-α-(2-methylpropyl)-γ-oxo-
20: [1,1'-Biphenyl]-4-butanoic acid, 2',4'-difluoro-α-(2-methylpropyl)-γ-oxo-
21: [1,1'-Biphenyl]-4-butanoic acid, 4'-methyl-α-(2-methylpropyl)-γ-oxo-
22: Benzenebutanoic acid, 4-chloro-α-(2-methylpropyl)-γ-oxo-
23: [1,1'-Biphenyl]-4-butanoic acid, α-(2-methylpropyl)-γ-oxo-4'-pentyl-
24: [1,1'-Biphenyl]-4-butanoic acid, 4'-hydroxy-α-(2-methylpropyl)-γ-oxo-
25: [1,1'-Biphenyl]-4-butanoic acid, 4'-chloro-β-methylene-γ-oxo-
26: [1,1'-Biphenyl]-4-butanoic acid, 4'-chloro-γ-hydroxy-α-(2-methylpropyl)-
27: [1,1'-Biphenyl]-4-butanoic acid, 4'-chloro-γ-hydroxy-α-(2-methylpropyl)-
28: 2(3H)-Furanone, 5-(4'-chloro[1,1'-biphenyl]-4-yl)dihydro-3-(2-methylpropyl)-
29: 2(3H)-Furanone, 5-(4'-chloro[1,1'-biphenyl]-4-yl)dihydro-3-(2-methylpropyl)-
30: [1,1'-Biphenyl]-4-butanoic acid, 4'-chloro-α-methylene-γ-oxo-
31: Benzenebutanoic acid, 4-methyl-α-methylene-γ-oxo-
32: [1,1'-Biphenyl]-4-butanoic acid, 2'-chloro-α-methylene-γ-oxo-
33: [1,1'-Biphenyl]-4-butanoic acid, 4'-chloro-α-methyl-'-oxo-
34: 2-Butenoic acid, 4-(4'-chloro[1,1'-biphenyl]-4-yl)-4-oxo-, (E)—
35: 2-Butenoic acid, 4-[4-(4-chlorophenoxy)phenyl]-4-oxo-, (E)—
36: [1,1'-Biphenyl]-4-butanoic acid, 4'-chloro-γ-oxo-α-pentyl-
37: Ethanone, 1-(4'-chloro[1,1'-biphenyl]-4-yl)-
38: [1,1'-Biphenyl]-4-butanoic acid, 4'-chloro-γ-hydroxy-α-methylene-
39: [1,1'-Biphenyl]-4-butanoic acid, 2'-fluoro-γ-hydroxy-
40: [1,1'-Biphenyl]-4-butanoic acid, 4'-iodo-γ-oxo-α-(3-phenylpropyl)-
41: [1,1'-Biphenyl]-4-butanoic acid, 4'-iodo-α-(2-methylpropyl)-γ-oxo-
42: [1,1'-Biphenyl]-4-butanoic acid, 4'-(3-ethoxy-3-oxo-1-propenyl)-γ-oxo-α-(3-phenylpropyl)-, (E)—
43: [1,1'-Biphenyl]-4-butanoic acid, 4'-(2-carboxyethenyl)-γ-oxo-α-(3-phenylpropyl)-, (E)—
44: [1,1'-Biphenyl]-4-butanoic acid, 4'-(3-ethoxy-3-oxopropyl)-α-(3-phenylpropyl)-
45: [1,1'-Biphenyl]-4-butanoic acid, 4'-(2-carboxyethyl)-α-(3-phenylpropyl)-
46: [1,1'-Biphenyl]-4-butanoic acid, 4'-cyano-α-(2-methylpropyl)-γ-oxo-
47: [1,1'-Biphenyl]-4-butanoic acid, 4'-[[(1,1-dimethylethoxy)carbonyl]amino]-γ-oxo-α-(3-phenylpropyl)-
48: [1,1'-Biphenyl]-4-butanoic acid, 4'-(1,1-dimethylethyl)-γ-oxo-α-(3-phenylpropyl)-
49: [1,1'-Biphenyl]-4-butanoic acid, 4'-[[[(1,1-dimethylethoxy)carbonyl]amino]methyl]-γ-oxo-α-(3-phenylpropyl)-
50: [1,1'-Biphenyl]-4-butanoic acid, 4'-(cyanomethyl)-γ-oxo-α-(3-phenylpropyl)-
51: [1,1'-Biphenyl]-4-butanoic acid, 4'-(methylthio)-γ-oxo-α-(3-phenylpropyl)-
52: [1,1'-Biphenyl]-4-butanoic acid, 4'-(2-chloroethoxy)-γ-oxo-α-(3-phenylpropyl)-
53: [1,1'-Biphenyl]-4-butanoic acid, 4'-(hydroxymethyl)-γ-oxo-α-(3-phenylpropyl)-
54: [1,1'-Biphenyl]-4-butanoic acid, 4'-(2-hydroxyethoxy)-γ-oxo-α-(3-phenylpropyl)-
55: [1,1'-Biphenyl]-4-butanoic acid, 4'-ethenyl-γ-oxo-α-(3-phenylpropyl)-
56: [1,1'-Biphenyl]-4-butanoic acid, 4'-cyano-γ-oxo-α-(3-phenylpropyl)-
57: [1,1'-Biphenyl]-4-butanoic acid, γ-oxo-α-(3-phenylpropyl)-4'-(1H-tetrazol-5-yl)-
58: [1,1'-Biphenyl]-4-butanoic acid, 4'-amino-γ-oxo-α-(3-phenylpropyl)-
59: [1,1'-Biphenyl]-4-butanoic acid, 4'-(aminomethyl)-γ-oxo-α-(3-phenylpropyl)-
60: [1,1'-Biphenyl]-4-butanoic acid, 4'-(dimethylamino)-γ-oxo-α-(3-phenylpropyl)-
61: 2-Pyridinebutanoic acid, 5-(4-ethylphenyl)-α-(2-methylpropyl)-γ-oxo-
62: [1,1'-Biphenyl]-4-butanoic acid, γ-oxo-α-(3-phenylpropyl)-4'-(trifluoromethyl)-
63: [1,1'-Biphenyl]-4-butanoic acid, 4'-nitro-γ-oxo-α-(3-phenylpropyl)-
64: [1,1'-Biphenyl]-4-butanoic acid, 3',4'-dichloro-α-(2-methylpropyl)-γ-oxo-
65: [1,1'-Biphenyl]-4-butanoic acid, 3',4'-dichloro-γ-oxo-α-(3-phenylpropyl)-
66: [1,1'-Biphenyl]-4-butanoic acid, 3',5'-dichloro-γ-oxo-α-(3-phenylpropyl)-
67: [1,1'-Biphenyl]-4-butanoic acid, 4'-(acetyloxy)-γ-oxo-α-(3-phenylpropyl)-
68: Benzenepentanoic acid, α-[2-[4-(5-chloro-2-thienyl)phenyl]-2-oxoethyl]-
69: [1,1'-Biphenyl]-4-butanoic acid, 4'-methoxy-γ-oxo-α-(3-phenylpropyl)-
70: [1,1'-Biphenyl]-4-butanoic acid, 3'-chloro-4'-fluoro-γ-oxo-α-(3-phenylpropyl)-
71: [1,1'-Biphenyl]-4-butanoic acid, 4'-ethoxy-γ-oxo-α-(3-phenylpropyl)-

72: Benzenepentanoic acid, α-[2-oxo-2-[4-(3-thienyl) phenyl]ethyl]-

73: [1,1'-Biphenyl]-4-butanoic acid, 2',4'-dichloro-γ-oxo-α-(3-phenylpropyl)-

74: [1,1'-Biphenyl]-4-butanoic acid, 4'-formyl-γ-oxo-α-(3-phenylpropyl)-

75: [1,1'-Biphenyl]-4-butanoic acid, γ-oxo-α-(3-phenylpropyl)-3',5'-bis(trifluoromethyl)-

76: Benzenepentanoic acid, α-[2-oxo-2-[4-(2-thienyl) phenyl]ethyl]-

77: [1,1'-Biphenyl]-4-butanoic acid, γ-oxo-α-(3-phenylpropyl)-3'-(trifluoromethyl)-

78: [1,1'-Biphenyl]-4-butanoic acid, 2'-formyl-γ-oxo-α-(3-phenylpropyl)-

79: [1,1'-Biphenyl]-4-butanoic acid, 4'-hydroxy-oxo-α-(3-phenylpropyl)-

80: [1,1'-Biphenyl]-4-butanoic acid, γ-oxo-α-(3-phenylpropyl)-4'-propoxy-

81: [1,1'-Biphenyl]-4-butanoic acid, γ-oxo-4'-(pentyloxy)-α-(3-phenylpropyl)-

82: [1,1'-Biphenyl]-4-butanoic acid, 4'-(hexyloxy)-γ-oxo-α-(3-phenylpropyl)-

83: [1,1'-Biphenyl]-4-butanoic acid, 4'-butoxy-γ-oxo-α-(3-phenylpropyl)-

84: [1,1'-Biphenyl]-4-butanoic acid, γ-oxo-4'-(3-phenylpropoxy)-α-(3-phenylpropyl)-

85: [1,1'-Biphenyl]-4-butanoic acid, 4'-(1-methylethoxy)-γ-oxo-α-(3-phenylpropyl)-

86: [1,1'-Biphenyl]-4-butanoic acid, 4'-(heptyloxy)-γ-oxo-α-(3-phenylpropyl)-

87: [1,1'-Biphenyl]-4-butanoic acid, 4'-chloro-γ-oxo-α-(3-phenylpropyl)-

88: [1,1'-Biphenyl]-4-butanoic acid, 4'-chloro-γ-oxo-α-(3-phenylpropyl)-, (R)-

89: [1,1'-Biphenyl]-4-butanoic acid, 4'-chloro-γ-oxo-α-(3-phenylpropyl)-, (S)-

90: [1,1'-Biphenyl]-4-butanoic acid, 4'-bromo-γ-oxo-α-(3-phenylpropyl)-, (S)-

91: [1,1'-Biphenyl]-4-butanoic acid, γ-oxo-α-(3-phenylpropyl)-

92: [1,1'-Biphenyl]-4-butanoic acid, 4'-chloro-α-ethyl-γ-oxo-

93: [1,1'-Biphenyl]-4-butanoic acid, 4'-chloro-γ-oxo-α-propyl-

94: [1,1'-Biphenyl]-4-butanoic acid, 4'-chloro-γ-oxo-α-2-propenyl-

95: [1,1'-Biphenyl]-4-butanoic acid, α-butyl-4'-chloro-γ-oxo-

96: [1,1'-Biphenyl]-4-butanoic acid, 4'-chloro-γ-oxo-α-2-propynyl-

97: [1,1'-Biphenyl]-4-butanoic acid, 4'-chloro-α-heptyl-γ-oxo-

98: [1,1'-Biphenyl]-4-butanoic acid, 4'-chloro-α-decyl-γ-oxo-

99: [1,1'-Biphenyl]-4-butanoic acid, 4'-nitro-γ-oxo-α-(2-phenylethyl)-

100: [1,1'-Biphenyl]-4-butanoic acid, 4'-amino-γ-oxo-α-(2-phenylethyl)-

101: [1,1'-Biphenyl]-4-butanoic acid, 4'-cyano-γ-oxo-α-(2-phenylethyl)-

102: [1,1'-Biphenyl]-4-butanoic acid, 4'-chloro-α-[2-(2-iodophenyl)ethyl]-γ-oxo- 103: [1,1'-Biphenyl]-4-butanoic acid, 4'-chloro-α-[2-[2-(methoxycarbonyl)phenyl]ethyl]-γ-oxo- 104: [1,1'-Biphenyl]-4-butanoic acid, 4'-chloro-γ-oxo-α-phenyl- 105: [1,1'-Biphenyl]-4-butanoic acid, 4'-chloro-γ-oxo-α-(phenylmethyl)-

106: [1,1'-Biphenyl]-4-butanoic acid, 4'-chloro-γ-oxo-α-(2-phenylethyl)-

107: [1,1'-Biphenyl]-4-butanoic acid, 4'-chloro-γ-oxo-α-(4-phenylbutyl)-

108: [1,1'-Biphenyl]-4-butanoic acid, 4'-chloro-γ-oxo-α-(5-phenylpentyl)-

109: [1,1'-Biphenyl]-4-butanoic acid, 4'-chloro-γ-oxo-α-(6-phenylhexyl)-

110: [1,1'-Biphenyl]-4-butanoic acid, α-([1,1'-biphenyl]-4-ylmethyl)-4'-chloro-γ-oxo- 111: [1,1'-Biphenyl]-4-butanoic acid, 4'-chloro-γ-oxo-α-(3-phenyl-2-propenyl)-, (E)—

112: [1,1'-Biphenyl]-4-butanoic acid, 4'-chloro-α-[3-(4-methylphenyl)propyl]-γ-oxo- 113: [1,1'-Biphenyl]-4-butanoic acid, 4'-chloro-α-[3-(4-chlorophenyl)propyl]-γ-oxo- 114: [1,1'-Biphenyl]-4-butanoic acid, 4'-chloro-α-[3-(4-methoxyphenyl)propyl]-γ-oxo- 115: [1,1'-Biphenyl]-4-butanoic acid, 4'-chloro-α-[2-(4-methoxyphenyl)ethyl]-γ-oxo- 116: [1,1'-Biphenyl]-4-butanoic acid, 4'-chloro-α-[2-(3-methoxyphenyl)ethyl]-γ-oxo- 117: [1,1'-Biphenyl]-4-butanoic acid, 4'-chloro-γ-oxo-α-(3-phenyl-2-propynyl)-

118: [1,1'-Biphenyl]-4-butanoic acid, 4'-chloro-α-[[(2,2-dimethyl-1-oxopropyl)thio]methyl]-γ-oxo- 119: [1,1'-Biphenyl]-4-butanoic acid, 4'-chloro-α-[[(2,2-dimethyl-1-oxopropyl)thio]methyl]-γ-oxo- 120: [1,1'-Biphenyl]-4-butanoic acid, 4'-chloro-α-[[(2,2-dimethyl-1-oxopropyl)thio]methyl]-γ-oxo- 121: [1,1'-Biphenyl]-4-butanoic acid, 4'-chloro-γ-oxo-α-[(phenylthio)methyl]-

122: [1,1'-Biphenyl]-4-butanoic acid, 4'-chloro-α-methyl-γ-oxo-α-(phenylthio)-

123: [1,1'-Biphenyl]-4-butanoic acid, 4'-chloro-γ-oxo-α-[(phenylthio)methyl]-, (S)—

124: [1,1'-Biphenyl]-4-butanoic acid, 4'-chloro-γ-oxo-α-[(phenylthio)methyl]-, (R)—

125: [1,1'-Biphenyl]-4-butanoic acid, 4'-chloro-γ-oxo-α-[(phenylsulfinyl)methyl]-, stereoisomer 126: [1,1'-Biphenyl]-4-butanoic acid, 4'-chloro-γ-oxo-α-[(phenylsulfinyl)methyl]-, stereoisomer 127: [1,1'-Biphenyl]-4-butanoic acid, 4'-chloro-γ-oxo-α-[(phenylsulfinyl)methyl]-, stereoisomer 128: [1,1'-Biphenyl]-4-butanoic acid, 4'-chloro-γ-oxo-α-[(phenylsulfinyl)methyl]-, stereoisomer 129: [1,1'-Biphenyl]-4-butanoic acid, 4'-chloro-γ-oxo-α-[(2-thienylthio)methyl]-

130: [1,1'-Biphenyl]-4-butanoic acid, α-[(acetylthio)methyl]-4'-chloro-γ-oxo-

131: [1,1'-Biphenyl]-4-butanoic acid, 4'-chloro-α-[[[(4-methoxyphenyl)methyl]thio]methyl]-γ-oxo- 132: [1,1'-Biphenyl]-4-butanoic acid, α-[(benzoylthio)methyl]-4'-chloro-γ-oxo- 133: [1,1'-Biphenyl]-4-butanoic acid, 4'-chloro-γ-oxo-α-[[(phenylmethyl)thio]methyl]-

134: [1,1'-Biphenyl]-4-butanoic acid, 4'-chloro-α-[[(4-hydroxyphenyl)thio]methyl]-γ-oxo- 135: [1,1'-Biphenyl]-4-butanoic acid, 4'-chloro-γ-oxo-α-[[(2-phenylethyl)thio]methyl]-

136: [1,1'-Biphenyl]-4-butanoic acid, 4'-chloro-α-[[(4-methoxyphenyl)thio]methyl]-γ-oxo- 137: [1,1'-Biphenyl]-4-butanoic acid, 4'-chloro-γ-oxo-α-[[(3-phenylpropyl)thio]methyl]-

138: [1,1'-Biphenyl]-4-butanoic acid, 4'-chloro-α-[[(4-fluorophenyl)thio]methyl]-γ-oxo- 139: [1,1'-Biphenyl]-4-butanoic acid, 4'-chloro-α-[[(4-chlorophenyl)thio]methyl]-γ-oxo- 140: [1,1'-Biphenyl]-4-butanoic acid, α-[[(4-bromophenyl)thio]methyl]-4'-chloro-γ-oxo- 141: [1,1'-Biphenyl]-4-butanoic acid, 4'-chloro-α-[[(4-methylphenyl)thio]methyl]-γ-oxo- 142: [1,1'-Biphenyl]-4-butanoic acid, 4'-chloro-α-[[(4-ethylphenyl)thio]methyl]-γ-oxo- 143: [1,1'-Biphenyl]-4-butanoic acid, 4'-chloro-α-[[[4-(1,1-dimethylethyl)phenyl]thio]methyl]-γ-oxo- 144: [1,1'-Biphenyl]-4-butanoic acid, 4'-chloro-α-[(cyclohexylthio)methyl]-γ-oxo- 145: [1,1'-Biphenyl]-4-butanoic acid, 4'-chloro-α-[[(3,4-dimethoxyphenyl)thio]methyl]-γ-oxo- 146: [1,1'-Biphenyl]-4-butanoic acid, 4'-chloro-α-[[(3,4-dichlorophenyl)thio]methyl]-γ-oxo- 147: [1,1'-Biphenyl]-4-butanoic acid, 4'-chloro-α-[[[2-(hydroxymethyl)phenyl]thio]methyl]-γ-oxo- 148: [1,1'-Biphenyl]-4-butanoic acid, 4'-chloro-α-[[(2-fluorophenyl)thio]methyl]-γ-oxo- 149: [1,1'-Biphenyl]-4-butanoic acid, α-[[(2-bromophenyl)thio]methyl]-4'-chloro-γ-oxo- 150: [1,1'-Biphenyl]-4-butanoic acid, 4'-chloro-α-[[(2-ethylphenyl)tbio]methyl]-γ-oxo- 151: [1,1'-Biphenyl]-4-butanoic acid, 4'-chloro-α-[[[2-(1-methylethyl)phenyl]thio]methyl]-γ-oxo- 152: [1,1'-Biphenyl]-4-butanoic acid, 4'-chloro-γ-oxo-α-[(4-pyridinylthio)methyl]-

153: [1,1'-Biphenyl]-4-butanoic acid, α-[[[4-(acetylamino)phenyl]tio]methyl]-4'-chloro-γ-oxo- 154: [1,1'-Biphenyl]-4-butanoic acid, 4'-chloro-α-[[(4-nitrophenyl)thio]methyl]-γ-oxo- 155: [1,1'-Biphenyl]-4-butanoic acid, α-[[[4-(2-carboxyethyl)phenyl]thio]methyl]-4'-chloro-γ-oxo- 156: [1,1'-Biphenyl]-4-butanoic acid, 4'-chloro-α-[(2-naphthalenylthio)methyl]-γ-oxo- 157: [1,1'-Biphenyl]-4-butanoic acid, 4'-chloro-α-[(1-naphthalenylthio)methyl]-γ-oxo- 158: [1,1'-Biphenyl]-4-butanoic acid, α-[[(3-bromophenyl)thio]methyl]-4'-chloro-γ-oxo- 159: [1,1'-Biphenyl]-4-butanoic acid, 4'-chloro-α-[[(2-methoxyphenyl)thio]methyl]-γ-oxo- 160: [1,1'-Biphenyl]-4-butanoic acid, 4'-chloro-α-[[(2-chlorophenyl)thio]methyl]-γ-oxo- 161: [1,1'-Biphenyl]-4-butanoic acid, 4'-chloro-α-[[(3-methylphenyl)thio]methyl]-γ-oxo- 162: [1,1'-Biphenyl]-4-butanoic acid, 4'-chloro-α-[[(2-methylphenyl)thio]methyl]-γ-oxo- 163: [1,1'-Biphenyl]-4-butanoic acid, α-[[(2-carboxyphenyl)thio]methyl]-4'-chloro-γ-oxo- 164: [1,1'-Biphenyl]-4-butanoic acid, 4'-chloro-α-[[(3-methoxyphenyl)thio]methyl]-γ-oxo- 165: [1,1'-Biphenyl]-4-butanoic acid, 4'-chloro-α-[[(3,5-dimethylphenyl)thio]methyl]-γ-oxo- 166: [1,1'-Biphenyl]-4-butanoic acid, 4'-chloro-γ-oxo-α-[[[3-(trifluoromethyl)phenyl]thio]methyl]-

167: [1,1'-Biphenyl]-4-butanoic acid, 4'-chloro-α-[[[4-(methoxycabonyl)phenyl]thio]methyl]-γ-oxo- 168: [1,1'-Biphenyl]-4-butanoic acid, α-[[[4-(carboxymethyl)phenyl]thio]methyl]-4'-chloro-γ-oxo- 169: [1,1'-Biphenyl]-4-butanoic acid, 4'-chloro-α-[[(1-methylethyl)thio]methyl]-γ-oxo- 170: [1,1'-Biphenyl]-4-butanoic acid, 4'-chloro-α-[[(2-hydroxyphenyl)thio]methyl]-γ-oxo- 171: [1,1'-Biphenyl]-4-butanoic acid, 4'-chloro-γ-oxo-α-[(8-quinolinylthio)methyl]-

172: [1,1'-Biphenyl]-4-butanoic acid, 4'-chloro-α-[[(3-chlorophenyl)thio]methyl]-γ-oxo- 173: [1,1'-Biphenyl]-4-butanoic acid, 4'-chloro-α-[[(3-fluorophenyl)thio]methyl]-γ-oxo- 174: [1,1'-Biphenyl]-4-butanoic acid, 4'-chloro-α-[[[2-(methoxycarbonyl)phenyl]thio]methyl]-γ-oxo- 175: [1,1'-Biphenyl]-4-butanoic acid, 4'-chloro-α-[[[2-[(methylamino)carbonyl]phenyl]thio]methyl]-γ-oxo- 176: [1,1'-Biphenyl]-4-butanoic acid, 4'-chloro-γ-oxo-α-(phenylthio)-

177: [1,1'-Biphenyl]-4-butanoic acid, 4'-chloro-γ-oxo-α-[(phenyhnethyl)thio]-

178: Benzenebutanoic acid, a-[(acetylthio)methyl]-4-methyl-γ-oxo-

179: [1,1'-Biphenyl]-4-butanoic acid, 4'-chloro-γ-oxo-β-[(2-thienylthio)methyl]-

180: [1,1'-Biphenyl]-4-butanoic acid, 4'-chloro-β-[[(2,2-dimethyl-1-oxopropyl)thio]methyl]-γ-oxo- 181: [1,1'-Biphenyl]-4-butanoic acid, 4'-chloro-γ-oxo-β-[(phenylthio)methyl]-

182: [1,1'-Biphenyl]-4-butanoic acid, β-[(acetylthio)methyl]-4'-chloro-γ-oxo-

183: Benzenebutanoic acid, α-(acetylthio)-4-(4-chlorophenoxy)-γ-oxo-

184: 4-Thiomorpholineacetic acid, α-[2-(4'-chloro[1,1'-biphenyl]-4-yl)-2-oxoethyl]-, hydrochloride 185: [1,1'-Biphenyl]-4-butanoic acid, 4'-chloro-α-[(diphenyhnethyl)amino]-γ-oxo-, hydrochloride 186: 4-Morpholineacetic acid, α-[2-(4'-chloro[1,1'-biphenyl]-4-yl)-2-oxoethyl]-3,5-dimethyl-, hydrochloride 187: [1,1'-Biphenyl]-4-butanoic acid, 4'-chloro-γ-oxo-α-[2-(phenylmethoxy)ethyl]-

188: [1,1'-Biphenyl]-4-butanoic acid, 4'-chloro-γ-oxo-α-[(trimethylsilyl)methyl]-

189: 2H-Isoindole-2-pentanoic acid, α-[2-(4'-chloro[1,1'-biphenyl]-4-yl)-2-oxoethyl]-1,3-dihydro-1,3-dioxo- 190: [1,1'-Biphenyl]-4-butanoic acid, 4'-chloro-α-[2-(dimethylamino)ethyl]-γ-oxo-, hydrochloride 191: [1,1'-Biphenyl]-4-butanoic acid, 4'-chloro-α-[2-(diethylamino)ethyl]-γ-oxo-, hydrochloride 192: [1,1'-Biphenyl]-4-butanoic acid, 4'-chloro-α-[3-(diethylamino)propyl]-γ-oxo-, trifluoroacetate 193: [1,1'-Biphenyl]-4-butanoic acid, 4'-chloro-α-[3-(methylthio)propyl]-γ-oxo- 194: 2H-Isoindole-2-butanoic acid, α-[2-(4'-chloro[1,1'-biphenyl]-4-yl)-2-oxoethyl]-1,3-dihydro-1,3-dioxo- 195: [1,1'-Biphenyl]-4-butanoic acid, 4'-chloro-α-[(2-methoxyethoxy)methyl]-γ-oxo- 196: [1,1'-Biphenyl]-4-butanoic acid, 4'-chloro-γ-oxo-α-[(phenylmethoxy)methyl]-

197: [1,1'-Biphenyl]-4-butanoic acid, 4'-chloro-α,α-dimethyl-γ-oxo-

198: [1,1'-Biphenyl]-4-butanoic acid, 4'-chloro-α,β-dimethyl-γ-oxo-, (R*,R*)—

199: [1,1'-Biphenyl]-4-butanoic acid, 4'-chloro-α,β-dimethyl-γ-oxo-, (R*,S*)—

200: Cyclohexanecarboxylic acid, 2-[(4'-chloro[1,1'-biphenyl]-4-yl)carbonyl]-, trans- 201: Cyclohexanecarboxylic acid, 2-[(4'-chloro[1,1'-biphenyl]-4-yl)carbonyl]-, cis- 202: Benzoic acid, 2-[(4'-chloro[1,1'-biphenyl]-4-yl)carbonyl]-

203: Cyclopentanecarboxylic acid, 2-[(4'-chloro[1,1'-biphenyl]-4-yl)carbonyl]-, cis- 204: Cyclopentanecarboxylic acid, 2-[(4'-chloro[1,1'-biphenyl]-4-yl)carbonyl]-, trans- 205: Cyclobutanecarboxylic acid, 2-[(4'-chloro[1,1'-biphenyl]-4-yl)carbonyl]-, cis- 206: Cyclobutanecarboxylic acid, 2-[(4'-chloro[1,1'-biphenyl]-4-yl)carbonyl]-, trans- 207: Cyclopropanecarboxylic acid, 2-[(4'-chloro[1,1'-biphenyl]-4-yl)carbonyl]-, cis- 208: Cyclopropanecarboxylic acid, 2-[(4'-chloro[1,1'-biphenyl]-4-yl)carbonyl]-, trans- 209: Cyclopentanecarboxylic acid, 2-[(4'-chloro[1,1'-biphenyl]-4-yl)carbonyl]-5-(phenylthio)-, (1α, 2β, 5β)-

210: Cyclopentanecarboxylic acid, 2-[(4'-chloro[1,1'-biphenyl]-4-yl)carbonyl]-5-(phenylthio)-, (1α, 2β, 5α)-

211: Cyclopentanecarboxylic acid, 2-[(4'-chloro[1,1'-biphenyl]-4-yl)carbonyl]-5-(phenylthio)-, [1S-(1α, 2β, 5β)]-

212: Cyclopentanecarboxylic acid, 2-[(4'-chloro[1,1'-biphenyl]-4-yl)carbonyl]-5-(phenylthio)-, [1R-(1α, 2β, 5β)]-

213: Cyclopentanecarboxylic acid, 2-[(4'-chloro[1,1'-biphenyl]-4-yl)carbonyl]-5-[(4-fluorophenyl)thio]-, (1α, 2β, 5β)-

214: Cyclopentanecarboxylic acid, 2-[(4'-chloro[1,1'-biphenyl]-4-yl)carbonyl]-5-[(4-fluorophenyl)thio]-, (1α, 2α, 5α)-

215: Cyclopentanecarboxylic acid, 2-[(4'-chloro[1,1'-biphenyl]-4-yl)carbonyl]-5-[(4-fluorophenyl)thio]-, (1α, 2β, 5α)-

216: Cyclopentanecarboxylic acid, 2-[(4'-chloro[1,1'-biphenyl]-4-yl)carbonyl]-5-[(2-methylphenyl)thio]-, (1α, 2β, 5β)-

217: Cyclopentanecarboxylic acid, 2-[(4'-chloro[1,1'-biphenyl]-4-yl)carbonyl]-5-[(2-methylphenyl)thio]-, (1α, 2α, 5α)-

218: Cyclopentanecarboxylic acid, 2-[(4'-chloro[1,1'-biphenyl]-4-yl)carbonyl]-5-[(2-methylphenyl)thio]-, (1α, 2β, 5α)-

219: Benzoic acid, 2-[[2-carboxy-3-[(4'-chloro[1,1'-biphenyl]-4-yl)carbonyl]cyclopentyl]thio]-, 1-methyl ester, (1α, 2β, 3α)-

220: Benzoic acid, 2-[[2-carboxy-3-[(4'-chloro[1,1'-biphenyl]-4-yl)carbonyl]cyclopentyl]thio]-, 1-methyl ester, (1α, 2α, 3α)-

221: Benzoic acid, 2-[[2-carboxy-3-[(4'-chloro[1,1'-biphenyl]-4-yl)carbonyl]cyclopentyl]thio]-, 1-methyl ester, (1α, 2α, 3β)-

222: Cyclopentanecarboxylic acid, 2-[(4'-chloro[1,1'-biphenyl]-4-yl)carbonyl]-5-[(4-chlorophenyl)thio]-, (1α, 2β, 5β)-

223: Cyclopentanecarboxylic acid, 2-[(4'-chloro[1,1'-biphenyl]-4-yl)carbonyl]-5-[(4-chlorophenyl)thio]-, (1α, 2β, 5α)-

224: Cyclopentanecarboxylic acid, 2-[(4'-ethoxy[1,1'-biphenyl]-4-yl)carbonyl]-5-(phenylthio)- (1α, 2β, 5β)-

225: Cyclopentanecarboxylic acid, 2-[(4'-ethoxy[1,1'-biphenyl]-4-yl)carbonyl]-5-(phenylthio)-, (1α, 2β, 5α)-

226: Cyclopentanecarboxylic acid, 2-[(4'-ethoxy[1,1'-biphenyl]-4-yl)carbonyl]-5-(phenylmethyl)-, (1α, 2β, 5β)-

227: Cyclopentanecarboxylic acid, 2-[(4'-chloro[1,1'-biphenyl]-4-yl)carbonyl]-5-(phenylmethyl)-, (1α, 2β, 5β)-

228: 3-Cyclohexene-1-carboxylic acid, 6-[(4'-chloro[1,1'-biphenyl]-4-yl)carbonyl]-3,4-dimethyl-, trans- 229: 3-Cyclohexene-1-carboxylic acid, 6-[(4'-chloro[1,1'-biphenyl]-4-yl)carbonyl]-,trans- 230: 3-Cyclohexene-1-carboxylic acid, 6-[(4'-chloro[1,1'-biphenyl]-4-yl)carbonyl]-3-methyl-, trans- 231: Bicyclo[2.2.2]oct-5-ene-2-carboxylic acid, 3-[(4'-chloro[1,1'-biphenyl]-4-yl)carbonyl]-, (2R*,3R*)-

232: Bicyclo[2.2.2]octane-2-carboxylic acid, 3-[(4'-chloro[1,1'-biphenyl]-4-yl)carbonyl]-, trans- 233: [1,1'-Biphenyl]-4-pentanoic acid, 4'-chloro-δ-oxo- 234: Cyclopentaneacetic acid, 1-[2-(4'-chloro[1,1'-biphenyl]-4-yl)-2-oxoethyl]- 235: [1,1'-Biphenyl]-4-pentanoic acid, 4'-chloro-β-methyl-δ-oxo- 236: [1,1'-Biphenyl]-4-pentanoic acid, 4'-chloro-β,β-dimethyl-δ-oxo- 237: [1,1'-Biphenyl]-4-pentanoic acid, 4'-chloro-β-ethyl-β-methyl-δ-oxo- 238: [1,1'-Biphenyl]-4-pentanoic acid, 4'-chloro-α,α-dimethyl-δ-oxo- 239: [1,1'-Biphenyl]-4-pentanoic acid, 4'-chloro-α-(2-methylpropyl)-δ-oxo- 240: Cyclohexaneacetic acid, 1-[2-(4'-chloro[1,1'-biphenyl]-4-yl)-2-oxoethyl]-

241: Cyclopentanepropanoic acid, 1-[(4'-chloro[1,1'-biphenyl]-4-yl)carbonyl]-

242: [1,1'-Biphenyl]-4-pentanoic acid, 4'-chloro-δ-oxo-α-(3-phenylpropyl)-

243: [1,1'-Biphenyl]-4-pentanoic acid, 4'-chloro-γ-(2-methylpropyl)-δ-oxo-

244: [1,1'-Biphenyl]-4-pentanoic acid, 4'-chloro-δ-oxo-γ-(3-phenylpropyl)-

245: 1-Hexanone, 1-(4'-bromo[1,1'-biphenyl]-4-yl)-6-phenyl-3-(1H-tetrazol-5-yl)-

246: Phosphonic acid, [1-[2-(4'-bromo[1,1'-biphenyl]-4-yl)-2-oxoethyl]-4-phenylbutyl]-

247: 2-Pyrrolidinecarboxamide, 1-[2-[2-(4'-chloro[1,1'-biphenyl]-4-yl)-2-oxoethyl]-4-methyl-1-oxopentyl]-N-methyl-, (2S)—

248: Benzenebutanoic acid, 4-(2-methyl-4-oxazolyl)-α-(2-methylpropyl)-γ-oxo-

249: Benzenebutanoic acid, α-(2-methylpropyl)-4-(2-methyl-4-thiazolyl)-γ-oxo-

250: 2-Thiophenebutanoic acid, 5-(4-chlorophenyl)-γ-oxo-α-(3-phenylpropyl)-

251: 2-Furanbutanoic acid, 5-(4-chlorophenyl)-γ-oxo-α-(3-phenylpropyl)-

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. Compounds having matrix metalloprotease inhibitory activity and the generalized formula:

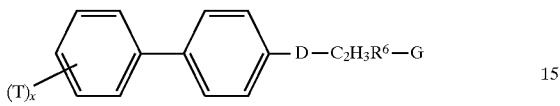

wherein
(a) T represents a substituent group, independently selected from the group consisting of halogen; alkyl; haloalkyl; alkenyl; alkynyl; —(CH$_2$)$_p$Q wherein p is 0 or an integer of 1–4; -alkenyl-Q wherein said alkenyl moiety comprises 2–4 carbons; wherein Q is selected from the group consisting of aryl, heteroaryl, —CN, —CHO, —NO$_2$, —CO$_2$R$^2$, —OCOR$^2$, —SOR$^3$, —SO$_2$R$^3$, —CON(R$^2$)$_2$, —SO$_2$N(R$^2$)$_2$, —COR$^2$, —N(R$^2$)$_2$, —N(R$^2$)COR$^2$, —N(R$^2$)CO$_2$R$^3$, —N(R$^2$)CON(R$^2$)$_2$, —OR$^4$, and —SR$^4$; wherein R$^2$ represents H, alkyl, aryl, heteroaryl, arylalkyl, or heteroarylalkyl; R$^3$ represents alkyl, aryl, heteroaryl, arylalkyl, or heteroaryl-alkyl; and R$^4$ represents H, alkyl, aryl, heteroaryl, arylalkyl, heteroaryl-alkyl, alkenyl, alkynyl, haloalkyl, acyl, or alkyleneoxy or polyalkyleneoxy terminated with H, alkyl, or phenyl;

and with the proviso that unsaturation in a moiety which is attached to Q or which is encompassed by Q is separated from any N, O, or S of Q by at least one carbon atom; and x is 0, 1, or 2;

(b) D represents

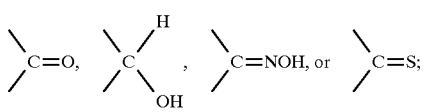

(c) R$^6$ contains at least two carbon atoms and is —(CH$_2$)$_t$R$^7$, wherein t is 0 or an integer of 1–5 and R$^7$ is selected from the group consisting of
*N-phthalimidoyl;
*N-(1,2-naphthalenedicarboximidoyl);
*N-(2,3-naphthalenedicarboximidoyl);
* N-(1,8-naphthalenedicarboximidoyl);
*N-indoloyl;
*N-(2-pyrrolodinonyl);
*N-succinimidoyl;
*N-maleimidoyl;
*3-hydantoinyl;
*1,2,4-urazolyl;
*amido;
*urethane;
*urea; and
*nonaromatic substituted or unsubstituted heterocycles containing and connected through a N atom, and comprising one additional 0 or S; and
*amino;

*and corresponding heteroaryl moieties in which the aryl portion of an aryl-containing R$^7$ group comprises 4–9 carbons and at least one N, O, or S heteroatom;

with the proviso that when R$^7$ is a nonaromatic heterocycle or an amino group, and t is 0, then x is 1 or 2; and and with the further proviso that aryl or heteroaryl portions of any of said T or R$^6$ groups optionally may bear up to two substituents selected from the group consisting of —(CH$_2$)$_y$C(R$^{11}$)(R$^{12}$)OH, —(CH$_2$)$_y$OR$^{11}$, —(CH$_2$)$_y$SR$^{11}$, —(CH$_2$)$_y$S(O)R$^{11}$, —(CH$_2$)$_y$S(O)$_2$R$^{11}$, —(CH$_2$)$_y$SO$_2$N(R$^{11}$)$_2$, —(CH$_2$)$_y$N(R$^{11}$)$_2$, —(CH$_2$)$_y$N(R$^{11}$)COR$^{12}$, —OC(R$^{11}$)$_2$O— in which both oxygen atoms are connected to the aryl ring, —(CH$_2$)$_y$COR$^{11}$, —(CH$_2$)$_y$CON(R$^{11}$)$_2$, —(CH$_2$)$_y$CO$_2$R$^{11}$, —(CH$_2$)$_y$OCOR$^{11}$, —halogen, —CHO, —CF$_3$, —NO$_2$, —CN, and —R$^{12}$, wherein
y is 0–4;
R$^{11}$ represents H or lower alkyl; and
R$^{12}$ represents lower alkyl; and (d) G represents —M,

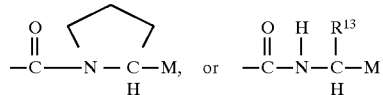

wherein
M represents —CO$_2$H, —CON(R$^{11}$)$_2$, or —CO$_2$R$^{12}$; and
R$^{13}$ represents any of the side chains of the 19 non-cyclic naturally occurring amino acids;
and pharmaceutically acceptable salts thereof.

2. A compound of claim 1 wherein said D unit is a carbonyl group.

3. A compound of claim 1 wherein said G unit is —CO$_2$H.

4. A compound of claim 1 wherein aryl portions of aryl-containing T and R$^6$ moieties contain only carbon in the rings.

5. A compound of claim 4 having the formula

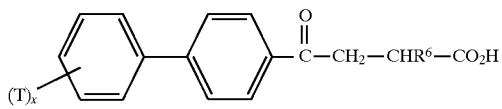

wherein
x is 1 or 2; and
one substituent T is located on the 4- position of the phenyl ring to which it is attached, relative to the bond of attachment between the two phenyl rings.

6. A composition having matrix metalloprotease inhibitory activity, comprising a compound of claim 1 and a pharmaceutically acceptable carrier.

7. A method of treating a mammal to achieve an effect, wherein the effect is: alleviation of osteoarthritis, rheumatoid arthritis, septic arthritis, periodontal disease, corneal ulceration, proteinuria, aneurysmal aortic disease, dystrophobic epidermolysis bullosa, conditions leading to inflammatory responses, osteopenias mediated by MMP activity, tempero mandibular joint disease, or demyelinating diseases of the nervous system; retardation of tumor metastasis or degenerative cartilage loss following traumatic joint injury;

reduction of coronary thrombosis from atherosclerotic plaque rupture; or improved birth control; the method comprising administering an amount of a compound of claim 1 which is effective to inhibit the activity of at least one matrix metalloprotease in said mammal thereby to achieve said effect.

8. Compounds having matrix metalloprotease inhibitory activity and the generalized formula:

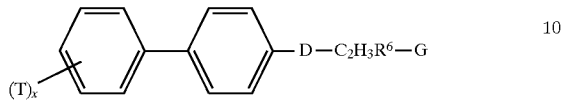

wherein
(a) each T represents a substituent group, independently selected from the group consisting of:
the halogens —F, —Cl, —Br, and —I;
alkyl of 1–10 carbons;
haloalkyl of 1–10 carbons;
alkenyl of 2–10 carbons;
alkynyl of 2–10 carbons;
—(CH$_2$)$_p$Q , wherein
p is 0 or an integer 1–4, and
—alkenyl—Q, wherein
said alkenyl moiety comprises 2–4 carbons; and
Q is selected from the group consisting of aryl of 6–10 carbons, heteroaryl comprising 4–9 carbons and at least one N, O, or S heteroatom, —CN, —CHO, —NO$_2$, —CO$_2$R$^2$, —OCOR$^2$, —SOR$^3$, —SO$_2$R$^3$, —CON(R$^2$)$_2$, —SO$_2$N(R$^2$)$_2$, —C(O)R$^2$, —N(R$^2$)$_2$, —N(R$^2$)COR$^2$, —N(R$^2$)CO$_2$R$^3$, —N(R$^2$)CON(R$^2$)$_2$, —CHN$_4$, —OR$^4$, and —SR$^4$;
wherein
R$^2$ represents H;
alkyl of 1–6 carbons;
aryl of 6–10 carbons;
heteroaryl comprising 4–9 carbons and at least one N, O, or S heteroatom; or
arylalkyl in which the aryl portion contains 6–10 carbons and the alkyl portion contains 1–4 carbons; or
heteroaryl-alkyl in which the heteroaryl portion comprises 4—9 carbons and at least one N, O, o r S heteroatom and the alkyl portion contains 1–4 carbons;
R$^3$ represents alkyl of 1–4 carbons;
aryl of 6–10 carbons;
heteroaryl comprising 4–9 carbons and at least one N, O, or S heteroatom; or
arylalkyl in which the aryl portion contains 6–10 carbons and the alkyl portion contains 1–4 carbons; or
heteroaryl-alkyl in which the heteroaryl portion comprises 4–9 carbons and at least one N, O, or S heteroatom and the alkyl portion contains 1–4 carbons;
R$^4$ represents H;
alkyl of 1–12 carbons;
aryl of 6–10 carbons;
heteroaryl comprising 4–9 carbons and at least one N, O, or S heteroatom;
arylalkyl in which the aryl portion contains 6–10 carbons and the alkyl portion contains 1–4 carbons;
heteroaryl-alkyl in which the heteroaryl portion comprises 4–9 carbons and at least one N, O, or S heteroatom and the alkyl portion contains 1–4 carbons;
alkenyl of 2–12 carbons;
alkynyl of 2–12 carbons;
—(C$_q$H$_{2q}$O)$_r$R$^5$ wherein q is 1–3; r is 1–3; and R$^5$ is H provided q is greater than 1, or alkyl of 1–4 carbons, or phenyl;
—(CH$_2$)$_s$X wherein s is 2–3 and X is halogen; or
—C(O)R$^2$;
and with the proviso that unsaturation in a moiety which is attached to Q or which is encompassed by Q is separated from any N, 0, or S of Q by at least one carbon atom, and x is 0, 1, or 2;
(b) D represents

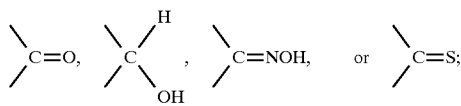

R$^6$ contains at least two carbon atoms and is —(CH$_2$)$_t$R$^7$
wherein
t is 0 or an integer of 1–5; and
R$^7$ is selected from the group consisting of

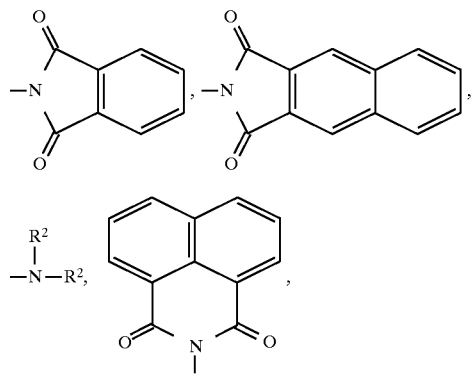

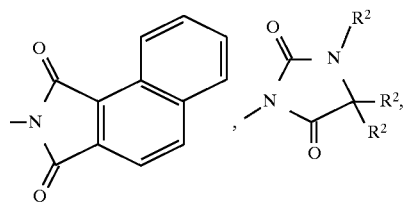

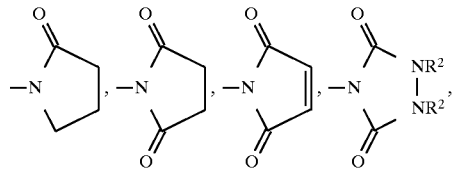

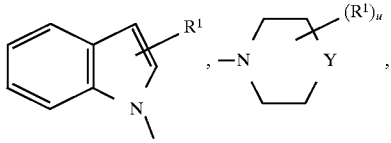

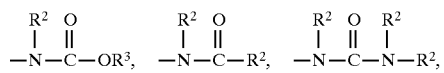

and corresponding heteroaryl moieties in which the aryl portion of an aryl-containing R$^7$ group comprises 4–9 carbons and at least one N, O, or S heteroatom;

wherein
Y represents O or S;
$R^1$, $R^2$, and $R^3$ are as defined above; and
u is 0, 1, or 2; and
with the proviso that when $R^7$ is $$-N\diagup\diagdown\diagup^{(R^1)_u}_{Y}\diagdown \quad \text{or} \quad -N-R^2, \atop R^2$$

and t is 0, then x is 1 or 2;
and with the further proviso that
aryl or heteroaryl portions of any of said T or $R^6$ groups optionally may bear up to two substituents selected from the group consisting of $-(CH_2)_yC(R^{11})(R^{12})OH$, $-(CH_2)_yOR^{11}$, $-(CH_2)_ySR^{11}$, $-(CH_2)_yS(O)R^{11}$, $-(CH_2)_yS(O)_2R^{11}$, $-(CH_2)_ySO_2N(R^{11})_2$, $-(CH_2)_yN(R^{11})_2$, $-(CH_2)_yN(R^{11})COR^{12}$, $-OC(R^{11})_2O-$ in which both oxygen atoms are connected to the aryl ring, $-(CH_2)_yCOR^{11}$, $-(CH_2)_yCON(R^{11})_2$, $-(CH_2)_yCO_2R^{11}$, $-(CH_2)_yOCOR^{11}$, $-halogen$, $-CHO$, $-CF_3$, $-NO_2$, $-CN$, and $-R^{12}$,
wherein
y is 0–4;
$R^{11}$ represents H or alkyl of 1–4 carbons; and
$R^{12}$ represents alkyl of 1–4 carbons; and
(d) G represents —M, $$\overset{O}{\underset{\|}{-C}}-\overset{H}{\underset{|}{N}}-\overset{\diagup\diagdown}{C}-M, \quad \text{or} \quad \overset{O}{\underset{\|}{-C}}-\overset{H}{\underset{|}{N}}-\overset{R^{13}}{\underset{|}{C}}-M$$

wherein
M represents $-CO_2H$, $-CON(R^{11})_2$, or $-CO_2R^{12}$; and p3 $R^{13}$ represents any of the side chains of the 19 noncyclic naturally occurring amino acids;
and pharmaceutically acceptable salts thereof.

9. A compound of claim 8 wherein said D unit is a carbonyl group.

10. A compound of claim 8 wherein said G unit is $-CO_2H$.

11. A compound of claim 8 wherein
aryl portions of aryl-containing T and $R^6$ moieties contain only carbon in the rings.

12. A compound of claim 11 having the formula $$(T)_x-\text{[biphenyl]}-\overset{O}{\underset{\|}{C}}-CH_2-CHR^6-CO_2H$$

wherein
x is 1 or 2; and
one substituent T is located on the 4- position of the phenyl ring to which it is attached, relative to the point of attachment between the two phenyl rings.

13. A composition having matrix metalloprotease inhibitory activity, comprising a compound of claim 8 and a pharmaceutically acceptable carrier.

14. A method of treating a mammal to achieve an effect, wherein the effect is: alleviation of osteoarthritis, rheumatoid arthritis, septic arthritis, periodontal disease, corneal ulceration, proteinuria, aneurysmal aortic disease, dystrophobic epidermolysis bullosa, conditions leading to inflammatory responses, osteopenias mediated by MMP activity, tempero mandibular joint disease, or demyelinating diseases of the nervous system; retardation of tumor metastasis or degenerative cartilage loss following traumatic joint injury; reduction of coronary thrombosis from atherosclerotic plaque rupture; or improved birth control; the method comprising administering an amount of a compound of claim 8 which is effective to inhibit the activity of at least one matrix metalloprotease in said human, thereby to achieve said effect.

15. A compound of claim 1, having the Chemical Abstracts name
2 H-Isoindole-2-pentanoic acid, α-[2-(4'-chloro[1,1'-biphenyl]-4-yl)-2-oxoethyl]-1,3-dihydro-1,3-dioxo- ; or
2 H-Isoindole-2-butanoic acid, α-[2-(4'-chloro[1,1'-biphenyl]-4-yl)-2-oxoethyl]-1,3-dihydro-1,3-dioxo-.

16. A compound of claim 8, having the Chemical Abstracts name
2 H-Isoindole-2-pentanoic acid, α-[2-(4'-chloro[1,1'-biphenyl]-4-yl)-2-oxoethyl]-1,3-dihydro-1,3-dioxo- ; or
2 H-Isoindole-2-butanoic acid, α-[2-(4'-chloro[1,1'-biphenyl]-4-yl)-2-oxoethyl]-1,3-dihydro- 1,3-dioxo-.

* * * * *